US011198876B2

(12) United States Patent
Bumcrot et al.

(10) Patent No.: US 11,198,876 B2
(45) Date of Patent: Dec. 14, 2021

(54) COMPOSITIONS AND METHODS FOR INHIBITING EXPRESSION OF TMPRSS6 GENE

(71) Applicant: ALNYLAM PHARMACEUTICALS, INC., Cambridge, MA (US)

(72) Inventors: David Bumcrot, Cambridge, MA (US); Brian Bettencourt, Groton, MA (US); Ivanka Toudjarska, Medford, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 71 days.

(21) Appl. No.: 16/121,265

(22) Filed: Sep. 4, 2018

(65) Prior Publication Data

US 2019/0119685 A1  Apr. 25, 2019

Related U.S. Application Data

(62) Division of application No. 14/866,148, filed on Sep. 25, 2015, now Pat. No. 10,100,312, which is a division of application No. 14/007,835, filed as application No. PCT/US2012/030786 on Mar. 28, 2012, now Pat. No. 9,175,290.

(60) Provisional application No. 61/568,942, filed on Dec. 9, 2011, provisional application No. 61/468,830, filed on Mar. 29, 2011.

(51) Int. Cl.
*C12N 15/11* (2006.01)
*C12N 15/113* (2010.01)
*A61K 31/713* (2006.01)

(52) U.S. Cl.
CPC ........ *C12N 15/1138* (2013.01); *A61K 31/713* (2013.01); *C12N 15/1137* (2013.01); *C12Y 304/21* (2013.01); *C12N 2310/14* (2013.01); *C12N 2310/315* (2013.01); *C12N 2310/321* (2013.01); *C12N 2310/344* (2013.01); *C12N 2310/346* (2013.01); *C12N 2310/351* (2013.01); *C12N 2320/30* (2013.01)

(58) Field of Classification Search
CPC ............ C12N 15/1138; C12N 15/1137; C12N 2310/14
See application file for complete search history.

(56) References Cited

U.S. PATENT DOCUMENTS

| 9,175,290 B2 | 11/2015 | Bumcrot et al. |
| 9,783,806 B2 | 10/2017 | Butler et al. |
| 2005/0246794 A1 | 11/2005 | Khvorova et al. |
| 2007/0093443 A1 | 4/2007 | Madison et al. |
| 2008/0125384 A1 | 5/2008 | Yang |
| 2009/0191263 A1 | 7/2009 | Reich et al. |
| 2009/0192104 A1 | 7/2009 | McSwiggen et al. |
| 2009/0203135 A1 | 8/2009 | Forst et al. |
| 2014/0194489 A1 | 7/2014 | Bumcrot et al. |
| 2014/0288158 A1 | 9/2014 | Rajeev et al. |

FOREIGN PATENT DOCUMENTS

| EP | 1752536 A1 | 2/2007 |
| WO | 9813526 A1 | 4/1998 |
| WO | 04045543 A2 | 6/2004 |
| WO | 2005116204 A1 | 12/2005 |
| WO | 2007053696 A2 | 5/2007 |
| WO | 2009073809 A2 | 6/2009 |
| WO | 2009082607 A2 | 7/2009 |
| WO | 2010/033246 A1 | 3/2010 |
| WO | 2010099341 A1 | 9/2010 |
| WO | 2010148013 A2 | 12/2010 |
| WO | 2012135246 A2 | 10/2012 |
| WO | 2013070786 A1 | 5/2013 |
| WO | 2014190157 A1 | 11/2014 |
| WO | 2016085852 A1 | 6/2016 |

OTHER PUBLICATIONS

AY358398 *Homo sapiens* clone DNA49152 PVAE354 (UNQ354) mRNA, complete cds. Published Oct. 3, 2003.
CR456446 *Homo sapiens* dJ1170K4.2 full length open reading frame (ORF) cDNA clone (cDNA clone C22ORF: pGEM.dJ1170K4. 2). Published Oct. 16, 2008.
CU013044 *Homo sapiens* TMPRSS6, mRNA (cDNA clone IMAGE:100000302), complete cds, with stop codon, in Gateway system. Published Oct. 7, 2008.
CU691658 Synthetic construct *Homo sapiens* gateway clone IMAGE-100019507 5' read TMPRSS6 mRNA. Published Feb. 23, 2008.
D'Aquino et al., The protein kinase Kin4 inhibits exit from mitosis in response to spindle position defects. Mol Cell. Jul. 22, 2005;19(2):223-34.
Database Biosis [Online] Biosciences Information Service, Philadelphia, PA, US, Nov. 2010, Finberg, K et al., "Tmprss6, An Inhibitor of Hepatic Bmp/Smad Signaling, is required for Hepcidin suppression and iron loading in a mouse model of beta-thalassemia", XP002737926, Database accession No. PREV201100422711 & Blood, vol. 116, No. 21, Nov. 2010, p. 75, 52nd Annual Meeting of the American Society of Hematology (ASH); Orlando, FL, USA; Dec. 4-7, 2010.
DI008490 Nucleic acid molecules encoding transmembrane serine proteases,the encoded proteins and methods based thereon. Feb. 21, 2008.
DI066240 Novel Polypeptides and Nucleic Acids Encoding the Same. Published Feb. 21, 2008.
DJ429262 Novel Polypeptides and Nucleic Acids Encoding the Same. Published Jun. 11, 2008.
DM117477 Transgenic Models for Different Genes and Their Use for Gene Characterization. Published Jun. 18, 2009.
DM180171 Modified Proteases That Inhibit Complement Activation. Published Aug. 26, 2009.

(Continued)

*Primary Examiner* — Ekaterina Poliakova-Georgantas
(74) *Attorney, Agent, or Firm* — McCarter & English, LLP; Maria Laccotripe Zacharakis; Amanda McFedries

(57) ABSTRACT

The invention relates to double-stranded ribonucleic acid (dsRNA) compositions targeting the TMPRSS6 gene, and methods of using such dsRNA compositions to inhibit expression of TMPRSS6.

23 Claims, 10 Drawing Sheets

Specification includes a Sequence Listing.

(56) References Cited

OTHER PUBLICATIONS

DM472417 Transgenic Models for Different Genes and Their Use for Gene Characterization. Published Jan. 21, 2010.
Elbashir et al., Functional anatomy of siRNAs for mediating efficient RNAi in *Drosophila melanogaster* embryo lysate. EMBO J. Dec. 3, 2001;20(23):6877-88.
FB762896 Sequence 1 from Patent WO2008009895. Published Dec. 18, 2008.
Finberg et al. "Tmprss6 is a genetic modifier of the Hfe-hemochromatosis phenotype in mice" Blood (2011) vol. 117, No. 17, pp. 4590-4599.
Finberg et al. "Tmprss6, an inhibitor of Hepatic Bmp/Smad Signaling, Is Required for Hepcidin Suppression and Iron Loading in a Mouse Model of ?-Thalassemia" Blood (2010) vol. 116, No. 21, Abstract No. 164.
Finberg et al., Down-regulation of Bmp/Smad signaling by Tmprss6 is required for maintenance of systemic iron homeostasis. Blood. May 6, 2010;115(18):3817-26. doi: 10.1182/blood-2009-05-224808. Epub Mar. 3, 2010.
GX268669 Sequence 168 from U.S. Pat. No. 7,723,488. Published Aug. 13, 2010.
HI141555 Sequence 4024 from Patent EP2052088. Published Nov. 2, 2010.
HV784394 JP 2010075209-A/109: Protease Screening Methods and Proteases Identified Thereby. Published Nov. 15, 2012.
HV848938 JP 2010500568-A/24256: Organ-Specific Proteins and Methods of Their Use. Published Nov. 15, 2012.
International Search Report and Written Opinion dated Sep. 4, 2012 from International Application No. PCT/US12/30786.
Kumiko Tei, et al., "RNAi Experiments—Q&A Self-Study Guide" 2006, published by Yodosha Co., Ltd., p. 52 and 53 and 88-96— Partial English Translation.
Lakhal et al., "Regulation of Type II Transmembrane Serine Proteinase TMPRSS6 by Hypoxia-Inducible Factors: New Link Between Hypoxia Signaling and Iron Homeostasis", J Bioi Chem., Feb. 2011, vol. 286(6), p. 4090-7. Epub Oct. 21, 2010.
Lakhal, S. et al. "Supplementary Data", Oct. 21, 2010, XP055180205, Retrieved from the Internet: URL:http:jwww.jbc.orgjcontentjsuppl/ 2010/ 10/21/M110.173096.DC1jjbc.M110.173096-1.pd f [retrieved on Mar. 30, 2015].
Lakhal, S. et al., "Regulation of Type II 1-15 Transmembrane Serine Proteinase TMPRSS6 by Hypoxia-inducible Factors: New Link Between Hypoxia Signaling and Iron Homeostasis", Journal of Biological Chemistry, vol. 286, No. 6, Feb. 11, 2011, pp. 4090-4097, XP055180203.
Maxson, J.E., et al., "Matriptase-2- and Proprotein Convertase-Cleaved Forms of Hemojuvelin Have Different Roles in the Down-Regulation of Hepcidin Expression", Journal of Biological Chemistry, vol. 285, No. 50, Dec. 10, 2010, pp. 39021-39028.
Maxson, J.E., et al., "Supplemental Methods", The Journal of Biological Chemistry, Dec. 10, 2010, XP055180076, Retrieved from the Internet: URL:http://www.jbc.org{content/suppl/2010/ 10/09/ M110.183160.DC1/jbc.M110.183160-1 pd f [retrieved on Mar. 30, 2015].
NCBI_NM_153609, *Homo sapiens* transmembrane protease, serine 6 (TMPRSS6), mRNA. Nov. 2006 [online]. (Retrieved on May 30, 2012). Retrieved from the Internet: <URL: http:llwww.ncbi.nlm. nih.gov/nuccore/56682967?sat=11&satkey=8411313> Definition; and Origin.
NM_001130556 Rattus norvegicus transmembrane serine protease 6 (Tmprss6), mRNA. (NM_001130556 XM_001074604 XM_001074630 XM_235768). Published Aug. 28, 2012.
Park et al. "Cloning and Characterization of TMPRSS6, a Novel Type 2 Transmembrane Serine Protease" Molecules and Cells (2005) vol. 19, No. 2, pp. 223-227.
Partial Supplementary European Search Report in European Application No. 12763700.7 dated Apr. 9, 2015.
Ramsay et al., Matriptase-2 (TMPRSS6): a proteolytic regulator of iron homeostasis. Haematologica. Jun. 2009;94(6):840-9. doi: 10.3324/ haematol.2008.001867. Epub Apr. 18, 2009.
Sisay, M.T. et al., "Identification of the First Low-Molecular-Weight Inhibitors of Matriptase-2", Journal of Medicinal Chemistry, vol. 53, No. 15, Aug. 12, 2010, pp. 5523-5535, XP055152881.
Velasco et al., Matriptase-2, a membrane-bound mosaic serine proteinase predominantly expressed in human liver and showing degrading activity against extracellular matrix proteins. J Biol Chem. Oct. 4, 2002;277(40):37637-46. Epub Jul. 30, 2002.
Extended European Search Report for European Application No. 19207174.4 dated May 18, 2020.

FIG. 1

```
   1 cttgagccag acccagtcca gctctggtgc ctgccctctg gtgcgagctg acctgagatg
  61 cacttccctc ctctgtgagc tgtctcggca cccacttgca gtcactgccg cctgatgttg
 121 ttactcttcc actccaaaag gatgcccgtg gccgaggccc cccaggtggc tggcgggcag
 181 ggggacggag gtgatggcga ggaagcggag ccggagggga tgttcaaggc ctgtgaggac
 241 tccaagagaa aagcccgggg ctacctccgc ctggtgcccc tgtttgtgct gctggccctg
 301 ctcgtgctgg cttcggcggg ggtgctactc tggtatttcc tagggtacaa ggcggaggtg
 361 atggtcagcc aggtgtactc aggcagtctg cgtgtactca atcgccactt ctcccaggat
 421 cttacccgcc gggaatctag tgccttccgc agtgaaaccg ccaaagccca gaagatgctc
 481 aaggagctca tcaccagcac ccgcctggga acttactaca actccagctc cgtctattcc
 541 tttggggagg gacccctcac ctgcttcttc tggttcattc tccaaatccc cgagcaccgc
 601 cggctgatgc tgagccccga ggtggtgcag gcactgctgg tggaggagct gctgtccaca
 661 gtcaacagct cggctgccgt ccctacagg gccgagtacg aagtggaccc cgagggccta
 721 gtgatcctgg aagccagtgt gaaagacata gctgcattga attccacgct gggttgttac
 781 cgctacagct acgtgggcca gggccaggtc ctccggctga ggggcctga ccacctggcc
 841 tccagctgcc tgtggcacct gcagggcccc aaggacctca tgctcaaact ccggctggag
 901 tggacgctgg cagagtgccg ggaccgactg gccatgtatg acgtggccgg gcccctggag
 961 aagaggctca tcacctcggt gtacggctgc agccgccagg agccgtggg ggaggttctg
1021 gcgtcggggg ccatcatggc ggtcgtctgg aagaagggcc tgcacagcta ctacgacccc
1081 ttcgtgctct ccgtgcagcc ggtggtcttc caggcctgtg aagtgaacct gacgctggac
1141 aacaggctcg actcccaggg cgtcctcagc accccgtact ccccagcta ctactcgccc
1201 caaacccact gctcctggca cctcacggtg ccctctctgg actacggctt ggccctctgg
1261 tttgatgcct atgcactgag gaggcagaag tatgatttgc cgtgcaccca gggccagtgg
1321 acgatccaga acaggaggct gtgtggcttg cgcatcctgc agccctacgc cgagaggatc
1381 cccgtggtgg ccacggccgg gatcaccatc aacttcacct cccagatctc cctcaccggg
1441 cccggtgtgc gggtgcacta tggcttgtac aaccagtcgg accctgccc tggagagttc
1501 ctctgttctg tgaatggact ctgtgtccct gcctgtgatg gggtcaagga ctgccccaac
1561 ggcctggatg agagaaactg cgtttgcaga gccacattcc agtgcaaaga ggacagcaca
1621 tgcatctcac tgcccaaggt ctgtgatggg cagcctgatt gtctcaacgg cagcgacgaa
1681 gagcagtgcc aggaaggggt gccatgtggg acattcacct ccagtgtga ggaccggagc
1741 tgcgtgaaga agcccaaccc gcagtgtgat gggcggcccg actgcaggga cggctcggat
1801 gaggagcact gtgactgtgg cctccaggc ccctccagcc gcattgttgg tggagctgtg
1861 tcctccgagg gtgagtggcc atggcaggcc agcctccagg ttcggggtcg acacatctgt
1921 gggggggccc tcatcgctga ccgctgggtg ataacagctg cccactgctt ccaggaggac
1981 agcatggcct ccacggtgct gtggaccgtg ttcctgggca aggtgtggca gaactcgcgc
2041 tggcctggag aggtgtcctt caaggtgagc cgcctgctcc tgcacccgta ccacgaagag
2101 gacagccatg actacgacgt ggcgctgctg cagctcgacc accggtggt gcgctcggcc
2161 gccgtgcgcc ccgtctgcct gccgcgcgc tcccacttct cgagcccgg cctgcactgc
2221 tggattacgg gctgggcgc cttgcgcgag ggcggcccca tcagcaacgc tctgcagaaa
2281 gtggatgtgc agttgatccc acaggacctg tgcagcgagg tctatcgcta ccaggtgacg
2341 ccacgcatgc tgtgtgccgg ctaccgcaag ggcaagaagg atgcctgtca gggtgactca
2401 ggtggtccgc tggtgtgcaa ggcactcagt ggccgctggt tcctggcggg gctggtcagc
2461 tggggcctgg gctgtggccg gctaactac ttcggcgtct acacccgcat acaggtgtg
2521 atcagctgga tccagcaagt ggtgacctga ggaactgccc cctgcaaag cagggcccac
2581 ctcctggact cagagagccc agggcaactg ccaagcaggg ggacaagtat tctggcgggg
2641 ggtggggag agagcaggcc ctgtggtggc aggaggtggc atcttgtctc gtccctgatg
2701 tctgctccag tgatggcagg aggatggaga agtgccagca gctggggtc aagacgtccc
2761 ctgaggaccc aggcccacac ccagcccttc tgcctccaa ttctctctcc tccgtcccct
2821 tcctccactg ctgcctaatg caaggcagtg gctcagcagc aagaatgctg gttctacatc
2881 ccgaggagtg tctgaggtgc gccccactct gtacagaggc tgtttgggca gccttgcctc
2941 cagagagcag attccagctt cggaagcccc tggtctaact tgggatctgg aatggaagg
3001 tgctcccatc ggaggggacc ctcagagccc tggagactgc caggtgggcc tgctgccact
3061 gtaagccaaa aggtggggaa gtcctgactc cagggtcctt gcccacccc tgcctgccac
3121 ctgggccctc acagcccaga ccctcactgg gaggtgagct cagctgccct ttggaataaa
3181 gctgcctgat caaaaaaaaa aaaaaaaaa aa
```

COMPOSITIONS AND METHODS FOR INHIBITING EXPRESSION OF TMPRSS6 GENE

CROSS-REFERENCE TO RELATED APPLICATIONS

This application is a divisional of U.S. application Ser. No. 14/866,148, filed Sep. 25, 2015, now U.S. Pat. No. 10,100,312, which is a divisional of U.S. application Ser. No. 14/007,835, filed Sep. 26, 2013, now U.S. Patent No. 9,1175,290, which is a national phase application under 35 U.S.C. § 371 of PCT International Application No. PCT/US2012/030786, filed Mar. 28, 2012, which claims the benefit of U.S. Provisional Application No. 61/468,830, filed Mar. 29, 2011, and U.S. Provisional Application No. 61/568, 942, filed Dec. 9, 2011. These prior applications are incorporated by reference herein in their entirety.

FIELD OF THE INVENTION

The invention relates to the specific inhibition of the expression of the TMPRSS6 gene.

BACKGROUND OF THE INVENTION

TMPRSS6 (Transmembrane Protease, Serine 6) encodes a type II serine protease and is expressed mainly in the liver. TMPRSS6 influences iron levels in the liver by binding and proteolytically degrading the hepcidin activator and BMP co-receptor HJV (hemojuvelin), which causes down-regulation of hepcidin levels.

TMPRSS6 consists of a short N-terminal intracytoplasmic tail, a type II transmembrane domain, a stem region composed of two extracellular CUB (complement factor Cls/Clr, urchin embryonic growth factor and BMP (bone morphogenetic protein)) domains, three LDLR (low-density-lipoprotein receptor class A) domains, and a C-terminal trypsin-like serine protease domain. There are also consensus sites for N-glycosylation in the extracellular domain, and a potential phosphorylation site in the intracytoplasmic tail region.

SUMMARY OF THE INVENTION

Described herein are compositions and methods that effect the RNA-induced silencing complex (RISC)-mediated cleavage of RNA transcripts of the TMPRSS6 gene, such as in a cell or mammal. Also described are compositions and methods for treating pathological conditions and diseases caused by the expression of a TMPRSS6 gene, such as a disorder characterized by iron overabundance (e.g., thalassemia, e.g., a β-thalassemia intermedia or an α-thalassemia). Also described are compositions and methods for decreasing or preventing iron absorption or mobilization, thereby ameliorating iron overload in certain pathological conditions. The methods and compositions described herein are generally useful for the treatment of hemochromatosis (iron build-up in the body).

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein inhibits the expression of TMPRSS6 in a cell or mammal. Alternatively, in another embodiment, the iRNA up-regulates the expression of TMPRSS6 in a cell or mammal.

The iRNAs included in the compositions featured herein encompass a double-stranded RNA (dsRNA) having an RNA strand (the antisense strand) having a region that is 30 nucleotides or less, generally 19-24 nucleotides in length, that is substantially complementary to at least part of an mRNA transcript of a TMPRSS6 gene. In one embodiment, the dsRNA comprises a region of at least 15 contiguous nucleotides.

In one embodiment, an iRNA for inhibiting expression of a TMPRSS6 gene includes at least two sequences that are complementary to each other. The iRNA includes a sense strand having a first sequence and an antisense strand having a second sequence. The antisense strand includes a nucleotide sequence that is substantially complementary to at least part of an mRNA encoding TMPRSS6, and the region of complementarity is 30 nucleotides or less, and at least 15 nucleotides in length. Generally, the iRNA is 19 to 24, e.g., 19 to 21 nucleotides in length. In some embodiments the iRNA is from about 15 to about 25 nucleotides in length, and in other embodiments the iRNA is from about 25 to about 30 nucleotides in length. The iRNA, upon contacting with a cell expressing TMPRSS6, inhibits the expression of a TMPRSS6 gene by at least 10%, at least 20%, at least 25%, at least 30%, at least 35% or at least 40% or more, such as when assayed by a method as described herein. In one embodiment, the TMPRSS6 iRNA is formulated in a stable nucleic acid lipid particle (SNALP).

In one embodiment, an iRNA featured herein includes a first sequence of a dsRNA that is selected from the group consisting of the sense sequences of Tables 2, 3 or 4 and a second sequence that is selected from the group consisting of the corresponding antisense sequences of Tables 2, 3 or 4. The iRNA molecules featured herein can include naturally occurring nucleotides or can include at least one modified nucleotide, including, but not limited to a 2'-O-methyl modified nucleotide, a nucleotide having a 5'-phosphorothioate group, and a terminal nucleotide linked to a cholesteryl derivative. Alternatively, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Generally, such a modified sequence will be based on a first sequence of said iRNA selected from the group consisting of the sense sequences of Tables 2, 3 or 4 and a second sequence selected from the group consisting of the antisense sequences of Tables 2, 3 or 4.

In one embodiment, an iRNA featured herein includes a sense strand of a TMPRSS6 dsRNA having a sequence selected from the group consisting of SEQ ID NO:111, SEQ ID NO:455, SEQ ID NO:109, SEQ ID NO:524, SEQ ID NO:89, SEQ ID NO:494, SEQ ID NO:445, SEQ ID NO:592, SEQ ID NO:47, and SEQ ID NO:540; and an antisense strand consisting of a sequence selected from the group consisting of SEQ ID NO:112, SEQ ID NO:456, SEQ ID NO:110, SEQ ID NO:525, SEQ ID NO:90, SEQ ID NO:495, SEQ ID NO:446, SEQ ID NO:593, SEQ ID NO:48 and SEQ ID NO:541.

In another embodiment, a composition containing a dsRNA targeting TMPRSS6 is administered to a subject who has elevated iron levels, e.g., elevated levels of iron in the liver. A subject who has elevated iron levels can be identified as a subject who has elevated serum iron levels (e.g., over 350 µg/dL, over 500 µg/dL or over 1000 µg/dL or more), elevated serum ferritin levels, or a transferrin saturation level greater than 40%, greater than 45%, greater than 50%, greater than 60% or more.

Mild-to-moderate iron overload is indicated by serum ferritin levels of 300-2500 µg/L, while levels >2500 µg/L are associated with an increased risk of cardiac disease. Serum ferritin>1000 µg/L has been shown to be associated with adverse outcomes in both primary and secondary iron overload. Serum ferritin levels higher than 200 µg/L in premenopausal women, and 300 µg/L in men and postmenopausal women indicate primary iron overload due to hemochromatosis, and ferritin levels higher than 1000 µg/L typically suggest liver damage due to iron overload. A subject having a serum ferritin level higher than 300 µg/L, 500 µg/L, 1000 µg/L, 1500 µg/L, 2000 µg/L, or 2500 µg/L or more is a candidate for treatment with a dsRNA targeting TMPRSS6.

In another embodiment, a composition containing a dsRNA targeting TMPRSS6 is administered to a subject who has elevated transferrin levels, e.g., transferrin levels greater than 400 mg/dL, greater than 500 mg/dL, greater than 1000 mg/dL or more)

Iron levels can also be measured by a TIBC (Total Iron Binding Capacity) test. The TIBC test measures the amount of iron that the blood would carry if the transferrin were fully saturated. Since transferrin is produced by the liver, the TIBC can be used to monitor liver function and nutrition. A subject having TIBC values greater than 400 µg/dL, greater than 500 µg/dL, or greater than 1000 µg/dL or more is a candidate for treatment with a dsRNA targeting TMPRSS6.

In one embodiment, administration of the dsRNA lowers iron levels, e.g., in the liver, or in serum, by at least 5%, e.g., by at least 10%, by at least 15%, at least 20%, at least 25%, at least 30%, at least 40%, at least 50%, or at least 60%, or more. In some embodiments, one or more of serum ferritin levels, serum transferrin levels, transferrin saturation levels or TIBC values are decreased by at least 5%, at least 10%, at least 15%, at least 20%, at least 25%, at least 30%, at least 40%, at least 50%, or at least 60%, or more, as compared to pretreatment levels. In another embodiment, the decrease in iron levels, decrease in serum ferritin levels, decrease in transferrin or transferrin saturation levels, or decrease in TIBC values is maintained for at least 5, 10, 20, 30, or 40 days or longer.

In one embodiment, the subject is selected, at least in part, on the basis of needing (as opposed to merely selecting a patient on the grounds of who happens to be in need of) lower iron levels.

In one embodiment, an iRNA as described herein targets a wildtype TMPRSS6 RNA transcript, and in another embodiment, the iRNA targets a mutant transcript (e.g., a TMPRSS6 RNA carrying an allelic variant). For example, an iRNA featured in the invention can target a polymorphic variant, such as a single nucleotide polymorphism (SNP), of TMPRSS6. In another embodiment, the iRNA targets both a wildtype and a mutant TMPRSS6 transcript. In yet another embodiment, the iRNA targets a transcript variant of TMPRSS6.

In one embodiment, an iRNA featured in the invention targets a non-coding region of a TMPRSS6 RNA transcript, such as the 5' or 3' untranslated region.

In one embodiment, an iRNA featured in the invention is delivered to the liver, e.g., hepatocytes of the liver or Kupffer cells, e.g., hypertrophic Kupffer cells.

In one aspect, embodiments featured in the invention provide a cell containing at least one of the iRNAs featured in the invention. The cell is generally a mammalian cell, such as a human cell.

In another aspect, embodiments featured in the invention provide a pharmaceutical composition for inhibiting the expression of a TMPRSS6 gene in an organism, generally a human subject. The composition typically includes one or more of the iRNAs described herein and a pharmaceutically acceptable carrier or delivery vehicle. In one embodiment, the composition is used for treating a disorder that causes increased iron levels, e.g., hemochromatosis. For example, the composition is useful for treating a thalassemia, such as β-thalassemia intermedia.

In another embodiment, the pharmaceutical composition is formulated for administration of a dosage regimen described herein, e.g., not more than once every two months, not more than once per month, not more than twice per month, not more than once every four weeks, not more than once every three weeks, not more than once every two weeks, or not more than once every week. In another embodiment, administration of the pharmaceutical composition can be maintained for a month or longer, e.g., one, two, three, or six months, or one year, or five years, or ten years, or longer, including the remaining lifetime of a subject.

In another embodiment, a composition containing an iRNA described herein, e.g., a dsRNA targeting TMPRSS6, is administered with a non-iRNA therapeutic agent, such as an agent known to treat hemochromatosis, or a disorder that causes hemochromatosis, such as a thalassemia. For example, an iRNA featured in the invention can be administered with an agent for treatment of a β thalassemia, e.g., β-thalassemia intermedia, or another disorder associated with increased iron levels.

In another embodiment, a TMPRSS6 iRNA is administered to a patient, and then the non-iRNA agent is administered to the patient (or vice versa). In another embodiment, a TMPRSS6 iRNA and the non-iRNA therapeutic agent are administered at the same time. In one embodiment, the agent is, for example, an agent that affects iron levels, such as an iron chelator (e.g., desferrioxamine), or folic acid.

In another aspect, provided herein is a method for inhibiting the expression of a TMPRSS6 gene in a cell by performing the following steps:
(a) introducing into the cell a double-stranded ribonucleic acid (dsRNA), wherein the dsRNA includes at least two sequences that are complementary to each other. The dsRNA has a sense strand having a first sequence and an antisense strand having a second sequence; the antisense strand has a region of complementarity that is substantially complementary to at least a part of an mRNA encoding TMPRSS6, and where the region of complementarity is 30 nucleotides or less, i.e., 15-30 nucleotides in length, and generally 19-24 nucleotides in length, and where the dsRNA, upon contact with a cell expressing TMPRSS6, inhibits expression of a TMPRSS6 gene by at least 10%, preferably at least 20%, at least 30%, at least 40% or more; and
(b) maintaining the cell produced in step (a) for a time sufficient to obtain degradation of the mRNA transcript of the TMPRSS6 gene, thereby inhibiting expression of a TMPRSS6 gene in the cell.

In another aspect, the invention provides methods and compositions useful for activating expression of a TMPRSS6 gene in a cell or mammal.

In another aspect, the invention provides a method for modulating the expression of a TMPRSS6 gene in a cell by performing the following steps:
(a) introducing into the cell a double-stranded ribonucleic acid (dsRNA), wherein the dsRNA includes at least two sequences that are complementary to each other. The dsRNA has a sense strand having a first sequence and an antisense strand having a second sequence; the antisense strand has a region of complementarity that is substantially complementary to at least a part of an mRNA encoding TMPRSS6, and where the region of complementarity is 30 nucleotides or less, i.e., 15-30 nucleotides in length, and generally 19-24 nucleotides in length, and where the dsRNA, upon contact with a cell expressing TMPRSS6, modulates expression of a TMPRSS6 gene by at least 10%, preferably at least 20%, at least 30%, at least 40% or more; and (b) maintaining the cell produced in step (a) for a time sufficient to obtain degradation or protection of the mRNA transcript of the TMPRSS6 gene, thereby modulating expression of a TMPRSS6 gene in the cell.

In one embodiment, the method is for inhibiting gene expression in a liver cell, such as a hepatocyte, or a Kupffer cell. In another embodiment, the method is for activating gene expression in a liver cell.

In other aspects, the invention provides methods for treating, preventing, reversing, or managing pathological processes mediated by TMPRSS6 expression, such as a disorder associated with hemochromatosis. In one embodiment, the method includes administering to a patient in need of such treatment, prevention, reversal, or management, a therapeutically or prophylactically effective amount of one or more of the iRNAs featured in the invention. In one embodiment the patient has a thalassemia, such as β-thalassemia intermedia. In another embodiment, administration of the iRNA targeting TMPRSS6 alleviates or relieves the severity of at least one symptom of a TMPRSS6-mediated disorder in the patient, such as a symptom associated with iron overload, e.g., joint pain, abdominal pain, or weakness.

In one aspect, the invention provides a vector for inhibiting the expression of a TMPRSS6 gene in a cell. In one embodiment, the vector includes at least one regulatory sequence operably linked to a nucleotide sequence that encodes at least one strand of an iRNA as described herein.

In another aspect, the invention provides a cell containing a vector for inhibiting the expression of a TMPRSS6 gene in a cell. The vector includes a regulatory sequence operably linked to a nucleotide sequence that encodes at least one strand of one of the iRNAs as described herein.

In yet another aspect, the invention provides a composition containing a TMPRSS6 iRNA, in combination with a second iRNA targeting a second gene involved in a pathological disease, and useful for treating the disease, e.g., a β-thalassemia. For example, a second iRNA can target a negative regulator of hepcidin, such as a hypoxia inducible factor, e.g., a HIF-1a or HIF-2a; GDF15; or TWSG1. In one embodiment, the second iRNA targets a gene involved in a second disorder that results from the β-thalassemia. For example, the second iRNA can target a gene involved in diabetes mellitus, thrombosis or osteopenia.

The details of various embodiments of the invention are set forth in the description below. Other features, objects, and advantages of the invention will be apparent from the description and the drawings, and from the claims.

DESCRIPTION OF THE DRAWINGS

FIG. 1 is the sequence of human TMPRSS6 mRNA (Ref. Seq. NM_153609.2, GI:56682967, Record dated Jan. 23, 2011, SEQ ID NO:1).

FIG. 6A depicts the effect of TMPRSS6 siRNA mediated silencing of TMPRSS6 on hemoglobin (HBG) in WT C57BL/6 mice 6 hours, 24 hours, 48 hours, 72 hours, 7 days, and 14 days post administration. FIG. 6B depicts the effect of TMPRSS6 siRNA mediated silencing of TMPRSS6 on hematocrit in WT C57BL/6 mice 6 hours, 24 hours, 48 hours, 72 hours, 7 days, and 14 days post administration.

FIG. 8A depicts the effect on the number of reticulocytes (%), FIG. 8B depicts the effect on the hemoglobin content of reticulocytes (CHr), and FIG. 8C depicts the effect on the number of mature red blood cells.

FIG. 9A depicts the effect on hematocrit (HCT) levels, FIG. 9B depicts the effect on hemoglobin (HGB), FIG. 9C depicts the effect on red blood cell (RBC) distribution width (RDW), and FIG. 9D depicts the effect on mean corpuscle value (MCV).

FIG. 10A depicts the effect on total spleen iron content, FIG. 10B depicts the effect on spleen weight, and FIG. 10C depicts the effect of TMPRSS6 siRNA mediated silencing of TMPRSS6 on the concentration of iron in the liver.

DETAILED DESCRIPTION OF THE INVENTION

Figure 2A:
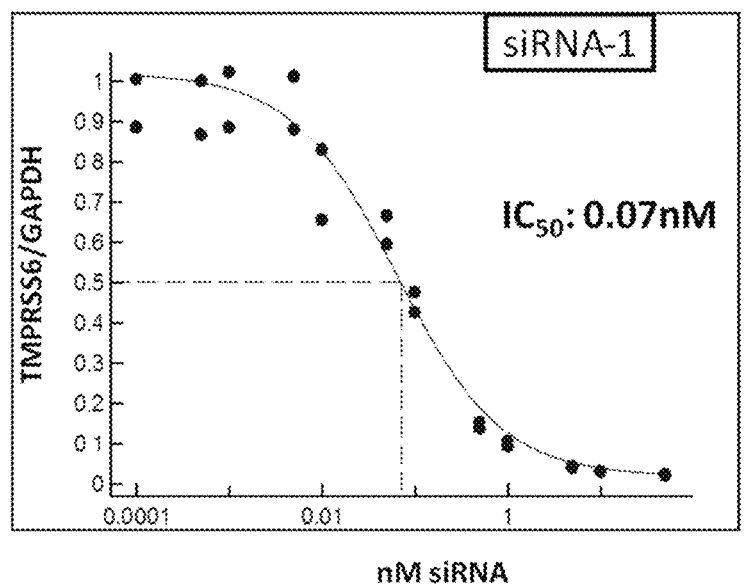
FIGS. 2A and 2B depict the potency of two chemically modified TMPRSS6 targeting siRNAs in the reduction of TMPRSS6 gene expression in primary mouse hepatocytes.

Described herein are iRNAs and methods of using them for inhibiting the expression of a TMPRSS6 gene in a cell or a mammal where the iRNA targets a TMPRSS6 gene. Also provided are compositions and methods for treating pathological conditions and diseases caused by TMPRSS6 gene expression, such as conditions associated with elevated levels of iron. iRNA directs the sequence-specific degradation of mRNA through a process known as RNA interference (RNAi). In an alternative embodiment, the iRNA activates the expression of a TMPRSS6 gene in a cell or mammal, where the iRNA targets a TMPRSS6 gene.

TMPRSS6 plays an important role in iron homeostasis as an inhibitor of HAMP gene expression. The HAMP gene encodes for the liver hormone hepcidin, which is a central regulator of iron homeostasis. Hepcidin binds to the iron exporter protein ferroportin (FPN1), which is localized mainly on absorptive enterocytes, hepatocytes and macrophages. Hepcidin binding to the extracellular domain of ferroportin leads to the internalization and degradation of ferroportin, thus decreasing the absorption of dietary iron from the intestine, and the release of iron from macrophages and hepatocytes. HAMP gene expression can be stimulated in response to iron through Bone Morphogenetic Protein (BMP)/Sons of Mothers Against Decapentaplegic (SMAD)-dependent signal transduction cascade mediated by the BMP-co-receptor hemojuvelin (HJV). The key role of TMPRSS6 in HAMP regulation is in the inhibition of BMP-mediated HAMP upregulation. TMPRSS6 inhibits BMP-mediated HAMP upregulation by cleaving the BMP co-receptor HJV, which is essential for BMP mediated HAMP upregulation; thus preventing BMP signaling, SMAD translocation to the nucleus, and HAMP transcriptional activation.

Several human and mouse studies have confirmed the role of TMPRSS6 in HAMP regulation and iron homeostasis (Du et al. Science 2008, Vol. 320, pp1088-1092; Folgueras et al. Blood 2008, Vol. 112, pp 2539-45). Studies have shown that loss of function mutations in TMPRSS6 can lead to the upregulation of hepcidin expression, causing an inherited iron deficiency anemia called iron refractory iron deficiency anemia (IRIDA) (Finberg. Seminars in Hematology 2009, Vol. 46, pp 378-86), which is characterized by elevated hepcidin levels, hypochromic microcytic anemia, low mean corpuscular volume (MCV), low transferrin saturation, poor absorption of oral iron, and incomplete response to parenteral iron. However, loss of function mutations in positive regulators of HAMP (e.g., BMP1, BMP4, and HFE) have been shown to downregulate hepcidin expression and cause iron overload disorders (Milet et al. Am J Hum Gen 2007, Vol. 81, pp 799-807; Finberg et al. Blood 2011, Vol. 117, pp 4590-9). In the primary iron overload disorders, collectively called hereditary hemochromatosis (HH), in anemias characterized by massive ineffective hematopoiesis, and in iron overload (secondary hemochromatosis), such as β-thalassemia intermedia (TI), hepcidin levels are low despite elevated serum iron concentrations and iron stores. A mouse model of β-thalassemia intermedia has demonstrated that the loss of TMPRSS6 expression leads to elevated levels of hepcidin (Finberg 2010 Oral Presentation: "TMPRSS6, an inhibitor of Hepatic BMP/Smad Signaling, is required for Hepcidin Suppression and Iron Loading in a Mouse Model of β-Thalassemia. American Society of Hematology Annual Meeting 2010, Abstract No.: 164).

The present invention describes methods and iRNA compositions for modulating the expression of a TMPRSS6 gene. In certain embodiments, expression of TMPRSS6 is reduced or inhibited using a TMPRSS6-specific iRNA, thereby leading to increase HAMP expression, and decreased serum iron levels. Thus, inhibition of TMPRSS6 gene expression or activity using the iRNA compositions featured in the invention can be a useful approach to therapies aimed at reducing the iron levels in a subject. Such inhibition can be useful for treating disorders associated with elevated iron levels, such as hemochromatosis or thalassemia, e.g., β-thalassemia.

The iRNAs of the compositions described herein include an RNA strand (the antisense strand) having a region which is 30 nucleotides or less in length, i.e., 15-30 nucleotides in length, generally 19-24 nucleotides in length, which region is substantially complementary to at least part of an mRNA transcript of a TMPRSS6 gene. The use of these iRNAs enables the targeted degradation of mRNAs of genes that are implicated in pathologies associated with TMPRSS6 expression in mammals. Very low dosages of TMPRSS6 iRNAs in particular can specifically and efficiently mediate RNAi, resulting in significant inhibition of expression of a TMPRSS6 gene. Using cell-based assays, the present inventors have demonstrated that iRNAs targeting TMPRSS6 can specifically and efficiently mediate RNAi, resulting in significant inhibition of expression of a TMPRSS6 gene. Thus, methods and compositions including these iRNAs are useful for treating pathological processes that can be mediated by down regulating TMPRSS6, such as in the treatment of a disorder that causes elevated iron levels, e.g., a hemochromatosis, or a β-thalassemia, e.g., β-thalassemia intermedia. The following detailed description discloses how to make and use compositions containing iRNAs to inhibit the expression of a TMPRSS6 gene, as well as compositions and methods for treating diseases and disorders caused by the expression of this gene.

Embodiments of the pharmaceutical compositions featured herein also include an iRNA having an antisense strand comprising a region which is 30 nucleotides or less in length, generally 19-24 nucleotides in length, which region is substantially complementary to at least part of an RNA transcript of a TMPRSS6 gene, together with a pharmaceutically acceptable carrier. Embodiments of compositions featured in the invention also include an iRNA having an antisense strand having a region of complementarity which is 30 nucleotides or less in length, generally 19-24 nucleotides in length, and is substantially complementary to at least part of an RNA transcript of a TMPRSS6 gene.

Accordingly, in some aspects, pharmaceutical compositions containing a TMPRSS6 iRNA and a pharmaceutically acceptable carrier, methods of using the compositions to inhibit expression of a TMPRSS6 gene, and methods of using the pharmaceutical compositions to treat diseases caused by expression of a TMPRSS6 gene are featured in the invention.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine can be replaced in the nucleotide sequences of dsRNA featured herein by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods described herein.

As used herein, "Transmembrane Protease, Serine 6" ("TMPSSR6") refers to a particular polypeptide expressed in a cell. TMPRSS6 is also known as matriptase-2, IRIDA (iron refractory iron-deficiency anemia), transmembrane protease serine 6, type II transmembrane serine protease 6, and membrane-bound mosaic serine proteinase matriptase-2. TMPRSS6 is a serine protease Type II transmembrane protein of approximately 899 amino acids in length. TMPRSS6 contains multiple domains, e.g., a short endo domain, a transmembrane domain, a sea urchin sperm protein/enteropeptidase domain/agrin (SEA) domain, two complement factor/urchin embryonic growth factor/BMP domains (CUB), three LDL-R class a domains (LDLa), and a trypsin-like serine protease domain with conserved His-Asp-Ser triad (HDS). The sequence of a human TMPRSS6 mRNA transcript can be found at NM_153609.2 (SEQ ID NO:1) (FIG. 1).

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of TMPRSS6 expression. Alternatively, in another embodiment, an iRNA as described herein activates TMPRSS6 expression.

As used herein, "target sequence" refers to a contiguous portion of the nucleotide sequence of an mRNA molecule formed during the transcription of a TMPRSS6 gene, including messenger RNA (mRNA) that is a product of RNA processing of a primary transcription product. The target portion of the sequence will be at least long enough to serve as a substrate for iRNA-directed cleavage at or near that portion. For example, the target sequence will generally be from 9-36 nucleotides in length, e.g., 15-30 nucleotides in length, including all sub-ranges there between. As non-limiting examples, the target sequence can be from 15-30 nucleotides, 15-26 nucleotides, 15-23 nucleotides, 15-22 nucleotides, 15-21 nucleotides, 15-20 nucleotides, 15-19 nucleotides, 15-18 nucleotides, 15-17 nucleotides, 18-30 nucleotides, 18-26 nucleotides, 18-23 nucleotides, 18-22 nucleotides, 18-21 nucleotides, 18-20 nucleotides, 19-30 nucleotides, 19-26 nucleotides, 19-23 nucleotides, 19-22 nucleotides, 19-21 nucleotides, 19-20 nucleotides, 20-30 nucleotides, 20-26 nucleotides, 20-25 nucleotides, 20-24 nucleotides, 20-23 nucleotides, 20-22 nucleotides, 20-21 nucleotides, 21-30 nucleotides, 21-26 nucleotides, 21-25 nucleotides, 21-24 nucleotides, 21-23 nucleotides, or 21-22 nucleotides.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs (bp), while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, can also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (an mRNA) refers to a polynucleotide that is substantially complementary to a contiguous portion of the mRNA of interest (e.g., an mRNA encoding TMPRSS6). For example, a polynucleotide is complementary to at least a part of a TMPRSS6 mRNA if the sequence is substantially complementary to a non-interrupted portion of an mRNA encoding TMPRSS6.

The term "double-stranded RNA" or "dsRNA," as used herein, refers to an iRNA that includes an RNA molecule or complex of molecules having a hybridized duplex region that comprises two anti-parallel and substantially complementary nucleic acid strands, which will be referred to as having "sense" and "antisense" orientations with respect to a target RNA. The duplex region can be of any length that permits specific degradation of a desired target RNA through a RISC pathway, but will typically range from 9 to 36 base pairs in length, e.g., 15-30 base pairs in length. Considering a duplex between 9 and 36 base pairs, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 and any sub-range therein between, including, but not limited to 15-30 base pairs, 15-26 base pairs, 15-23 base pairs, 15-22 base pairs, 15-21 base pairs, 15-20 base pairs, 15-19 base pairs, 15-18 base pairs, 15-17 base pairs, 18-30 base pairs, 18-26 base pairs, 18-23 base pairs, 18-22 base pairs, 18-21 base pairs, 18-20 base pairs, 19-30 base pairs, 19-26 base pairs, 19-23 base pairs, 19-22 base pairs, 19-21 base pairs, 19-20 base pairs, 20-30 base pairs, 20-26 base pairs, 20-25 base pairs, 20-24 base pairs, 20-23 base pairs, 20-22 base pairs, 20-21 base pairs, 21-30 base pairs, 21-26 base pairs, 21-25 base pairs, 21-24 base pairs, 21-23 base pairs, or 21-22 base pairs. dsRNAs generated in the cell by processing with Dicer and similar enzymes are generally in the range of 19-22 base pairs in length. One strand of the duplex region of a dsDNA comprises a sequence that is substantially complementary to a region of a target RNA. The two strands forming the duplex structure can be from a single RNA molecule having at least one self-complementary region, or can be formed from two or more separate RNA molecules. Where the duplex region is formed from two strands of a single molecule, the molecule can have a duplex region separated by a single stranded chain of nucleotides (herein referred to as a "hairpin loop") between the 3'-end of one strand and the 5'-end of the respective other strand forming the duplex structure. The hairpin loop can comprise at least one unpaired nucleotide; in some embodiments the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can be covalently connected. Where the two strands are connected covalently by means other than a hairpin loop, the connecting structure is referred to as a "linker." The term "siRNA" is also used herein to refer to a dsRNA as described above.

The skilled artisan will recognize that the term "RNA molecule" or "ribonucleic acid molecule" encompasses not only RNA molecules as expressed or found in nature, but also analogs and derivatives of RNA comprising one or more ribonucleotide/ribonucleoside analogs or derivatives as described herein or as known in the art. Strictly speaking, a "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein. The RNA can be modified in the nucleobase structure or in the ribose-phosphate backbone structure, e.g., as described herein below. However, the molecules comprising ribonucleoside analogs or derivatives must retain the ability to form a duplex. As non-limiting examples, an RNA molecule can also include at least one modified ribonucleoside including but not limited to a 2'-O-methyl modified nucleoside, a nucleoside comprising a 5' phosphorothioate group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-amino-modified nucleoside, 2'-alkyl-modified nucleoside, morpholino nucleoside, a phosphoramidate or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, at least 20 or more, up to the entire length of the dsRNA molecule. The modifications need not be the same for each of such a plurality of modified ribonucleosides in an RNA molecule. In one embodiment, modified RNAs contemplated for use in methods and compositions described herein are peptide nucleic acids (PNAs) that have the ability to form the required duplex structure and that permit or mediate the specific degradation of a target RNA via a RISC pathway.

In one aspect, a modified ribonucleoside includes a deoxyribonucleoside. In such an instance, an iRNA agent can comprise one or more deoxynucleosides, including, for example, a deoxynucleoside overhang(s), or one or more deoxynucleosides within the double stranded portion of a dsRNA. However, it is self evident that under no circumstances is a double stranded DNA molecule encompassed by the term "iRNA."

In one aspect, an RNA interference agent includes a single stranded RNA that interacts with a target RNA sequence to direct the cleavage of the target RNA. Without wishing to be bound by theory, long double stranded RNA introduced into plants and invertebrate cells is broken down into siRNA by a Type III endonuclease known as Dicer (Sharp et al., Genes Dev. 2001, 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleaves the target to induce silencing (Elbashir, et al., (2001) Genes Dev. 15:188). Thus, in one aspect the invention relates to a single stranded RNA that promotes the formation of a RISC complex to effect silencing of the target gene.

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) may be on the sense strand, the antisense strand or any combination thereof. Furthermore, the nucleotide(s) of an overhang can be present on the 5' end, 3' end or both ends of either an antisense or sense strand of a dsRNA.

In one embodiment, the antisense strand of a dsRNA has a 1-10 nucleotide overhang at the 3' end and/or the 5' end. In one embodiment, the sense strand of a dsRNA has a 1-10 nucleotide overhang at the 3' end and/or the 5' end. In another embodiment, one or more of the nucleotides in the overhang is replaced with a nucleoside thiophosphate.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double-stranded over its entire length.

The term "antisense strand" or "guide strand" refers to the strand of an iRNA, e.g., a dsRNA, which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally, the most tolerated mismatches are in the terminal regions, e.g., within 5, 4, 3, or 2 nucleotides of the 5' and/or 3' terminus.

The term "sense strand," or "passenger strand" as used herein, refers to the strand of an iRNA that includes a region that is substantially complementary to a region of the antisense strand as that term is defined herein.

As used herein, in one embodiment, the term "SNALP" refers to a stable nucleic acid-lipid particle. A SNALP represents a vesicle of lipids coating a reduced aqueous interior comprising a nucleic acid such as an iRNA or a plasmid from which an iRNA is transcribed. SNALPs are described, e.g., in U.S. Patent Application Publication Nos. 20060240093, 20070135372, and in International Application No. WO 2009082817. Examples of "SNALP" formulations are described elsewhere herein.

"Introducing into a cell," when referring to an iRNA, means facilitating or effecting uptake or absorption into the cell, as is understood by those skilled in the art. Absorption or uptake of an iRNA can occur through unaided diffusive or active cellular processes, or by auxiliary agents or devices. The meaning of this term is not limited to cells in vitro; an iRNA can also be "introduced into a cell," wherein the cell is part of a living organism. In such an instance, introduction into the cell will include the delivery to the organism. For example, for in vivo delivery, iRNA can be injected into a tissue site or administered systemically. In vivo delivery can also be by a β-glucan delivery system, such as those described in U.S. Pat. Nos. 5,032,401 and 5,607,677, and U.S. Publication No. 2005/0281781 which are hereby incorporated by reference in their entirety. In vitro introduction into a cell includes methods known in the art such as electroporation and lipofection. Further approaches are described herein below or are known in the art.

As used herein, the term "modulate the expression of," refers to at an least partial "inhibition" or partial "activation" of TMPRSS6 gene expression in a cell treated with an iRNA composition as described herein compared to the expression of TMPRSS6 in an untreated cell.

The terms "activate," "enhance," "up-regulate the expression of," "increase the expression of," and the like, in so far as they refer to a TMPRSS6 gene, herein refer to the at least partial activation of the expression of a TMPRSS6 gene, as manifested by an increase in the amount of TMPRSS6 mRNA, which can be isolated from or detected in a first cell or group of cells in which a TMPRSS6 gene is transcribed and which has or have been treated such that the expression of a TMPRSS6 gene is increased, as compared to a second cell or group of cells substantially identical to the first cell or group of cells but which has or have not been so treated (control cells).

In one embodiment, expression of a TMPRSS6 gene is activated by at least about 10%, 15%, 20%, 25%, 30%, 35%, 40%, 45%, or 50% by administration of an iRNA as described herein. In some embodiments, a TMPRSS6 gene is activated by at least about 60%, 70%, or 80% by administration of an iRNA featured in the invention. In some embodiments, expression of a TMPRSS6 gene is activated by at least about 85%, 90%, or 95% or more by administration of an iRNA as described herein. In some embodiments, the TMPRSS6 gene expression is increased by at least 1-fold, at least 2-fold, at least 5-fold, at least 10-fold, at least 50-fold, at least 100-fold, at least 500-fold, at least 1000 fold or more in cells treated with an iRNA as described herein compared to the expression in an untreated cell. Activation of expression by small dsRNAs is described, for example, in Li et al., 2006 Proc. Natl. Acad. Sci. U.S.A. 103:17337-42, and in US20070111963 and US2005226848, each of which is incorporated herein by reference.

The terms "silence," "inhibit the expression of," "down-regulate the expression of," "suppress the expression of," and the like, in so far as they refer to a TMPRSS6 gene, herein refer to the at least partial suppression of the expression of a TMPRSS6 gene, as manifested by a reduction of the amount of TMPRSS6 mRNA which can be isolated from or detected in a first cell or group of cells in which a TMPRSS6 gene is transcribed and which has or have been treated such that the expression of a TMPRSS6 gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition can be given in terms of a reduction of a parameter that is functionally linked to TMPRSS6 gene expression, e.g., the amount of protein encoded by a TMPRSS6 gene, or the number of cells displaying a certain phenotype, e.g., a decrease in iron levels, or in iron absorption. In principle, TMPRSS6 gene silencing can be determined in any cell expressing TMPRSS6, either constitutively or by genomic engineering, and by any appropriate assay.

For example, in certain instances, expression of a TMPRSS6 gene is suppressed by at least about 10%, 15%, 20%, 25%, 30%, 35%, 40%, 45%, or 50% by administration of an iRNA featured in the invention. In some embodiments, a TMPRSS6 gene is suppressed by at least about 60%, 70%, or 80% by administration of an iRNA described herein. In some embodiments, a TMPRSS6 gene is suppressed by at least about 85%, 90%, 95%, 98%, 99%, or more, by administration of an iRNA as described herein.

As used herein in the context of TMPRSS6 expression, the terms "treat," "treatment," and the like, refer to relief from or alleviation of pathological processes mediated by TMPRSS6 expression. In the context of the present invention insofar as it relates to any of the other conditions recited herein below (other than pathological processes mediated by TMPRSS6 expression), the terms "treat," "treatment," and the like mean to relieve or alleviate at least one symptom associated with such condition, or to slow or reverse the progression or anticipated progression of such condition, such as slowing the progression of a hemochromatosis, such as a β-thalassemia.

By "lower" in the context of a disease marker or symptom is meant a statistically significant decrease in such level. The decrease can be, for example, at least 10%, at least 20%, at least 30%, at least 40% or more, and is preferably down to a level accepted as within the range of normal for an individual without such disorder.

As used herein, the phrases "therapeutically effective amount" and "prophylactically effective amount" refer to an amount that provides a therapeutic benefit in the treatment, prevention, or management of pathological processes mediated by TMPRSS6 expression or an overt symptom of pathological processes mediated by TMPRSS6 expression.

The specific amount that is therapeutically effective can be readily determined by an ordinary medical practitioner, and can vary depending on factors known in the art, such as, for example, the type of pathological processes mediated by TMPRSS6 expression, the patient's history and age, the stage of pathological processes mediated by TMPRSS6 expression, and the administration of other agents that inhibit pathological processes mediated by TMPRSS6 expression.

As used herein, a "pharmaceutical composition" comprises a pharmacologically effective amount of an iRNA and a pharmaceutically acceptable carrier. As used herein, "pharmacologically effective amount," "therapeutically effective amount" or simply "effective amount" refers to that amount of an iRNA effective to produce the intended pharmacological, therapeutic or preventive result. For example, if a given clinical treatment is considered effective when there is at least a 10% reduction in a measurable parameter associated with a disease or disorder, a therapeutically effective amount of a drug for the treatment of that disease or disorder is the amount necessary to effect at least a 10% reduction in that parameter. For example, a therapeutically effective amount of an iRNA targeting TMPRSS6 can reduce TMPRSS6 protein levels by at least 10%.

As used herein, the term "thalassemia" refers to an inherited recessive blood disorder. A loss-of-function mutation results in reduced rate of synthesis or no synthesis of one of the globin chains that makes up hemoglobin, and causes a deficiency in normal globin proteins. Thalassemia patients produce a deficiency of either α globin (called α-thalassemia), β globin (called β-thalassemia) or, in rare cases, β globin. In α-thalassemia, an excess of β chains form unstable tetramers, which have abnormal oxygen dissociation curves. β-thalassemias can be minor, major or intermedia.

β globin chains are encoded by a single gene called the HBB (hemoglobin, β) gene. β-thalassemia minor occurs in patients carrying one mutant β-thalassemia allele, and one wildtype allele. This condition has no effect on blood iron levels, and patients do not require treatment. β-thalassemia major results when a patient carries two knock-out mutant β-thalassemia alleles. Excess iron accumulates in these patients, and the excess iron is stored primarily in hypertrophic Kupffer cells. Patients with β-thalassemia major are typically treated with chronic blood transfusion therapy, iron chelation, splenectomy and allogeneic hematopoietic transplantation. β-thalassemia intermedia results when a patient carries one knock-out allele of the β-thalassemia gene and one partial loss-of-function allele. Excess iron accumulates in these patients, and the excess iron is stored primarily in hepatocytes. Patients with thalassemia major and thalassemia intermedia have anemia (hypoxia), which leads to an increase in EPO (erythropoietin) and consequently, dramatic compensatory and ineffective erythropoiesis (the production of red blood cells by stem cells in bone marrow). Patients with thalassemia intermedia sometimes develop hepatosplenomegaly, jaundice, osteopenia, thrombotic events, leg ulcers, pulmonary hypotension, congestive heart failure, diabetes mellitus, growth hormone deficiency, hypothyroidism, hypoparathyroidism, hypogonadism, and facial deformities.

As used herein, the term "hemochromatosis" refers to a disorder, which results in too much iron being absorbed from the gastrointestinal tract. Hemochromatosis occurs in two forms: primary and secondary. Primary hemochromatosis, the most common genetic disorder in the United States (affecting an estimated 1 of every 200 to 300 Americans), is usually caused by a specific genetic problem that causes too much iron to be absorbed. Secondary, or acquired, hemochromatosis, can be caused by diseases such as thalassemia or sideroblastic anemia. Secondary hemochromatosis sometimes develops in patients with hemolytic anemia and chronic alcoholism. Symptoms of hemochromatosis include abdominal pain, joint pain, fatigue, lack of energy, weakness, darkening of the skin (often referred to as "bronzing"), and loss of body hair.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Agents included in drug formulations are described further herein below.

As used herein, a "subject" is a mammal, e.g. a dog, horse, cat, and other non-human primates. In a preferred embodiment, a subject is a human.

As used herein, the term "LNPXX", wherein the "XX" are numerals, is also referred to as "AFXX" herein. For example, LNP09 is also referred to AF09 and LNP12 is also known as or referred to as AF12.

As used herein, the term "comprising" or "comprises" is used in reference to compositions, methods, and respective component(s) thereof, that are essential to the invention, yet open to the inclusion of unspecified elements, whether essential or not.

As used herein, the term "consisting essentially of" refers to those elements required for a given embodiment. The term permits the presence of elements that do not materially affect the basic and novel or functional characteristic(s) of that embodiment featured in the invention.

The term "consisting of" refers to compositions, methods, and respective components thereof as described herein, which are exclusive of any element not recited in that description of the embodiment.

II. Double-Stranded Ribonucleic Acid (dsRNA)

Described herein are iRNA agents that modulate the expression of the TMPRSS6 gene. In one embodiment, the iRNA agent includes double-stranded ribonucleic acid (dsRNA) molecules for inhibiting the expression of a TMPRSS6 gene in a cell or mammal, e.g., in a human having elevated iron levels, such as in a patient with a β-thalassemia, or a hemachromatosis. The dsRNA includes an antisense strand having a region of complementarity which is complementary to at least a part of an mRNA formed in the expression of a TMPRSS6 gene. The region of complementarity is 30 nucleotides or less in length, generally 19-24 nucleotides in length, and where the dsRNA, upon contact with a cell expressing the TMPRSS6 gene, inhibits the expression of the TMPRSS6 gene by at least 10% as assayed by, for example, a PCR or branched DNA (bDNA)-based method, or by a protein-based method, such as by Western blot. In one embodiment, the iRNA agent activates the expression of a TMPRSS6 gene in a cell or mammal. Expression of a TMPRSS6 gene in cell culture, such as in COS cells, HeLa cells, primary hepatocytes, HepG2 cells, primary cultured cells or in a biological sample from a subject, can be assayed by measuring TMPRSS6 mRNA levels, such as by bDNA or TaqMan® assay, or by measuring protein levels, such as by immunofluorescence analysis, using, for example, Western blotting or flow cytometric techniques.

A dsRNA includes two RNA strands that are complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of a TMPRSS6 gene. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

One of skill in the art will also recognize that the duplex region is a primary functional portion of a dsRNA, e.g., a duplex region of 9 to 36, e.g., 15-30 base pairs. Thus, in one embodiment, to the extent that it becomes processed to a functional duplex of, e.g., 15-30 base pairs that targets a desired RNA for cleavage, an RNA molecule or complex of RNA molecules having a duplex region greater than 30 base pairs is a dsRNA. Thus, an ordinarily skilled artisan will recognize that in one embodiment, an miRNA is a dsRNA. In another embodiment, a dsRNA is not a naturally occurring miRNA. In another embodiment, an iRNA agent useful to target TMPRSS6 expression is not generated in the target cell by cleavage of a larger dsRNA.

A dsRNA as described herein can further include one or more single-stranded nucleotide overhangs. The dsRNA can be synthesized by standard methods known in the art as further discussed below, e.g., by use of an automated DNA synthesizer, such as are commercially available from, for example, Biosearch, Applied Biosystems, Inc. In one embodiment, a TMPRSS6 gene is a human TMPRSS6 gene. In another embodiment the TMPRSS6 gene is a mouse or a rat TMPRSS6 gene. The sequence of mouse TMPRSS6 mRNA can be found at GenBank Accession No. NM_027902 (GI:125656151, Record dated Dec. 28, 2010). The sequence of rat TMPRSS6 mRNA can be found at GenBank Accession No. NM_001130556.1 (GI:194474097, Record dated Jan. 17, 2011). In specific embodiments, the first sequence is a sense strand of a dsRNA that includes a sense sequence of one of Tables 2, 3 or 4 and the second sequence is an antisense strand of a dsRNA that includes an antisense sequence of one of Tables 2, 3 or 4. Alternative dsRNA agents that target elsewhere in the target sequence provided in Tables 2, 3 or 4 can readily be determined using the target sequence and the flanking TMPRSS6 sequence.

In one aspect, a dsRNA will include at least two nucleotide sequences, a sense and an antisense sequence, whereby the sense strand is selected from the groups of sequences provided in Tables 2, 3 or 4. In this aspect, one of the two sequences is complementary to the other of the two sequences, with one of the sequences being substantially complementary to a sequence of an mRNA generated in the expression of a TMPRSS6 gene. As such, in this aspect, a dsRNA will include two oligonucleotides, where one oligonucleotide is described as the sense strand in Tables 2, 3 or 4 and the second oligonucleotide is described as the corresponding antisense strand of the sense strand from Tables 2, 3 or 4. As described elsewhere herein and as known in the art, the complementary sequences of a dsRNA can also be contained as self-complementary regions of a single nucleic acid molecule, as opposed to being on separate oligonucleotides.

The skilled person is well aware that dsRNAs having a duplex structure of between 20 and 23, but specifically 21, base pairs have been hailed as particularly effective in inducing RNA interference (Elbashir et al., EMBO 2001, 20:6877-6888). However, others have found that shorter or longer RNA duplex structures can be effective as well. In the embodiments described above, by virtue of the nature of the oligonucleotide sequences provided in Tables 2, 3 or 4 dsRNAs described herein can include at least one strand of a length of minimally 21 nt. It can be reasonably expected that shorter duplexes having one of the sequences of Tables 2, 3 or 4 minus only a few nucleotides on one or both ends may be similarly effective as compared to the dsRNAs described above. Hence, dsRNAs having a partial sequence of at least 15, 16, 17, 18, 19, 20, or more contiguous nucleotides from one of the sequences of Tables 2, 3 or 4 and differing in their ability to inhibit the expression of a TMPRSS6 gene by not more than 5, 10, 15, 20, 25, or 30% inhibition from a dsRNA comprising the full sequence, are contemplated according to the invention.

In addition, the RNAs provided in Tables 2, 3 or 4 identify a site in a TMPRSS6 transcript that is susceptible to RISC-mediated cleavage. As such, the present invention further features iRNAs that target within one of such sequences. As used herein, an iRNA is said to target within a particular site of an RNA transcript if the iRNA promotes cleavage of the transcript anywhere within that particular site. Such an iRNA will generally include at least 15 contiguous nucleotides from one of the sequences provided in Tables 2, 3 or 4 coupled to additional nucleotide sequences taken from the region contiguous to the selected sequence in a TMPRSS6 gene.

While a target sequence is generally 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window"

or "mask" of a given size (as a non-limiting example, 21 nucleotides) is literally or figuratively (including, e.g., in silico) placed on the target RNA sequence to identify sequences in the size range that may serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Thus, while the sequences identified, for example, in Tables 2, 3 or 4 represent effective target sequences, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified, e.g., in Tables 2, 3 or 4 further optimization could be achieved by systematically either adding or removing nucleotides to generate longer or shorter sequences and testing those sequences generated by walking a window of the longer or shorter size up or down the target RNA from that point. Again, coupling this approach to generating new candidate targets with testing for effectiveness of iRNAs based on those target sequences in an inhibition assay as known in the art or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes, etc.) as an expression inhibitor.

An iRNA as described herein can contain one or more mismatches to the target sequence. In one embodiment, an iRNA as described herein contains no more than 3 mismatches. If the antisense strand of the iRNA contains mismatches to a target sequence, it is preferable that the area of mismatch not be located in the center of the region of complementarity. If the antisense strand of the iRNA contains mismatches to the target sequence, it is preferable that the mismatch be restricted to be within the last 5 nucleotides from either the 5' or 3' end of the region of complementarity. For example, for a 23 nucleotide iRNA agent RNA strand which is complementary to a region of a TMPRSS6 gene, the RNA strand generally does not contain any mismatch within the central 13 nucleotides. The methods described herein or methods known in the art can be used to determine whether an iRNA containing a mismatch to a target sequence is effective in inhibiting the expression of a TMPRSS6 gene. Consideration of the efficacy of iRNAs with mismatches in inhibiting expression of a TMPRSS6 gene is important, especially if the particular region of complementarity in a TMPRSS6 gene is known to have polymorphic sequence variation within the population.

In one embodiment, at least one end of a dsRNA has a single-stranded nucleotide overhang of 1 to 4, generally 1 or 2 nucleotides. Such dsRNAs having at least one nucleotide overhang have unexpectedly superior inhibitory properties relative to their blunt-ended counterparts. In yet another embodiment, the RNA of an iRNA, e.g., a dsRNA, is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to, RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6, 239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$—[known as a methylene (methylimino) or MMI backbone], —$CH_2$—O—N($CH_3$)—$CH_2$, —$CH_2$—N($CH_3$)—N($CH_3$)—$CH_2$— and —N($CH_3$)—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$)$_n$$OCH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$)]$_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples herein below.

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, Oreg. et al., (2007) *Mol Canc Ther* 6(3):833-843; Grunweller, A. et al., (2003) *Nucleic Acids Research* 31(12):3185-3193).

Representative U.S. Patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA of an iRNA featured in the invention involves chemically linking to the RNA one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

In one embodiment, a ligand alters the distribution, targeting or lifetime of an iRNA agent into which it is incorporated. In preferred embodiments a ligand provides an enhanced affinity for a selected target, e.g., molecule, cell or cell type (e.g., a liver cell, such as a hepatocyte), compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an a helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a PK modulator. As used herein, a "PK modulator" refers to a pharmacokinetic modulator. PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbaone are also amenable to the present invention as ligands (e.g. as PK modulating ligands). In addition, aptamers that bind serum components (e.g. serum proteins) are also suitable for use as PK modulating ligands in the embodiments described herein.

For macromolecular drugs and hydrophilic drug molecules, which cannot easily cross bilayer membranes, entrapment in endosomal/lysosomal compartments of the cell is thought to be the biggest hurdle for effective delivery to their site of action. In recent years, a number of approaches and strategies have been devised to address this problem. For liposomal formulations, the use of fusogenic lipids in the formulation have been the most common approach (Singh, R. S., Goncalves, C. et al. (2004). On the Gene Delivery Efficacies of pH-Sensitive Cationic Lipids via Endosomal Protonation. A Chemical Biology Investigation. Chem. Biol. 11, 713-723.). Other components, which exhibit pH-sensitive endosomolytic activity through protonation and/or pH-induced conformational changes, include charged polymers and peptides. Examples may be found in Hoffman, A. S., Stayton, P. S. et al. (2002). Design of "smart" polymers that can direct intracellular drug delivery. Polymers Adv. Technol. 13, 992-999; Kakudo, Chaki, T., S. et al. (2004). Transferrin-Modified Liposomes Equipped with a pH-Sensitive Fusogenic Peptide: An Artificial Virallike Delivery System. Biochemistry 436, 5618-5628; Yessine, M. A. and Leroux, J. C. (2004). Membrane-destabilizing polyanions: interaction with lipid bilayers and endosomal escape of biomacromolecules. Adv. Drug Deliv. Rev. 56, 999-1021; Oliveira, S., van Rooy, I. et al. (2007). Fusogenic peptides enhance endosomal escape improving iRNA-induced silencing of oncogenes. Int. J. Pharm. 331, 211-4. They have generally been used in the context of drug delivery systems, such as liposomes or lipoplexes. For folate receptor-mediated delivery using liposomal formulations, for instance, a pH-sensitive fusogenic peptide has been incorporated into the liposomes and shown to enhance the activity through improving the unloading of drug during the uptake process (Turk, M. J., Reddy, J. A. et al. (2002). Characterization of a novel pH-sensitive peptide that enhances drug release from folate-targeted liposomes at endosomal pHs is described in Biochim. Biophys. Acta 1559, 56-68).

In certain embodiments, the endosomolytic components of the present invention can be polyanionic peptides or peptidomimetics which show pH-dependent membrane activity and/or fusogenicity. A peptidomimetic can be a small protein-like chain designed to mimic a peptide. A peptidomimetic can arise from modification of an existing peptide in order to alter the molecule's properties, or the synthesis of a peptide-like molecule using unnatural amino acids or their analogs. In certain embodiments, they have improved stability and/or biological activity when compared to a peptide. In certain embodiments, the endosomolytic component assumes its active conformation at endosomal pH (e.g., pH 5-6). The "active" conformation is that conformation in which the endosomolytic component promotes lysis of the endosome and/or transport of the modular composition featured in the invention, or its any of its components (e.g., a nucleic acid), from the endosome to the cytoplasm of the cell.

Libraries of compounds can be screened for their differential membrane activity at endosomal pH versus neutral pH using a hemolysis assay. Promising candidates isolated by this method may be used as components of the modular compositions featured in the invention. A method for identifying an endosomolytic component for use in the compositions and methods of the present invention may comprise: providing a library of compounds; contacting blood cells with the members of the library, wherein the pH of the medium in which the contact occurs is controlled; determining whether the compounds induce differential lysis of blood cells at a low pH (e.g., about pH 5-6) versus neutral pH (e.g., about pH 7-8).

Exemplary endosomolytic components include the GALA peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In certain embodiments, the endosomolytic component can contain a chemical group (e.g., an amino acid) which will undergo a change in charge or protonation in response to a change in pH. The endosomolytic component may be linear or branched. Exemplary primary sequences of endosomolytic components include $H_2N$-(AALEALAEALEALAEALEA-LAEAAAAGGC)-CO2H (SEQ ID NO:2); $H_2N$-(AA-LAEALAEALAEALAEALAEALAAAAGGC)-CO2H (SEQ ID NO:3); and $H_2N$-(ALEALAEALEALAEA)-CONH2 (SEQ ID NO:4).

In certain embodiments, more than one endosomolytic component can be incorporated into the iRNA agent featured in the invention. In some embodiments, this will entail incorporating more than one of the same endosomolytic component into the iRNA agent. In other embodiments, this will entail incorporating two or more different endosomolytic components into iRNA agent.

These endosomolytic components can mediate endosomal escape by, for example, changing conformation at endosomal pH. In certain embodiments, the endosomolytic components can exist in a random coil conformation at neutral pH and rearrange to an amphipathic helix at endosomal pH. As a consequence of this conformational transition, these peptides may insert into the lipid membrane of the endosome, causing leakage of the endosomal contents into the cytoplasm. Because the conformational transition is pH-dependent, the endosomolytic components can display little or no fusogenic activity while circulating in the blood (pH~7.4). "Fusogenic activity," as used herein, is defined as that activity which results in disruption of a lipid membrane by the endosomolytic component. One example of fusogenic activity is the disruption of the endosomal membrane by the endosomolytic component, leading to endosomal lysis or leakage and transport of one or more components of the modular composition featured in the invention (e.g., the nucleic acid) from the endosome into the cytoplasm.

In addition to hemolysis assays, as described herein, suitable endosomolytic components can be tested and identified by a skilled artisan using other methods. For example, the ability of a compound to respond to, e.g., change charge depending on, the pH environment can be tested by routine methods, e.g., in a cellular assay. In certain embodiments, a test compound is combined with or contacted with a cell, and the cell is allowed to internalize the test compound, e.g., by endocytosis. An endosome preparation can then be made from the contacted cells and the endosome preparation compared to an endosome preparation from control cells. A change, e.g., a decrease, in the endosome fraction from the contacted cell vs. the control cell indicates that the test compound can function as a fusogenic agent. Alternatively, the contacted cell and control cell can be evaluated, e.g., by microscopy, e.g., by light or electron microscopy, to determine a difference in the endosome population in the cells. The test compound and/or the endosomes can labeled, e.g., to quantify endosomal leakage.

In another type of assay, an iRNA agent described herein is constructed using one or more test or putative fusogenic agents. The iRNA agent can be labeled for easy visualization. The ability of the endosomolytic component to promote endosomal escape, once the iRNA agent is taken up by the cell, can be evaluated, e.g., by preparation of an endosome preparation, or by microscopy techniques, which enable visualization of the labeled iRNA agent in the cytoplasm of the cell. In certain other embodiments, the inhibition of gene expression, or any other physiological parameter, may be used as a surrogate marker for endosomal escape.

In other embodiments, circular dichroism spectroscopy can be used to identify compounds that exhibit a pH-dependent structural transition.

A two-step assay can also be performed, wherein a first assay evaluates the ability of a test compound alone to respond to changes in pH, and a second assay evaluates the ability of a modular composition that includes the test compound to respond to changes in pH.

Lipid Conjugates

In one ligand, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an α-helical agent, which preferably has a lipophilic and a lipophobic phase.

Cell Permeation Peptides

Peptides suitable for use with the present invention can be a natural peptide, e.g., tat or antennapedia peptide, a synthetic peptide, or a peptidomimetic. Furthermore, the peptide can be a modified peptide, for example peptide can comprise non-peptide or pseudo-peptide linkages, and D-amino acids. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO:5). An RFGF analogue (e.g., amino acid sequence AALLPVL-LAAP (SEQ ID NO:6)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO:7)) and the *Drosophila Antennapedia* protein (RQIKIWFQNRRMKWKK (SEQ ID NO:8)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991).

Preferably, the peptide or peptidomimetic tethered to the lipid is a cell-targeting peptide such as an arginine-glycine-aspartic acid (RGD)-peptide, or RGD mimic A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an dsRNA agent to tumors of a variety of other tissues, including the lung, kidney, spleen, or liver (Aoki et al., Cancer Gene Therapy 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver a iRNA agent to a tumor cell expressing $\alpha v \beta_3$ (Haubner et al., Jour. Nucl. Med., 42:326-336, 2001).

Peptides that target markers enriched in proliferating cells can be used. E.g., RGD containing peptides and peptidomimetics can target cancer cells, in particular cells that exhibit an $\alpha v \beta 3$ integrin. Thus, one could use RGD peptides, cyclic peptides containing RGD, RGD peptides that include D-amino acids, as well as synthetic RGD mimics. In addition to RGD, one can use other moieties that target the $\alpha v \beta 3$ integrin ligand. Generally, such ligands can be used to control proliferating cells and angiogeneis.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

Carbohydrate Conjugates

In some embodiments, the iRNA oligonucleotides described herein further comprise carbohydrate conjugates. The carbohydrate conjugates are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include $C_5$ and above (preferably $C_5$-$C_8$) sugars; di- and trisaccharides include sugars having two or three monosaccharide units (preferably $C_5$-$C_8$).

In one embodiment, the carbohydrate conjugate is selected from the group consisting of:

Formula II

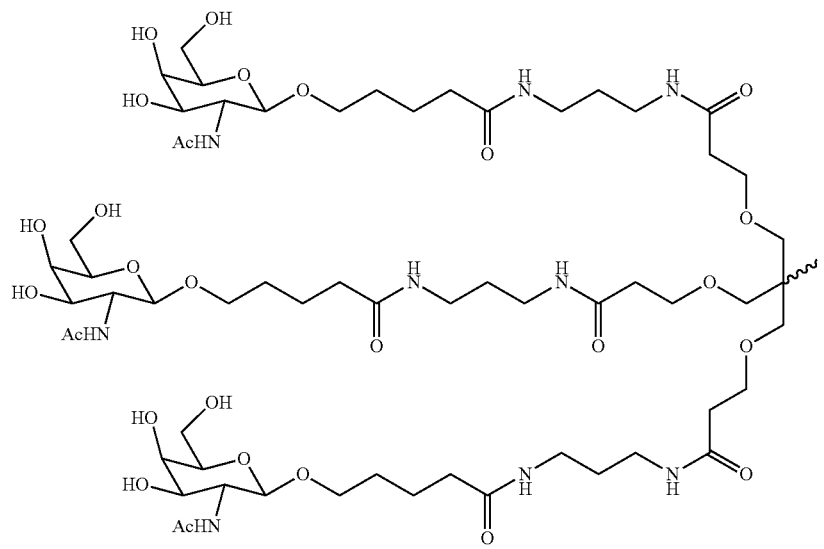

,

-continued
Formula III
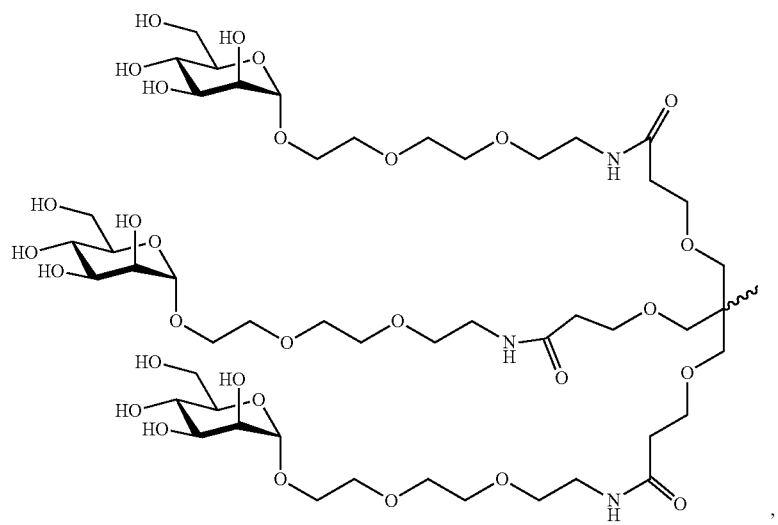
Formula IV
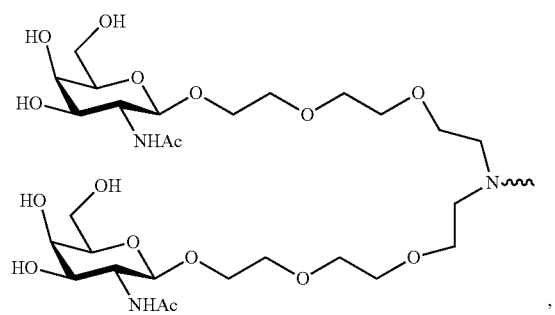
Formula V
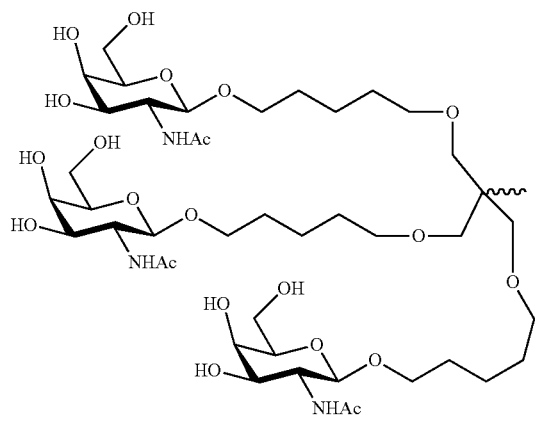
Formula VI
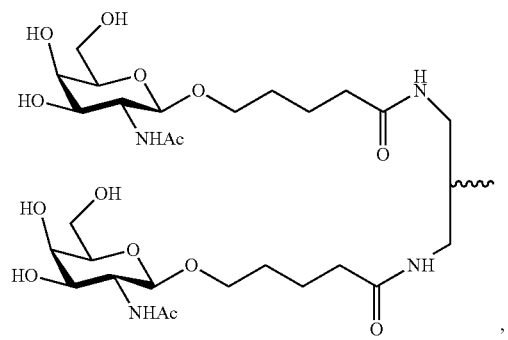
Formula VII
Formula VIII
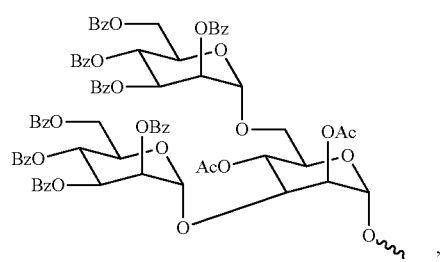

-continued
Formula IX
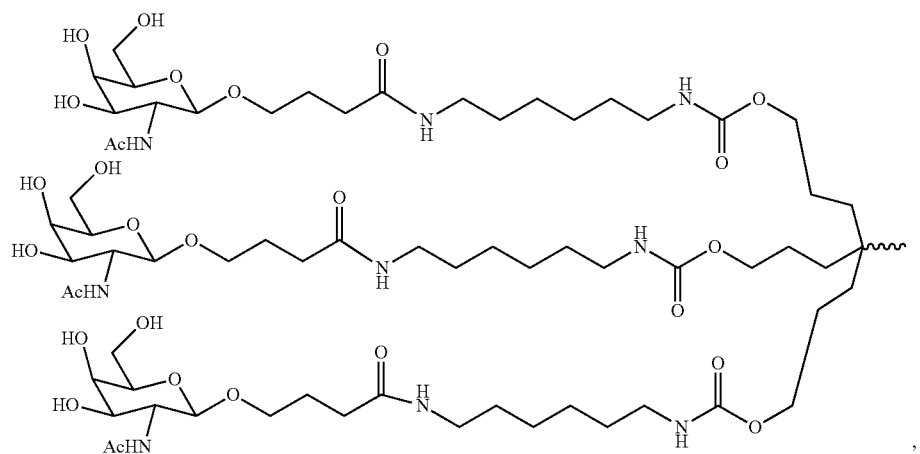
Formula X
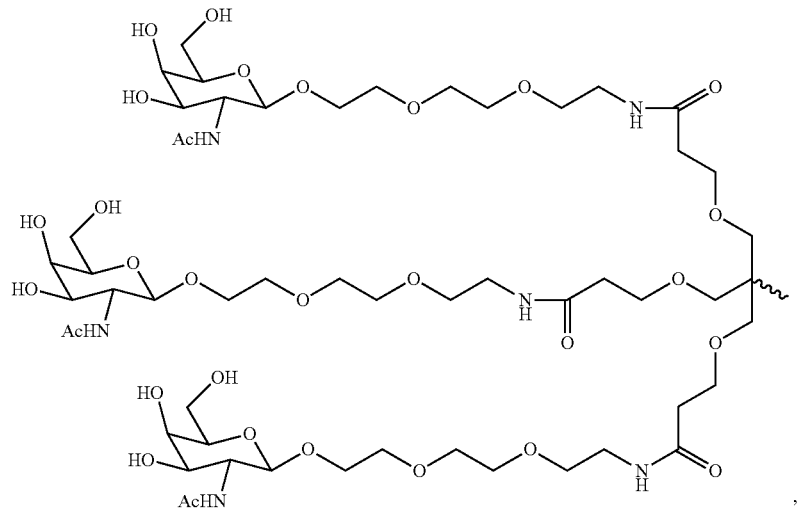
Formula XI
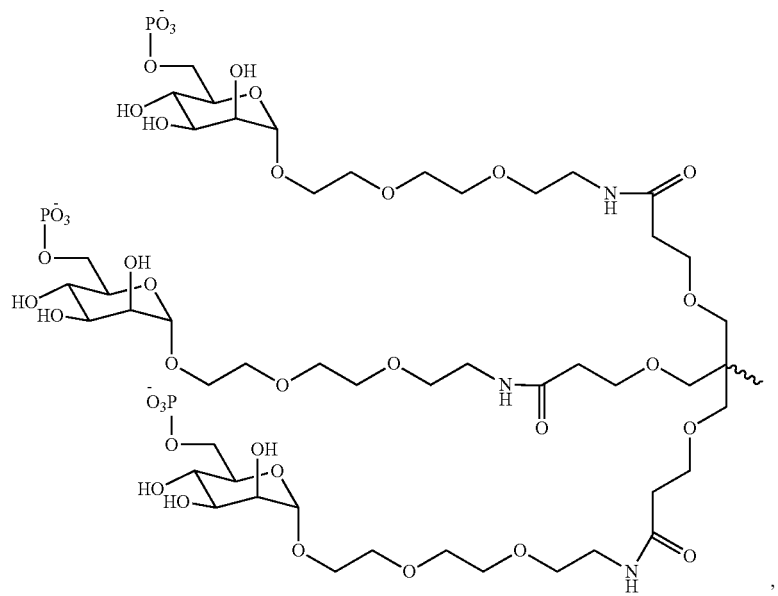

Formula XII
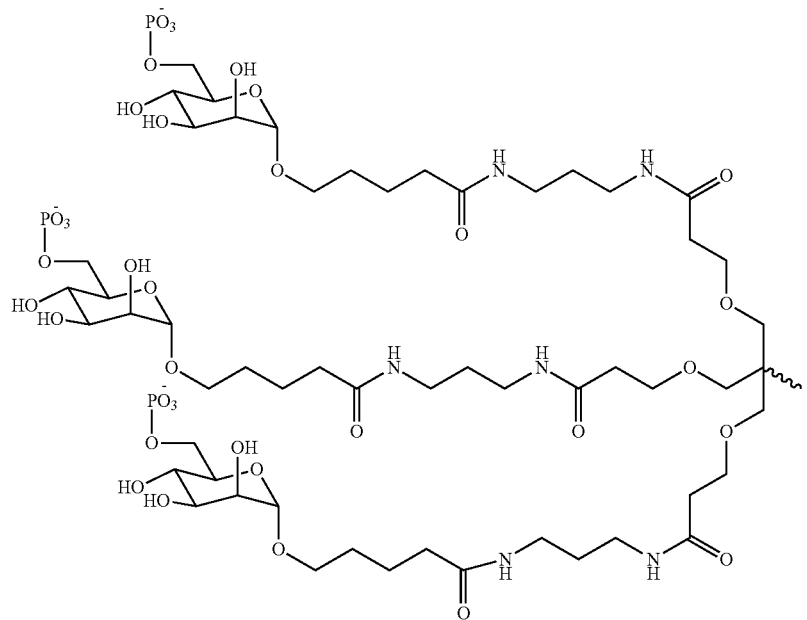
Formula XIII
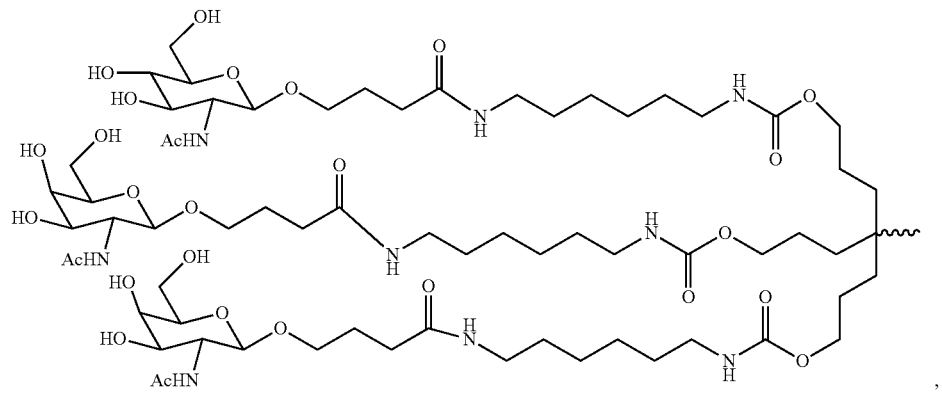
Formula XIV
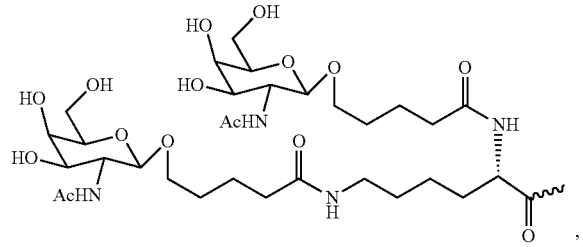
Formula XV
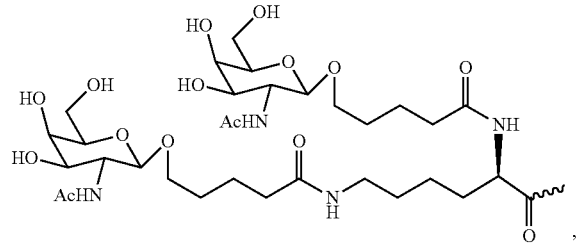
Formula XVI
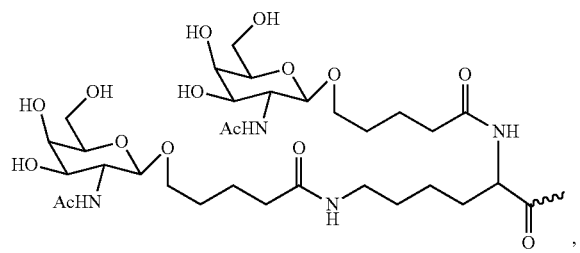
Formula XVII
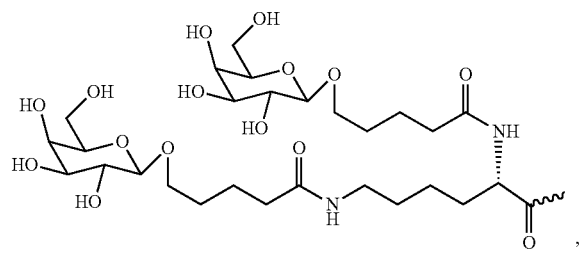

-continued
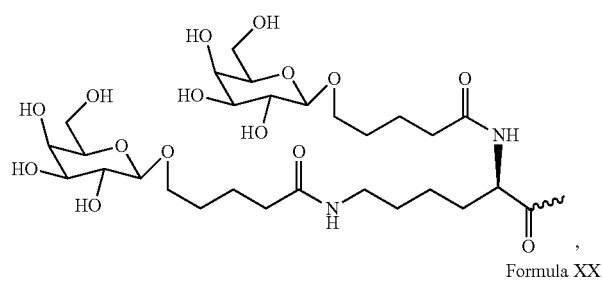
Formula XVIII
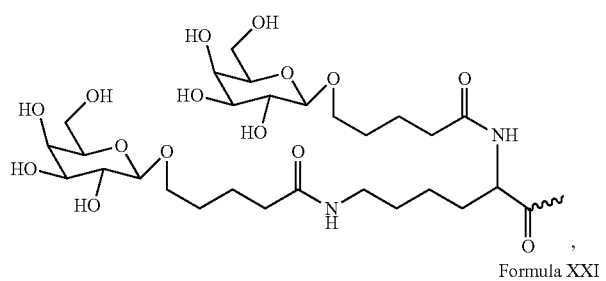
Formula XIX
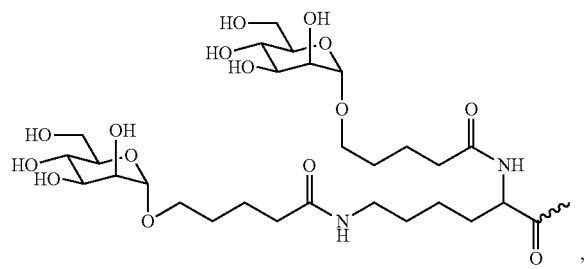
Formula XX
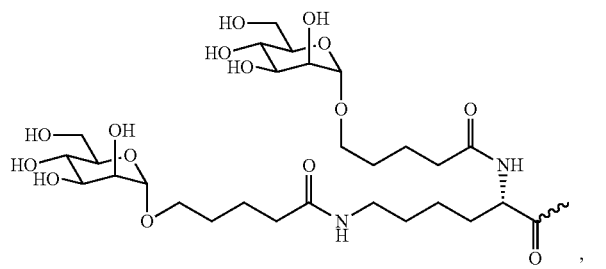
Formula XXI
Formula XXII
i.e., Formula II - Formula XXII.
Another representative carbohydrate conjugate for use in the embodiments described herein includes, but is not limited to, (Formula XXIII)
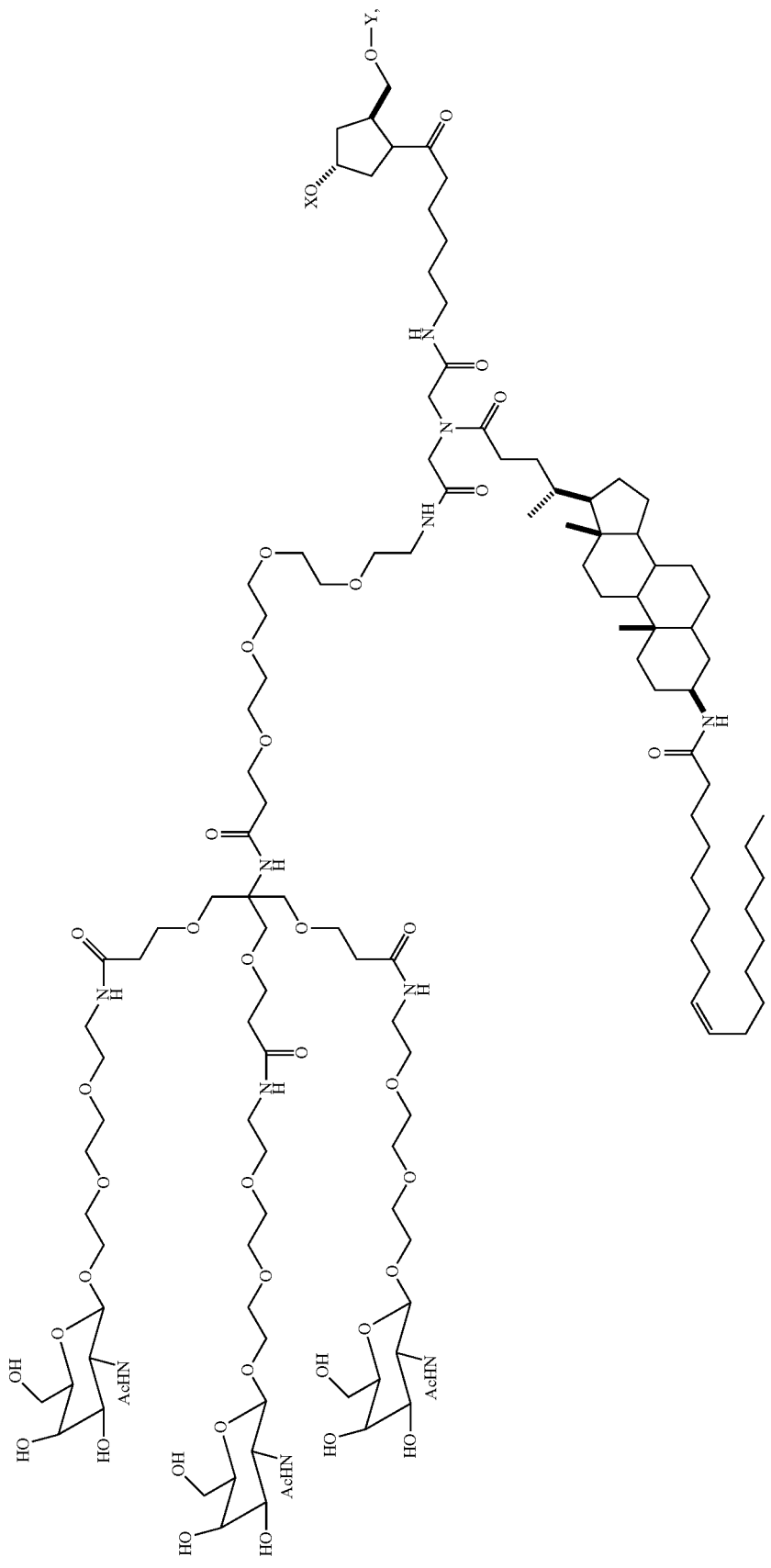

when one of X or Y is an oligonucleotide, the other is a hydrogen.

In some embodiments, the carbohydrate conjugate further comprises other ligand such as, but not limited to, PK modulator, endosomolytic ligand, and cell permeation peptide.

Linkers

In some embodiments, the conjugates described herein can be attached to the iRNA oligonucleotide with various linkers that can be cleavable or non cleavable.

The term "linker" or "linking group" means an organic moiety that connects two parts of a compound. Linkers typically comprise a direct bond or an atom such as oxygen or sulfur, a unit such as $NR^8$, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, $N(R^8)$, C(O), substituted or unsubstituted aryl, substituted or unsubstituted heteroaryl, substituted or unsubstituted heterocyclic; where $R^8$ is hydrogen, acyl, aliphatic or substituted aliphatic. In one embodiment, the linker is between 1-24 atoms, preferably 4-24 atoms, preferably 6-18 atoms, more preferably 8-18 atoms, and most preferably 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula—NHCHR$^A$C(O)NHCHR$^B$C(O)—, where R$^A$ and R$^B$ are the R groups of the two adjacent amino acids. These candidates can be evaluated using methods analogous to those described above.

Representative carbohydrate conjugates with linkers include, but are not limited to, (Formula XXIV)

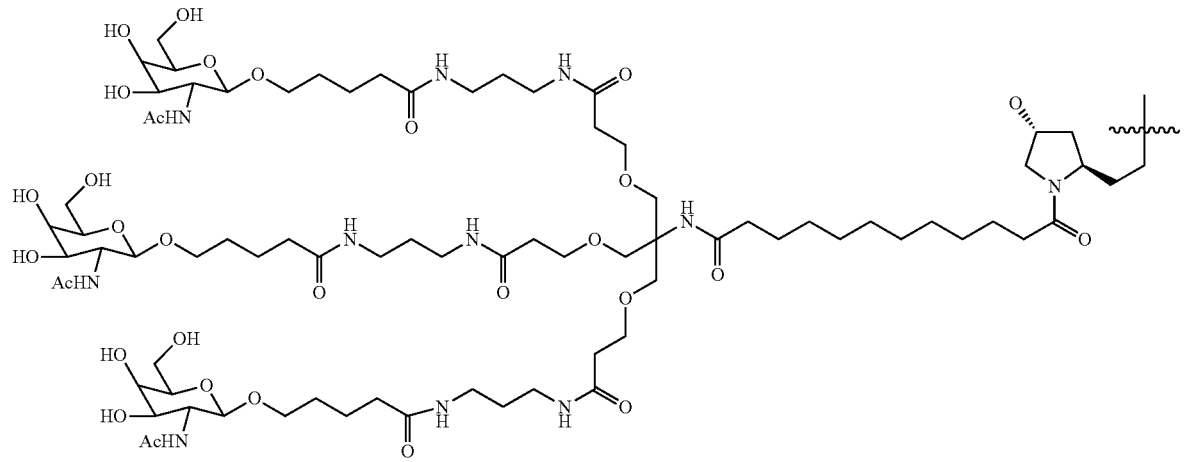

, (Formula XXV)
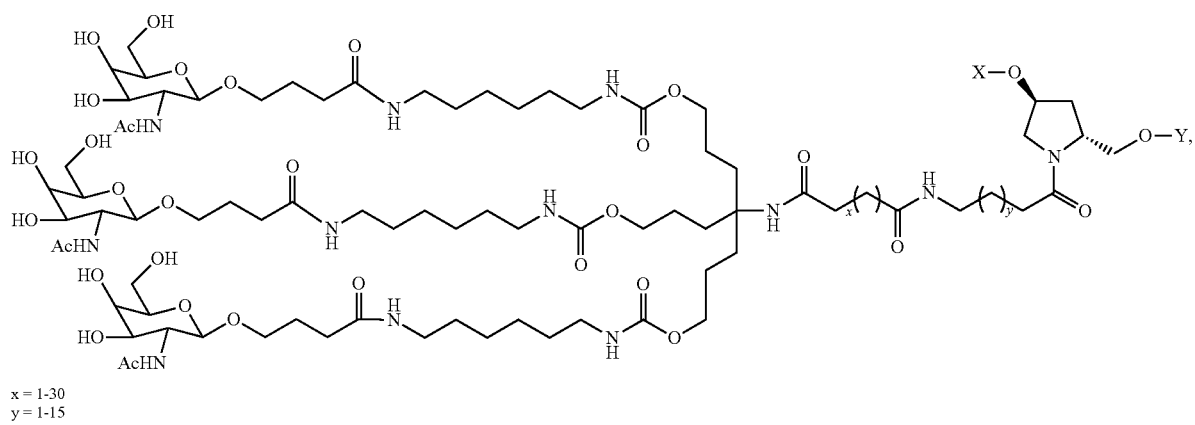
x = 1-30
y = 1-15
(Formula XXVI)
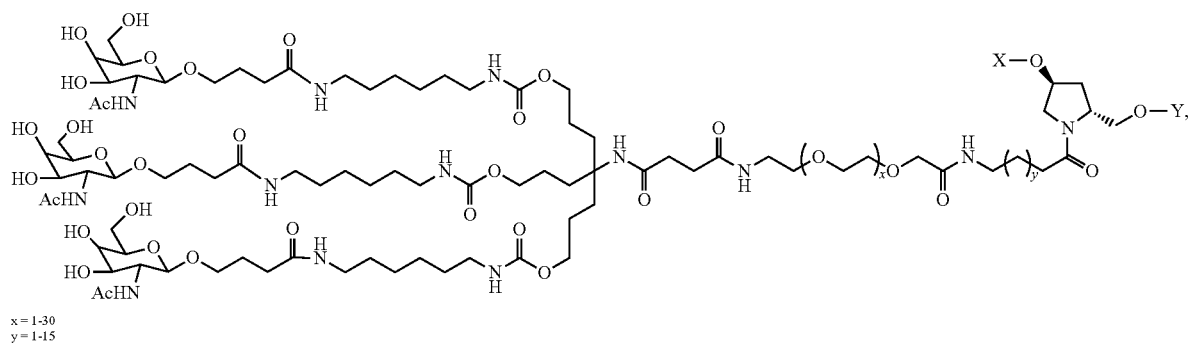
x = 1-30
y = 1-15
(Formula XXVII)
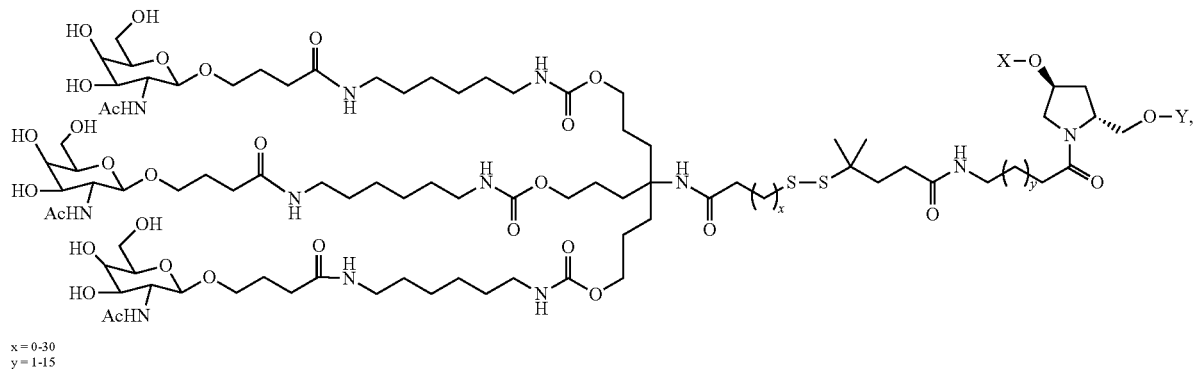
x = 0-30
y = 1-15
(Formula XXVIII)
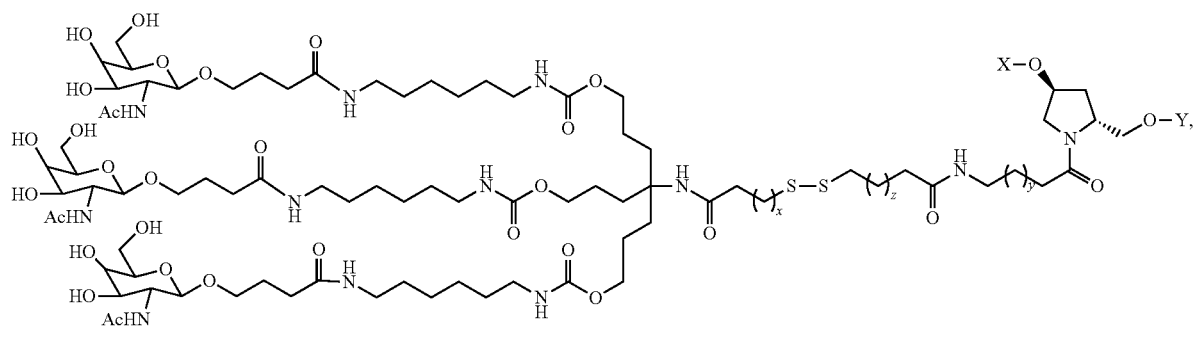
x = 0-30
y = 1-15
z = 1-20

(Formula XXIX)

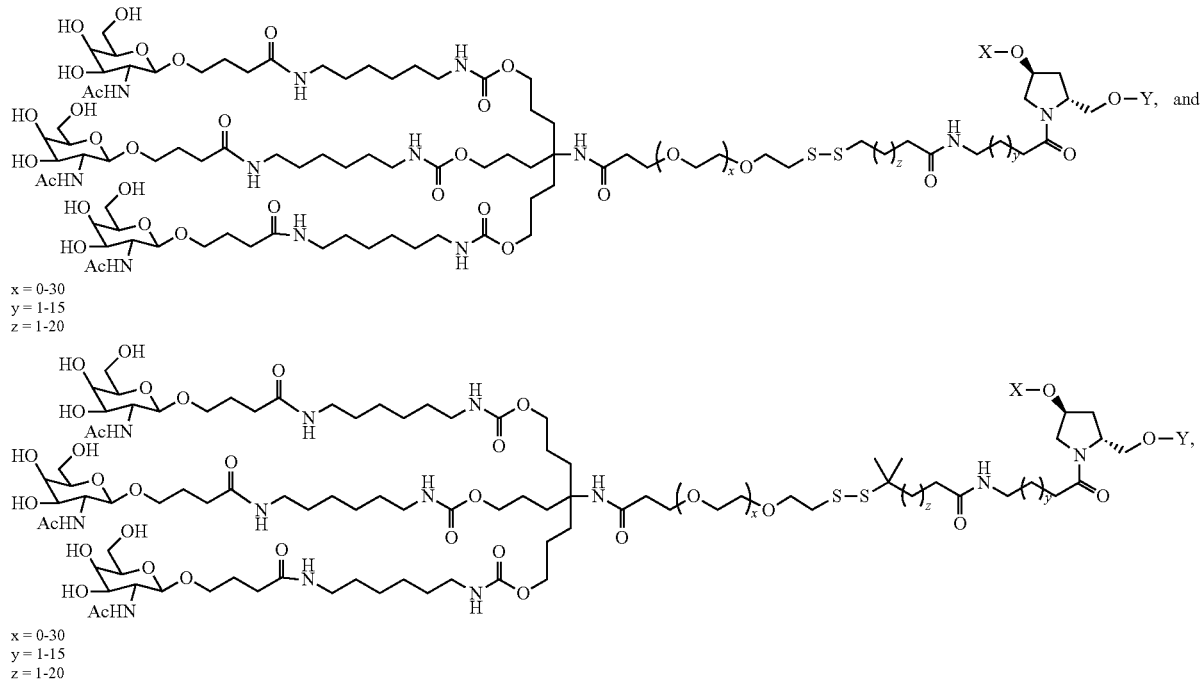

x = 0-30
y = 1-15
z = 1-20 x = 0-30
y = 1-15
z = 1-20 when one of X or Y is an oligonucleotide, the other is a hydrogen.

Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; each of which is herein incorporated by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds. "Chimeric" iRNA compounds or "chimeras," in the context of this invention, are iRNA compounds, preferably dsRNAs, which contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., Biochem. Biophys. Res. Comm., 2007, 365(1):54-61; Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such RNA conjugates have been listed above. Typical conjugation protocols involve the synthesis of an RNA bearing an amino linker at one or more positions of the sequence. The amino group is then reacted with the molecule being conjugated using appropriate coupling or activating reagents. The conjugation reaction may be performed either with the RNA still bound to the solid support or following cleavage of the RNA, in solution phase. Purification of the RNA conjugate by HPLC typically affords the pure conjugate.

Delivery of iRNA

The delivery of an iRNA to a subject in need thereof can be achieved in a number of different ways. In vivo delivery can be performed directly by administering a composition comprising an iRNA, e.g. a dsRNA, to a subject. Alternatively, delivery can be performed indirectly by administering one or more vectors that encode and direct the expression of the iRNA.

Direct Delivery of an iRNA Composition

In general, any method of delivering a nucleic acid molecule can be adapted for use with an iRNA (see e.g., Akhtar S. and Julian RL. (1992) Trends Cell. Biol. 2(5): 139-144 and WO94/02595, which are incorporated herein by reference in their entireties). However, there are three factors that are important to consider in order to successfully deliver an iRNA molecule in vivo: (a) biological stability of the delivered molecule, (2) preventing non-specific effects, and (3) accumulation of the delivered molecule in the target tissue. The non-specific effects of an iRNA can be minimized by local administration, for example by direct injection or implantation into a tissue (as a non-limiting example, a tumor) or topically administering the preparation. Local administration to a treatment site maximizes local concentration of the agent, limits the exposure of the agent to systemic tissues that may otherwise be harmed by the agent or that may degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J., et al (2004) Retina 24:132-138) and subretinal injections in mice (Reich, S J., et al (2003) Mol. Vis. 9:210-216) were both shown to prevent neovascularization in an experimental model of age-related macular degeneration. In addition, direct intratumoral injection of a dsRNA in mice reduces tumor volume (Pille, J., et al (2005) Mol. Ther.11:267-274) and can prolong survival of tumor-bearing mice (Kim, W J., et al (2006) Mol. Ther. 14:343-350; Li, S., et al (2007) Mol. Ther. 15:515-523). RNA interference has also shown success with local delivery to the CNS by direct injection (Dorn, G., et al. (2004) Nucleic Acids 32:e49; Tan, P H., et al (2005) Gene Ther. 12:59-66; Makimura, H., et al (2002) BMC Neurosci. 3:18; Shishkina, G T., et al (2004) Neuroscience 129:521-528; Thakker, E R., et al (2004) Proc. Natl. Acad. Sci. U.S.A. 101:17270-17275; Akaneya, Y., et al (2005) J. Neurophysiol. 93:594-602) and to the lungs by intranasal administration (Howard, K A., et al (2006) Mol. Ther. 14:476-484; Zhang, X., et al (2004) J. Biol. Chem. 279:10677-10684; Bitko, V., et al (2005) Nat. Med. 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) Nature 432:173-178). Conjugation of an iRNA to an aptamer has been shown to inhibit tumor growth and mediate tumor regression in a mouse model of prostate cancer (McNamara, J O., et al (2006) Nat. Biotechnol. 24:1005-1015). In an alternative embodiment, the iRNA can be delivered using drug delivery systems such as a nanoparticle, a dendrimer, a polymer, a liposome, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) Journal of Controlled Release 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) J. Mol. Biol 327:761-766; Verma, U N., et al (2003) Clin. Cancer Res. 9:1291-1300; Arnold, A S et al (2007) J. Hypertens. 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) Nature 441:111-114), cardiolipin (Chien, P Y., et al (2005) Cancer Gene Ther. 12:321-328; Pal, A., et al (2005) Int J. Oncol. 26:1087-1091), polyethyleneimine (Bonnet M E., et al (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A., et al (2007) Biochem. Soc. Trans. 35:61-67; Yoo, H., et al (1999) Pharm. Res. 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

Vector Encoded iRNAs

In another aspect, iRNA targeting the TMPRSS6 gene can be expressed from transcription units inserted into DNA or RNA vectors (see, e.g., Couture, A, et al., TIG. (1996), 12:5-10; Skillern, A., et al., International PCT Publication No. WO 00/22113, Conrad, PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., Proc. Natl. Acad. Sci. USA (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, the strands of a dsRNA are expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

iRNA expression plasmids can be transfected into target cells as a complex with cationic lipid carriers (e.g., Oligofectamine) or non-cationic lipid-based carriers (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct may be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, FASEB J. 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-β-D1-thiogalactopyranoside (IPTG). A person skilled in the art would be able to choose the appropriate regulatory/promoter sequence based on the intended use of the iRNA transgene.

In a specific embodiment, viral vectors that contain nucleic acid sequences encoding an iRNA can be used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding an iRNA are cloned into one or more vectors, which facilitates delivery of the nucleic acid into a patient. More detail about retroviral vectors can be found, for example, in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). A suitable AV vector for expressing an iRNA featured in the invention, a method for constructing the recombinant AV vector, and a method for delivering the vector into target cells, are described in Xia H et al. (2002), Nat. Biotech. 20: 1006-1010.

Use of Adeno-associated virus (AAV) vectors is also contemplated (Walsh et al., Proc. Soc. Exp. Biol. Med. 204:289-300 (1993); U.S. Pat. No. 5,436,146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J.

Virol, 70: 520-532; Samulski R et al. (1989), J. Virol. 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

Another preferred viral vector is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), J Virol 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

III. Pharmaceutical Compositions Containing iRNA

In one embodiment, provided herein are pharmaceutical compositions containing an iRNA and a pharmaceutically acceptable carrier. The pharmaceutical composition containing the iRNA is useful for treating a disease or disorder associated with the expression or activity of a TMPRSS6 gene, such as pathological processes mediated by TMPRSS6 expression. Such pharmaceutical compositions are formulated based on the mode of delivery. One example is compositions that are formulated for systemic administration via parenteral delivery, e.g., by intravenous (IV) delivery.

The pharmaceutical compositions featured herein are administered in dosages sufficient to inhibit expression of TMPRSS6 genes. In general, a suitable dose of iRNA will be in the range of 0.01 to 200.0 milligrams per kilogram body weight of the recipient per day, generally in the range of 1 to 50 mg per kilogram body weight per day. For example, the dsRNA can be administered at 0.05 mg/kg, 0.5 mg/kg, 1 mg/kg, 1.5 mg/kg, 2 mg/kg, 3 mg/kg, 10 mg/kg, 20 mg/kg, 30 mg/kg, 40 mg/kg, or 50 mg/kg per single dose. The pharmaceutical composition may be administered once daily, or once weekly, or once monthly, or once every other month. The composition can alternatively be administered twice per week or twice per month, or once every two, three or four weeks. In some embodiments, the iRNA is administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the present invention. In this embodiment, the dosage unit contains a corresponding multiple of the daily dose.

The effect of a single dose on TMPRSS6 levels can be long lasting, such that subsequent doses are administered at not more than 3, 4, or 5 day intervals, or at not more than 1, 2, 3, or 4 week intervals.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

Advances in mouse genetics have generated a number of mouse models for the study of various human diseases, such as pathological processes mediated by TMPRSS6 expression. Such models can be used for in vivo testing of iRNA, as well as for determining a therapeutically effective dose. A suitable mouse model is, for example, a mouse containing a transgene expressing human TMPRSS6.

The present invention also includes pharmaceutical compositions and formulations that include the iRNA compounds featured in the invention. The pharmaceutical compositions of the present invention may be administered in a number of ways depending upon whether local or systemic treatment is desired and upon the area to be treated. Administration may be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The iRNA can be delivered in a manner to target a particular tissue, such as the liver (e.g., the hepatocytes of the liver).

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention may be encapsulated within liposomes or may form complexes thereto, in particular to cationic liposomes. Alternatively, iRNAs may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

Liposomal Formulations

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to traverse intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap nucleic acids rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al. S.T.P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{1215G}$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describes PEG-containing liposomes that can be further derivatized with functional moieties on their surfaces.

A number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include a dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Nucleic Acid Lipid Particles

In one embodiment, a TMPRSS6 dsRNA featured in the invention is fully encapsulated in the lipid formulation, e.g., to form a SPLP, pSPLP, SNALP, or other nucleic acid-lipid particle. As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1.

The cationic lipid can be, for example, N,N-dioleyl-N,N-dimethylammonium chloride (DODAC), N,N-distearyl-N,N-dimethylammonium bromide (DDAB), N-(I-(2,3-dioleyloxy)propyl)-N,N,N-trimethylammonium chloride (DOTAP), N-(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyedidodecan-2-ol (Tech G1), or a mixture thereof. The cationic lipid may comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2,2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The non-cationic lipid may be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid may be from about 5 mol % to about 90 mol %, about 10 mol %, or about 58 mol % if cholesterol is included, of the total lipid present in the particle.

The conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($C]_8$). The conjugated lipid that prevents aggregation of particles may be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

LNP01

In one embodiment, the lipidoid ND98.4HCl (MW 1487) (see U.S. patent application Ser. No. 12/056,230, filed Mar. 26, 2008, which is herein incorporated by reference in its entirety), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

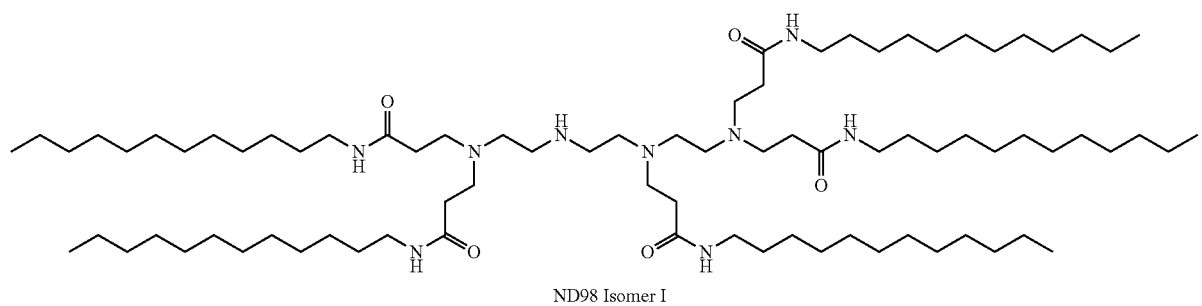

Formula I

ND98 Isomer I

LNP01 formulations are described, e.g., in International Application Publication No. WO 2008/042973, which is hereby incorporated by reference.

Additional exemplary lipid-dsRNA formulations are as follows:

|  | Cationic Lipid | cationic lipid/non-cationic lipid/cholesterol/PEG-lipid conjugate Lipid:siRNA ratio |
|---|---|---|
| SNALP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~7:1 |
| S-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~11:1 |
| LNP09 | 2'2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (C12-200) | C12-200/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |

-continued

|  | Cationic Lipid | cationic lipid/non-cationic lipid/cholesterol/PEG-lipid conjugate Lipid:siRNA ratio |
|---|---|---|
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: distearoylphosphatidylcholine
DPPC: dipalmitoylphosphatidylcholine
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000)

SNALP (1,2-Dilinolenyloxy-N,N-dimethylaminopropane (DLinDMA)) comprising formulations are described in International Publication No. WO2009/127060, filed Apr. 15, 2009, which is hereby incorporated by reference.

XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Ser. No. 61/185,712, filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.

MC3 comprising formulations are described, e.g., in U.S. Provisional Ser. No. 61/244,834, filed Sep. 22, 2009, U.S. Provisional Ser. No. 61/185,800, filed Jun. 10, 2009, and International Application No. PCT/US10/28224, filed Jun. 10, 2010, which are hereby incorporated by reference.

ALNY-100 comprising formulations are described, e.g., International patent application number PCT/US09/63933, filed on Nov. 10, 2009, which is hereby incorporated by reference.

C12-200 comprising formulations are described in U.S. Provisional Ser. No. 61/175,770, filed May 5, 2009 and International Application No. PCT/US10/33777, filed May 5, 2010, which are hereby incorporated by reference.

As used herein, the term "LNPXX", wherein the "XX" are numerals, is also referred to as "AFXX" herein. For example, LNP09 is also referred to AF09 and LNP12 is also known as or referred to as AF12.

Synthesis of Cationic Lipids

Any of the compounds, e.g., cationic lipids and the like, used in the nucleic acid-lipid particles featured in the invention can be prepared by known organic synthesis techniques, including the methods described in more detail in the Examples. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(=O)alkyl, —C(=O)alkenyl, and —C(=O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle can be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl," "optionally substituted alkenyl," "optionally substituted alkynyl," "optionally substituted acyl," and "optionally substituted heterocycle" means that, when substituted, at least one hydrogen atom is replaced with a substituent. In the case of an oxo substituent (═O) two hydrogen atoms are replaced. In this regard, substituents include oxo, halogen, heterocycle, —CN, —OR$^x$, —NR$^x$R$^y$, —NR$^x$C(═O)R$^y$, —NR$^x$SO$_2$R$^y$, —C(═O)R$^x$, —C(═O)OR$^x$, —C(═O)NR$^x$R$^y$, —SO$_n$R$^x$ and —SO$_n$NR$^x$R$^y$, wherein n is 0, 1 or 2, R$^x$ and R$^y$ are the same or different and independently hydrogen, alkyl or heterocycle, and each of said alkyl and heterocycle substituents may be further substituted with one or more of oxo, halogen, —OH, —CN, alkyl, —OR$^x$, heterocycle, —NR$^x$R$^y$, —NR$^x$C(═O)R$^y$, —NR$^x$SO$_2$R$^y$, —C(═O)R$^x$, —C(═O)OR$^x$, —C(═O)NR$^x$R$^y$, —SO$_n$R$^x$ and —SO$_n$NR$^x$R$^y$.

"Halogen" means fluoro, chloro, bromo and iodo.

In some embodiments, the methods featured in the invention can require the use of protecting groups. Protecting group methodology is well known to those skilled in the art (see, for example, Protective Groups in Organic Synthesis, Green, T. W. et al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments, an "alcohol protecting group" is used. An "alcohol protecting group" is any group which decreases or eliminates unwanted reactivity of an alcohol functional group. Protecting groups can be added and removed using techniques well known in the art.

Synthesis of Formula A

In some embodiments, nucleic acid-lipid particles featured in the invention are formulated using a cationic lipid of formula A:

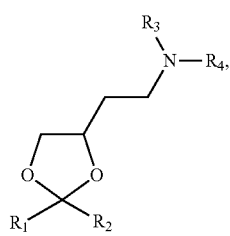

where R1 and R2 are independently alkyl, alkenyl or alkynyl, each can be optionally substituted, and R3 and R4 are independently lower alkyl or R3 and R4 can be taken together to form an optionally substituted heterocyclic ring. In some embodiments, the cationic lipid is XTC (2,2-Dilinoleyl-4-dimethylaminoethyl-[1,3]-dioxolane). In general, the lipid of formula A above may be made by the following Reaction Schemes 1 or 2, wherein all substituents are as defined above unless indicated otherwise.

Scheme 1

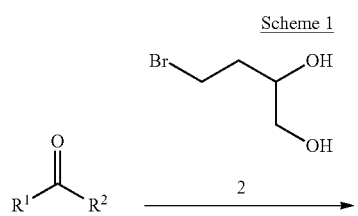

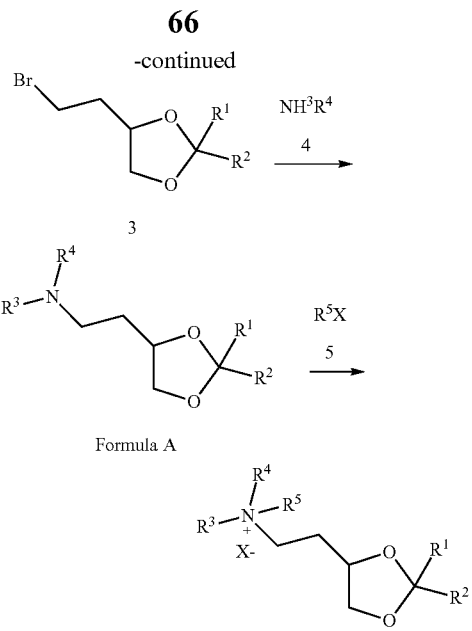

Formula A

Lipid A, where R$_1$ and R$_2$ are independently alkyl, alkenyl or alkynyl, each can be optionally substituted, and R$_3$ and R$_4$ are independently lower alkyl or R$_3$ and R$_4$ can be taken together to form an optionally substituted heterocyclic ring, can be prepared according to Scheme 1. Ketone 1 and bromide 2 can be purchased or prepared according to methods known to those of ordinary skill in the art. Reaction of 1 and 2 yields ketal 3. Treatment of ketal 3 with amine 4 yields lipids of formula A. The lipids of formula A can be converted to the corresponding ammonium salt with an organic salt of formula 5, where X is anion counter ion selected from halogen, hydroxide, phosphate, sulfate, or the like.

Scheme 2

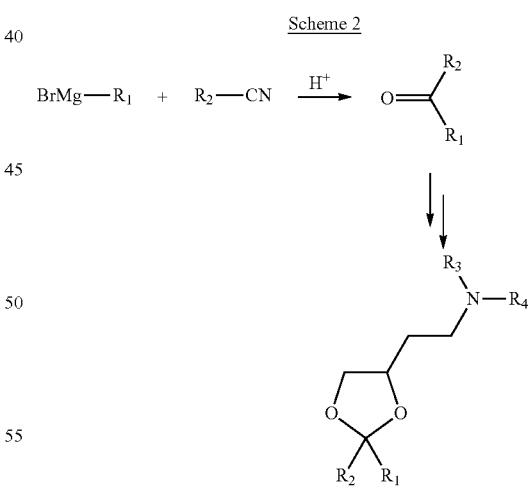

Alternatively, the ketone 1 starting material can be prepared according to Scheme 2. Grignard reagent 6 and cyanide 7 can be purchased or prepared according to methods known to those of ordinary skill in the art. Reaction of 6 and 7 yields ketone 1. Conversion of ketone 1 to the corresponding lipids of formula A is as described in Scheme 1.

Synthesis of MC3

Preparation of DLin-M-C3-DMA (i.e., (6Z,9Z,28Z,31Z)-heptatriaconta-6,9,28,31-tetraen-19-yl4-(dimethylamino)

butanoate) was as follows. A solution of (6Z,9Z,28Z,31Z)-heptatriaconta-6,9,28,31-tetraen-19-ol (0.53 g), 4-N,N-dimethylaminobutyric acid hydrochloride (0.51 g), 4-N,N-dimethylaminopyridine (0.61 g) and 1-ethyl-3-(3-dimethylaminopropyl)carbodiimide hydrochloride (0.53 g) in dichloromethane (5 mL) was stirred at room temperature overnight. The solution was washed with dilute hydrochloric acid followed by dilute aqueous sodium bicarbonate. The organic fractions were dried over anhydrous magnesium sulphate, filtered and the solvent removed on a rotovap. The residue was passed down a silica gel column (20 g) using a 1-5% methanol/dichloromethane elution gradient. Fractions containing the purified product were combined and the solvent removed, yielding a colorless oil (0.54 g).

Synthesis of ALNY-100

Synthesis of ketal 519 [ALNY-100] was performed using the following scheme 3:

washed successively with 1N HCl solution (1×100 mL) and saturated NaHCO3 solution (1×50 mL). The organic layer was then dried over anhyd. Na2SO4 and the solvent was evaporated to give crude material which was purified by silica gel column chromatography to get 516 as sticky mass. Yield: 11 g (89%). 1H-NMR (CDCl3, 400 MHz): δ=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H] −232.3 (96.94%).

Synthesis of 517A and 517B

The cyclopentene 516 (5 g, 0.02164 mol) was dissolved in a solution of 220 mL acetone and water (10:1) in a single neck 500 mL RBF and to it was added N-methyl morpholine-N-oxide (7.6 g, 0.06492 mol) followed by 4.2 mL of 7.6% solution of OsO4 (0.275 g, 0.00108 mol) in tert-butanol at room temperature. After completion of the reaction (~ 3 h), the mixture was quenched with addition of solid

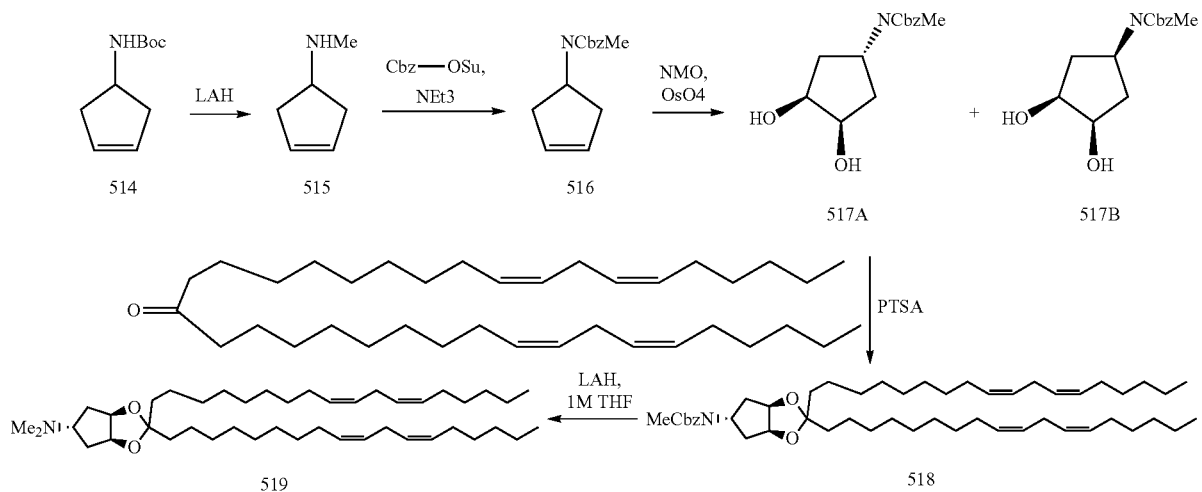

Synthesis of 515

To a stirred suspension of LiAlH4 (3.74 g, 0.09852 mol) in 200 ml anhydrous THF in a two neck RBF (1 L), was added a solution of 514 (10 g, 0.04926 mol) in 70 mL of THF slowly at 0° C. under nitrogen atmosphere. After complete addition, reaction mixture was warmed to room temperature and then heated to reflux for 4 h. Progress of the reaction was monitored by TLC. After completion of reaction (by TLC) the mixture was cooled to 0 0C and quenched with careful addition of saturated Na2SO4 solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g 1H-NMR (DMSO, 400 MHz): δ=9.34 (broad, 2H), 5.68 (s, 2H), 3.74 (m, 1H), 2.66-2.60 (m, 2H), 2.50-2.45 (m, 5H).

Synthesis of 516

To a stirred solution of compound 515 in 100 mL dry DCM in a 250 mL two neck RBF, was added NEt3 (37.2 mL, 0.2669 mol) and cooled to 0 0C under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was Na2SO3 and resulting mixture was stirred for 1.5 h at room temperature. Reaction mixture was diluted with DCM (300 mL) and washed with water (2×100 mL) followed by saturated NaHCO3 (1×50 mL) solution, water (1×30 mL) and finally with brine (1×50 mL). Organic phase was dried over an.Na2SO4 and solvent was removed in vacuum. Silica gel column chromatographic purification of the crude material was afforded a mixture of diastereomers, which were separated by prep HPLC. Yield: ~6 g crude 517A-Peak-1 (white solid), 5.13 g (96%). 1H-NMR (DMSO, 400 MHz): δ=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS-[M+H]−266.3, [M+NH4+]−283.5 present, HPLC-97.86%. Stereochemistry confirmed by X-ray.

Synthesis of 518

Using a procedure analogous to that described for the synthesis of compound 505, compound 518 (1.2 g, 41%) was obtained as a colorless oil. 1H-NMR (CDCl3, 400 MHz): δ=7.35-7.33 (m, 4H), 7.30-7.27 (m, 1H), 5.37-5.27 (m, 8H), 5.12 (s, 2H), 4.75 (m, 1H), 4.58-4.57 (m, 2H), 2.78-2.74 (m, 7H), 2.06-2.00 (m, 8H), 1.96-1.91 (m, 2H), 1.62 (m, 4H), 1.48 (m, 2H), 1.37-1.25 (br m, 36H), 0.87 (m, 6H). HPLC-98.65%.

General Procedure for the Synthesis of Compound 519

A solution of compound 518 (1 eq) in hexane (15 mL) was added in a drop-wise fashion to an ice-cold solution of LAH in THF (1 M, 2 eq). After complete addition, the mixture was heated at 40° C. over 0.5 h then cooled again on an ice bath. The mixture was carefully hydrolyzed with saturated aqueous Na2SO4 then filtered through celite and reduced to an oil. Column chromatography provided the pure 519 (1.3 g, 68%) which was obtained as a colorless oil. 13C NMR ☐=130.2, 130.1 (x2), 127.9 (x3), 112.3, 79.3, 64.4, 44.7, 38.3, 35.4, 31.5, 29.9 (x2), 29.7, 29.6 (x2), 29.5 (x3), 29.3 (x2), 27.2 (x3), 25.6, 24.5, 23.3, 226, 14.1; Electrospray MS (+ve): Molecular weight for C44H80NO2 (M+H)+ Calc. 654.6, Found 654.6.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total dsRNA concentration in the formulation, as well as the entrapped fraction, is estimated using a dye exclusion assay. A sample of the formulated dsRNA can be incubated with an RNA-binding dye, such as Ribogreen (Molecular Probes) in the presence or absence of a formulation disrupting surfactant, e.g., 0.5% Triton-X100. The total dsRNA in the formulation can be determined by the signal from the sample containing the surfactant, relative to a standard curve. The entrapped fraction is determined by subtracting the "free" dsRNA content (as measured by the signal in the absence of surfactant) from the total dsRNA content. Percent entrapped dsRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. In some embodiments, oral formulations are those in which dsRNAs featured in the invention are administered in conjunction with one or more penetration enhancers surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention may be delivered orally, in granular form including sprayed dried particles, or complexed to form micro or nanoparticles. DsRNA complexing agents include poly-amino acids; polyimines; polyacrylates; poly-alkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Additional Formulations
Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of iRNAs and nucleic acids are formulated as microemulsions. A microemulsion may be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191, 105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention may also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

Bile salts: The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus, the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating Agents: Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of β-diketones (enamines) (see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of iRNAs at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000™ (Invitrogen; Carlsbad, Calif.), 293fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPass$^a$ D1 Transfection Reagent (New England Biolabs; Ipswich, Mass., USA), LyoVec™/LipoGen™ (Invivogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances that increase the viscosity of the suspension including, for example, sodium carboxymethylcellulose, sorbitol and/or dextran. The suspension may also contain stabilizers.

In some embodiments, pharmaceutical compositions featured in the invention include (a) one or more iRNA compounds and (b) one or more anti-cytokine biologic agents which function by a non-RNAi mechanism. Examples of such biologics include, biologics that target IL1β (e.g., anakinra), IL6 (e.g., tocilizumab), or TNF (e.g., etanercept, infliximab, adlimumab, or certolizumab).

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein lies generally within a range of circulating concentrations that include the ED50 with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration, as discussed above, the iRNAs described herein can be administered in combination with other known agents effective in treatment of pathological processes mediated by TMPRSS6 expression. In any event, the administering physician can adjust the amount and timing of iRNA administration on the basis of results observed using standard measures of efficacy known in the art or described herein.

Methods for Treating Diseases Caused by Expression of a TMPRSS6 Gene

The invention relates in particular to the use of an iRNA targeting TMPRSS6 and compositions containing at least one such iRNA for the treatment of a TMPRSS6-mediated disorder or disease. For example, a composition containing an iRNA targeting a TMPRSS6 gene is used for treatment of a disorder associated with elevated iron levels, such as a thalassemia, (e.g., β-thalassemia intermedia or α-thalassemia), primary hemochromatosis, secondary hemochromatosis, severe juvenile hemochromatosis, sideroblastic anemia, hemolytic anemia, dyserythropoietic anemia, or sickle-cell anemia. In one embodiment, a TMPRSS6 iRNA is used to treat a hemoglobinopathy. The TMPRSS6 iRNAs featured in the invention can also be used to treat elevated levels of iron due to other conditions, such as, chronic alcoholism.

In thalassemias, the bone marrow synthesizes insufficient amounts of a hemoglobin chain; this in turn reduces the production of red blood cells and causes anemia. Either the α or the β chain may be affected, but β thalassemias are more common; newborn babies are healthy because their bodies still produce HbF, which does not have β chains; during the first few months of life, the bone marrow switches to producing HbA, and symptoms start to appear.

β-thalassemias result from mutation with either non-expressing ($β^0$) or low expressing ($β^+$) alleles of the HBB gene. β-thalassemias vary in severity depending on the genotype, and include minor/trait β-thalassemia ($β/β^0$ or $β/β+$), intermedia β-thalassemia ($β^0/β+$), and major β-thalassemia $β^0/β^0$ or $β^+/β^+$).

Thalassemia intermedia (TI) typically presents with little hemolysis, while major β-thalassemia (TM) is typically accompanied by abundant hemolysis which causes, e.g., anemia and splenomegaly; and highly ineffective erythropoiesis, which causes bone marrow drive (skeletal changes, oteopenia), increased erythropoietin synthesis, hepato-splenomegaly, consumption of haematinics (megablastic anemia), and high uric acid in blood. The iRNAs featured in the invention, e.g., TMPRSS6 iRNAs, are better suited for treating the iron overload that typically accompanies thalassemia's that are more TI like (e.g., for treating individuals having a $β^0/β+$, $β/β^0$ or $β/β+$ genotype).

Symptoms of β-thalassemias also include, e.g., complication due to therapy, e.g., iron overload, which causes endocrinopathy, liver fibrosis and cardiac fibrosis. Administration of an iRNA agent that targets TMPRSS6 can be effective to treat one or more of these symptoms.

α-thalassemias result from mutation with either non-expressing ($α^0$) or low expressing ($α^+$) alleles of the HBA1 or HBA2 genes. α-thalassemias vary in severity depending on the genotype, and include trait thalassemia (–α/αα), Hb Bart and Hydrops fetalis ($α^0/α^0$), α-Thalaseemia minor (--/αα), (–α/–α), and HbH disease (--/–α). Lower α-globin chains are produced, resulting in an excess of β chains in adults and excess γ chains in newborns. The excess β chains form unstable tetramers (called Hemoglobin H or HbH of 4 beta chains), which have abnormal oxygen dissociation curves. Administration of an iRNA agent that targets TMPRSS6 can be effective to treat iron overload in a subject who has an α-thalassemias.

Symptoms of hemochromatosis include, e.g., abdominal pain, joint pain, fatigue, lack of energy, weakness, darkening of the skin (often referred to as "bronzing"), and loss of body hair. Administration of an iRNA agent that targets TMPRSS6 can be effective to treat one or more of these symptoms.

Other symptoms associated with iron overload include increased risk for liver disease (cirrhosis, cancer), heart attack or heart failure, diabetes mellitus, osteoarthritis, osteoporosis, metabolic syndrome, hypothyroidism, hypogonadism, and in some cases premature death. Iron mismanagement resulting in overload can also accelerate such neurodegenerative diseases as Alzheimer's, early-onset Parkinson's, Huntington's, epilepsy and multiple sclerosis. Administration of an iRNA that targets TMPRSS6, e.g., an iRNA described in Tables 2, 3 or 4 can treat one or more of these symptoms, or prevent the development or progression of a disease or disorder that is aggravated by increased iron levels.

The invention further relates to the use of an iRNA or a pharmaceutical composition thereof, e.g., for treating a disorder associated with elevated iron levels, in combination with other pharmaceuticals and/or other therapeutic methods, e.g., with known pharmaceuticals and/or known therapeutic methods, such as, for example, those which are currently employed for treating these disorders. For example, in certain embodiments, an iRNA targeting TMPRSS6 is administered in combination with, e.g., iron chelators (e.g., desferroxamine), folic acid, a blood transfusion, a phlebotomy, agents to manage ulcers, agents to increase fetal hemoglobin levels (e.g., hydroxyurea), agents to control infection (e.g., antibiotics and antivirals), agents to treat thrombotic state, or a stem cell or bone marrow transplant. A stem cell transplant can utilize stem cells from an umbilical cord, such as from a relative, e.g., a sibling. Exemplary iron chelators include desferroxamine, Deferasirox (Exjade), deferoprone, vitamin E, wheat germ oil, tocophersolan, and indicaxanthin.

The iRNA and an additional therapeutic agent can be administered in the same composition, e.g., parenterally, or the additional therapeutic agent can be administered as part of a separate composition or by another method described herein. Administration of the TMPRSS6 iRNA and the additional therapeutic agent can be at the same time, or at different times and, in any order.

The invention features a method of administering an iRNA agent targeting TMPRSS6 to a patient having a disease or disorder mediated by TMPRSS6 expression, such as a disorder associated with elevated iron levels. Administration of the dsRNA can lower iron levels, lower ferritin levels, and/or lower transferrin saturation levels. For example, administration of the dsRNA can lower serum iron levels and/or lower serum ferritin levels. Transferrin saturation levels can be lowered by 5%, 10%, 15%, 20%, 25% or more. Transferrin saturation levels can be lowered to below 50%, below 45%, below 40%, below 35%, below 35% or lower. Transferrin saturation is a measure of the amount of iron bound to serum transferrin, and corresponds to the ratio of serum iron and total iron-binding capacity.

By "lower" in this context is meant a statistically significant decrease in such level. The decrease can be, for example, at least 10%, at least 20%, at least 30%, at least 40% or more, and is preferably down to a level accepted as within the range of normal for an individual without such disorder.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, the levels of transferrin saturation or serum ferritin can be monitored for efficacy of a given treatment regime.

Iron level tests are typically performed on a sample of a patient's blood. An iron level test measure the amount of iron in the blood serum that is being carried by the proteins trasferrin. A TIBC (Total iron-binding capacity) test measures the amount of iron that the blood would carry if the transferrin were fully saturated. Since transferrin is produced by the liver, the TIBC can be used to monitor liver function and nutrition. The transferrin test is a direct measure of transferrin (also called siderophilin) levels in the blood. The saturation level of transferrin can be calculated by dividing the serum iron level by the TIBC. The ferritin test measures the level of a protein in the blood that stores iron for later use by the body.

The iRNA treatments described herein can be used to treat individuals having elevated iron levels, as may be indicated by iron levels in serum e.g., iron levels measuring greater than 350 µg/dL, greater than 500 µg/dL, greater than 1000 µg/dL, or more. In an embodiment, elevated levels of iron in serum, e.g., greater than 15, 20, 25, or 30 mg/g dry weight.

The iRNA treatments described herein can be used to treat individuals having elevated iron levels, as may be indicated by elevated ferritin levels in serum, e.g., ferritin levels measuring greater than 300 µg/L, greater than 500 µg/L, greater than 1000 µg/L, greater than 1500 µg/L, greater than 2000 µg/L, greater than 2500 µg/L, or 3000 µg/L, or more.

The iRNA treatments described herein can be used to treat individuals having elevated iron levels, as may be indicated by elevated transferrin levels in serum, e.g., transferrin levels measuring greater than 400 mg/dL, greater than 500 mg/L, greater than 1000 mg/dL, or more.

The iRNA treatments described herein can be used to treat individuals having moderately elevated iron levels, as may be indicated by moderately elevated transferrin saturation levels, e.g., saturation levels of 40%, 45%, or 50% or more. In addition, the treatment described herein may also be used to prevent elevated iron levels in individuals with only minor elevations in transferrin saturation. One of skill in the art can easily monitor the transferrin saturation levels in subjects receiving treatment with iRNA as described herein and assay for a reduction in transferrin saturation levels of at least 5% or 10%.

The iRNA treatments described herein can be used to treat individuals having elevated iron levels, as may be indicated by a TIBC value greater than 400 µg/dL, greater than 500 µg/dL, or greater than 1000 µg/dL, or more.

In some embodiments, individuals in need of treatment with a TMPRSS6 siRNA have decreased hematocrit levels, decreased hemoglobin levels, increased red blood cell distribution width, increased number of reticulocytes, decreased number of mature red blood cells, increased unsaturated iron binding capacity, decreased ineffective erythropoiesis, decreased extradedullary hematopoiesis, and/or decreased HAMP1 expression levels.

A patient can be further monitored by assay of blood sugar (glucose) level or a fetoprotein level, by echocardiogram (e.g., to examine the heart's function), electrocardiogram (ECG) (e.g., to look at the electrical activity of the heart), imaging tests (such as CT scans, MRI and ultrasound), and liver function tests. Excess iron staining or iron concentrations can be measured on liver biopsy samples, or to confirm the extent of liver damage, e.g., the stage of liver disease.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted disease severity grading scale.

Patients can be administered a therapeutic amount of iRNA, such as 0.01 mg/kg, 0.05 mg/kg, 0.1 mg/kg, 0.5 mg/kg, 1.0 mg/kg, 1.5 mg/kg, 2.0 mg/kg, or 2.5 mg/kg dsRNA. The iRNA can be administered by intravenous infusion over a period of time, such as over a 5 minute, 10 minute, 15 minute, 20 minute, or 25 minute period. The administration is repeated, for example, on a regular basis, such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the iRNA can reduce TMPRSS6 levels, e.g., in a cell, tissue, blood, urine or other compartment of the patient by at least 10%, at least 15%, at least 20%, at least 25%, at least 30%, at least 40%, at least 50%, at least 60%, at least 70%, at least 80% or at least 90% or more.

Before administration of a full dose of the iRNA, patients can be administered a smaller dose, such as a 5% infusion reaction, and monitored for adverse effects, such as an allergic reaction or a worsening of symptoms. In another example, the patient can be monitored for unwanted immunostimulatory effects, such as increased cytokine (e.g., TNF-α or INF-α) levels.

Many disorders associated with elevated iron levels are hereditary. Therefore, a patient in need of a TMPRSS6 iRNA may be identified by taking a family history. A healthcare provider, such as a doctor, nurse, or family member, can take a family history before prescribing or administering a TMPRSS6 dsRNA. A DNA test may also be performed on the patient to identify a mutation in the TMPRSS6 gene, before a TMPRSS6 dsRNA is administered to the patient. For example, diagnosis of hereditary hemochromatosis can be confirmed by identifying the two HFE (Hemochromatosis) gene mutations C282Y and H63D, according to GenBank Accession No. CAB07442.1 (GI: 1890180, record dated Oct. 23, 2008).

Owing to the inhibitory effects on TMPRSS6 expression, a composition according to the invention or a pharmaceutical composition prepared therefrom can enhance the quality of life.

Methods for Modulating Expression of a TMPRSS6 Gene

In yet another aspect, the invention provides a method for modulating (e.g., inhibiting or activating) the expression of a TMPRSS6 gene in a mammal.

In one embodiment, the method includes administering a composition featured in the invention to the mammal such that expression of the target TMPRSS6 gene is decreased, such as for an extended duration, e.g., at least two, three, four days or more, e.g., one week, two weeks, three weeks, or four weeks or longer. The effect of the decreased target TMPRSS6 gene preferably results in a decrease in iron absorption and/or mobilization in the body. Decreased iron absorption or mobilization can be manifested by an observed decrease in serum ferritin levels, serum or liver iron levels, and/or serum transferrin saturation levels. In some embodiments, one or more of serum ferritin levels, serum or liver iron levels, or serum transferrin saturation levels are decreased by at least 5%, at least 10%, at least 15%, at least 20%, at least 25%, at least 30%, at least 40%, at least 50%, or at least 60%, or more, as compared to pretreatment levels. In some embodiments, serum ferritin levels are decreased by at least 10%, at least 15%, at least 20%, at least 25%, at least 30%, at least 40%, at least 50%, or at least 60%, or more, as compared to pretreatment levels.

In another embodiment, the method includes administering a composition as described herein to a mammal such that expression of the target TMPRSS6 gene is increased by e.g., at least 10% compared to an untreated animal. In some embodiments, the activation of TMPRSS6 occurs over an extended duration, e.g., at least two, three, four days or more, e.g., one week, two weeks, three weeks, four weeks, or more. Without wishing to be bound by theory, an iRNA can activate TMPRSS6 expression by stabilizing the TMPRSS6 mRNA transcript, interacting with a promoter in the genome, and/or inhibiting an inhibitor of TMPRSS6 expression.

The iRNAs useful for the methods and compositions featured in the invention specifically target RNAs (primary or processed) of the target TMPRSS6 gene. Compositions and methods for inhibiting the expression of these TMPRSS6 genes using iRNAs can be prepared and performed as described elsewhere herein.

In one embodiment, the method includes administering a composition containing an iRNA, where the iRNA includes a nucleotide sequence that is complementary to at least a part of an RNA transcript of the TMPRSS6 gene of the mammal to be treated. When the organism to be treated is a mammal such as a human, the composition may be administered by any means known in the art including, but not limited to oral, intraperitoneal, or parenteral routes, including intracranial (e.g., intraventricular, intraparenchymal and intrathecal), intravenous, intramuscular, subcutaneous, transdermal, airway (aerosol), nasal, rectal, and topical (including buccal and sublingual) administration. In certain embodiments, the compositions are administered by intravenous infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Interference RNA (iRNA) Synthesis

Source of Reagents

Where the source of a reagent is not specifically given herein, such reagent may be obtained from any supplier of reagents for molecular biology at a quality/purity standard for application in molecular biology.

Oligonucleotide Synthesis

Applicants have used several different methods to generate the iRNA molecules described herein. This Example describes one approach that has been used. The ordinarily skilled artisan can use any method known in the art to prepare iRNAs as described herein.

Oligonucleotides are synthesized on an AKTAoligopilot synthesizer. Commercially available controlled pore glass solid support (dT-CPG, 500 Å, Prime Synthesis) and RNA phosphoramidites with standard protecting groups, 5'-O-dimethoxytrityl N6-benzoyl-2'-t-butyldimethylsilyl-adenosine-3'-O-N,N'-diisopropyl-2-cyanoethylphosphoramidite, 5-O-dimethoxytrityl-N4-acetyl-2'-t-butyldimethylsilyl-cytidine-3'-O-N,N'-diisopropyl-2-cyanoethylphosphoramidite, 5'-O-dimethoxytrityl-N2-isobutryl-2'-t-butyldimethylsilyl-guanosine-3'-O-N,N'-diisopropyl-2-cyanoethylphosphoramidite, and 5'-O-dimethoxytrityl-2'-t-butyldimethylsilyl-uridine-3'-O-N,N'-diisopropyl-2-cyanoethylphosphoramidite (Pierce Nucleic Acids Technologies) were used for the oligonucleotide synthesis. The 2'-F phosphoramidites, 5'-O-dimethoxytrityl-N4-acetyl-2'-fluro-cytidine-3'-O-N,N'-diisopropyl-2-cyanoethyl-phosphoramidite and 5'-O-dimethoxytrityl-2'-fluro-uridine-3'-O-N,N'-diisopropyl-2-cyanoethyl-phosphoramidite are purchased from (Promega). All phosphoramidites are used at a concentration of 0.2M in acetonitrile ($CH_3CN$) except for guanosine which is used at 0.2M concentration in 10% THF/ANC (v/v). Coupling/recycling time of 16 minutes is used. The activator is 5-ethyl thiotetrazole (0.75M, American International Chemicals); for the PO-oxidation iodine/water/pyridine is used and for the PS-oxidation PADS (2%) in 2,6-lutidine/ACN (1:1 v/v) is used.

3'-ligand conjugated strands are synthesized using solid support containing the corresponding ligand. For example, the introduction of cholesterol unit in the sequence is performed from a hydroxyprolinol-cholesterol phosphoramidite. Cholesterol is tethered to trans-4-hydroxyprolinol via a 6-aminohexanoate linkage to obtain a hydroxyprolinol-cholesterol moiety. 5'-end Cy-3 and Cy-5.5 (fluorophore) labeled iRNAs are synthesized from the corresponding Quasar-570 (Cy-3) phosphoramidite are purchased from Biosearch Technologies. Conjugation of ligands to 5'-end and or internal position is achieved by using appropriately protected ligand-phosphoramidite building block. An extended 15 min coupling of 0.1 M solution of phosphoramidite in anhydrous $CH_3CN$ in the presence of 5-(ethylthio)-1H-tetrazole activator to a solid-support-bound oligonucleotide. Oxidation of the internucleotide phosphite to the phosphate is carried out using standard iodine-water as reported (1) or by treatment with tert-butyl hydroperoxide/acetonitrile/water (10:87:3) with 10 min oxidation wait time conjugated oligonucleotide. Phosphorothioate is introduced by the oxidation of phosphite to phosphorothioate by using a sulfur transfer reagent such as DDTT (purchased from AM Chemicals), PADS and or Beaucage reagent. The cholesterol phosphoramidite is synthesized in house and used at a concentration of 0.1 M in dichloromethane. Coupling time for the cholesterol phosphoramidite is 16 minutes.

Deprotection I (Nucleobase Deprotection)

After completion of synthesis, the support is transferred to a 100 mL glass bottle (VWR). The oligonucleotide is cleaved from the support with simultaneous deprotection of base and phosphate groups with 80 mL of a mixture of ethanolic ammonia [ammonia: ethanol (3:1)] for 6.5 h at 55° C. The bottle is cooled briefly on ice and then the ethanolic ammonia mixture is filtered into a new 250-mL bottle. The CPG is washed with 2×40 mL portions of ethanol/water (1:1 v/v). The volume of the mixture is then reduced to ~ 30 mL by roto-vap. The mixture is then frozen on dry ice and dried under vacuum on a speed vac.

Deprotection II (Removal of 2'-TBDMS Group)

The dried residue is resuspended in 26 mL of triethylamine, triethylamine trihydrofluoride (TEA•3HF) or pyridine-HF and DMSO (3:4:6) and heated at 60° C. for 90 minutes to remove the tert-butyldimethylsilyl (TBDMS) groups at the 2' position. The reaction is then quenched with 50 mL of 20 mM sodium acetate and the pH is adjusted to 6.5. Oligonucleotide is stored in a freezer until purification.

Analysis

The oligonucleotides are analyzed by high-performance liquid chromatography (HPLC) prior to purification and selection of buffer and column depends on nature of the sequence and or conjugated ligand.

HPLC Purification

The ligand-conjugated oligonucleotides are purified by reverse-phase preparative HPLC. The unconjugated oligonucleotides are purified by anion-exchange HPLC on a TSK gel column packed in house. The buffers are 20 mM sodium phosphate (pH 8.5) in 10% $CH_3CN$ (buffer A) and 20 mM sodium phosphate (pH 8.5) in 10% $CH_3CN$, 1M NaBr (buffer B). Fractions containing full-length oligonucleotides are pooled, desalted, and lyophilized. Approximately 0.15 OD of desalted oligonucleotides are diluted in water to 150 μL and then pipetted into special vials for CGE and LC/MS analysis. Compounds are then analyzed by LC-ESMS and CGE.

iRNA Preparation

For the general preparation of iRNA, equimolar amounts of sense and antisense strand are heated in 1×PBS at 95° C. for 5 min and slowly cooled to room temperature. Integrity of the duplex is confirmed by HPLC analysis.

Nucleic acid sequences are represented below using standard nomenclature, and specifically the abbreviations of Table 1.

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | adenosine |
| C | cytidine |
| G | guanosine |
| T | thymidine |
| U | uridine |
| N | any nucleotide (G, A, C, T or U) |
| a | 2'-O-methyladenosine |
| c | 2'-O-methylcytidine |
| g | 2'-O-methylguanosine |
| u | 2'-O-methyluridine |
| dT | 2'-deoxythymidine |
| s | phosphorothioate linkage |

Example 2

TMPRSS6 siRNA Design

Transcripts siRNAs targeting TMPRSS6 were designed and synthesized. The design used human transcript NM_153609.2 (SEQ ID NO:1, FIG. 1) from the NCBI Refseq collection.

siRNA duplexes were designed with 100% identity to the TMPRSS6 gene.

A total of 655 sense and 655 antisense human TMPRSS6 derived siRNA oligos were designed. The oligos are presented in Table 2. Additional sense and antisense human TMPRSS6 derived siRNA oligos are presented in Table 3. Sense and antisense human TMPRSS6 derived siRNA oligos with modifications are presented in Table 4.

TABLE 2

Sense and antisense strand sequences of human TMPRSS6 dsRNAs

| position of 5' base on transcript (NM_153609.2, (SEQ ID NO: 1) | Sense Sequence (5' to 3') | SEQ ID NO: | Antisense Sequence (5' to 3') | SEQ ID NO: |
|---|---|---|---|---|
| 36 | CUCUGGUGCGAGCUGACCU | 9 | AGGUCAGCUCGCACCAGAG | 10 |
| 46 | AGCUGACCUGAGAUGCACU | 11 | AGUGCAUCUCAGGUCAGCU | 12 |

TABLE 2-continued

Sense and antisense strand sequences of human TMPRSS6 dsRNAs

| position of 5' base on transcript (NM_153609.2, (SEQ ID NO: 1) | Sense Sequence (5' to 3') | SEQ ID NO: | Antisense Sequence (5' to 3') | SEQ ID NO: |
|---|---|---|---|---|
| 72 | UCUGUGAGCUGUCUCGGCA | 13 | UGCCGAGACAGCUCACAGA | 14 |
| 78 | AGCUGUCUCGGCACCCACU | 15 | AGUGGGUGCCGAGACAGCU | 16 |
| 79 | GCUGUCUCGGCACCCACUU | 17 | AAGUGGGUGCCGAGACAGC | 18 |
| 100 | AGUCACUGCCGCCUGAUGU | 19 | ACAUCAGGCGGCAGUGACU | 20 |
| 104 | ACUGCCGCCUGAUGUUGUU | 21 | AACAACAUCAGGCGGCAGU | 22 |
| 105 | CUGCCGCCUGAUGUUGUUA | 23 | UAACAACAUCAGGCGGCAG | 24 |
| 107 | GCCGCCUGAUGUUGUUACU | 25 | AGUAACAACAUCAGGCGGC | 26 |
| 110 | GCCUGAUGUUGUUACUCUU | 27 | AAGAGUAACAACAUCAGGC | 28 |
| 124 | CUCUUCCACUCCAAAAGGA | 29 | UCCUUUUGGAGUGGAAGAG | 30 |
| 131 | ACUCCAAAAGGAUGCCCGU | 31 | ACGGGCAUCCUUUUGGAGU | 32 |
| 233 | GUGAGGACUCCAAGAGAAA | 33 | UUUCUCUUGGAGUCCUCAC | 34 |
| 311 | CUUCGGCGGGGUGCUACU | 35 | AGUAGCACCCCCGCCGAAG | 36 |
| 313 | UCGGCGGGGUGCUACUCU | 37 | AGAGUAGCACCCCCGCCGA | 38 |
| 316 | GCGGGGUGCUACUCUGGU | 39 | ACCAGAGUAGCACCCCCGC | 40 |
| 318 | GGGGGUGCUACUCUGGUAU | 41 | AUACCAGAGUAGCACCCCC | 42 |
| 319 | GGGGUGCUACUCUGGUAUU | 43 | AAUACCAGAGUAGCACCCC | 44 |
| 329 | UCUGGUAUUUCCUAGGGUA | 45 | UACCCUAGGAAAUACCAGA | 46 |
| 331 | UGGUAUUUCCUAGGGUACA | 47 | UGUACCCUAGGAAAUACCA | 48 |
| 332 | GGUAUUUCCUAGGGUACAA | 49 | UUGUACCCUAGGAAAUACC | 50 |
| 363 | GGUCAGCCAGGUGUACUCA | 51 | UGAGUACACCUGGCUGACC | 52 |
| 367 | AGCCAGGUGUACUCAGGCA | 53 | UGCCUGAGUACACCUGGCU | 54 |
| 375 | GUACUCAGGCAGUCUGCGU | 55 | ACGCAGACUGCCUGAGUAC | 56 |
| 377 | ACUCAGGCAGUCUGCGUGU | 57 | ACACGCAGACUGCCUGAGU | 58 |
| 380 | CAGGCAGUCUGCGUGUACU | 59 | AGUACACGCAGACUGCCUG | 60 |
| 382 | GGCAGUCUGCGUGUACUCA | 61 | UGAGUACACGCAGACUGCC | 62 |
| 383 | GCAGUCUGCGUGUACUCAA | 63 | UUGAGUACACGCAGACUGC | 64 |
| 384 | CAGUCUGCGUGUACUCAAU | 65 | AUUGAGUACACGCAGACUG | 66 |
| 389 | UGCGUGUACUCAAUCGCCA | 67 | UGGCGAUUGAGUACACGCA | 68 |
| 391 | CGUGUACUCAAUCGCCACU | 69 | AGUGGCGAUUGAGUACACG | 70 |
| 392 | GUGUACUCAAUCGCCACUU | 71 | AAGUGGCGAUUGAGUACAC | 72 |
| 394 | GUACUCAAUCGCCACUUCU | 73 | AGAAGUGGCGAUUGAGUAC | 74 |
| 406 | CACUUCUCCCAGGAUCUUA | 75 | UAAGAUCCUGGGAGAAGUG | 76 |
| 418 | GAUCUUACCCGCCGGGAAU | 77 | AUUCCCGGCGGGUAAGAUC | 78 |
| 420 | UCUUACCCGCCGGGAAUCU | 79 | AGAUUCCCGGCGGGUAAGA | 80 |
| 421 | CUUACCCGCCGGGAAUCUA | 81 | UAGAUUCCCGGCGGGUAAG | 82 |
| 423 | UACCCGCCGGGAAUCUAGU | 83 | ACUAGAUUCCCGGCGGGUA | 84 |

TABLE 2-continued

Sense and antisense strand sequences of human TMPRSS6 dsRNAs

| position of 5' base on transcript (NM_153609.2, (SEQ ID NO: 1) | Sense Sequence (5' to 3') | SEQ ID NO: | Antisense Sequence (5' to 3') | SEQ ID NO: |
|---|---|---|---|---|
| 427 | CGCCGGGAAUCUAGUGCCU | 85 | AGGCACUAGAUUCCCGGCG | 86 |
| 428 | GCCGGGAAUCUAGUGCCUU | 87 | AAGGCACUAGAUUCCCGGC | 88 |
| 446 | UCCGCAGUGAAACCGCCAA | 89 | UUGGCGGUUUCACUGCGGA | 90 |
| 447 | CCGCAGUGAAACCGCCAAA | 91 | UUUGGCGGUUUCACUGCGG | 92 |
| 502 | CGCCUGGGAACUUACUACA | 93 | UGUAGUAAGUUCCCAGGCG | 94 |
| 503 | GCCUGGGAACUUACUACAA | 95 | UUGUAGUAAGUUCCCAGGC | 96 |
| 505 | CUGGGAACUUACUACAACU | 97 | AGUUGUAGUAAGUUCCCAG | 98 |
| 517 | UACAACUCCAGCUCCGUCU | 99 | AGACGGAGCUGGAGUUGUA | 100 |
| 518 | ACAACUCCAGCUCCGUCUA | 101 | UAGACGGAGCUGGAGUUGU | 102 |
| 520 | AACUCCAGCUCCGUCUAUU | 103 | AAUAGACGGAGCUGGAGUU | 104 |
| 541 | UUUGGGGAGGGACCCCUCA | 105 | UGAGGGGUCCCUCCCCAAA | 106 |
| 550 | GGACCCCUCACCUGCUUCU | 107 | AGAAGCAGGUGAGGGGUCC | 108 |
| 563 | GCUUCUUCUGGUUCAUUCU | 109 | AGAAUGAACCAGAAGAAGC | 110 |
| 566 | UCUUCUGGUUCAUUCUCCA | 111 | UGGAGAAUGAACCAGAAGA | 112 |
| 593 | AGCACCGCCGGCUGAUGCU | 113 | AGCAUCAGCCGGCGGUGCU | 114 |
| 680 | UCCCUACAGGGCCGAGUA | 115 | UACUCGGCCCUGUAGGGGA | 116 |
| 683 | CCUACAGGGCCGAGUACGA | 117 | UCGUACUCGGCCCUGUAGG | 118 |
| 686 | ACAGGGCCGAGUACGAAGU | 119 | ACUUCGUACUCGGCCCUGU | 120 |
| 689 | GGGCCGAGUACGAAGUGGA | 121 | UCCACUUCGUACUCGGCCC | 122 |
| 710 | CCGAGGGCCUAGUGAUCCU | 123 | AGGAUCACUAGGCCCUCGG | 124 |
| 735 | CAGUGUGAAAGACAUAGCU | 125 | AGCUAUGUCUUUCACACUG | 126 |
| 759 | GAAUUCCACGCUGGGUUGU | 127 | ACAACCCAGCGUGGAAUUC | 128 |
| 760 | AAUUCCACGCUGGGUUGUU | 129 | AACAACCCAGCGUGGAAUU | 130 |
| 766 | ACGCUGGGUUGUUACCGCU | 131 | AGCGGUAACAACCCAGCGU | 132 |
| 767 | CGCUGGGUUGUUACCGCUA | 133 | UAGCGGUAACAACCCAGCG | 134 |
| 769 | CUGGGUUGUUACCGCUACA | 135 | UGUAGCGGUAACAACCCAG | 136 |
| 772 | GGUUGUUACCGCUACAGCU | 137 | AGCUGUAGCGGUAACAACC | 138 |
| 776 | GUUACCGCUACAGCUACGU | 139 | ACGUAGCUGUAGCGGUAAC | 140 |
| 872 | AGGACCUCAUGCUCAAACU | 141 | AGUUUGAGCAUGAGGUCCU | 142 |
| 878 | UCAUGCUCAAACUCCGGCU | 143 | AGCCGGAGUUUGAGCAUGA | 144 |
| 970 | AUCACCUCGGUGUACGGCU | 145 | AGCCGUACACCGAGGUGAU | 146 |
| 973 | ACCUCGGUGUACGGCUGCA | 147 | UGCAGCCGUACACCGAGGU | 148 |
| 1033 | AUCAUGGCGGUCGUCUGGA | 149 | UCCAGACGACCGCCAUGAU | 150 |
| 1034 | UCAUGGCGGUCGUCUGGAA | 151 | UUCCAGACGACCGCCAUGA | 152 |
| 1067 | GCUACUACGACCCCUUCGU | 153 | ACGAAGGGGUCGUAGUAGC | 154 |
| 1091 | CCGUGCAGCCGGUGGUCUU | 155 | AAGACCACCGGCUGCACGG | 156 |

TABLE 2-continued

Sense and antisense strand sequences of human TMPRSS6 dsRNAs

| position of 5' base on transcript (NM_153609.2, (SEQ ID NO: 1) | Sense Sequence (5' to 3') | SEQ ID NO: | Antisense Sequence (5' to 3') | SEQ ID NO: |
|---|---|---|---|---|
| 1106 | UCUUCCAGGCCUGUGAAGU | 157 | ACUUCACAGGCCUGGAAGA | 158 |
| 1114 | GCCUGUGAAGUGAACCUGA | 159 | UCAGGUUCACUUCACAGGC | 160 |
| 1118 | GUGAAGUGAACCUGACGCU | 161 | AGCGUCAGGUUCACUUCAC | 162 |
| 1133 | CGCUGGACAACAGGCUCGA | 163 | UCGAGCCUGUUGUCCAGCG | 164 |
| 1135 | CUGGACAACAGGCUCGACU | 165 | AGUCGAGCCUGUUGUCCAG | 166 |
| 1162 | GUCCUCAGCACCCCGUACU | 167 | AGUACGGGGUGCUGAGGAC | 168 |
| 1163 | UCCUCAGCACCCCGUACUU | 169 | AAGUACGGGGUGCUGAGGA | 170 |
| 1168 | AGCACCCCGUACUUCCCCA | 171 | UGGGGAAGUACGGGGUGCU | 172 |
| 1185 | CAGCUACUACUCGCCCCAA | 173 | UUGGGGCGAGUAGUAGCUG | 174 |
| 1186 | AGCUACUACUCGCCCCAAA | 175 | UUUGGGGCGAGUAGUAGCU | 176 |
| 1190 | ACUACUCGCCCCAAACCCA | 177 | UGGGUUUGGGGCGAGUAGU | 178 |
| 1195 | UCGCCCCAAACCCACUGCU | 179 | AGCAGUGGGUUUGGGGCGA | 180 |
| 1211 | GCUCCUGGCACCUCACGGU | 181 | ACCGUGAGGUGCCAGGAGC | 182 |
| 1231 | CCCUCUCUGGACUACGGCU | 183 | AGCCGUAGUCCAGAGAGGG | 184 |
| 1244 | ACGGCUUGGCCCUCUGGUU | 185 | AACCAGAGGGCCAAGCCGU | 186 |
| 1245 | CGGCTTGGCCCTCTGG777 | 187 | AAACCAGAGGGCCAAGCCG | 188 |
| 1247 | GCUUGGCCCUCUGGUUUGA | 189 | UCAAACCAGAGGGCCAAGC | 190 |
| 1254 | CCUCUGGUUUGAUGCCUAU | 191 | AUAGGCAUCAAACCAGAGG | 192 |
| 1285 | CAGAAGUAUGAUUUGCCGU | 193 | ACGGCAAAUCAUACUUCUG | 194 |
| 1288 | AAGUAUGAUUUGCCGUGCA | 195 | UGCACGGCAAAUCAUACUU | 196 |
| 1292 | AUGAUUUGCCGUGCACCCA | 197 | UGGGUGCACGGCAAAUCAU | 198 |
| 1306 | ACCCAGGGCCAGUGGACGA | 199 | UCGUCCACUGGCCCUGGGU | 200 |
| 1310 | AGGGCCAGUGGACGAUCCA | 201 | UGGAUCGUCCACUGGCCCU | 202 |
| 1312 | GGCCAGUGGACGAUCCAGA | 203 | UCUGGAUCGUCCACUGGCC | 204 |
| 1313 | GCCAGUGGACGAUCCAGAA | 205 | UUCUGGAUCGUCCACUGGC | 206 |
| 1360 | CAGCCCUACGCCGAGAGGA | 207 | UCCUCUCGGCGUAGGGCUG | 208 |
| 1443 | CGGUGUGCGGGUGCACUAU | 209 | AUAGUGCACCCGCACACCG | 210 |
| 1447 | GUGCGGGUGCACUAUGGCU | 211 | AGCCAUAGUGCACCCGCAC | 212 |
| 1448 | UGCGGGUGCACUAUGGCUU | 213 | AAGCCAUAGUGCACCCGCA | 214 |
| 1451 | GGGUGCACUAUGGCUUGUA | 215 | UACAAGCCAUAGUGCACCC | 216 |
| 1454 | UGCACUAUGGCUUGUACAA | 217 | UUGUACAAGCCAUAGUGCA | 218 |
| 1486 | UGCCCUGGAGAGUUCCUCU | 219 | AGAGGAACUCUCCAGGGCA | 220 |
| 1565 | UGGAUGAGAGAAACUGCGU | 221 | ACGCAGUUUCUCUCAUCCA | 222 |
| 1611 | GGACAGCACAUGCAUCUCA | 223 | UGAGAUGCAUGUGCUGUCC | 224 |
| 1613 | ACAGCACAUGCAUCUCACU | 225 | AGUGAGAUGCAUGUGCUGU | 226 |
| 1634 | CCAAGGUCUGUGAUGGGCA | 227 | UGCCCAUCACAGACCUUGG | 228 |

TABLE 2-continued

Sense and antisense strand sequences of human TMPRSS6 dsRNAs

| position of 5' base on transcript (NM_153609.2, (SEQ ID NO: 1) | Sense Sequence (5' to 3') | SEQ ID NO: | Antisense Sequence (5' to 3') | SEQ ID NO: |
|---|---|---|---|---|
| 1646 | AUGGGCAGCCUGAUUGUCU | 229 | AGACAAUCAGGCUGCCCAU | 230 |
| 1649 | GGCAGCCUGAUUGUCUCAA | 231 | UUGAGACAAUCAGGCUGCC | 232 |
| 1654 | CCUGAUUGUCUCAACGGCA | 233 | UGCCGUUGAGACAAUCAGG | 234 |
| 1662 | UCUCAACGGCAGCGACGAA | 235 | UUCGUCGCUGCCGUUGAGA | 236 |
| 1687 | UGCCAGGAAGGGGUGCCAU | 237 | AUGGCACCCCUUCCUGGCA | 238 |
| 1696 | GGGGUGCCAUGUGGGACAU | 239 | AUGUCCCACAUGGCACCCC | 240 |
| 1699 | GUGCCAUGUGGGACAUUCA | 241 | UGAAUGUCCCACAUGGCAC | 242 |
| 1703 | CAUGUGGGACAUUCACCUU | 243 | AAGGUGAAUGUCCCACAUG | 244 |
| 1723 | CAGUGUGAGGACCGGAGCU | 245 | AGCUCCGGUCCUCACACUG | 246 |
| 1745 | UGAAGAAGCCCAACCCGCA | 247 | UGCGGGUUGGGCUUCUUCA | 248 |
| 1749 | GAAGCCCAACCCGCAGUGU | 249 | ACACUGCGGGUUGGGCUUC | 250 |
| 1830 | CCCCUCCAGCCGCAUUGUU | 251 | AACAAUGCGGCUGGAGGGG | 252 |
| 1897 | CAGGUUCGGGGUCGACACA | 253 | UGUGUCGACCCCGAACCUG | 254 |
| 1898 | AGGUUCGGGUCGACACAU | 255 | AUGUGUCGACCCCGAACCU | 256 |
| 1900 | GUUCGGGGUCGACACAUCU | 257 | AGAUGUGUCGACCCCGAAC | 258 |
| 1935 | CGCUGACCGCUGGGUGAUA | 259 | UAUCACCCAGCGGUCAGCG | 260 |
| 1936 | GCUGACCGCUGGGUGAUAA | 261 | UUAUCACCCAGCGGUCAGC | 262 |
| 1938 | UGACCGCUGGGUGAUAACA | 263 | UGUUAUCACCCAGCGGUCA | 264 |
| 1941 | CCGCUGGGUGAUAACAGCU | 265 | AGCUGUUAUCACCCAGCGG | 266 |
| 1997 | UGCUGUGGACCGUGUUCCU | 267 | AGGAACACGGUCCACAGCA | 268 |
| 2023 | GUGUGGCAGAACUCGCGCU | 269 | AGCGCGAGUUCUGCCACAC | 270 |
| 2078 | UCCUGCACCCGUACCACGA | 271 | UCGUGGUACGGGUGCAGGA | 272 |
| 2079 | CCUGCACCCGUACCACGAA | 273 | UUCGUGGUACGGGUGCAGG | 274 |
| 2081 | UGCACCCGUACCACGAAGA | 275 | UCUUCGUGGUACGGGUGCA | 276 |
| 2186 | CGCGCUCCCACUUCUUCGA | 277 | UCGAAGAAGUGGGAGCGCG | 278 |
| 2209 | GGCCUGCACUGCUGGAUUA | 279 | UAAUCCAGCAGUGCAGGCC | 280 |
| 2215 | CACUGCUGGAUUACGGGCU | 281 | AGCCCGUAAUCCAGCAGUG | 282 |
| 2283 | GGAUGUGCAGUUGAUCCCA | 283 | UGGGAUCAACUGCACAUCC | 284 |
| 2311 | UGCAGCGAGGUCUAUCGCU | 285 | AGCGAUAGACCUCGCUGCA | 286 |
| 2312 | GCAGCGAGGUCUAUCGCUA | 287 | UAGCGAUAGACCUCGCUGC | 288 |
| 2315 | GCGAGGUCUAUCGCUACCA | 289 | UGGUAGCGAUAGACCUCGC | 290 |
| 2320 | GUCUAUCGCUACCAGGUGA | 291 | UCACCUGGUAGCGAUAGAC | 292 |
| 2333 | AGGUGACGCCACGCAUGCU | 293 | AGCAUGCGUGGCGUCACCU | 294 |
| 2335 | GUGACGCCACGCAUGCUGU | 295 | ACAGCAUGCGUGGCGUCAC | 296 |
| 2337 | GACGCCACGCAUGCUGUGU | 297 | ACACAGCAUGCGUGGCGUC | 298 |
| 2470 | GGCUGUGGCCGGCCUAACU | 299 | AGUUAGGCCGGCCACAGCC | 300 |

TABLE 2-continued

Sense and antisense strand sequences of human TMPRSS6 dsRNAs

| position of 5' base on transcript (NM_153609.2, (SEQ ID NO: 1) | Sense Sequence (5' to 3') | SEQ ID NO: | Antisense Sequence (5' to 3') | SEQ ID NO: |
|---|---|---|---|---|
| 2471 | GCUGUGGCCGGCCUAACUA | 301 | UAGUUAGGCCGGCCACAGC | 302 |
| 2473 | UGUGGCCGGCCUAACUACU | 303 | AGUAGUUAGGCCGGCCACA | 304 |
| 2480 | GGCCUAACUACUUCGGCGU | 305 | ACGCCGAAGUAGUUAGGCC | 306 |
| 2482 | CCUAACUACUUCGGCGUCU | 307 | AGACGCCGAAGUAGUUAGG | 308 |
| 2483 | CUAACUACUUCGGCGUCUA | 309 | UAGACGCCGAAGUAGUUAG | 310 |
| 2485 | AACUACUUCGGCGUCUACA | 311 | UGUAGACGCCGAAGUAGUU | 312 |
| 2501 | ACACCCGCAUCACAGGUGU | 313 | ACACCUGUGAUGCGGGUGU | 314 |
| 2506 | CGCAUCACAGGUGUGAUCA | 315 | UGAUCACACCUGUGAUGCG | 316 |
| 2525 | GCUGGAUCCAGCAAGUGGU | 317 | ACCACUUGCUGGAUCCAGC | 318 |
| 2551 | GGAACUGCCCCCCUGCAAA | 319 | UUUGCAGGGGGGCAGUUCC | 320 |
| 2671 | AGGAGGUGGCAUCUUGUCU | 321 | AGACAAGAUGCCACCUCCU | 322 |
| 2674 | AGGUGGCAUCUUGUCUCGU | 323 | ACGAGACAAGAUGCCACCU | 324 |
| 2678 | GGCAUCUUGUCUCGUCCCU | 325 | AGGGACGAGACAAGAUGCC | 326 |
| 2680 | CAUCUUGUCUCGUCCCUGA | 327 | UCAGGGACGAGACAAGAUG | 328 |
| 2681 | AUCUUGUCUCGUCCCUGAU | 329 | AUCAGGGACGAGACAAGAU | 330 |
| 2739 | CAGCUGGGGGUCAAGACGU | 331 | ACGUCUUGACCCCCAGCUG | 332 |
| 2744 | GGGGGUCAAGACGUCCCCU | 333 | AGGGGACGUCUUGACCCCC | 334 |
| 2746 | GGGUCAAGACGUCCCCUGA | 335 | UCAGGGGACGUCUUGACCC | 336 |
| 2825 | CCACUGCUGCCUAAUGCAA | 337 | UUGCAUUAGGCAGCAGUGG | 338 |
| 2829 | UGCUGCCUAAUGCAAGGCA | 339 | UGCCUUGCAUUAGGCAGCA | 340 |
| 2835 | CUAAUGCAAGGCAGUGGCU | 341 | AGCCACUGCCUUGCAUUAG | 342 |
| 2857 | CAGCAAGAAUGCUGGUUCU | 343 | AGAACCAGCAUUCUUGCUG | 344 |
| 2894 | GAGGUGCGCCCCACUCUGU | 345 | ACAGAGUGGGGCGCACCUC | 346 |
| 2958 | CUUCGGAAGCCCCUGGUCU | 347 | AGACCAGGGGCUUCCGAAG | 348 |
| 2960 | UCGGAAGCCCCUGGUCUAA | 349 | UUAGACCAGGGGCUUCCGA | 350 |
| 2962 | GGAAGCCCCUGGUCUAACU | 351 | AGUUAGACCAGGGGCUUCC | 352 |
| 2963 | GAAGCCCCUGGUCUAACUU | 353 | AAGUUAGACCAGGGGCUUC | 354 |
| 2968 | CCCUGGUCUAACUUGGGAU | 355 | AUCCCAAGUUAGACCAGGG | 356 |
| 2970 | CUGGUCUAACUUGGGAUCU | 357 | AGAUCCCAAGUUAGACCAG | 358 |
| 2975 | CUAACUUGGGAUCUGGGAA | 359 | UUCCCAGAUCCCAAGUUAG | 360 |
| 3006 | CCAUCGGAGGGACCCUCA | 361 | UGAGGGUCCCUCCGAUGG | 362 |
| 3045 | UGGGCCUGCUGCCACUGUA | 363 | UACAGUGGCAGCAGGCCCA | 364 |
| 3046 | GGGCCUGCUGCCACUGUAA | 365 | UUACAGUGGCAGCAGGCCC | 366 |
| 3052 | GCUGCCACUGUAAGCCAAA | 367 | UUUGGCUUACAGUGGCAGC | 368 |
| 3056 | CCACUGUAAGCCAAAAGGU | 369 | ACCUUUUGGCUUACAGUGG | 370 |
| 3071 | AGGUGGGGAAGUCCUGACU | 371 | AGUCAGGACUUCCCCACCU | 372 |

TABLE 2-continued

Sense and antisense strand sequences of human TMPRSS6 dsRNAs

| position of 5' base on transcript (NM_153609.2, (SEQ ID NO: 1) | Sense Sequence (5' to 3') | SEQ ID NO: | Antisense Sequence (5' to 3') | SEQ ID NO: |
|---|---|---|---|---|
| 3174 | GAAUAAAGCUGCCUGAUCA | 373 | UGAUCAGGCAGCUUUAUUC | 374 |
| 3175 | AAUAAAGCUGCCUGAUCAA | 375 | UUGAUCAGGCAGCUUUAUU | 376 |
| 3180 | AGCUGCCUGAUCAAAAAAA | 377 | UUUUUUUGAUCAGGCAGCU | 378 |

TABLE 3

Unmodified sense and antisense strand sequences of human TMPRSS6 dsRNAs

| Duplex ID | SEQ ID NO.: (sense) | Sense Trans seq | Position in NM_153609.2 | Position in NM_153609.2 | SEQ ID NO.: (antisense) | Antisense Trans seq |
|---|---|---|---|---|---|---|
| AD-46230.1 | 43 | GGGGUGCUACUCUGGUAUU | 319 | 319-337 | 44 | AAUACCAGAGUAGCACCCC |
| AD-46231.1 | 111 | UCUUCUGGUUCAUUCUCCA | 566 | 566-584 | 112 | UGGAGAAUGAACCAGAAGA |
| AD-46232.1 | 131 | ACGCUGGGUUGUUACCGCU | 766 | 766-784 | 132 | AGCGGUAACAACCCAGCGU |
| AD-46233.1 | 193 | CAGAAGUAUGAUUUGCCGU | 1285 | 1285-1303 | 194 | ACGGCAAAUCAUACUUCUG |
| AD-46234.1 | 259 | CGCUGACCGCUGGGUGAUA | 1935 | 1935-1953 | 260 | UAUCACCCAGCGGUCAGCG |
| AD-46235.1 | 45 | UCUGGUAUUUCCUAGGGUA | 329 | 329-347 | 46 | UACCCUAGGAAAUACCAGA |
| AD-46236.1 | 117 | CCUACAGGGCCGAGUACGA | 683 | 683-701 | 118 | UCGUACUCGGCCCUGUAGG |
| AD-46237.1 | 133 | CGCUGGGUUGUUACCGCUA | 767 | 767-785 | 134 | UAGCGGUAACAACCCAGCG |
| AD-46238.1 | 203 | GGCCAGUGGACGAUCCAGA | 1312 | 1312-1330 | 204 | UCUGGAUCGUCCACUGGCC |
| AD-46239.1 | 263 | UGACCGCUGGGUGAUAACA | 1938 | 1938-1956 | 264 | UGUUAUCACCCAGCGGUCA |
| AD-46240.1 | 51 | GGUCAGCCAGGUGUACUCA | 363 | 363-381 | 52 | UGAGUACACCUGGCUGACC |
| AD-46241.1 | 379 | CUACAGGGCCGAGUACGAA | 684 | 684-702 | 380 | UUCGUACUCGGCCCUGUAG |
| AD-46242.1 | 135 | CUGGGUUGUUACCGCUACA | 769 | 769-787 | 136 | UGUAGCGGUAACAACCCAG |
| AD-46243.1 | 217 | UGCACUAUGGCUUGUACAA | 1454 | 1454-1472 | 218 | UUGUACAAGCCAUAGUGCA |
| AD-46244.1 | 604 | CCUGGAGAGGUGUCCUUCA | 2044 | 2044-2062 | 605 | UGAAGGACACCUCUCCAGG |
| AD-46244.2 | 604 | CCUGGAGAGGUGUCCUUCA | 2044 | 2044-2062 | 605 | UGAAGGACACCUCUCCAGG |
| AD-46245.1 | 53 | AGCCAGGUGUACUCAGGCA | 367 | 367-385 | 54 | UGCCUGAGUACACCUGGCU |
| AD-46246.1 | 119 | ACAGGGCCGAGUACGAAGU | 686 | 686-704 | 120 | ACUUCGUACUCGGCCCUGU |
| AD-46247.1 | 137 | GGUUGUUACCGCUACAGCU | 772 | 772-790 | 138 | AGCUGUAGCGGUAACAACC |
| AD-46248.1 | 381 | UGUGAUGGGGUCAAGGACU | 1534 | 1534-1552 | 382 | AGUCCUUGACCCCAUCACA |
| AD-46249.1 | 383 | CUGGAGAGGUGUCCUUCAA | 2045 | 2045-2063 | 384 | UUGAAGGACACCUCUCCAG |
| AD-46250.1 | 89 | UCCGCAGUGAAACCGCCAA | 446 | 446-464 | 90 | UUGGCGGUUUCACUGCGGA |
| AD-46251.1 | 121 | GGGCCGAGUACGAAGUGGA | 689 | 689-707 | 122 | UCCACUUCGUACUCGGCCC |
| AD-46252.1 | 385 | GGACCGACUGGCCAUGUAU | 921 | 921-939 | 386 | AUACAUGGCCAGUCGGUCC |
| AD-46253.1 | 606 | CAACGGCCUGGAUGAGAGA | 1557 | 1557-1575 | 607 | UCUCUCAUCCAGGCCGUUG |
| AD-46253.2 | 606 | CAACGGCCUGGAUGAGAGA | 1557 | 1557-1575 | 607 | UCUCUCAUCCAGGCCGUUG |
| AD-46254.1 | 387 | AGUUGAUCCCACAGGACCU | 2291 | 2291-2309 | 388 | AGGUCCUGUGGGAUCAACU |
| AD-46255.1 | 91 | CCGCAGUGAAACCGCCAAA | 447 | 447-465 | 92 | UUUGGCGGUUUCACUGCGG |

TABLE 3-continued

Unmodified sense and antisense strand sequences of human TMPRSS6 dsRNAs

| Duplex ID | SEQ ID NO.: (sense) | Sense Trans seq | Position in NM_153609.2 | Position in NM_153609.2 | SEQ ID NO.: (antisense) | Antisense Trans seq |
|---|---|---|---|---|---|---|
| AD-46256.1 | 123 | CCGAGGGCCUAGUGAUCCU | 710 | 710-728 | 124 | AGGAUCACUAGGCCCUCGG |
| AD-46257.1 | 169 | UCCUCAGCACCCCGUACUU | 1163 | 1163-1181 | 170 | AAGUACGGGGUGCUGAGGA |
| AD-46258.1 | 253 | CAGGUUCGGGGUCGACACA | 1897 | 1897-1915 | 254 | UGUGUCGACCCCGAACCUG |
| AD-46259.1 | 293 | AGGUGACGCCACGCAUGCU | 2333 | 2333-2351 | 294 | AGCAUGCGUGGCGUCACCU |
| AD-46260.1 | 389 | AAACCGCCAAAGCCCAGAA | 455 | 455-473 | 390 | UUCUGGGCUUUGGCGGUUU |
| AD-46261.1 | 125 | CAGUGUGAAAGACAUAGCU | 735 | 735-753 | 126 | AGCUAUGUCUUUCACACUG |
| AD-46262.1 | 183 | CCCUCUCUGGACUACGGCU | 1231 | 1231-1249 | 184 | AGCCGUAGUCCAGAGAGGG |
| AD-46263.1 | 257 | GUUCGGGGUCGACACAUCU | 1900 | 1900-1918 | 258 | AGAUGUGUCGACCCCGAAC |
| AD-46264.1 | 391 | UGUGUGCCGGCUACCGCAA | 2351 | 2351-2369 | 392 | UUGCGGUAGCCGGCACACA |
| AD-46265.1 | 109 | GCUUCUUCUGGUUCAUUCU | 563 | 563-581 | 110 | AGAAUGAACCAGAAGAAGC |
| AD-46266.1 | 393 | AUUCCACGCUGGGUUGUUA | 761 | 761-779 | 394 | UAACAACCCAGCGUGGAAU |
| AD-46267.1 | 185 | ACGGCUUGGCCCUCUGGUU | 1244 | 1244-1262 | 186 | AACCAGAGGGCCAAGCCGU |
| AD-46268.1 | 395 | UCGCUGACCGCUGGGUGAU | 1934 | 1934-1952 | 396 | AUCACCCAGCGGUCAGCGA |
| AD-46269.1 | 608 | AGUGGUGACCUGAGGAACU | 2538 | 2538-2556 | 609 | AGUUCCUCAGGUCACCACU |
| AD-46269.2 | 608 | AGUGGUGACCUGAGGAACU | 2538 | 2538-2556 | 609 | AGUUCCUCAGGUCACCACU |
| AD-46270.1 | 397 | CAAGCAGGGGACAAGUAU | 2612 | 2612-2630 | 398 | AUACUUGUCCCCUGCUUG |
| AD-46271.1 | 399 | UGAUGUCUGCUCCAGUGAU | 2696 | 2696-2714 | 400 | AUCACUGGAGCAGACAUCA |
| AD-46272.1 | 359 | CUAACUUGGGAUCUGGGAA | 2975 | 2975-2993 | 360 | UUCCCAGAUCCCAAGUUAG |
| AD-46273.1 | 47 | UGGUAUUUCCUAGGGUACA | 331 | 331-349 | 48 | UGUACCCUAGGAAAUACCA |
| AD-46273.2 | 47 | UGGUAUUUCCUAGGGUACA | 331 | 331-349 | 48 | UGUACCCUAGGAAAUACCA |
| AD-46273.3 | 47 | UGGUAUUUCCUAGGGUACA | 331 | 331-349 | 48 | UGUACCCUAGGAAAUACCA |
| AD-46274.1 | 401 | GAGGUGUCCUUCAAGGUGA | 2050 | 2050-2068 | 402 | UCACCUUGAAGGACACCUC |
| AD-46276.1 | 403 | AAGCAGGGGACAAGUAUU | 2613 | 2613-2631 | 404 | AAUACUUGUCCCCUGCUU |
| AD-46277.1 | 331 | CAGCUGGGGGUCAAGACGU | 2739 | 2739-2757 | 332 | ACGUCUUGACCCCCAGCUG |
| AD-46278.1 | 405 | CUUGGGAUCUGGGAAUGGA | 2979 | 2979-2997 | 406 | UCCAUUCCCAGAUCCCAAG |
| AD-46279.1 | 407 | GGUAUUUCCUAGGGUACAA | 332 | 332-350 | 408 | UUGUACCCUAGGAAAUACC |
| AD-46280.1 | 409 | GGCUACCGCAAGGGCAAGA | 2359 | 2359-2377 | 410 | UCUUGCCCUUGCGGUAGCC |
| AD-46282.1 | 411 | GCAGGGGACAAGUAUUCU | 2615 | 2615-2633 | 412 | AGAAUACUUGUCCCCUGC |
| AD-46283.1 | 413 | GCUCAGCAGCAAGAAUGCU | 2851 | 2851-2869 | 414 | AGCAUUCUUGCUGCUGAGC |
| AD-46284.1 | 415 | UUGGGAUCUGGGAAUGGAA | 2980 | 2980-2998 | 416 | UUCCAUUCCCAGAUCCCAA |
| AD-46285.1 | 417 | CCAAAGCCCAGAAGAUGCU | 461 | 461-479 | 418 | AGCAUCUUCUGGGCUUUGG |
| AD-46286.1 | 419 | GCUACCGCAAGGGCAAGAA | 2360 | 2360-2378 | 420 | UUCUUGCCCUUGCGGUAGC |
| AD-46286.2 | 419 | GCUACCGCAAGGGCAAGAA | 2360 | 2360-2378 | 420 | UUCUUGCCCUUGCGGUAGC |
| AD-46288.1 | 423 | UGGUGGCAGGAGGUGGCAU | 2664 | 2664-2682 | 424 | AUGCCACCUCCUGCCACCA |
| AD-46289.1 | 425 | CCCACUCUGUACAGAGGCU | 2903 | 2903-2921 | 426 | AGCCUCUGUACAGAGUGGG |
| AD-46290.1 | 427 | CUCACAGCCCAGACCCUCA | 3128 | 3128-3146 | 428 | UGAGGGUCUGGGCUGUGAG |
| AD-46291.1 | 429 | CCUCUCUGGACUACGGCUU | 1232 | 1232-1250 | 430 | AAGCCGUAGUCCAGAGAGG |

TABLE 3-continued

Unmodified sense and antisense strand sequences of human TMPRSS6 dsRNAs

| Duplex ID | SEQ ID NO.: (sense) | Sense Trans seq | Position in NM_153609.2 | Position in NM_153609.2 | SEQ ID NO.: (antisense) | Antisense Trans seq |
|---|---|---|---|---|---|---|
| AD-46293.1 | 431 | GUGGCAGGAGGUGGCAUCU | 2666 | 2666-2684 | 432 | AGAUGCCACCUCCUGCCAC |
| AD-46294.1 | 433 | UUCGGAAGCCCCUGGUCUA | 2959 | 2959-2977 | 434 | UAGACCAGGGGCUUCCGAA |
| AD-46295.1 | 435 | AGCUCAGCUGCCCUUUGGA | 3157 | 3157-3175 | 436 | UCCAAAGGGCAGCUGAGCU |
| AD-46296.1 | 437 | GGCCUGGAUGAGAGAAACU | 1561 | 1561-1579 | 438 | AGUUUCUCUCAUCCAGGCC |
| AD-46297.1 | 439 | UGGCAGGAGGUGGCAUCUU | 2667 | 2667-2685 | 440 | AAGAUGCCACCUCCUGCCA |
| AD-46298.1 | 349 | UCGGAAGCCCCUGGUCUAA | 2960 | 2960-2978 | 350 | UUAGACCAGGGGCUUCCGA |
| AD-46299.1 | 421 | GCUCAGCUGCCCUUUGGAA | 3158 | 3158-3176 | 422 | UUCCAAAGGGCAGCUGAGC |
| AD-46299.2 | 421 | GCUCAGCUGCCCUUUGGAA | 3158 | 3158-3176 | 422 | UUCCAAAGGGCAGCUGAGC |
| AD-46300.1 | 441 | ACUGUGACUGUGGCCUCCA | 1808 | 1808-1826 | 442 | UGGAGGCCACAGUCACAGU |
| AD-46301.1 | 321 | AGGAGGUGGCAUCUUGUCU | 2671 | 2671-2689 | 322 | AGACAAGAUGCCACCUCCU |
| AD-46302.1 | 443 | CCCCUGGUCUAACUUGGGA | 2967 | 2967-2985 | 444 | UCCCAAGUUAGACCAGGGG |
| AD-46303.1 | 445 | UCAGCUGCCCUUUGGAAUA | 3160 | 3160-3178 | 446 | UAUUCCAAAGGGCAGCUGA |
| AD-46304.1 | 447 | UCGGGGUCGACACAUCUGU | 1902 | 1902-1920 | 448 | ACAGAUGUGUCGACCCCGA |
| AD-46305.1 | 449 | GUCCCUGAUGUCUGCUCCA | 2691 | 2691-2709 | 450 | UGGAGCAGACAUCAGGGAC |
| AD-46306.1 | 355 | CCCUGGUCUAACUUGGGAU | 2968 | 2968-2986 | 356 | AUCCCAAGUUAGACCAGGG |
| AD-46307.1 | 610 | CAGCUGCCCUUUGGAAUAA | 3161 | 3161-3179 | 611 | UUAUUCCAAAGGGCAGCUG |
| AD-46307.2 | 610 | CAGCUGCCCUUUGGAAUAA | 3161 | 3161-3179 | 611 | UUAUUCCAAAGGGCAGCUG |
| AD-46308.1 | 451 | UCAUCGCUGACCGCUGGGU | 1931 | 1931-1949 | 452 | ACCCAGCGGUCAGCGAUGA |

TABLE 4

Modified sense and antisense strand sequences of human TMPRSS6 dsRNAs

| Duplex ID | SEQ ID NO.: (sense) | Sense sequence | Position in NM_153609.2 | Position in NM_153609.2 | SEQ ID NO.: (anti-sense) | Antisense sequence |
|---|---|---|---|---|---|---|
| AD-46230.1 | 453 | GGGGuGcuAcucuGGuAuudTsdT | 319 | 319-337 | 454 | AAuACcAGAGuAGcACCCCdTsdT |
| AD-46231.1 | 455 | ucuucuGGuucAuucuccAdTsdT | 566 | 566-584 | 456 | UGGAGAAUGAACcAGAAGAdTsdT |
| AD-46232.1 | 457 | AcGcuGGGuuGuuAccGcudTsdT | 766 | 766-784 | 458 | AGCGGuAAcAACCcAGCGUdTsdT |
| AD-46233.1 | 459 | cAGAAGuAuGAuuuGccGudTsdT | 1285 | 1285-1303 | 460 | ACGGcAAAUcAuACUUCUGdTsdT |
| AD-46234.1 | 461 | cGcuGAccGcuGGGuGAuAdTsdT | 1935 | 1935-1953 | 462 | uAUcACCcAGCGGUcAGCGdTsdT |
| AD-46235.1 | 463 | ucuGGuAuuccuAGGGuAdTsdT | 329 | 329-347 | 464 | uACCCuAGGAAAuACcAGAdTsdT |
| AD-46236.1 | 465 | ccuAcAGGGccGAGuAcGAdTsdT | 683 | 683-701 | 466 | UCGuACUCGGCCCUGuAGGdTsdT |
| AD-46237.1 | 467 | cGcuGGGuuGuuAccGcuAdTsdT | 767 | 767-785 | 468 | uAGCGGuAAcAACCcAGCGdTsdT |
| AD-46238.1 | 469 | GGccAGuGGAcGAuccAGAdTsdT | 1312 | 1312-1330 | 470 | UCUGGAUCGUCcACUGGCCdTsdT |
| AD-46239.1 | 471 | uGAccGcuGGGuGAuAAcAdTsdT | 1938 | 1938-1956 | 472 | UGUuAUcACCcAGCGGUcAdTsdT |
| AD-46240.1 | 473 | GGucAGccAGGuGuAcucAdTsdT | 363 | 363-381 | 474 | UGAGuAcACCUGGCUGACCdTsdT |
| AD-46241.1 | 475 | cuAcAGGGccGAGuAcGAAdTsdT | 684 | 684-702 | 476 | UUCGuACUCGGCCCUGuAGdTsdT |
| AD-46242.1 | 478 | cuGGGuuGuuAccGcuAcAdTsdT | 769 | 769-787 | 479 | UGuAGCGGuAAcAACCcAGdTsdT |

TABLE 4-continued

Modified sense and antisense strand sequences of human TMPRSS6 dsRNAs

| Duplex ID | SEQ ID NO.: (sense) | Sense sequence | Position in NM_153609.2 | Position in NM_153609.2 | SEQ ID NO.: (anti-sense) | Antisense sequence |
|---|---|---|---|---|---|---|
| AD-46243.1 | 480 | uGcAcuAuGGcuuGuAcAAdTsdT | 1454 | 1454-1472 | 481 | UUGuAcAAGCcAuAGUGcAdTsdT |
| AD-46244.1 | 482 | ccuGGAGAGGuGuccuucAdTsdT | 2044 | 2044-2062 | 483 | UGAAGGAcACCUCUCcAGGdTsdT |
| AD-46244.2 | 482 | ccuGGAGAGGuGuccuucAdTsdT | 2044 | 2044-2062 | 483 | UGAAGGAcACCUCUCcAGGdTsdT |
| AD-46245.1 | 484 | AGccAGGuGuAcucAGGcAdTsdT | 367 | 367-385 | 485 | UGCCUGAGuAcACCUGGCUdTsdT |
| AD-46246.1 | 486 | AcAGGGccGAGuAcGAAGudTsdT | 686 | 686-704 | 487 | ACUUCGuACUCGGCCCUGUdTsdT |
| AD-46247.1 | 488 | GGuuGuuAccGcuAcAGcudTsdT | 772 | 772-790 | 489 | AGCUGuAGCGGuAAcAACCdTsdT |
| AD-46248.1 | 490 | uGuGAuGGGucAAGGAcudTsdT | 1534 | 1534-1552 | 491 | AGUCCUUGACCCcAUcAcAdTsdT |
| AD-46249.1 | 492 | cuGGAGAGGuGuccuucAAdTsdT | 2045 | 2045-2063 | 493 | UUGAAGGAcACCUCUCcAGGdTsdT |
| AD-46250.1 | 494 | uccGcAGuGAAAccGccAAdTsdT | 446 | 446-464 | 495 | UUGGCGGUUUcACUGCGGAdTsdT |
| AD-46251.1 | 496 | GGGccGAGuAcGAAGuGGAdTsdT | 689 | 689-707 | 497 | UCcACUUCGuACUCGGCCCdTsdT |
| AD-46252.1 | 498 | GGAccGAcuGGccAuGuAudTsdT | 921 | 921-939 | 499 | AuAcAUGGCcAGUCGGUCCdTsdT |
| AD-46253.1 | 500 | cAAcGGccuGGAuGAGAGAdTsdT | 1557 | 1557-1575 | 501 | UCUCUcAUCcAGGCCGUUGdTsdT |
| AD-46253.2 | 500 | cAAcGGccuGGAuGAGAGAdTsdT | 1557 | 1557-1575 | 501 | UCUCUcAUCcAGGCCGUUGdTsdT |
| AD-46254.1 | 502 | AGuuGAucccAcAGGAccudTsdT | 2291 | 2291-2309 | 503 | AGGUCCUGUGGGAUcAACUdTsdT |
| AD-46255.1 | 504 | ccGcAGuGAAAccGccAAAdTsdT | 447 | 447-465 | 505 | UUUGGCGGUUUcACUGCGGdTsdT |
| AD-46256.1 | 506 | ccGAGGGccuAGuGAuccudTsdT | 710 | 710-728 | 507 | AGGAUcACuAGGCCCUCGGdTsdT |
| AD-46257.1 | 508 | uccucAGcAccccGuAcuudTsdT | 1163 | 1163-1181 | 509 | AAGuACGGGGUGCUGAGGAdTsdT |
| AD-46258.1 | 510 | cAGGuucGGGGucGAcAcAdTsdT | 1897 | 1897-1915 | 511 | UGUGUCGACCCCGAACCUGdTsdT |
| AD-46259.1 | 512 | AGGuGAcGccAcGcAuGcudTsdT | 2333 | 2333-2351 | 513 | AGcAUGCGUGGCGUcACCUdTsdT |
| AD-46260.1 | 514 | AAAccGccAAAGcccAGAAdTsdT | 455 | 455-473 | 515 | UUCUGGGCUUUGGCGGUUUdTsdT |
| AD-46261.1 | 516 | cAGuGuGAAAGAcAuAGcudTsdT | 735 | 735-753 | 517 | AGCuAUGUCUUUcAcACUGdTsdT |
| AD-46262.1 | 518 | ccucucucuGGAcuAcGGcudTsdT | 1231 | 1231-1249 | 519 | AGCCGuAGUCcAGAGAGGGdTsdT |
| AD-46263.1 | 520 | GuucGGGGucGAcAcAucudTsdT | 1900 | 1900-1918 | 521 | AGAUGUGUCGACCCCGAACdTsdT |
| AD-46264.1 | 522 | uGuGuGccGGcuAccGcAAdTsdT | 2351 | 2351-2369 | 523 | UUGCGGuAGCCGGcAcAcAdTsdT |
| AD-46265.1 | 524 | GcuucuucGGuucAuucudTsdT | 563 | 563-581 | 525 | AGAAUGAACcAGAAGAAGCdTsdT |
| AD-46266.1 | 526 | AuuccAcGcuGGGuuGuuAdTsdT | 761 | 761-779 | 527 | uAAcAACCcAGCGUGGAAUdTsdT |
| AD-46267.1 | 528 | AcGGcuuGGcccucuGGuudTsdT | 1244 | 1244-1262 | 529 | AACcAGAGGGCcAAGCCGUdTsdT |
| AD-46268.1 | 530 | ucGcuGAccGcuGGGuGAudTsdT | 1934 | 1934-1952 | 531 | AUcACCcAGCGGUcAGCGAdTsdT |
| AD-46269.1 | 532 | AGuGGuGAccuGAGGAAcudTsdT | 2538 | 2538-2556 | 533 | AGUUCCUcAGGUcACcACUdTsdT |
| AD-46269.2 | 532 | AGuGGuGAccuGAGGAAcudTsdT | 2538 | 2538-2556 | 533 | AGUUCCUcAGGUcACcACUdTsdT |
| AD-46270.1 | 534 | cAAGcAGGGGGAcAAGuAudTsdT | 2612 | 2612-2630 | 535 | AuACUUGUCCCCCUGCUUGdTsdT |
| AD-46271.1 | 536 | uGAuGucuGcuccAGuGAudTsdT | 2696 | 2696-2714 | 537 | AUcACUGGAGcAGAcAUcAdTsdT |
| AD-46272.1 | 538 | cuAAcuGGGAucuGGGAAdTsdT | 2975 | 2975-2993 | 539 | UUCCcAGAUCCcAAGUuAGdTsdT |
| AD-46273.1 | 540 | uGGuAuuuccuAGGGuAcAdTsdT | 331 | 331-349 | 541 | UGuACCCuAGGAAAuACcAdTsdT |
| AD-46273.2 | 540 | uGGuAuuuccuAGGGuAcAdTsdT | 331 | 331-349 | 541 | UGuACCCuAGGAAAuACcAdTsdT |
| AD-46273.3 | 540 | uGGuAuuuccuAGGGuAcAdTsdT | 331 | 331-349 | 541 | UGuACCCuAGGAAAuACcAdTsdT |

TABLE 4-continued

Modified sense and antisense strand sequences of human TMPRSS6 dsRNAs

| Duplex ID | SEQ ID NO.: (sense) | Sense sequence | Position in NM_153609.2 | Position in NM_153609.2 | SEQ ID NO.: (anti-sense) | Antisense sequence |
|---|---|---|---|---|---|---|
| AD-46274.1 | 542 | GAGGuGuccuucAAGGuGAdTsdT | 2050 | 2050-2068 | 543 | UcACCUUGAAGGAcACCUCdTsdT |
| AD-46276.1 | 544 | AAGcAGGGGGAcAAGuAuudTsdT | 2613 | 2613-2631 | 545 | AAuACUUGUCCCCUGCUUdTsdT |
| AD-46277.1 | 546 | cAGcuGGGGGucAAGAcGudTsdT | 2739 | 2739-2757 | 547 | ACGUCUUGACCCcCAGCUGdTsdT |
| AD-46278.1 | 548 | cuuGGGAucuGGGAAuGGAdTsdT | 2979 | 2979-2997 | 549 | UCcAUUCCcAGAUCCcAAGdTsdT |
| AD-46279.1 | 550 | GGuAuuccuAGGGuAcAAdTsdT | 332 | 332-350 | 551 | UUGuACCCuAGGAAAuACCdTsdT |
| AD-46280.1 | 552 | GGcuAccGcAAGGGcAAGAdTsdT | 2359 | 2359-2377 | 553 | UCUUGCCCUUGCGGuAGCCdTsdT |
| AD-46282.1 | 554 | GcAGGGGGAcAAGuAuucudTsdT | 2615 | 2615-2633 | 555 | AGAAuACUUGUCCCCUGCdTsdT |
| AD-46283.1 | 556 | GcucAGcAGcAAGAAuGcudTsdT | 2851 | 2851-2869 | 557 | AGcAUUCUUGCUGCUGAGdTsdT |
| AD-46284.1 | 558 | uuGGGAucuGGGAAuGGAAdTsdT | 2980 | 2980-2998 | 559 | UUCcAUUCCcAGAUCCcAAdTsdT |
| AD-46285.1 | 560 | ccAAAGcccAGAAGAuGcudTsdT | 461 | 461-479 | 561 | AGcAUCUUCUGGGCUUUGGdTsdT |
| AD-46286.1 | 562 | GcuAccGcAAGGGcAAGAAdTsdT | 2360 | 2360-2378 | 563 | UUCUUGCCCUUGCGGuAGCdTsdT |
| AD-46286.2 | 562 | GcuAccGcAAGGGcAAGAAdTsdT | 2360 | 2360-2378 | 563 | UUCUUGCCCUUGCGGuAGCdTsdT |
| AD-46288.1 | 564 | uGGuGGcAGGAGGuGGcAudTsdT | 2664 | 2664-2682 | 565 | AUGCcACCUCCUGCcACcAdTsdT |
| AD-46289.1 | 566 | cccAcucuGuAcAGAGGcudTsdT | 2903 | 2903-2921 | 567 | AGCCUCUGuAcAGAGUGGGdTsdT |
| AD-46290.1 | 568 | cucAcAGcccAGAcccucAdTsdT | 3128 | 3128-3146 | 569 | UGAGGGUCUGGGCUGUGAGdTsdT |
| AD-46291.1 | 570 | ccucucuGGAcuAcGGcuudTsdT | 1232 | 1232-1250 | 571 | AAGCCGuAGUCcAGAGAGGdTsdT |
| AD-46293.1 | 572 | GuGGcAGGAGGuGGcAucudTsdT | 2666 | 2666-2684 | 573 | AGAUGCcACCUCCUGCcACdTsdT |
| AD-46294.1 | 574 | uucGGAAGccccuGGucuAdTsdT | 2959 | 2959-2977 | 575 | uAGAccAGGGGCUUCCGAAdTsdT |
| AD-46295.1 | 576 | AGcuAGcuGcccuuuGGAdTsdT | 3157 | 3157-3175 | 577 | UCcAAAGGGcAGCUGAGCUdTsdT |
| AD-46296.1 | 578 | GGccuGGAuGAGAGAAAcudTsdT | 1561 | 1561-1579 | 579 | AGUUUCUCUcAUCcAGGCCdTsdT |
| AD-46297.1 | 580 | uGGcAGGAGGuGGcAucuudTsdT | 2667 | 2667-2685 | 581 | AAGAUGCcACCUCCUGCcAdTsdT |
| AD-46298.1 | 582 | ucGGAAGccccuGGucuAAdTsdT | 2960 | 2960-2978 | 583 | UuAGAccAGGGGCUUCCGAdTsdT |
| AD-46299.1 | 584 | GcucAGcuGcccuuuGGAAdTsdT | 3158 | 3158-3176 | 585 | UUCcAAAGGGcAGCUGAGCdTsdT |
| AD-46299.2 | 584 | GcucAGcuGcccuuuGGAAdTsdT | 3158 | 3158-3176 | 585 | UUCcAAAGGGcAGCUGAGCdTsdT |
| AD-46300.1 | 586 | AcuGuGAcuGuGGccuccAdTsdT | 1808 | 1808-1826 | 587 | UGGAGGCcAcAGUcAcAGUdTsdT |
| AD-46301.1 | 588 | AGGAGGuGGcAucuuGucudTsdT | 2671 | 2671-2689 | 589 | AGAcAAGAUGCcACCUCCUdTsdT |
| AD-46302.1 | 590 | ccccuGGucuAAcuuGGGAdTsdT | 2967 | 2967-2985 | 591 | UCCcAAGUuAGAccAGGGGdTsdT |
| AD-46303.1 | 592 | ucAGcuGcccuuuGGAAuAdTsdT | 3160 | 3160-3178 | 593 | uAUUCcAAAGGGcAGCUGAdTsdT |
| AD-46304.1 | 594 | ucGGGGucGAcAcAucuGudTsdT | 1902 | 1902-1920 | 595 | AcAGAUGUGUCGACCCCGAdTsdT |
| AD-46305.1 | 596 | GucccuGAuGucuGcuccAdTsdT | 2691 | 2691-2709 | 597 | UGGAGcAGAcAUcAGGGACdTsdT |
| AD-46306.1 | 598 | cccuGGucuAAcuuGGGAudTsdT | 2968 | 2968-2986 | 599 | AUCCcAAGUuAGAccAGGGdTsdT |
| AD-46307.1 | 600 | cAGcuGcccuuuGGAAuAAdTsdT | 3161 | 3161-3179 | 601 | UuAUUCcAAAGGGcAGCUGdTsdT |
| AD-46307.2 | 600 | cAGcuGcccuuuGGAAuAAdTsdT | 3161 | 3161-3179 | 201 | UuAUUCcAAAGGGcAGCUGdTsdT |
| AD-46308.1 | 602 | ucAucGcuGAccGcuGGGudTsdT | 1931 | 1931-1949 | 603 | ACCcAGCGGUcAGCGAUGAdTsdT |

Synthesis of TMPRSS6 Sequences

TMPRSS6 iRNA sequences can be synthesized on a MerMade 192 synthesizer at 1 μmol scale.

Endolight chemistry can be applied as detailed below.
All pyrimidines (cytosine and uridine) in the sense strand contained 2'-O-Methyl bases (2' O-Methyl C and 2'-O-Methyl U)
In the antisense strand, pyrimidines adjacent to (towards 5' position) ribo A nucleoside can be replaced with their corresponding 2-O-Methyl nucleosides A two base dTsdT extension at 3' end of both sense and anti sense sequences can be introduced
The sequence file can be converted to a text file to make it compatible for loading in the MerMade 192 synthesis software Synthesis, Cleavage and Deprotection The synthesis of TMPRSS6 sequences use solid supported oligonucleotide synthesis using phosphoramidite chemistry.

The synthesis of the above sequences can be performed at 1 μm scale in 96 well plates. The amidite solutions can be prepared at 0.1M concentration and ethyl thio tetrazole (0.6M in Acetonitrile) can be used as activator.

The synthesized sequences can be cleaved and deprotected in 96 well plates, using methylamine in the first step and fluoride reagent in the second step. The crude sequences can be precipitated using acetone: ethanol (80:20) mix and the pellets re-suspended in 0.02M sodium acetate buffer. Samples from each sequence can be analyzed by LC-MS to confirm the identity, and by UV for quantification. A selected set of samples can also be analyzed by IEX chromatography to determine purity.

Purification and Desalting

All sequences can be purified on AKTA explorer purification system using Source 15Q column. Sample injection and collection can be performed in 96 well (1.8 mL-deep well) plates. A single peak corresponding to the full length sequence can be collected in the eluent. The purified sequences can be desalted on a Sephadex G25 column using AKTA purifier. The desalted TMPRSS6 sequences can be analyzed for concentration (by UV measurement at A260) and purity (by ion exchange HPLC). The single strands can then be submitted for annealing.

Example 3

In Vitro Screening of TMPRSS6 siRNA Duplexes for TMPRSS6 Knockdown Activity

TMPRSS6 siRNA duplexes were screened for the ability to knockdown TMPRSS6 expression in vitro. Single dose screening, dose response screening, and viability of host cells were evaluated.

In Vitro Screening:

Cell Culture and Transfections for Single Dose and Dose Response Studies:

HeLa or Hep3B cells (ATCC, Manassas, Va.) were grown to near confluence at 37° C. in an atmosphere of 5% $CO_2$ in X (ATCC) supplemented with 10% FBS, streptomycin, and glutamine (ATCC) before being released from the plate by trypsinization. Transfection was carried out by adding 14.8 μl of Opti-MEM plus 0.2 μl of Lipofectamine RNAiMax per well (Invitrogen, Carlsbad Calif. cat #13778-150) to 5 μl of siRNA duplexes per well into a 96-well plate and incubated at room temperature for 15 minutes. 80 μl of complete growth media without antibiotic containing~$2 \times 10^4$ HeLa or Hep3B cells were then added to the siRNA mixture. Cells were incubated for either 24 or 120 hours prior to RNA purification. Single dose experiments were performed at 10 nM and 0.1 nM final duplex concentration and dose response experiments were done at 10, 1, 0.5, 0.1, 0.05, 0.01, 0.005, 0.001, 0.0005, 0.0001, 0.00005, 0.00001 nM final duplex concentration.

Total RNA Isolation Using DYNABEADS® mRNA Isolation Kit (Invitrogen, Part #: 610-12):

Cells were harvested and lysed in 150 μl of Lysis/Binding Buffer then mixed for 5 minutes at 850 rpm using an Eppendorf® Thermomixer (the mixing speed was the same throughout the process). Ten microliters of magnetic beads and 80 μl of Lysis/Binding Buffer mixture were added to a round bottom plate and mixed for 1 minute. Magnetic beads were captured using a magnetic stand and the supernatant was removed without disturbing the beads. After removing the supernatant, the lysed cells were added to the remaining beads and mixed for 5 minutes. After removing the supernatant, the magnetic beads were washed twice with 150 μl of Wash Buffer A and mixed for one minute. The beads were captured again and the supernatant was removed. The beads were then washed with 150 μl Wash Buffer B, captured and the supernatant was removed. Beads were next washed with 150 μl Elution Buffer, captured and supernatant removed. The beads were then allowed to dry for two minutes. After drying, 50 μl of Elution Buffer was added and mixed for five minutes at 70° C. The beads were captured on a magnet for five minutes. 40 μl of supernatant was removed and added to another 96 well plate.

cDNA Synthesis Using ABI High Capacity cDNA Reverse Transcription Kit (Applied Biosystems, Foster City, Calif., Cat #4368813):

A master mix of 2 μl of 10× Buffer, 0.8 μl of 25× dNTPs, 2 μl of Random primers, 1 μl of Reverse Transcriptase, 1 μl of RNase inhibitor and 3.2 μl of H2O per reaction were added into 10 μl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Real Time PCR:

2 μl of cDNA were added to a master mix containing 0.5 μl GAPDH TaqMan Probe (Applied Biosystems Cat #4326317E), 0.5 μl TMPRSS6 TaqMan probe (Applied Biosystems cat # Hs00542184_ml) and 5 μl Lightcycler 480 probe master mix (Roche Cat #04887301001) per well in a 384 well 50 plates (Roche cat #04887301001). Real time PCR was done in an ABI 7900HT Real Time PCR system (Applied Biosystems) using the ΔΔCt(RQ) assay. Each duplex was tested in two independent transfections and each transfection was assayed in duplicate, unless otherwise noted in the summary tables.

To calculate relative fold change, real time data were analyzed using the ΔΔCt method and normalized to assays performed with cells transfected with 10 nM AD-1955, or mock transfected cells. IC50s were calculated using a 4 parameter fit model using XLFit and normalized to cells transfected with AD-1955 over the same dose range, or to its own lowest dose.

Viability screens. HeLa or Hep3B cells (ATCC, Manassas, Va.) were grown to near confluence at 37° C. in an atmosphere of 5% $CO_2$ in X (ATCC) supplemented with 10% FBS, streptomycin, and glutamine (ATCC) before being released from the plate by trypsinization. Cell viability was measured on days 3 and 5 in HeLa and Hep3B cells following transfection with 100, 10, 1, 0.1, 0.01 and 0.0001 nM siRNA. Cells were plated at a density of $2.5 \times 10^3$-$5 \times 10^3$ cells per well in 96 well plates. Each siRNA was assayed in triplicate and the data averaged. siRNAs targeting PLK1 and AD-19200 were included as positive controls for loss of viability and AD-1955 as a negative control. PLK1 and AD-19200 result in a dose dependant loss of viability. To measure viability, 20 ul of CellTiter Blue (Promega) was added to each well of the 96 well plates after 3 and 5 days and incubated at 37° C. for 2 hours. Plates were then read in a Spectrophotometer (Molecular Devices) at $560_{Ex}/590_{Em}$. Viability was expressed as the average value of light units from three replicate transfections +/− standard deviation.

In Vitro Knockdown of TMPRSS6 Expression by TMPRSS6 siRNA Duplexes.

Table 5 presents data indicating the knockdown of TMPRSS6 in Hep3B cells transfected with siRNAs targeting TMPRSS6. The data is expressed as a fraction of TMPRSS6 message remaining in cells transfected with siRNAs targeting TMPRSS6, relative to cells transfected with a negative control siRNA, AD-1955. Cells that were not treated ("naïve" cells) served as a second negative control. All siRNAs were tested at least twice, and qPCR reactions were also performed in duplicate. Single dose experiments were performed at 10 nM and 0.1 nM final siRNA duplex concentration.

TABLE 5

TMPRSS6 expression in single dose screen in vitro.

| Duplex ID | 10 nM Ave | 0.1 nM Ave | 10 nM SD | 0.1 nM SD |
|---|---|---|---|---|
| AD-46230.1 | 0.89 | 1.14 | 0.036 | 0.145 |
| AD-46230.1 | 0.85 | 1.22 | 0.039 | 0.063 |
| AD-46231.1 | 0.11 | 0.29 | 0.017 | 0.007 |
| AD-46232.1 | 0.78 | 0.87 | 0.03 | 0.023 |
| AD-46233.1 | 0.6 | 0.98 | 0.033 | 0.046 |
| AD-46234.1 | 0.79 | 1.06 | 0.082 | 0.068 |
| AD-46235.1 | 0.18 | 0.87 | 0.009 | 0.066 |
| AD-46235.1 | 0.18 | 0.96 | 0.009 | 0.132 |
| AD-46236.1 | 0.15 | 1.06 | 0.007 | 0.036 |
| AD-46237.1 | 0.81 | 0.98 | 0.043 | 0.027 |
| AD-46238.1 | 0.71 | 0.99 | 0.069 | 0.031 |
| AD-46239.1 | 0.83 | 1.3 | 0.035 | 0.073 |
| AD-46240.1 | 0.89 | 0.99 | 0.027 | 0.079 |
| AD-46240.1 | 0.88 | 1 | 0.009 | 0.034 |
| AD-46241.1 | 0.6 | 0.9 | 0.029 | 0.029 |
| AD-46242.1 | 0.81 | 0.91 | 0.016 | 0.049 |
| AD-46243.1 | 0.82 | 0.87 | 0.029 | 0.066 |
| AD-46244.1 | 0.19 | 0.43 | 0.018 | 0.028 |
| AD-46245.1 | 0.48 | 0.79 | 0.148 | 0.016 |
| AD-46245.1 | 0.51 | 0.82 | 0.147 | 0.028 |
| AD-46246.1 | 0.39 | 0.89 | 0.012 | 0.043 |
| AD-46247.1 | 0.84 | 0.9 | 0.047 | 0.019 |
| AD-46248.1 | 0.68 | 0.95 | 0.059 | 0.075 |
| AD-46249.1 | 0.17 | 0.29 | 0.005 | 0.152 |
| AD-46250.1 | 0.19 | 0.53 | 0.017 | 0.011 |
| AD-46251.1 | 0.16 | 0.47 | 0.007 | 0.005 |
| AD-46252.1 | 1.04 | 1.08 | 0.031 | 0.038 |
| AD-46253.1 | 0.27 | 0.45 | 0.02 | 0.031 |
| AD-46254.1 | 1.03 | 1.08 | 0.221 | 0.021 |
| AD-46255.1 | 0.52 | 0.84 | 0.029 | 0.036 |
| AD-46256.1 | 0.81 | 1.02 | 0.025 | 0.015 |
| AD-46257.1 | 0.64 | 0.97 | 0.016 | 0.076 |
| AD-46258.1 | 0.91 | 0.98 | 0.054 | 0.059 |
| AD-46259.1 | 0.77 | 1.03 | 0.052 | 0.067 |
| AD-46260.1 | 1.24 | 1 | 0.634 | 0.031 |
| AD-46261.1 | 0.12 | 0.19 | 0.007 | 0.006 |
| AD-46262.1 | 0.58 | 1.27 | 0.016 | 0.024 |
| AD-46263.1 | 0.79 | 0.95 | 0.03 | 0.021 |
| AD-46264.1 | 0.93 | 1.16 | 0.052 | 0.095 |
| AD-46265.1 | 0.09 | 0.47 | 0.007 | 0.017 |
| AD-46266.1 | 0.25 | 0.8 | 0.024 | 0.018 |
| AD-46267.1 | 0.65 | 0.84 | 0.058 | 0.02 |
| AD-46268.1 | 0.92 | 1 | 0.008 | 0.048 |
| AD-46269.1 | 0.37 | 0.52 | 0.037 | 0.024 |
| AD-46270.1 | 0.26 | 0.55 | 0.01 | 0.03 |
| AD-46271.1 | 0.35 | 0.8 | 0.044 | 0.029 |
| AD-46272.1 | 0.62 | 0.91 | 0.015 | 0.061 |
| AD-46273.1 | 0.18 | 0.3 | 0.02 | 0.012 |
| AD-46274.1 | 0.88 | 0.85 | 0.04 | 0.016 |
| AD-46276.1 | 0.33 | 0.64 | 0.024 | 0.024 |
| AD-46277.1 | 0.85 | 0.89 | 0.12 | 0.026 |
| AD-46278.1 | 0.24 | 0.7 | 0.019 | 0.059 |
| AD-46279.1 | 0.55 | 0.79 | 0.008 | 0.025 |
| AD-46280.1 | 0.96 | 0.84 | 0.059 | 0.042 |
| AD-46282.1 | 0.21 | 0.47 | 0.017 | 0.004 |
| AD-46283.1 | 0.62 | 1.01 | 0.05 | 0.03 |
| AD-46284.1 | 0.42 | 0.78 | 0.016 | 0.019 |
| AD-46285.1 | 0.37 | 0.86 | 0.014 | 0.042 |
| AD-46286.1 | 0.19 | 0.49 | 0.019 | 0.027 |
| AD-46288.1 | 0.65 | 0.88 | 0.052 | 0.032 |
| AD-46289.1 | 0.89 | 0.92 | 0.062 | 0.032 |
| AD-46290.1 | 0.83 | 0.9 | 0.035 | 0.029 |
| AD-46291.1 | 0.65 | 0.87 | 0.014 | 0.014 |
| AD-46293.1 | 0.31 | 0.68 | 0.012 | 0.054 |
| AD-46294.1 | 0.25 | 0.7 | 0.015 | 0.031 |
| AD-46295.1 | 0.2 | 0.42 | 0.004 | 0.029 |
| AD-46296.1 | 0.43 | 0.83 | 0.012 | 0.043 |
| AD-46297.1 | 0.3 | 0.6 | 0.009 | 0.017 |
| AD-46298.1 | 0.91 | 0.91 | 0.08 | 0.008 |
| AD-46299.1 | 0.26 | 0.57 | 0.018 | 0.052 |
| AD-46300.1 | 0.98 | 0.91 | 0.037 | 0.024 |
| AD-46301.1 | 0.65 | 0.87 | 0.018 | 0.051 |
| AD-46302.1 | 0.92 | 1.01 | 0.021 | 0.048 |
| AD-46303.1 | 0.13 | 0.43 | 0.008 | 0.019 |
| AD-46304.1 | 1.11 | 1.01 | 0.016 | 0.056 |
| AD-46305.1 | 0.21 | 0.73 | 0.029 | 0.011 |
| AD-46306.1 | 0.84 | 0.96 | 0.114 | 0.092 |
| AD-46307.1 | 0.27 | 0.49 | 0.007 | 0.019 |
| AD-46308.1 | 0.69 | 0.83 | 0.02 | 0.024 |
| Naïve | 1.04 | 1.06 | 0.021 | 0.018 |
| Naïve | 1.07 | 1.29 | 0.065 | 0.059 |
| AD-1955 | 0.85 | 0.85 | 0.055 | 0.071 |
| AD-1955 | 1.1 | 0.97 | 0.034 | 0.04 |
| AD-1955 | 1 | 0.98 | 0.036 | 0.058 |
| AD-1955 | 1.04 | 0.98 | 0.053 | 0.049 |
| AD-1955 | 1.04 | 1.08 | 0.021 | 0.039 |
| AD-1955 | 0.98 | 1.19 | 0.049 | 0.058 |

$IC_{50}$ of Select TMPRSS6 siRNA Duplexes in In Vitro Dose Response Screen.

Table 6 presents the $IC_{50}$ values of select TMPRSS6 siRNA duplexes determined from in vitro dose response screens. TMPRSS6 siRNA duplexes that were efficacious in the 10 nM and 0.1 nM single dose screen (Table 5), were tested for TMPRSS6 knockdown activity in a dose response at 1 and 5 days following transfection in Hep3B cells. Dose response experiments were conducted at 10, 1, 0.5, 0.1, 0.05, 0.01, 0.005, 0.001, 0.0005, 0.0001, 0.00005, 0.00001 nM final siRNA duplex concentration. For normalization, knockdown of TMPRSS6 was measured relative to the non-targeting control, AD-1955, or the value obtained at the lowest siRNA concentration for each duplex tested.

TABLE 6

$IC_{50}$ of select TMPRSS6 siRNA duplexes in in vitro dose response screen.

| | Normalized to low dose | | Normalized to AD-1955 | |
|---|---|---|---|---|
| Duplex ID | Day 1 (nM) | Day 5 (nM) | Day 1 (nM) | Day 5 (nM) |
| AD-46250.1 | 0.57 | 0.08 | 0.22 | 0.04 |
| AD-46265.1 | 0.14 | 0.07 | 0.2 | 0.03 |
| AD-46231.1 | 0.07 | 0.04 | 0.06 | 0.02 |

TABLE 6-continued

IC$_{50}$ of select TMPRSS6 siRNA duplexes in in vitro dose response screen.

| | Normalized to low dose | | Normalized to AD-1955 | |
|---|---|---|---|---|
| Duplex ID | Day 1 (nM) | Day 5 (nM) | Day 1 (nM) | Day 5 (nM) |
| AD-46251.1 | 0.27 | 0.1 | 0.37 | 0.07 |
| AD-46261.1 | 0.04 | 0.09 | 0.08 | 0.05 |
| AD-46253.1 | 0.78 | 0.07 | 0.35 | 0.13 |
| AD-46244.1 | 0.14 | 0.13 | 0.2 | 0.32 |
| AD-46269.1 | 0.06 | 0.57 | 0.07 | 1.16 |
| AD-46270.1 | 0.94 | No IC50 | 0 | No IC50 |
| AD-46282.1 | 1.16 | No IC50 | 0.02 | No IC50 |
| AD-46297.1 | 0.05 | No IC50 | 0.08 | No IC50 |
| AD-46299.1 | 0.01 | 3.89 | 0.03 | 0.69 |
| AD-46303.1 | 0.01 | 2.47 | 0.03 | 0.04 |
| AD-46307.1 | 1.02 | 0.02 | 2.68 | 0.15 |
| AD-46273.1 | 0.23 | 0.03 | 0.72 | 0.1 |
| AD-46286.1 | 0.22 | 0.46 | 0.53 | 0.46 |
| AD-46249.1 | 0.27 | 1.96 | 0.31 | 5.87 |
| AD-46295.1 | 0.76 | 0.31 | 0.24 | 0.1 |

In vitro Viability Screening of HeLa and HEP3B Cell Lines Transfected with TMPRSS6 siRNA Duplexes.

Table 7 presents viability data of HeLa and HEP3B cell lines transfected with TMPRSS6 siRNA duplexes. Viability data are expressed as average raw fluorescence units, where smaller values represent lower viability. Error is expressed as standard deviation from three replicate transfections.

TABLE 7

Viability of HeLa and HEP3B cell lines transfected with TMPRSS6 siRNA duplexes.

| | HeLa Day 3 10 nM | HeLa Day 3 1 nM | HeLa Day 3 0.1 nM | HeLa Day 3 0.01 nM | HeLa Day 3 0.001 nM | HeLa Day 3 0.0001 nM | HeLa Day 3 10 nM SD | HeLa Day 3 1 nM SD | HeLa Day 3 0.1 nM SD | HeLa Day 3 0.01 nM SD | HeLa Day 3 0.001 nM SD | HeLa Day 3 0.0001 nM SD |
|---|---|---|---|---|---|---|---|---|---|---|---|---|
| AD-46250.1 | 5260 | 13504 | 29520 | 30542 | 30924 | 30956 | 150 | 62 | 272 | 220 | 799 | 751 |
| AD-46265.1 | 12234 | 29940 | 32497 | 33323 | 32124 | 32882 | 968 | 884 | 1071 | 946 | 707 | 595 |
| AD-46231.1 | 25177 | 28407 | 32021 | 32650 | 33375 | 32704 | 710 | 420 | 127 | 1697 | 356 | 667 |
| AD-46251.1 | 29528 | 30151 | 30215 | 32163 | 31743 | 31726 | 416 | 102 | 31 | 1588 | 518 | 1091 |
| AD-46261.1 | 16677 | 26331 | 30594 | 31681 | 32847 | 31544 | 390 | 277 | 431 | 1375 | 681 | 583 |
| AD-46253.1 | 21580 | 28887 | 30953 | 31684 | 32457 | 31491 | 1158 | 437 | 524 | 944 | 229 | 455 |
| AD-46244.1 | 13230 | 16369 | 26545 | 31359 | 32753 | 32280 | 197 | 165 | 255 | 357 | 589 | 1318 |
| AD-46269.1 | 9978 | 19514 | 29290 | 30839 | 31529 | 31173 | 597 | 360 | 1406 | 400 | 743 | 626 |
| AD-46270.1 | 17543 | 17834 | 31180 | 31087 | 32793 | 31314 | 370 | 1026 | 771 | 552 | 391 | 1293 |
| AD-46282.1 | 29055 | 32421 | 31840 | 31006 | 34287 | 32185 | 446 | 618 | 430 | 855 | 323 | 133 |
| AD-46297.1 | 8126 | 16696 | 28128 | 33928 | 33955 | 32322 | 193 | 598 | 733 | 895 | 1266 | 392 |
| AD-46299.1 | 31922 | 30196 | 30880 | 30447 | 31900 | 32608 | 1459 | 617 | 58 | 194 | 773 | 964 |
| AD-46303.1 | 27309 | 28325 | 27975 | 29319 | 30310 | 30935 | 1363 | 572 | 421 | 295 | 306 | 95 |
| AD-46307.1 | 33156 | 33240 | 32059 | 33072 | 32135 | 33307 | 667 | 258 | 775 | 1164 | 102 | 286 |
| AD-46273.1 | 24465 | 29130 | 30417 | 33043 | 34639 | 31876 | 142 | 768 | 271 | 261 | 853 | 800 |
| AD-46286.1 | 3640 | 9590 | 29713 | 33138 | 32877 | 30814 | 34 | 631 | 371 | 1185 | 1641 | 599 |
| AD-46249.1 | 17315 | 25591 | 30443 | 31599 | 32719 | 29855 | 981 | 258 | 578 | 482 | 1412 | 886 |
| AD-46295.1 | 30565 | 31730 | 30772 | 31777 | 32874 | 30916 | 403 | 261 | 1223 | 1880 | 981 | 441 |
| AD-19200 | 9727 | 15752 | 31352 | 32521 | 30110 | 30650 | 648 | 699 | 763 | 1543 | 55 | 9 |
| PLK | 1166 | 1626 | 27849 | 29902 | 30512 | 30273 | 23 | 44 | 91 | 299 | 362 | 563 |
| AD-1955 | 26502 | 30164 | 30267 | 31906 | 33309 | 30906 | 5669 | 134 | 353 | 645 | 233 | 696 |
| Naïve | 32821 | 32311 | 30805 | 31683 | 33238 | 31470 | 1455 | 631 | 555 | 557 | 288 | 164 |
| Naïve | 33594 | 32373 | 32005 | 34024 | 35629 | 33401 | 554 | 253 | 754 | 899 | 55 | 649 |
| Naïve | 30695 | 30651 | 29956 | 31377 | 32734 | 32527 | 304 | 299 | 807 | 874 | 646 | 225 |

| | HeLa Day 5 10 nM | HeLa Day 5 1 nM | HeLa Day 5 0.1 nM | HeLa Day 5 0.01 nM | HeLa Day 5 0.001 nM | HeLa Day 5 0.0001 nM | HeLa Day 5 10 nM SD | HeLa Day 5 1 nM SD | HeLa Day 5 0.1 nM SD | HeLa Day 5 0.01 nM SD | HeLa Day 5 0.001 nM SD | HeLa Day 5 0.0001 nM SD |
|---|---|---|---|---|---|---|---|---|---|---|---|---|
| AD-46250.1 | 2344 | 25502 | 46627 | 44986 | 46479 | 46070 | 44 | 1916 | 157 | 913 | 598 | 2016 |
| AD-46265.1 | 10411 | 46611 | 48725 | 47425 | 47238 | 47942 | 300 | 327 | 602 | 1479 | 2145 | 1690 |
| AD-46231.1 | 41079 | 46963 | 48575 | 48060 | 47467 | 48500 | 1645 | 319 | 243 | 998 | 1821 | 1203 |
| AD-46251.1 | 42551 | 47044 | 49088 | 48229 | 47755 | 48719 | 1597 | 420 | 162 | 1105 | 1434 | 1232 |
| AD-46261.1 | 37500 | 46441 | 48702 | 47953 | 47776 | 48878 | 689 | 441 | 451 | 1447 | 1614 | 1159 |
| AD-46253.1 | 31772 | 45899 | 48606 | 47801 | 47693 | 49237 | 1310 | 65 | 648 | 1550 | 1365 | 789 |
| AD-46244.1 | 11597 | 28046 | 46020 | 47413 | 47670 | 49430 | 967 | 527 | 395 | 1336 | 937 | 869 |
| AD-46269.1 | 10704 | 37735 | 47496 | 47629 | 47496 | 49194 | 317 | 161 | 198 | 1359 | 1502 | 986 |
| AD-46270.1 | 16356 | 26284 | 48520 | 48011 | 48016 | 49358 | 382 | 663 | 497 | 1121 | 1024 | 681 |
| AD-46282.1 | 22372 | 42327 | 47297 | 47478 | 47450 | 49349 | 656 | 715 | 343 | 1513 | 2057 | 883 |
| AD-46297.1 | 4228 | 26993 | 47037 | 47269 | 46961 | 48993 | 41 | 657 | 593 | 1847 | 1574 | 639 |
| AD-46299.1 | 45283 | 45485 | 46334 | 43966 | 42922 | 46772 | 1088 | 908 | 382 | 2057 | 3580 | 1131 |
| AD-46303.1 | 42669 | 46358 | 46240 | 45624 | 46200 | 46764 | 849 | 183 | 791 | 890 | 90 | 539 |
| AD-46307.1 | 47710 | 47466 | 47974 | 47671 | 47911 | 48505 | 273 | 539 | 680 | 399 | 238 | 309 |
| AD-46273.1 | 36834 | 45018 | 47522 | 47912 | 48316 | 48804 | 680 | 432 | 104 | 619 | 308 | 248 |
| AD-46286.1 | 2970 | 31215 | 47504 | 47883 | 48062 | 48999 | 515 | 1262 | 1093 | 826 | 87 | 541 |
| AD-46249.1 | 20356 | 44959 | 48534 | 47988 | 48053 | 49145 | 884 | 1033 | 1238 | 1045 | 619 | 530 |
| AD-46295.1 | 46448 | 48014 | 49195 | 48654 | 48432 | 49355 | 685 | 1021 | 746 | 1183 | 645 | 407 |
| AD-19200 | 26444 | 35772 | 39724 | 48377 | 48373 | 49509 | 725 | 1009 | 1246 | 540 | 762 | 408 |

TABLE 7-continued

Viability of HeLa and HEP3B cell lines transfected with TMPRSS6 siRNA duplexes.

| | | | | | | | | | | | | |
|---|---|---|---|---|---|---|---|---|---|---|---|---|
| PLK | 1105 | 1804 | 37258 | 47955 | 47893 | 49416 | 44 | 95 | 1110 | 781 | 474 | 515 |
| AD-1955 | 44857 | 47272 | 48354 | 48050 | 48668 | 49721 | 322 | 388 | 756 | 880 | 585 | 490 |
| Naïve | 48734 | 48454 | 48549 | 47246 | 48004 | 49067 | 850 | 303 | 743 | 1166 | 349 | 102 |
| Naïve | 48318 | 47839 | 45252 | 47098 | 47128 | 48914 | 969 | 527 | 223 | 797 | 548 | 526 |
| Naïve | 45189 | 45096 | 45508 | 44334 | 45177 | 47004 | 1327 | 938 | 579 | 1342 | 930 | 350 |

| | Hep3B Day 3 10 nM | Hep3B Day 3 1 nM | Hep3B Day 3 0.1 nM | Hep3B Day 3 0.01 nM | Hep3B Day 3 0.001 nM | Hep3B Day 3 0.0001 nM | Hep3B Day 3 10 nM SD | Hep3B Day 3 1 nM SD | Hep3B Day 3 0.1 nM SD | Hep3B Day 3 0.01 nM SD | Hep3B Day 3 0.001 nM SD | Hep3B Day 3 0.0001 nM SD |
|---|---|---|---|---|---|---|---|---|---|---|---|---|
| AD-46250.1 | 4495 | 4905 | 6786 | 7022 | 6122 | 6033 | 225 | 105 | 56 | 85 | 151 | 49 |
| AD-46265.1 | 6453 | 6990 | 6917 | 6685 | 6165 | 5974 | 187 | 79 | 103 | 70 | 121 | 21 |
| AD-46231.1 | 6478 | 7042 | 6808 | 6444 | 6173 | 5987 | 97 | 19 | 35 | 66 | 131 | 69 |
| AD-46251.1 | 5663 | 5990 | 6084 | 6241 | 5869 | 6298 | 445 | 38 | 73 | 69 | 63 | 88 |
| AD-46261.1 | 5380 | 6025 | 5824 | 6325 | 5801 | 6076 | 376 | 14 | 29 | 67 | 81 | 65 |
| AD-46253.1 | 5417 | 6078 | 5840 | 6113 | 5568 | 6503 | 549 | 29 | 103 | 81 | 20 | 72 |
| AD-46244.1 | 4743 | 5479 | 5884 | 6078 | 6170 | 6593 | 29 | 43 | 51 | 168 | 60 | 70 |
| AD-46269.1 | 2788 | 2958 | 5479 | 5878 | 5899 | 5739 | 64 | 14 | 97 | 215 | 80 | 22 |
| AD-46270.1 | 4378 | 4720 | 5579 | 6127 | 6066 | 6522 | 235 | 94 | 167 | 17 | 43 | 260 |
| AD-46282.1 | 5096 | 5932 | 6258 | 5988 | 6068 | 6724 | 101 | 34 | 32 | 107 | 59 | 20 |
| AD-46297.1 | 1134 | 1325 | 4477 | 6051 | 6199 | 6626 | 40 | 64 | 80 | 101 | 134 | 55 |
| AD-46299.1 | 5875 | 5836 | 6251 | 5872 | 6016 | 6726 | 47 | 64 | 39 | 54 | 81 | 104 |
| AD-46303.1 | 6879 | 7060 | 6801 | 6793 | 6306 | 6827 | 43 | 32 | 59 | 60 | 126 | 65 |
| AD-46307.1 | 6951 | 6826 | 6613 | 6511 | 6119 | 7093 | 97 | 148 | 46 | 82 | 97 | 91 |
| AD-46273.1 | 6628 | 6749 | 6711 | 6839 | 6237 | 6958 | 122 | 24 | 59 | 59 | 48 | 109 |
| AD-46286.1 | 5384 | 5405 | 5755 | 6469 | 6299 | 6207 | 81 | 5 | 45 | 33 | 95 | 58 |
| AD-46249.1 | 3955 | 4239 | 5214 | 6549 | 6171 | 6537 | 141 | 70 | 134 | 37 | 35 | 27 |
| AD-46295.1 | 6186 | 6535 | 5776 | 6500 | 6247 | 6252 | 96 | 34 | 141 | 35 | 41 | 35 |
| AD-19200 | 2304 | 3860 | 5592 | 6634 | 6063 | 6111 | 95 | 24 | 43 | 41 | 67 | 74 |
| PLK | 1484 | 1668 | 3385 | 6283 | 5714 | 6015 | 36 | 52 | 130 | 94 | 112 | 143 |
| AD-1955 | 5718 | 5826 | 5633 | 6356 | 6369 | 6460 | 27 | 60 | 16 | 80 | 108 | 122 |
| Naïve | 5799 | 6503 | 6350 | 6351 | 6002 | 6449 | 69 | 98 | 44 | 40 | 72 | 66 |
| Naïve | 5623 | 6550 | 5950 | 6103 | 5574 | 6489 | 23 | 49 | 37 | 82 | 59 | 93 |
| Naïve | 5895 | 6021 | 5550 | 5908 | 5573 | 6769 | 72 | 27 | 55 | 90 | 64 | 42 |

| | Hep3B Day 5 10 nM | Hep3B Day 5 1 nM | Hep3B Day 5 0.1 nM | Hep3B Day 5 0.01 nM | Hep3B Day 5 0.001 nM | Hep3B Day 5 0.0001 nM | Hep3B Day 5 10 nM SD | Hep3B Day 5 1 nM SD | Hep3B Day 5 0.1 nM SD | Hep3B Day 5 0.01 nM SD | Hep3B Day 5 0.001 nM SD | Hep3B Day 5 0.0001 nM SD |
|---|---|---|---|---|---|---|---|---|---|---|---|---|
| AD-46250.1 | 4758 | 5572 | 9636 | 12294 | 11079 | 10674 | 311 | 285 | 180 | 901 | 575 | 403 |
| AD-46265.1 | 9937 | 12543 | 10822 | 13430 | 12967 | 12089 | 323 | 1714 | 1094 | 107 | 1407 | 704 |
| AD-46231.1 | 12650 | 13786 | 11763 | 13765 | 14003 | 13857 | 1002 | 422 | 1551 | 177 | 213 | 320 |
| AD-46251.1 | 8543 | 9397 | 10581 | 13642 | 12990 | 13568 | 518 | 1054 | 707 | 289 | 1247 | 475 |
| AD-46261.1 | 10459 | 11700 | 11735 | 13764 | 13738 | 13210 | 148 | 1308 | 459 | 277 | 712 | 210 |
| AD-46253.1 | 11125 | 12124 | 11533 | 14213 | 13967 | 11946 | 473 | 1531 | 772 | 262 | 679 | 1015 |
| AD-46244.1 | 7330 | 7939 | 10428 | 12695 | 13584 | 11852 | 451 | 416 | 1104 | 61 | 358 | 1473 |
| AD-46269.1 | 2316 | 2442 | 11476 | 13621 | 12821 | 11090 | 507 | 623 | 574 | 299 | 831 | 298 |
| AD-46270.1 | 6643 | 5235 | 11774 | 12788 | 13487 | 11895 | 179 | 386 | 709 | 1032 | 635 | 760 |
| AD-46282.1 | 7767 | 10214 | 12650 | 12859 | 12980 | 11175 | 214 | 1116 | 569 | 1282 | 925 | 169 |
| AD-46297.1 | 1012 | 1124 | 9438 | 12403 | 12063 | 11599 | 47 | 96 | 162 | 990 | 1118 | 83 |
| AD-46299.1 | 13643 | 13396 | 12404 | 12113 | 12782 | 12913 | 1585 | 2086 | 202 | 896 | 1040 | 1209 |
| AD-46303.1 | 10567 | 12918 | 10617 | 11203 | 11189 | 11260 | 456 | 1263 | 106 | 309 | 310 | 153 |
| AD-46307.1 | 13787 | 14089 | 11830 | 13512 | 13489 | 12773 | 208 | 467 | 900 | 60 | 504 | 203 |
| AD-46273.1 | 13801 | 13484 | 12719 | 14212 | 14305 | 12499 | 386 | 219 | 1250 | 382 | 128 | 176 |
| AD-46286.1 | 5783 | 6472 | 10990 | 14352 | 14424 | 12234 | 93 | 78 | 472 | 632 | 103 | 649 |
| AD-46249.1 | 3763 | 5086 | 10729 | 14293 | 14283 | 12608 | 269 | 124 | 453 | 570 | 443 | 633 |
| AD-46295.1 | 14870 | 15096 | 11289 | 14697 | 14336 | 12000 | 539 | 224 | 453 | 698 | 689 | 903 |
| AD-19200 | 1546 | 6337 | 10310 | 14261 | 13551 | 11486 | 132 | 379 | 456 | 250 | 646 | 754 |
| PLK | 1337 | 1636 | 6996 | 14661 | 13860 | 12555 | 31 | 79 | 759 | 740 | 423 | 296 |
| AD-1955 | 11717 | 12560 | 12164 | 14504 | 13008 | 11077 | 1146 | 1210 | 1289 | 392 | 1405 | 56 |
| Naïve | 13989 | 14873 | 11512 | 14022 | 13458 | 11399 | 404 | 316 | 267 | 412 | 635 | 114 |
| Naïve | 14167 | 14550 | 11269 | 14247 | 13793 | 11771 | 197 | 426 | 230 | 640 | 664 | 888 |
| Naïve | 13857 | 14632 | 10432 | 13485 | 14164 | 12808 | 231 | 1150 | 474 | 546 | 177 | 1028 |

Example 4

TMPRSS6 siRNA Duplex Lead Selection

Figure 2B:
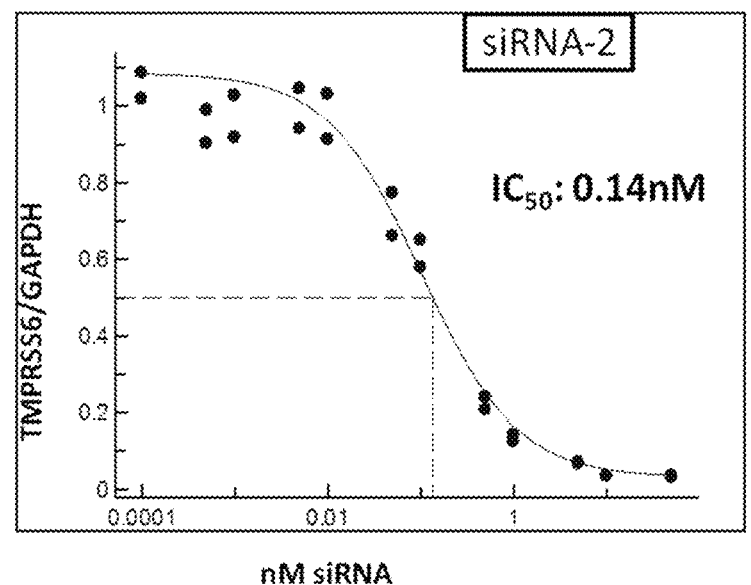

To select specific TMPRSS6 siRNAs for use in further in vivo experimentation, chemically modified siRNAs were screened by transfection in HEP3B human hepatoma cells for TMPRSS6 gene silencing activity. Two highly potent siRNAs with minimal predicted off-target potential and with multi-species reactivity, including human cynomolgus monkey, rat, and mouse, were selected for evaluation in vivo. Potency of the two selected TMPRSS6 siRNAs was also confirmed in primary mouse hepatocytes, wherein both TMPRSS6 siRNA-1 (AD-46273) and TMPRSS6 siRNA-2 (AD-46286) demonstrated strong TMPRSS6 gene silencing activity, with TMPRSS6 siRNA-1 (AD-46273) demonstrating an $IC_{50}$ of 70 pM (FIG. 2A) and TMPRSS6 siRNA-2 (AD-46286) demonstrating an $IC_{50}$ of 140 pM (FIG. 2B).

Example 5

The Effect of TMPRSS6 siRNA Mediated Silencing of TMPRSS6 in WT C57BL/6 Mice The Effect of TMPRSS6 siRNA on TMPRSS6 and HAMP1 mRNA Expression in WT C57BL/6 Mice.

Figure 3A:
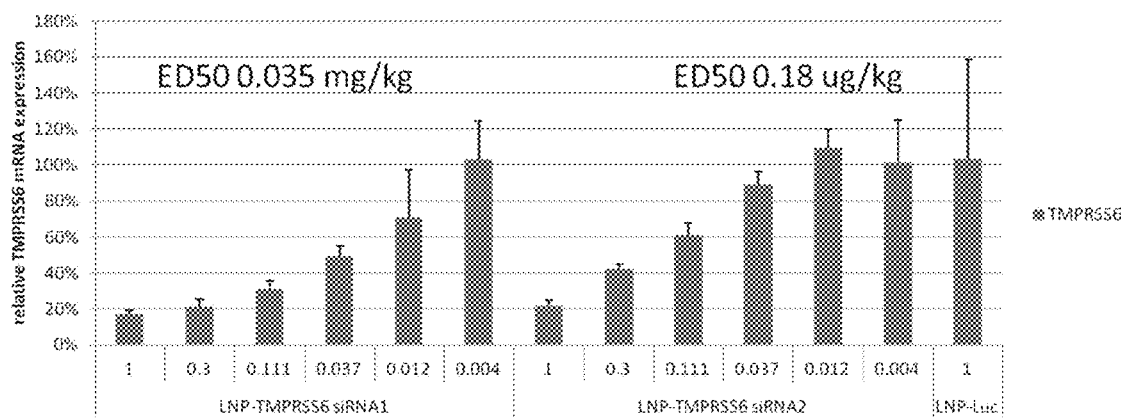
FIGS. 3A and 3B depict the effect of LNP-TMPRSS6 siRNA-1 (AD-46273) and LNP-TMPRSS6 siRNA-2 (AD-46286), on TMPRSS6 and HAMP1 gene expression, respectively, in WT C57BL/6 mice.
Figure 3B:
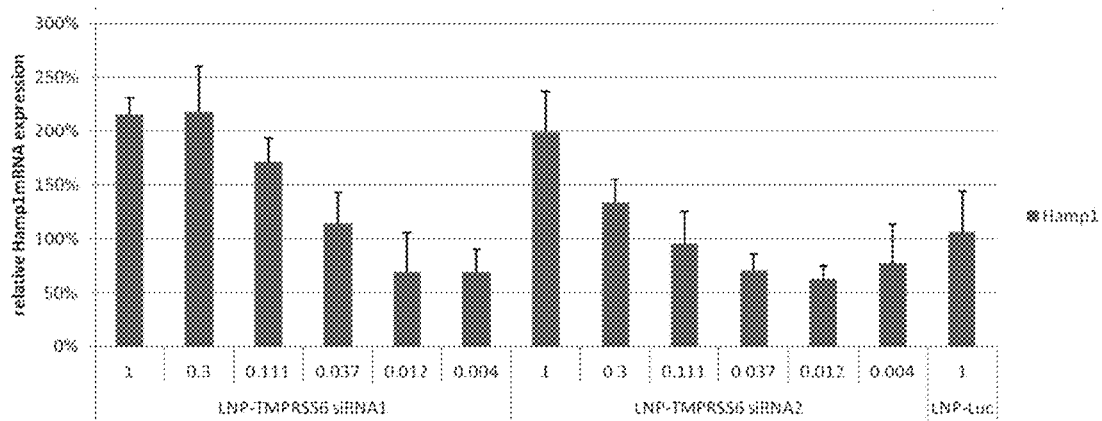

In order to evaluate the effect of LNP-TMPRSS6 siRNA-1 (AD-46273) and LNP-TMPRSS6 siRNA-2 (AD-46286) in vivo, eight week old female WT C57BL/6 mice were dosed via tail vein IV injection with 1 mg/kg LNP-TMPRSS6 siRNA-1 (AD-46273) or LNP-TMPRSS6 siRNA-2 (AD-46286) or LNP-AD-19551 (siRNA targeting the non-mammalian gene LUCIFERASE). The TMPRSS6 siRNAs were formulated with LNP11 (MC3). The mice were sacrificed 24 hours post dosing, and livers removed, flash frozen, and ground into powder. A small amount (~20 mg) of liver powder was disrupted in lysis buffer and used for mRNA analysis by TaqMan®. A total of five mice were used per group. The data are expressed as a percent of LNP-Luc control ratios of target TMPRSS6 mRNA relative to B-actin mRNA. As shown in FIG. 3A, there was a specific and potent dose dependent inhibition of liver TMPRSS6 mRNA expression by LNP-TMPRSS6 siRNA-1 (AD-46273) and LNP-TMPRSS6 siRNA-2 (AD-46286) (data represent mean+/−standard deviation), with an $ED_{50}$ of 0.035 mg/kg, and an $ED_{50}$ of 0.18 mg/kg, respectively. As shown in FIG. 3B, there was also a dose dependent inhibition of liver HAMP1 mRNA expression by LNP-TMPRSS6 siRNA-1 (AD-46273) and LNP-TMPRSS6 siRNA-2 (AD-46286).

The Duration of TMPRSS6 siRNA Mediated Silencing of TMPRSS6 and HAMP1 Gene Expression in WT C57BL/6 Mice.

Figure 4:
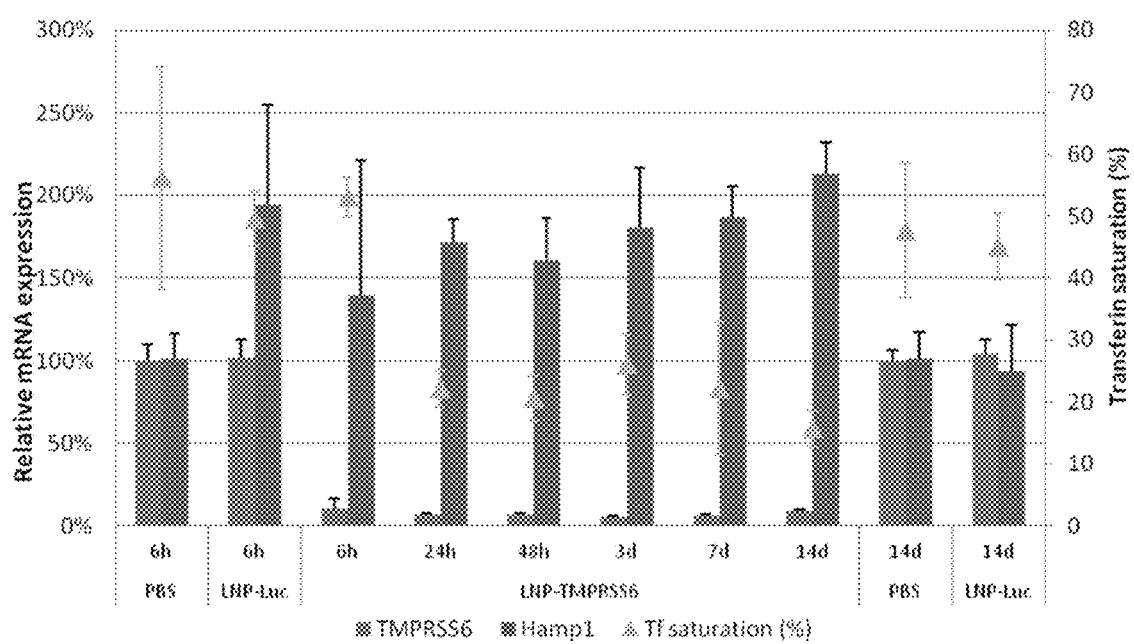
FIG. 4 depicts the duration of the TMPRSS6 siRNA mediated effects on TMPRSS6 gene expression, HAMP1 gene expression, and serum iron levels in WT C57BL/6 mice.

In order to evaluate the duration of the TMPRSS6 siRNA mediated knockdown of TMPRSS6 and HAMP1 gene expression, eight week old WT C57BL/6 mice were administered a single 1 mg/kg dose via tail vein IV injection with LNP-TMPRSS6 siRNA-1 (AD-46273), or LNP-Luc control (LNP-AD-1955), or PBS; all siRNA agents were delivered as LNP11 formulations. The mice were sacrificed at 6 hours, 24 hours, 48 hours, 3 days, 7 days, and 14 days. The mRNA expression level of TMPRSS6 and HAMP1 in the liver was analyzed using TaqMan® assay and normalized to B-actin. Five mice were used per group, and the data is represented in FIG. 4 as mean+/− standard deviation. As shown in FIG. 4, 1 mg/kg single dose of LNP-TMPRSS6 siRNA-1 (AD-46273) knocked down TMPRSS6 mRNA expression as early as six hours post dosing, and reduced TMPRSS6 mRNA expression to approximately 90% of LNP-Luc control or PBS control for the duration of the two week time period. HAMP1 gene expression was increased starting 24 hours post dosing and was maintained for the duration of the two week time period, with a maximum increase of 200% of control on day 14 post dosing (FIG. 4). In addition, serum iron levels were assayed as the percentage of transferrin (Tf) saturation using an Olympus AU 400. The level of transferrin saturation was calculated as the ratio of serum iron to total iron binding capacity (TIBC) and is expressed as a percent of transferrin saturation. The percent of transferrin saturation was reduced by approximately 50% starting 24 hours post dosing and maintained over the two week time period, indicating that the circulating iron levels in the serum were decreased (FIG. 4). Level of TMPRSS6 siRNA mediated silencing of TMPRSS6 necessary to maintain the TMPRSS6 siRNA mediated effects on HAMP1 gene expression and serum iron levels in WT C57BL/6 Mice.

Figure 5:
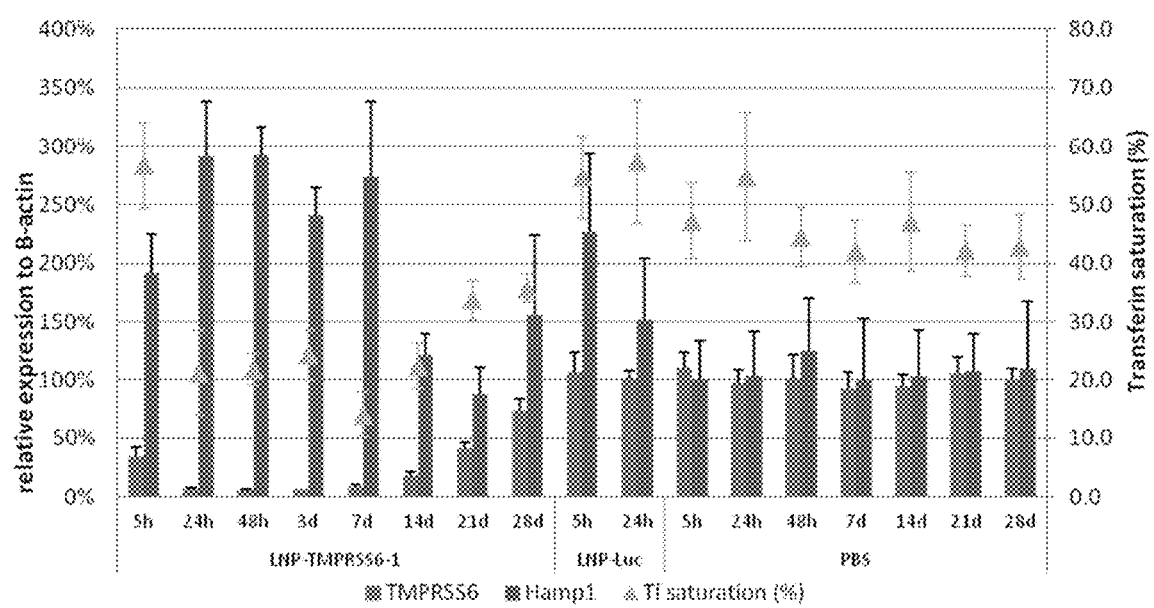
FIG. 5 depicts the level of TMPRSS6 siRNA mediated silencing of TMPRSS6 necessary to maintain the TMPRSS6 siRNA mediated effects on HAMP1 gene expression and serum iron levels in WT C57BL/6 mice.

In order to evaluate the level of TMPRSS6 siRNA mediated silencing of TMPRSS6 necessary to maintain the TMPRSS6 siRNA mediated effects on HAMP1 gene expression and serum iron levels in WT C57BL/6 mice; C57BL/6 mice were dosed with 0.3 mg/kg LNP-TMPRSS6 siRNA-1 (AD-46273), or LNP-Luc control, or PBS; all siRNA agents were delivered as LNP11 formulations. The mice were sacrificed at 5 hours, 24 hours, 48 hours, 3 days, 7 days, 14 days, 21, days, and 28 days post dosing. The mRNA expression level of TMPRSS6 and HAMP1 was analyzed using TaqMan® assay and normalized to B-actin. Five mice were used per group, and the data is represented in FIG. 5 as mean+/−standard deviation. As shown in FIG. 5, the maximal reduction of TMPRSS6 gene expression of 90% was achieved 24 hours post dosing and maintained up until day three post dosing. At day seven post dosing, TMPRSS6 gene expression was reduced by approximately 85%; HAMP1 gene expression was induced to approximately 250% of control; and transferrin saturation (%) was reduced by approximately 50% (FIG. 5). At day 21 post dosing, TMPRSS6 gene expression was reduced by approximately 40%; HAMP1 gene expression had normalized; and serum iron levels, as measured by transferrin saturation (%), began to return to normal levels (FIG. 5). In summary, maximal knockdown of TMPRSS6 mRNA expression was achieved at 24 hours post dosing and returned to approximately 50% of normal expression levels by 3 weeks post dosing; hepcidin mRNA levels were increased as early as 24 hours and maintained up to seven days post dosing; hepcidin levels returned to control levels on day fourteen post dosing; and transferrin saturation, as an indicator of circulating iron levels, was reduced by 50% of control levels as early as 24 hours post dosing, and was normalized towards week four. Thus the data presented in FIG. 5 illustrates that more than 50% TMPRSS6 silencing is required to maintain the LNP-TMPRSS6 siRNA-1 (AD-46273) mediated effects on HAMP1 gene expression and serum iron levels.

The Effect of TMPRSS6 siRNA Mediated Silencing of TMPRSS6 on Hematological Parameters in WT C57BL/6 Mice.

Figure 6A:
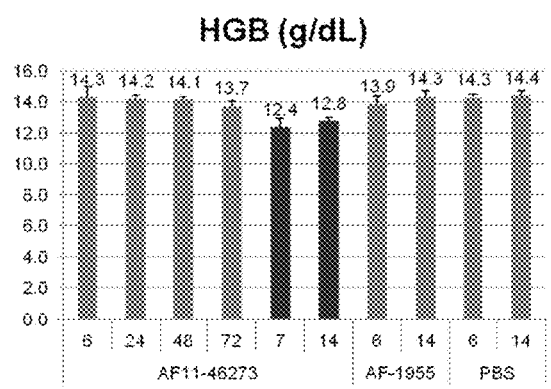
FIGS. 6A and 6B depict the effect of TMPRSS6 siRNA mediated silencing of TMPRSS6 on hematological parameters in WT C57BL/6 mice.
Figure 6B:
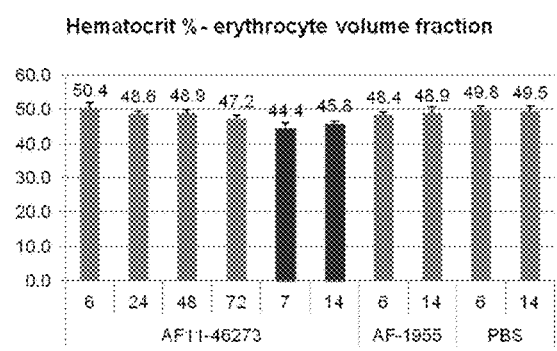

In order to evaluate the effect of TMPRSS6 siRNA mediated silencing of TMPRSS6 on hematological parameters, including hemoglobin (HGB) and hematocrit; WT C57BL/6 mice were dosed with 1 mg/kg single dose of TMPRSS6 siRNA-1 (AD-46273) or LNP-Luc control, or PBS; and subsequently sacrificed at different time points up to two weeks post dosing. Hematological parameters including, hemoglobin (HGB), hematocrit, mean corpuscular volume (MCV), mean corpuscular hemoglobin (MCH), mean corpuscular hemoglobin concentration (MCHC), and the reticulocyte hemoglobin content (Chr) were assayed using Advia 120 analyzer. As shown in FIGS. 6A and 6B, silencing of TMPRSS6 in Th3/+ mice led to a decrease HGB (FIG. 6A), and a decrease in hematocrit (FIG. 6B) in WT C57BL/6 mice. There was a similar effect on mean corpuscular volume (MCV), mean corpuscular hemoglobin (MCH), mean corpuscular hemoglobin concentration (MCHC), and the reticulocyte hemoglobin content (Chr).

Example 6

The Effect of TMPRSS6 siRNA Mediated Silencing of TMPRSS6 in Thalassemic Mice (Th3/+)

The Effect of TMPRSS6 siRNA Mediated Silencing of TMPRSS6 on Serum Iron Parameters in Thalassemic Mice (Th3/+).

Figure 7:
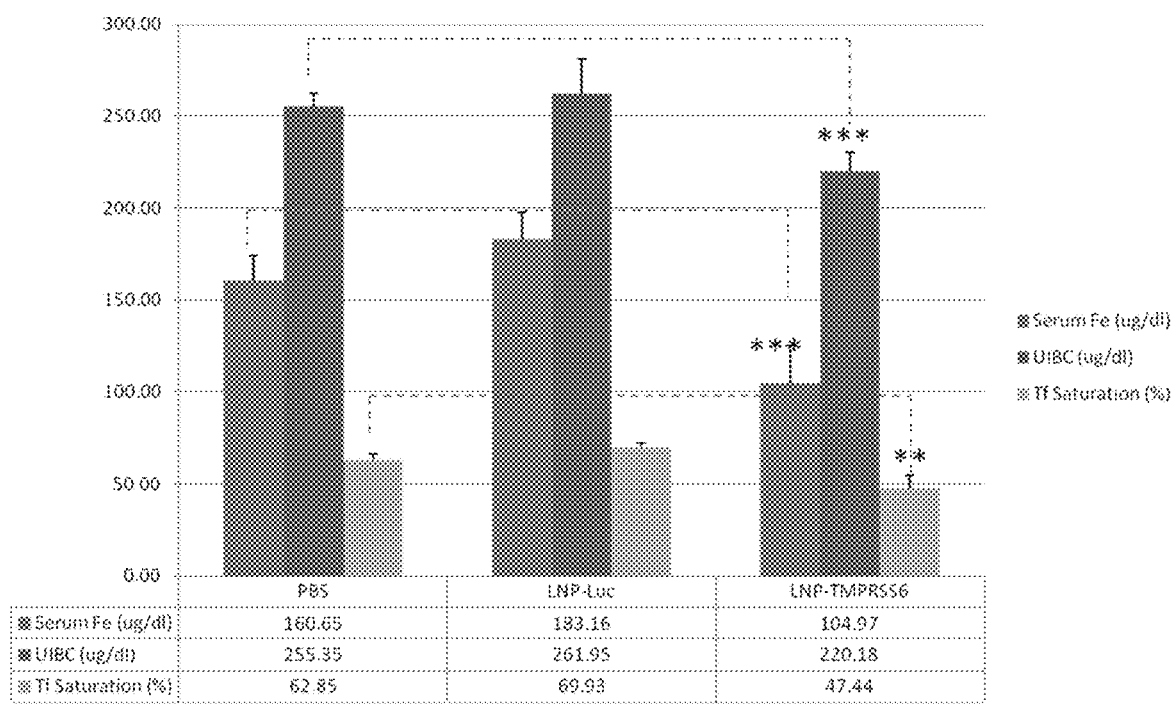
FIG. 7 depicts the effect of TMPRSS6 siRNA mediated silencing of TMPRSS6 on serum iron parameters in thalassemic mice (Th3/+), including serum iron levels, unsaturated iron binding capacity (UIBC) levels, and transferrin saturation levels.

To evaluate the effect of TMPRSS6 siRNA mediated silencing of TMPRSS6 on serum iron parameters, including iron levels, unsaturated iron-binding capacity (UIBC), and Tf saturation in thalassemic mice (Th3/+), six week old Th3/+ mice were dosed via tail vein injection with 1 mg/kg LNP-TMPRSS6 siRNA-1 (AD-46273), or LNP-Luc control, or PBS, and the mice were sacrificed two weeks post dosing. Five mice were used per group, and data represented in FIG. 7 as mean+/−standard deviation, with  denoting a P-value<0.01 and * denoting a P-value<0.001. As shown in FIG. 7, silencing of TMPRSS6 in Th3/+ mice led to a significant reduction of serum iron, UIBC, and Tf saturation compared to the control PBS group.

The Effect of TMPRSS6 siRNA Mediated Silencing of TMPRSS6 on Reticulocyte and Erthyrocyte Parameters in Thalassemic Mice (Th3/+).

Figure 8A:
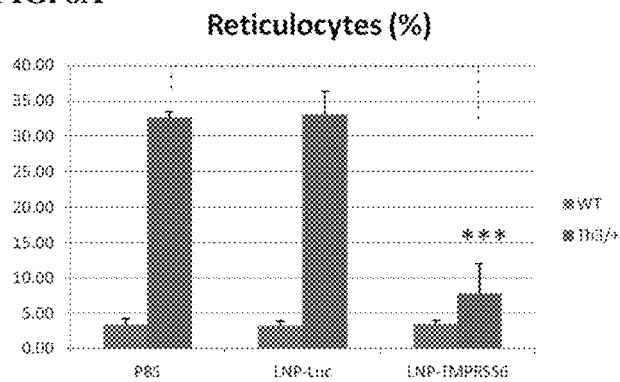
FIGS. 8A to 8C depict the effects of TMPRSS6 siRNA mediated silencing of TMPRSS6 on reticulocyte and erythrocyte parameters in thalassemic mice (Th3/+).
Figure 8B:
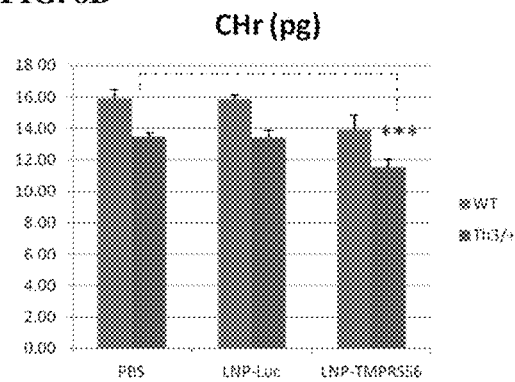
Figure 8C:
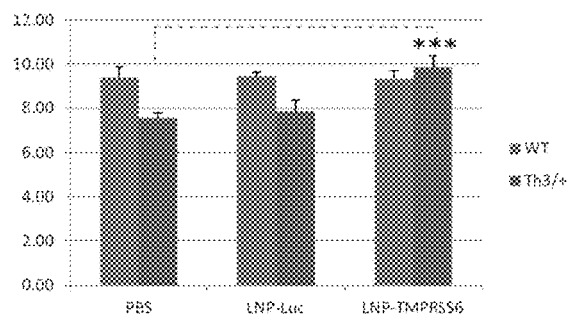

To evaluate the effect of TMPRSS6 siRNA mediated silencing of TMPRSS6 on reticulocyte and erythrocyte parameters, including reticulocyte number, reticulocyte hemoglobin content (CHr), and erythrocyte number (RBC), in thalassemic mice (Th3/+); six week old Th3/+ mice were dosed via tail vein injection, with 1 mg/kg LNP-TMPRSS6 siRNA-1 (AD-46273), or LNP-Luc control, or PBS, and the mice were sacrificed two weeks post dosing. Reticulocyte and erythrocyte parameters, including reticulocyte number, reticulocyte hemoglobin content (CHr), and erythrocyte number (RBC) were assayed using Advia 120 analyzer. Five mice were used per group, and the data is represented in FIGS. 8A-8C as mean+/−standard deviation, with  denoting a P-value<0.01 and * denoting a P-value<0.001. As shown in FIGS. 8A and 8B, respectively, silencing of TMPRSS6 in Th3/+ mice led to a significant reduction in the number of reticulocytes as well as the hemoglobin content of reticulocytes (Chr). In addition, silencing of TMPRSS6 in Th3/+ mice led to a significant increase in the number of mature erythrocytes (RBC) (FIG. 8C), demonstrating a significant improvement in ineffective erythropoiesis, extramedullary hematopoiesis, and red blood cell production.

The Effect of TMPRSS6 siRNA Mediated Silencing of TMPRSS6 on Hematological Parameters in Thalassemic Mice (Th3/+).

Figure 9A:
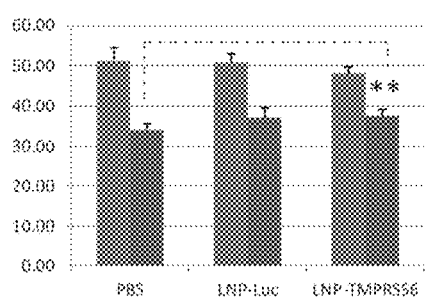
FIGS. 9A to 9D depicts the effect of TMPRSS6 siRNA mediated silencing of TMPRSS6 on hematological parameters in thalassemic mice (Th3/+).
Figure 9B:
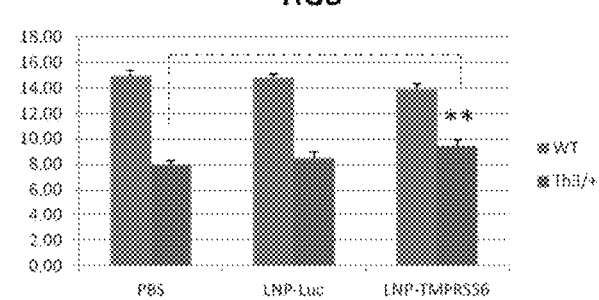
Figure 9C:
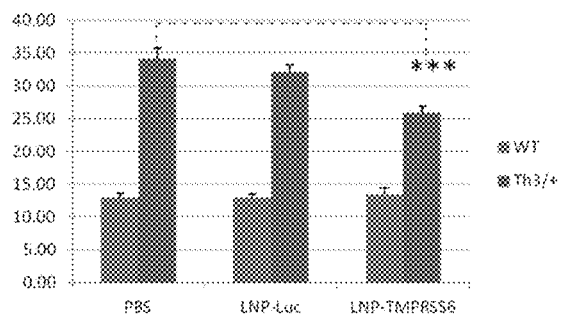
Figure 9D:
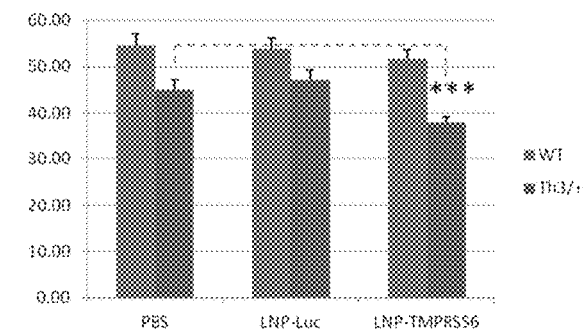

To evaluate the effect of TMPRSS6 siRNA mediated silencing of TMPRSS6 on hematological parameters, including hematocrit (HCT), hemoglobin (HGB), red blood cell distribution width (RDW), and mean corpuscle value (MCV) in thalassemic mice (Th3/+); six week old Th3/+ mice were dosed via tail vein injection, with 1 mg/kg LNP-TMPRSS6 siRNA-1 (AD-46273), or LNP-Luc control, or PBS, and the mice were sacrificed two weeks post dosing. Hematological paramters including hematocrit (HCT), hemoglobin (HGB), red blood cell distribution width (RDW), and mean corpuscle value (MCV); were assayed using Advia 120 analyzer. Five mice were used per group, and the data is represented in FIG. 9 as mean+/−standard deviation, with  denoting a P-value<0.01 and * denoting a P-value<0.001. Silencing of TMPRSS6 in Th3/+ mice led to a significant increase in HCT (FIG. 9A), a significant increase in HGB (FIG. 9B), a significant decrease in RDW (FIG. 9C), and a significant decrease in MCV (FIG. 9D). The data presented in FIG. 9 illustrates a normalization of the β-thalassemia phenotype in these hematological parameters post administration of the LNP-TMPRSS6 siRNA-1 (AD-46273).

The Effect of TMPRSS6 siRNA Mediated Silencing of TMPRSS6 on Peripheral Blood Morphology in Thalassemic Mice (Th3/+).

To evaluate the effect of TMPRSS6 siRNA mediated silencing of TMPRSS6 on peripheral blood morphology in thalassemic mice (Th3/+); six week old Th3/+ mice were dosed via tail vein injection with, 1 mg/kg LNP-TMPRSS6 siRNA-1 (AD-46273) or LNP-Luc control, and the mice were sacrificed two weeks post dosing. May-Grunwald/Gimsa stain at 10× magnification showed a marked decrease in polychromasia in the Th3/+ mice treated with the TMPRSS6 siRNA compared to control, representative of the decreased reticulocyte number as well as an overall trend toward normalization of the mature red blood cell morphology. May-Grunwald/Gimsa stain at 10× magnification also showed slight anisocytosis was induced by the WT TMPRSS6 siRNA animal when compared to WT control animal.

The Effect of TMPRSS6 siRNA Mediated Silencing of TMPRSS6 on Splenic Architecture in Thalassemic Mice (Th3/+).

To evaluate the effect of TMPRSS6 siRNA mediated silencing of TMPRSS6 on splenic architecture in thalassemic mice (Th3/+); six week old Th3/+ mice were dosed via tail vein injection, with 1 mg/kg LNP-TMPRSS6 siRNA-1 (AD-46273), or LNP-Luc control, or PBS, and mice were sacrificed two weeks post dosing. Hematoxylin and eosin (H&E) stain at 10× magnification showed Th3/+ mice treated with the TMPRSS6 siRNA compared to control had a normalization of splenic architecture, including a reduction in sinusoidal extramedullary erythropoiesis and the reappearance of white pulp nodules.

The Effect of TMPRSS6 siRNA Mediated Silencing of TMPRSS6 on Spleen and Liver Iron Content in Thalassemic Mice (Th3/+).

Figure 10A:
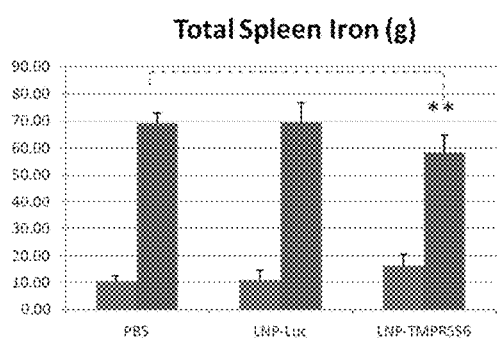
FIGS. 10A to 10C depict the effect of TMPRSS6 siRNA mediated silencing of TMPRSS6 on spleen and liver iron content in thalassemic mice (Th3/+).
Figure 10B:
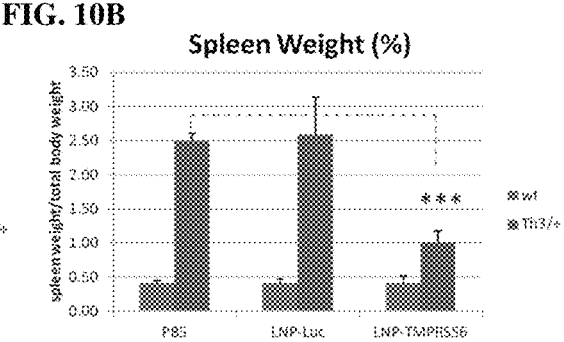
Figure 10C:
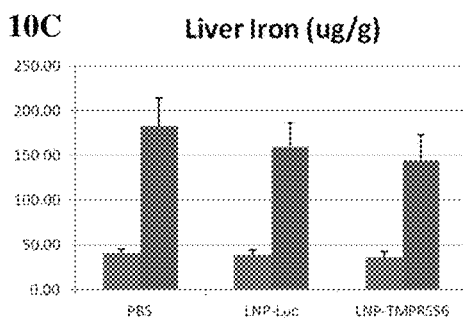

To evaluate the effect of TMPRSS6 siRNA mediated silencing of TMPRSS6 on spleen and liver iron content in thalassemic mice (Th3/+); six week old Th3/+ mice were dosed via tail vein injection, with 1 mg/kg LNP-TMPRSS6 siRNA-1 (AD-46273), or LNP-Luc control, or PBS, and the mice were sacrificed two weeks post dosing. Five mice were used per group, and the data is represented in FIGS. 10A-10C as mean+/−standard deviation, with  denoting a P-value<0.01 and * denoting a P-value<0.001. Silencing of TMPRSS6 in Th3/+ mice led to a significant reduction of spleen iron content and spleen weight (FIG. 10A and FIG. 10B, respectively), indicating a normalization of extramedullary hematopoiesis. A trend towards a reduction liver iron content was also observed, but was not statistically significant (FIG. 10C).

The above results demonstrate that silencing of TMPRSS6 by systemic administration of formulated siRNAs increases HAMP expression to levels sufficient to ameliorate the phenotype in a mouse model of β-thalassemia intermedia. Therefore, LNP-TMPRSS6-siRNAs are being developed for congenital iron overload disorders characterized by abnormally low hepcidin levels, (e.g., β-thalassemia intermedia and hereditary hemochromatosis).

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A double-stranded ribonucleic acid (dsRNA) agent for inhibiting expression of TMPRSS6 in a cell, wherein said dsRNA agent comprises a sense strand and an antisense strand forming a double-stranded region, wherein the antisense strand comprises the nucleotide sequence of any one of 5'-UCcAAAGGGcAGCUGAGCUdTsdT-3' (SEQ ID NO: 577), 5'-UUCcAAAGGGcAGCUGAGCdTsdT-3' (SEQ ID NO: 585), 5'-uAUUCcAAAGGGcAGCUGAdTsdT-3' (SEQ ID NO: 593), or 5'-UuAUUCcAAAGGGcAGCUGdTsdT-3 (SEQ ID NO: 601), wherein a, g, c and u are 2'-O-methyl (2'-OMe) A, G, C, and U; dT is a deoxy-thymine nucleotide;

and s is a phosphorothioate linkage.

2. The dsRNA agent of claim 1, wherein each strand is no more than 30 nucleotides in length.

3. The dsRNA agent of claim 1, wherein at least one strand comprises a 3' overhang of at least 1 nucleotide or at least 2 nucleotides.

4. The dsRNA agent of claim 1, further comprising a ligand.

5. The dsRNA agent of claim 4, wherein the ligand is conjugated to the 3' end of the sense strand of the dsRNA agent.

6. A cell containing the dsRNA agent of claim 1.

7. A pharmaceutical composition for inhibiting expression of a TMPRSS6 gene comprising the dsRNA agent of claim 1.

8. The pharmaceutical composition of claim 7, further comprising a lipid formulation.

9. A method of inhibiting TMPRSS6 expression in a cell, the method comprising:

(a) introducing into the cell the dsRNA agent of claim 1; and (b) maintaining the cell produced in step (a) for a time sufficient to obtain degradation of the mRNA transcript of a TMPRSS6 gene, thereby inhibiting expression of the TMPRSS6 gene in the cell.

10. The method of claim 9, wherein the TMPRSS6 expression is inhibited by at least 30%.

11. A method of treating a disorder mediated by TMPRSS6 expression comprising administering to a human in need of such treatment a therapeutically effective amount of the dsRNA agent of claim 1.

12. The method of claim 11, wherein the human has a disorder associated with hemochromatosis, a β-thalassemia, or β-thalassemia intermedia.

13. The method of claim 11, wherein the human has a β-thalassemia and wherein the administration of the dsRNA agent to the subject causes a decrease in iron in the serum of the subject by at least 10%.

14. The method of claim 11, wherein the dsRNA agent is administered at a concentration of 0.01 mg/kg-5 mg/kg bodyweight of the subject.

15. The dsRNA agent of claim 1, wherein the antisense strand consists of a nucleotide sequence selected from the group consisting of
5'-UCcAAAGGGcAGCUGAGCUdTsdT-3' (SEQ ID NO: 577),
5'-UUCcAAAGGGcAGCUGAGCdTsdT-3' (SEQ ID NO: 585),
5'-uAUUCcAAAGGGcAGCUGAdTsdT-3' (SEQ ID NO: 593), and
5'-UuAUUCcAAAGGGcAGCUGdTsdT-3' (SEQ ID NO: 601),
wherein a, g, c and u are 2'-O-methyl (2'-OMe) A, G, C, and U; dT is a deoxy-thymine nucleotide; and s is a phosphorothioate linkage.

16. The dsRNA of claim 1, wherein the sense strand comprises the nucleotide sequence of any one of
5'-AGcucAGcuGcccuuuGGAdTsdT-3' (SEQ ID NO: 576),
5'-GcucAGcuGcccuuuGGAAdTsdT-3' (SEQ ID NO: 584),
5'-ucAGcuGcccuuuGGAAuAdTsdT-3' (SEQ ID NO: 592), or
5'-cAGcuGcccuuuGGAAuAAdTsdT-3' (SEQ ID NO: 600),
wherein a, g, c and u are 2'-O-methyl (2'-OMe) A, G, C, and U; dT is a deoxy-thymine nucleotide; and s is a phosphorothioate linkage.

17. The dsRNA of claim 1,
wherein the antisense strand comprises the nucleotide sequence of 5' UCcAAAGGGcAGCUGAGCUdTsdT-3' (SEQ ID NO: 577) and the sense strand comprises the nucleotide sequence of 5'-AGcucAGcuGcccuuuGAdTsdT-3' (SEQ ID NO: 576);
wherein the antisense strand comprises the nucleotide sequence of 5'-UUCcAAAGGGcAGCUGAGCdTsdT-3' (SEQ ID NO: 585) and the sense strand comprises the nucleotide sequence of 5'-GcucAGcuGcccuuuGAAdTsdT-3' (SEQ ID NO: 584);
wherein the antisense strand comprises the nucleotide sequence of 5'-uAUUCcAAAGGGcAGCUGAdTsdT-3' (SEQ ID NO: 593) and the sense strand comprises the nucleotide sequence of 5'-ucAGcuGcccuuuGAAuAdTsdT-3' (SEQ ID NO: 592); or
wherein the antisense strand comprises the nucleotide sequence of 5'-UuAUUCcAAAGGGcAGCUGdTsdT-3' (SEQ ID NO: 601) and the sense strand comprises the nucleotide sequence of 5'-cAGcuGcccuuuGAAuAAdTsdT-3' (SEQ ID NO: 600), and
wherein a, g, c and u are 2'-O-methyl (2'-OMe) A, G, C, and U; dT is a deoxy-thymine nucleotide; and s is a phosphorothioate linkage.

18. The dsRNA agent of claim 1, wherein at least one end of the dsRNA is blunt.

19. The dsRNA agent of claim 1, wherein the dsRNA comprises a duplex region between 15-30 base pairs.

20. The dsRNA agent of claim 4, wherein the ligand is a cell or tissue targeting group chosen from a lectin, a glycoprotein, a lipid, or an antibody that binds to a specified cell type.

21. The dsRNA agent of claim 4, wherein the ligand is a multivalent galactose, N-acetyl-galactosamine, an N-acetyl-galacosamine multivalent mannose, or a cholesterol.

22. The dsRNA agent of claim 1, wherein the sense strand consists of a nucleotide sequence selected from the group consisting of
5'-AGcucAGcuGcccuuuGGAdTsdT-3' (SEQ ID NO: 576),
5'-GcucAGcuGcccuuuGGAAdTsdT-3' (SEQ ID NO: 584),
5'-ucAGcuGcccuuuGGAAuAdTsdT-3' (SEQ ID NO: 592), and
5'-cAGcuGcccuuuGGAAuAAdTsdT-3' (SEQ ID NO: 600),
wherein a, g, c and u are 2'-O-methyl (2'-OMe) A, G, C, and U; dT is a deoxy-thymine nucleotide; and s is a phosphorothioate linkage.

23. The dsRNA agent of claim 22, wherein the antisense strand consists of a nucleotide sequence selected from the group consisting of
5'-UCcAAAGGGcAGCUGAGCUdTsdT-3' (SEQ ID NO: 577),
5'-UUCcAAAGGGcAGCUGAGCdTsdT-3' (SEQ ID NO: 585),
5'-uAUUCcAAAGGGcAGCUGAdTsdT-3' (SEQ ID NO: 593), and
5'-UuAUUCcAAAGGGcAGCUGdTsdT-3' (SEQ ID NO: 601); and
wherein the sense strand consists of a nucleotide sequence selected from the group consisting of
5'-AGcucAGcuGcccuuuGGAdTsdT-3' (SEQ ID NO: 576),
5'-GcucAGcuGcccuuuGGAAdTsdT-3' (SEQ ID NO: 584),
5'-ucAGcuGcccuuuGGAAuAdTsdT-3' (SEQ ID NO: 592), and
5'-cAGcuGcccuuuGGAAuAAdTsdT-3' (SEQ ID NO: 600),
wherein a, g, c and u are 2'-O-methyl (2'-OMe) A, G, C, and U; dT is a deoxy-thymine nucleotide; and s is a phosphorothioate linkage.

* * * * *

SEQUENCE LISTING

<160> NUMBER OF SEQ ID NOS: 611

<210> SEQ ID NO 1
<211> LENGTH: 3212
<212> TYPE: DNA
<213> ORGANISM: Homo sapiens

<400> SEQUENCE: 1

| | | | | | |
|---|---|---|---|---|---|
| cttgagccag | acccagtcca | gctctggtgc | ctgccctctg | gtgcgagctg | acctgagatg | 60 |
| cacttccctc | ctctgtgagc | tgtctcggca | cccacttgca | gtcactgccg | cctgatgttg | 120 |
| ttactcttcc | actccaaaag | gatgcccgtg | gccgaggccc | ccaggtggc | tggcgggcag | 180 |
| ggggacggag | gtgatggcga | ggaagcggag | ccggagggga | tgttcaaggc | ctgtgaggac | 240 |
| tccaagagaa | aagcccgggg | ctacctccgc | ctggtgcccc | tgtttgtgct | gctggccctg | 300 |
| ctcgtgctgg | cttcggcggg | ggtgctactc | tggtatttcc | tagggtacaa | ggcggaggtg | 360 |
| atggtcagcc | aggtgtactc | aggcagtctg | cgtgtactca | atcgccactt | ctcccaggat | 420 |
| cttacccgcc | gggaatctag | tgccttccgc | agtgaaaccg | ccaaagccca | gaagatgctc | 480 |
| aaggagctca | tcaccagcac | ccgcctggga | acttactaca | actccagctc | cgtctattcc | 540 |
| tttgggagg | gacccctcac | ctgcttcttc | tggttcattc | tccaaatccc | cgagcaccgc | 600 |
| cggctgatgc | tgagccccga | ggtggtgcag | gcactgctgg | tggaggagct | gctgtccaca | 660 |
| gtcaacagct | cggctgccgt | ccctacagg | gccgagtacg | aagtggaccc | cgagggccta | 720 |
| gtgatcctgg | aagccagtgt | gaaagacata | gctgcattga | attccacgct | gggttgttac | 780 |
| cgctacagct | acgtgggcca | gggccaggtc | ctccggctga | aggggcctga | ccacctggcc | 840 |
| tccagctgcc | tgtggcacct | gcagggcccc | aaggacctca | tgctcaaact | ccggctggag | 900 |
| tggacgctgg | cagagtgccg | ggaccgactg | gccatgtatg | acgtggccgg | gcccctggag | 960 |
| aagaggctca | tcacctcggt | gtacggctgc | agccgccagg | agcccgtggt | ggaggttctg | 1020 |
| gcgtcggggg | ccatcatggc | ggtcgtctgg | aagaagggcc | tgcacagcta | ctacgacccc | 1080 |
| ttcgtgctct | ccgtgcagcc | ggtggtcttc | caggcctgtg | aagtgaacct | gacgctggac | 1140 |
| aacaggctcg | actcccaggg | cgtcctcagc | accccgtact | tccccagcta | ctactcgccc | 1200 |
| caaacccact | gctcctggca | cctcacggtg | ccctctctgg | actacggctt | ggccctctgg | 1260 |
| tttgatgcct | atgcactgag | gaggcagaag | tatgatttgc | cgtgcaccca | gggccagtgg | 1320 |
| acgatccaga | acaggaggct | gtgtggcttg | cgcatcctgc | agcccctacgc | cgagaggatc | 1380 |
| cccgtggtgg | ccacggccgg | gatcaccatc | aacttcacct | cccagatctc | cctcaccggg | 1440 |
| cccggtgtgc | gggtgcacta | tggcttgtac | aaccagtcgg | accctgccc | tggagagttc | 1500 |
| ctctgttctg | tgaatggact | ctgtgtccct | gcctgtgatg | gggtcaagga | ctgccccaac | 1560 |
| ggcctggatg | agagaaactg | cgtttgcaga | gccacattcc | agtgcaaaga | ggacagcaca | 1620 |
| tgcatctcac | tgcccaaggt | ctgtgatggg | cagcctgatt | gtctcaacgg | cagcgacgaa | 1680 |
| gagcagtgcc | aggaagggggt | gccatgtggg | acattcacct | tccagtgtga | ggaccggagc | 1740 |
| tgcgtgaaga | agcccaaccc | gcagtgtgat | ggcggcccg | actgcaggga | cggctcggat | 1800 |
| gaggagcact | gtgactgtgg | cctccagggc | ccctccagcc | gcattgttgg | tggagctgtg | 1860 |
| tcctccgagg | gtgagtggcc | atggcaggcc | agcctccagg | ttcggggtcg | acacatctgt | 1920 |
| ggggggccc | tcatcgctga | ccgctgggtg | ataacagctg | cccactgctt | ccaggaggac | 1980 |
| agcatggcct | ccacggtgct | gtggaccgtg | ttcctgggca | aggtgtggca | gaactcgcgc | 2040 |
| tggcctggag | aggtgtcctt | caaggtgagc | cgcctgctcc | tgcacccgta | ccacgaagag | 2100 |

```
gacagccatg actacgacgt ggcgctgctg cagctcgacc acccggtggt gcgctcggcc    2160
gccgtgcgcc ccgtctgcct gcccgcgcgc tcccacttct tcgagcccgg cctgcactgc    2220
tggattacgg gctggggcgc cttgcgcgag ggcggcccca tcagcaacgc tctgcagaaa    2280
gtggatgtgc agttgatccc acaggacctg tgcagcgagg tctatcgcta ccaggtgacg    2340
ccacgcatgc tgtgtgccgg ctaccgcaag ggcaagaagg atgcctgtca gggtgactca    2400
ggtggtccgc tggtgtgcaa ggcactcagt ggccgctggt tcctggcggg gctggtcagc    2460
tggggcctgg gctgtggccg gcctaactac ttcggcgtct acacccgcat cacaggtgtg    2520
atcagctgga tccagcaagt ggtgacctga ggaactgccc ccctgcaaag cagggcccac    2580
ctcctggact cagagagccc agggcaactg ccaagcaggg gacaagtat tctggcgggg    2640 ggtgggggag agagcaggcc ctgtggtggc aggaggtggc atcttgtctc gtccctgatg    2700
tctgctccag tgatggcagg aggatggaga agtgccagca gctgggggtc aagacgtccc    2760
ctgaggaccc aggcccacac ccagcccttc tgcctcccaa ttctctctcc tccgtccct     2820 tcctccactg ctgcctaatg caaggcagtg gctcagcagc aagaatgctg gttctacatc    2880
ccgaggagtg tctgaggtgc gccccactct gtacagaggc tgtttgggca gccttgcctc    2940
cagagagcag attccagctt cggaagcccc tggtctaact tgggatctgg gaatggaagg    3000
tgctcccatc ggaggggacc ctcagagccc tggagactgc caggtgggcc tgctgccact    3060
gtaagccaaa aggtggggaa gtcctgactc cagggtcctt gccccacccc tgcctgccac    3120
ctgggccctc acagcccaga ccctcactgg gaggtgagct cagctgccct ttggaataaa    3180
gctgcctgat caaaaaaaaa aaaaaaaaaa aa                                  3212

<210> SEQ ID NO 2
<211> LENGTH: 29
<212> TYPE: PRT
<213> ORGANISM: Unknown
<220> FEATURE:
<223> OTHER INFORMATION: Description of Unknown: Exemplary primary
      peptide of endosomolytic components

<400> SEQUENCE: 2

Ala Ala Leu Glu Ala Leu Ala Glu Ala Leu Glu Ala Leu Ala Glu Ala
1               5                   10                  15

Leu Glu Ala Leu Ala Glu Ala Ala Ala Ala Gly Gly Cys
            20                  25

<210> SEQ ID NO 3
<211> LENGTH: 30
<212> TYPE: PRT
<213> ORGANISM: Unknown
<220> FEATURE:
<223> OTHER INFORMATION: Description of Unknown: Exemplary primary
      peptide of endosomolytic components

<400> SEQUENCE: 3

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Ala Gly Gly Cys
            20                  25                  30

<210> SEQ ID NO 4
<211> LENGTH: 15
<212> TYPE: PRT
<213> ORGANISM: Unknown
<220> FEATURE:
```

```
<223> OTHER INFORMATION: Description of Unknown: Exemplary primary
      peptide of endosomolytic components

<400> SEQUENCE: 4

Ala Leu Glu Ala Leu Ala Glu Ala Leu Glu Ala Leu Ala Glu Ala
1               5                   10                  15

<210> SEQ ID NO 5
<211> LENGTH: 16
<212> TYPE: PRT
<213> ORGANISM: Unknown
<220> FEATURE:
<223> OTHER INFORMATION: Description of Unknown: Hydrophobic membrane
      translocation peptide

<400> SEQUENCE: 5

Ala Ala Val Ala Leu Leu Pro Ala Val Leu Leu Ala Leu Leu Ala Pro
1               5                   10                  15

<210> SEQ ID NO 6
<211> LENGTH: 11
<212> TYPE: PRT
<213> ORGANISM: Unknown
<220> FEATURE:
<223> OTHER INFORMATION: Description of Unknown: Hydrophobic membrane
      translocation peptide

<400> SEQUENCE: 6

Ala Ala Leu Leu Pro Val Leu Leu Ala Ala Pro
1               5                   10

<210> SEQ ID NO 7
<211> LENGTH: 13
<212> TYPE: PRT
<213> ORGANISM: Human immunodeficiency virus

<400> SEQUENCE: 7

Gly Arg Lys Lys Arg Arg Gln Arg Arg Arg Pro Pro Gln
1               5                   10

<210> SEQ ID NO 8
<211> LENGTH: 16
<212> TYPE: PRT
<213> ORGANISM: Drosophila sp.

<400> SEQUENCE: 8

Arg Gln Ile Lys Ile Trp Phe Gln Asn Arg Arg Met Lys Trp Lys Lys
1               5                   10                  15

<210> SEQ ID NO 9
<211> LENGTH: 19
<212> TYPE: RNA
<213> ORGANISM: Homo sapiens

<400> SEQUENCE: 9
cucuggugcg agcugaccu                                              19

<210> SEQ ID NO 10
<211> LENGTH: 19
<212> TYPE: RNA
<213> ORGANISM: Homo sapiens

<400> SEQUENCE: 10
aggucagcuc gcaccagag                                              19
```

```
<210> SEQ ID NO 11
<211> LENGTH: 19
<212> TYPE: RNA
<213> ORGANISM: Homo sapiens

<400> SEQUENCE: 11
agcugaccug agaugcacu                                                    19

<210> SEQ ID NO 12
<211> LENGTH: 19
<212> TYPE: RNA
<213> ORGANISM: Homo sapiens

<400> SEQUENCE: 12
agugcaucuc aggucagcu                                                    19

<210> SEQ ID NO 13
<211> LENGTH: 19
<212> TYPE: RNA
<213> ORGANISM: Homo sapiens

<400> SEQUENCE: 13
ucugugagcu gucucggca                                                    19

<210> SEQ ID NO 14
<211> LENGTH: 19
<212> TYPE: RNA
<213> ORGANISM: Homo sapiens

<400> SEQUENCE: 14
ugccgagaca gcucacaga                                                    19

<210> SEQ ID NO 15
<211> LENGTH: 19
<212> TYPE: RNA
<213> ORGANISM: Homo sapiens

<400> SEQUENCE: 15
agcugucucg gcacccacu                                                    19

<210> SEQ ID NO 16
<211> LENGTH: 19
<212> TYPE: RNA
<213> ORGANISM: Homo sapiens

<400> SEQUENCE: 16
agugggugcc gagacagcu                                                    19

<210> SEQ ID NO 17
<211> LENGTH: 19
<212> TYPE: RNA
<213> ORGANISM: Homo sapiens

<400> SEQUENCE: 17
gcugucucgg cacccacuu                                                    19

<210> SEQ ID NO 18
<211> LENGTH: 19
<212> TYPE: RNA
<213> ORGANISM: Homo sapiens

<400> SEQUENCE: 18
aagugggugc cgagacagc                                                    19
```

```
<210> SEQ ID NO 19
<211> LENGTH: 19
<212> TYPE: RNA
<213> ORGANISM: Homo sapiens

<400> SEQUENCE: 19
agucacugcc gccugaugu                                                    19

<210> SEQ ID NO 20
<211> LENGTH: 19
<212> TYPE: RNA
<213> ORGANISM: Homo sapiens

<400> SEQUENCE: 20
acaucaggcg gcagugacu                                                    19

<210> SEQ ID NO 21
<211> LENGTH: 19
<212> TYPE: RNA
<213> ORGANISM: Homo sapiens

<400> SEQUENCE: 21
acugccgccu gauguuguu                                                    19

<210> SEQ ID NO 22
<211> LENGTH: 19
<212> TYPE: RNA
<213> ORGANISM: Homo sapiens

<400> SEQUENCE: 22
aacaacauca ggcggcagu                                                    19

<210> SEQ ID NO 23
<211> LENGTH: 19
<212> TYPE: RNA
<213> ORGANISM: Homo sapiens

<400> SEQUENCE: 23
cugccgccug auguuguua                                                    19

<210> SEQ ID NO 24
<211> LENGTH: 19
<212> TYPE: RNA
<213> ORGANISM: Homo sapiens

<400> SEQUENCE: 24
uaacaacauc aggcggcag                                                    19

<210> SEQ ID NO 25
<211> LENGTH: 19
<212> TYPE: RNA
<213> ORGANISM: Homo sapiens

<400> SEQUENCE: 25
gccgccugau guuguuacu                                                    19

<210> SEQ ID NO 26
<211> LENGTH: 19
<212> TYPE: RNA
<213> ORGANISM: Homo sapiens

<400> SEQUENCE: 26
aguaacaaca ucaggcggc                                                    19
```

```
<210> SEQ ID NO 27
<211> LENGTH: 19
<212> TYPE: RNA
<213> ORGANISM: Homo sapiens

<400> SEQUENCE: 27
gccugauguu guuacucuu                                                  19

<210> SEQ ID NO 28
<211> LENGTH: 19
<212> TYPE: RNA
<213> ORGANISM: Homo sapiens

<400> SEQUENCE: 28
aagaguaaca acaucaggc                                                  19

<210> SEQ ID NO 29
<211> LENGTH: 19
<212> TYPE: RNA
<213> ORGANISM: Homo sapiens

<400> SEQUENCE: 29
cucuuccacu ccaaaagga                                                  19

<210> SEQ ID NO 30
<211> LENGTH: 19
<212> TYPE: RNA
<213> ORGANISM: Homo sapiens

<400> SEQUENCE: 30
uccuuuugga guggaagag                                                  19

<210> SEQ ID NO 31
<211> LENGTH: 19
<212> TYPE: RNA
<213> ORGANISM: Homo sapiens

<400> SEQUENCE: 31
acuccaaaag gaugcccgu                                                  19

<210> SEQ ID NO 32
<211> LENGTH: 19
<212> TYPE: RNA
<213> ORGANISM: Homo sapiens

<400> SEQUENCE: 32
acgggcaucc uuuuggagu                                                  19

<210> SEQ ID NO 33
<211> LENGTH: 19
<212> TYPE: RNA
<213> ORGANISM: Homo sapiens

<400> SEQUENCE: 33
gugaggacuc caagagaaa                                                  19

<210> SEQ ID NO 34
<211> LENGTH: 19
<212> TYPE: RNA
<213> ORGANISM: Homo sapiens

<400> SEQUENCE: 34
```

| | |
|---|---|
| uuucucuugg aguccucac | 19 |

<210> SEQ ID NO 35
<211> LENGTH: 19
<212> TYPE: RNA
<213> ORGANISM: Homo sapiens

<400> SEQUENCE: 35

| | |
|---|---|
| cuucggcggg ggugcuacu | 19 |

<210> SEQ ID NO 36
<211> LENGTH: 19
<212> TYPE: RNA
<213> ORGANISM: Homo sapiens

<400> SEQUENCE: 36

| | |
|---|---|
| aguagcaccc ccgccgaag | 19 |

<210> SEQ ID NO 37
<211> LENGTH: 19
<212> TYPE: RNA
<213> ORGANISM: Homo sapiens

<400> SEQUENCE: 37

| | |
|---|---|
| ucggcggggg ugcuacucu | 19 |

<210> SEQ ID NO 38
<211> LENGTH: 19
<212> TYPE: RNA
<213> ORGANISM: Homo sapiens

<400> SEQUENCE: 38

| | |
|---|---|
| agaguagcac ccccgccga | 19 |

<210> SEQ ID NO 39
<211> LENGTH: 19
<212> TYPE: RNA
<213> ORGANISM: Homo sapiens

<400> SEQUENCE: 39

| | |
|---|---|
| gcggggugc uacucuggu | 19 |

<210> SEQ ID NO 40
<211> LENGTH: 19
<212> TYPE: RNA
<213> ORGANISM: Homo sapiens

<400> SEQUENCE: 40

| | |
|---|---|
| accagaguag caccccgc | 19 |

<210> SEQ ID NO 41
<211> LENGTH: 19
<212> TYPE: RNA
<213> ORGANISM: Homo sapiens

<400> SEQUENCE: 41

| | |
|---|---|
| gggggugcua cucugguau | 19 |

<210> SEQ ID NO 42
<211> LENGTH: 19
<212> TYPE: RNA
<213> ORGANISM: Homo sapiens

<400> SEQUENCE: 42

```
auaccagagu agcaccccc                                           19

<210> SEQ ID NO 43
<211> LENGTH: 19
<212> TYPE: RNA
<213> ORGANISM: Homo sapiens

<400> SEQUENCE: 43
ggggugcuac ucugguauu                                           19

<210> SEQ ID NO 44
<211> LENGTH: 19
<212> TYPE: RNA
<213> ORGANISM: Homo sapiens

<400> SEQUENCE: 44
aauaccagag uagcacccc                                           19

<210> SEQ ID NO 45
<211> LENGTH: 19
<212> TYPE: RNA
<213> ORGANISM: Homo sapiens

<400> SEQUENCE: 45
ucugguauuu ccuagggua                                           19

<210> SEQ ID NO 46
<211> LENGTH: 19
<212> TYPE: RNA
<213> ORGANISM: Homo sapiens

<400> SEQUENCE: 46
uacccuagga aauaccaga                                           19

<210> SEQ ID NO 47
<211> LENGTH: 19
<212> TYPE: RNA
<213> ORGANISM: Homo sapiens

<400> SEQUENCE: 47
ugguauuucc uaggguaca                                           19

<210> SEQ ID NO 48
<211> LENGTH: 19
<212> TYPE: RNA
<213> ORGANISM: Homo sapiens

<400> SEQUENCE: 48
uguacccuag gaaauacca                                           19

<210> SEQ ID NO 49
<211> LENGTH: 19
<212> TYPE: RNA
<213> ORGANISM: Homo sapiens

<400> SEQUENCE: 49
gguauuuccu aggguacaa                                           19

<210> SEQ ID NO 50
<211> LENGTH: 19
<212> TYPE: RNA
<213> ORGANISM: Homo sapiens
```

```
<400> SEQUENCE: 50
uuguacccua ggaaauacc                                              19

<210> SEQ ID NO 51
<211> LENGTH: 19
<212> TYPE: RNA
<213> ORGANISM: Homo sapiens

<400> SEQUENCE: 51
ggucagccag guguacuca                                              19

<210> SEQ ID NO 52
<211> LENGTH: 19
<212> TYPE: RNA
<213> ORGANISM: Homo sapiens

<400> SEQUENCE: 52
ugaguacacc uggcugacc                                              19

<210> SEQ ID NO 53
<211> LENGTH: 19
<212> TYPE: RNA
<213> ORGANISM: Homo sapiens

<400> SEQUENCE: 53
agccaggugu acucaggca                                              19

<210> SEQ ID NO 54
<211> LENGTH: 19
<212> TYPE: RNA
<213> ORGANISM: Homo sapiens

<400> SEQUENCE: 54
ugccugagua caccuggcu                                              19

<210> SEQ ID NO 55
<211> LENGTH: 19
<212> TYPE: RNA
<213> ORGANISM: Homo sapiens

<400> SEQUENCE: 55
guacucaggc agucugcgu                                              19

<210> SEQ ID NO 56
<211> LENGTH: 19
<212> TYPE: RNA
<213> ORGANISM: Homo sapiens

<400> SEQUENCE: 56
acgcagacug ccugaguac                                              19

<210> SEQ ID NO 57
<211> LENGTH: 19
<212> TYPE: RNA
<213> ORGANISM: Homo sapiens

<400> SEQUENCE: 57
acucaggcag ucugcgugu                                              19

<210> SEQ ID NO 58
<211> LENGTH: 19
<212> TYPE: RNA
<213> ORGANISM: Homo sapiens
```

```
<400> SEQUENCE: 58
acacgcagac ugccugagu                                                19

<210> SEQ ID NO 59
<211> LENGTH: 19
<212> TYPE: RNA
<213> ORGANISM: Homo sapiens

<400> SEQUENCE: 59
caggcagucu gcguguacu                                                19

<210> SEQ ID NO 60
<211> LENGTH: 19
<212> TYPE: RNA
<213> ORGANISM: Homo sapiens

<400> SEQUENCE: 60
aguacacgca gacugccug                                                19

<210> SEQ ID NO 61
<211> LENGTH: 19
<212> TYPE: RNA
<213> ORGANISM: Homo sapiens

<400> SEQUENCE: 61
ggcagucugc guguacuca                                                19

<210> SEQ ID NO 62
<211> LENGTH: 19
<212> TYPE: RNA
<213> ORGANISM: Homo sapiens

<400> SEQUENCE: 62
ugaguacacg cagacugcc                                                19

<210> SEQ ID NO 63
<211> LENGTH: 19
<212> TYPE: RNA
<213> ORGANISM: Homo sapiens

<400> SEQUENCE: 63
gcagucugcg uguacucaa                                                19

<210> SEQ ID NO 64
<211> LENGTH: 19
<212> TYPE: RNA
<213> ORGANISM: Homo sapiens

<400> SEQUENCE: 64
uugaguacac gcagacugc                                                19

<210> SEQ ID NO 65
<211> LENGTH: 19
<212> TYPE: RNA
<213> ORGANISM: Homo sapiens

<400> SEQUENCE: 65
cagucugcgu guacucaau                                                19

<210> SEQ ID NO 66
<211> LENGTH: 19
<212> TYPE: RNA
```

<213> ORGANISM: Homo sapiens

<400> SEQUENCE: 66
auugaguaca cgcagacug                    19

<210> SEQ ID NO 67
<211> LENGTH: 19
<212> TYPE: RNA
<213> ORGANISM: Homo sapiens

<400> SEQUENCE: 67
ugcguguacu caaucgcca                    19

<210> SEQ ID NO 68
<211> LENGTH: 19
<212> TYPE: RNA
<213> ORGANISM: Homo sapiens

<400> SEQUENCE: 68
uggcgauuga guacacgca                    19

<210> SEQ ID NO 69
<211> LENGTH: 19
<212> TYPE: RNA
<213> ORGANISM: Homo sapiens

<400> SEQUENCE: 69
cguguacuca aucgccacu                    19

<210> SEQ ID NO 70
<211> LENGTH: 19
<212> TYPE: RNA
<213> ORGANISM: Homo sapiens

<400> SEQUENCE: 70
aguggcgauu gaguacacg                    19

<210> SEQ ID NO 71
<211> LENGTH: 19
<212> TYPE: RNA
<213> ORGANISM: Homo sapiens

<400> SEQUENCE: 71
guguacucaa ucgccacuu                    19

<210> SEQ ID NO 72
<211> LENGTH: 19
<212> TYPE: RNA
<213> ORGANISM: Homo sapiens

<400> SEQUENCE: 72
aaguggcgau ugaguacac                    19

<210> SEQ ID NO 73
<211> LENGTH: 19
<212> TYPE: RNA
<213> ORGANISM: Homo sapiens

<400> SEQUENCE: 73
guacucaauc gccacuucu                    19

<210> SEQ ID NO 74
<211> LENGTH: 19

<212> TYPE: RNA
<213> ORGANISM: Homo sapiens

<400> SEQUENCE: 74
agaaguggcg auugaguac                                                  19

<210> SEQ ID NO 75
<211> LENGTH: 19
<212> TYPE: RNA
<213> ORGANISM: Homo sapiens

<400> SEQUENCE: 75
cacuucuccc aggaucuua                                                  19

<210> SEQ ID NO 76
<211> LENGTH: 19
<212> TYPE: RNA
<213> ORGANISM: Homo sapiens

<400> SEQUENCE: 76
uaagauccug ggagaagug                                                  19

<210> SEQ ID NO 77
<211> LENGTH: 19
<212> TYPE: RNA
<213> ORGANISM: Homo sapiens

<400> SEQUENCE: 77
gaucuuaccc gccgggaau                                                  19

<210> SEQ ID NO 78
<211> LENGTH: 19
<212> TYPE: RNA
<213> ORGANISM: Homo sapiens

<400> SEQUENCE: 78
auucccggcg gguaagauc                                                  19

<210> SEQ ID NO 79
<211> LENGTH: 19
<212> TYPE: RNA
<213> ORGANISM: Homo sapiens

<400> SEQUENCE: 79
ucuuacccgc cgggaaucu                                                  19

<210> SEQ ID NO 80
<211> LENGTH: 19
<212> TYPE: RNA
<213> ORGANISM: Homo sapiens

<400> SEQUENCE: 80
agauucccgg cggguaaga                                                  19

<210> SEQ ID NO 81
<211> LENGTH: 19
<212> TYPE: RNA
<213> ORGANISM: Homo sapiens

<400> SEQUENCE: 81
cuuacccgcc gggaaucua                                                  19

<210> SEQ ID NO 82

```
<211> LENGTH: 19
<212> TYPE: RNA
<213> ORGANISM: Homo sapiens

<400> SEQUENCE: 82
uagauucccg gcgguaag                                                    19

<210> SEQ ID NO 83
<211> LENGTH: 19
<212> TYPE: RNA
<213> ORGANISM: Homo sapiens

<400> SEQUENCE: 83
uacccgccgg gaaucuagu                                                   19

<210> SEQ ID NO 84
<211> LENGTH: 19
<212> TYPE: RNA
<213> ORGANISM: Homo sapiens

<400> SEQUENCE: 84
acuagauucc cggcgggua                                                   19

<210> SEQ ID NO 85
<211> LENGTH: 19
<212> TYPE: RNA
<213> ORGANISM: Homo sapiens

<400> SEQUENCE: 85
cgccgggaau cuagugccu                                                   19

<210> SEQ ID NO 86
<211> LENGTH: 19
<212> TYPE: RNA
<213> ORGANISM: Homo sapiens

<400> SEQUENCE: 86
aggcacuaga uucccggcg                                                   19

<210> SEQ ID NO 87
<211> LENGTH: 19
<212> TYPE: RNA
<213> ORGANISM: Homo sapiens

<400> SEQUENCE: 87
gccgggaauc uagugccuu                                                   19

<210> SEQ ID NO 88
<211> LENGTH: 19
<212> TYPE: RNA
<213> ORGANISM: Homo sapiens

<400> SEQUENCE: 88
aaggcacuag auucccggc                                                   19

<210> SEQ ID NO 89
<211> LENGTH: 19
<212> TYPE: RNA
<213> ORGANISM: Homo sapiens

<400> SEQUENCE: 89
uccgcaguga aaccgccaa                                                   19
```

```
<210> SEQ ID NO 90
<211> LENGTH: 19
<212> TYPE: RNA
<213> ORGANISM: Homo sapiens

<400> SEQUENCE: 90
uuggcgguuu cacugcgga                                                19

<210> SEQ ID NO 91
<211> LENGTH: 19
<212> TYPE: RNA
<213> ORGANISM: Homo sapiens

<400> SEQUENCE: 91
ccgcagugaa accgccaaa                                                19

<210> SEQ ID NO 92
<211> LENGTH: 19
<212> TYPE: RNA
<213> ORGANISM: Homo sapiens

<400> SEQUENCE: 92
uuuggcgguu ucacugcgg                                                19

<210> SEQ ID NO 93
<211> LENGTH: 19
<212> TYPE: RNA
<213> ORGANISM: Homo sapiens

<400> SEQUENCE: 93
cgccugggaa cuuacuaca                                                19

<210> SEQ ID NO 94
<211> LENGTH: 19
<212> TYPE: RNA
<213> ORGANISM: Homo sapiens

<400> SEQUENCE: 94
uguaguaagu ucccaggcg                                                19

<210> SEQ ID NO 95
<211> LENGTH: 19
<212> TYPE: RNA
<213> ORGANISM: Homo sapiens

<400> SEQUENCE: 95
gccugggaac uuacuacaa                                                19

<210> SEQ ID NO 96
<211> LENGTH: 19
<212> TYPE: RNA
<213> ORGANISM: Homo sapiens

<400> SEQUENCE: 96
uuguaguaag uucccaggc                                                19

<210> SEQ ID NO 97
<211> LENGTH: 19
<212> TYPE: RNA
<213> ORGANISM: Homo sapiens

<400> SEQUENCE: 97
cugggaacuu acuacaacu                                                19
```

```
<210> SEQ ID NO 98
<211> LENGTH: 19
<212> TYPE: RNA
<213> ORGANISM: Homo sapiens

<400> SEQUENCE: 98
aguuguagua aguucccag                                                     19

<210> SEQ ID NO 99
<211> LENGTH: 19
<212> TYPE: RNA
<213> ORGANISM: Homo sapiens

<400> SEQUENCE: 99
uacaacucca gcuccgucu                                                     19

<210> SEQ ID NO 100
<211> LENGTH: 19
<212> TYPE: RNA
<213> ORGANISM: Homo sapiens

<400> SEQUENCE: 100
agacggagcu ggaguugua                                                     19

<210> SEQ ID NO 101
<211> LENGTH: 19
<212> TYPE: RNA
<213> ORGANISM: Homo sapiens

<400> SEQUENCE: 101
acaacuccag cuccgucua                                                     19

<210> SEQ ID NO 102
<211> LENGTH: 19
<212> TYPE: RNA
<213> ORGANISM: Homo sapiens

<400> SEQUENCE: 102
uagacggagc uggaguugu                                                     19

<210> SEQ ID NO 103
<211> LENGTH: 19
<212> TYPE: RNA
<213> ORGANISM: Homo sapiens

<400> SEQUENCE: 103
aacuccagcu ccgucuauu                                                     19

<210> SEQ ID NO 104
<211> LENGTH: 19
<212> TYPE: RNA
<213> ORGANISM: Homo sapiens

<400> SEQUENCE: 104
aauagacgga gcuggaguu                                                     19

<210> SEQ ID NO 105
<211> LENGTH: 19
<212> TYPE: RNA
<213> ORGANISM: Homo sapiens

<400> SEQUENCE: 105
uuuggggagg gaccccuca                                                     19
```

```
<210> SEQ ID NO 106
<211> LENGTH: 19
<212> TYPE: RNA
<213> ORGANISM: Homo sapiens

<400> SEQUENCE: 106
ugaggggucc cuccccaaa                                              19

<210> SEQ ID NO 107
<211> LENGTH: 19
<212> TYPE: RNA
<213> ORGANISM: Homo sapiens

<400> SEQUENCE: 107
ggaccccuca ccugcuucu                                              19

<210> SEQ ID NO 108
<211> LENGTH: 19
<212> TYPE: RNA
<213> ORGANISM: Homo sapiens

<400> SEQUENCE: 108
agaagcaggu gagggucc                                               19

<210> SEQ ID NO 109
<211> LENGTH: 19
<212> TYPE: RNA
<213> ORGANISM: Homo sapiens

<400> SEQUENCE: 109
gcuucuucug guucauucu                                              19

<210> SEQ ID NO 110
<211> LENGTH: 19
<212> TYPE: RNA
<213> ORGANISM: Homo sapiens

<400> SEQUENCE: 110
agaaugaacc agaagaagc                                              19

<210> SEQ ID NO 111
<211> LENGTH: 19
<212> TYPE: RNA
<213> ORGANISM: Homo sapiens

<400> SEQUENCE: 111
ucuucugguu cauucucca                                              19

<210> SEQ ID NO 112
<211> LENGTH: 19
<212> TYPE: RNA
<213> ORGANISM: Homo sapiens

<400> SEQUENCE: 112
uggagaauga accagaaga                                              19

<210> SEQ ID NO 113
<211> LENGTH: 19
<212> TYPE: RNA
<213> ORGANISM: Homo sapiens

<400> SEQUENCE: 113
```

-continued agcaccgccg gcugaugcu                                                        19

<210> SEQ ID NO 114
<211> LENGTH: 19
<212> TYPE: RNA
<213> ORGANISM: Homo sapiens

<400> SEQUENCE: 114
agcaucagcc ggcggugcu                                                        19

<210> SEQ ID NO 115
<211> LENGTH: 19
<212> TYPE: RNA
<213> ORGANISM: Homo sapiens

<400> SEQUENCE: 115
uccccuacag ggccgagua                                                        19

<210> SEQ ID NO 116
<211> LENGTH: 19
<212> TYPE: RNA
<213> ORGANISM: Homo sapiens

<400> SEQUENCE: 116
uacucggccc uguagggga                                                        19

<210> SEQ ID NO 117
<211> LENGTH: 19
<212> TYPE: RNA
<213> ORGANISM: Homo sapiens

<400> SEQUENCE: 117
ccuacagggc cgaguacga                                                        19

<210> SEQ ID NO 118
<211> LENGTH: 19
<212> TYPE: RNA
<213> ORGANISM: Homo sapiens

<400> SEQUENCE: 118
ucguacucgg cccuguagg                                                        19

<210> SEQ ID NO 119
<211> LENGTH: 19
<212> TYPE: RNA
<213> ORGANISM: Homo sapiens

<400> SEQUENCE: 119
acagggccga guacgaagu                                                        19

<210> SEQ ID NO 120
<211> LENGTH: 19
<212> TYPE: RNA
<213> ORGANISM: Homo sapiens

<400> SEQUENCE: 120
acuucguacu cggcccugu                                                        19

<210> SEQ ID NO 121
<211> LENGTH: 19
<212> TYPE: RNA
<213> ORGANISM: Homo sapiens

<400> SEQUENCE: 121

| | |
|---|---|
| gggccgagua cgaagugga | 19 |

<210> SEQ ID NO 122
<211> LENGTH: 19
<212> TYPE: RNA
<213> ORGANISM: Homo sapiens

<400> SEQUENCE: 122

| | |
|---|---|
| uccacuucgu acucggccc | 19 |

<210> SEQ ID NO 123
<211> LENGTH: 19
<212> TYPE: RNA
<213> ORGANISM: Homo sapiens

<400> SEQUENCE: 123

| | |
|---|---|
| ccgagggccu agugauccu | 19 |

<210> SEQ ID NO 124
<211> LENGTH: 19
<212> TYPE: RNA
<213> ORGANISM: Homo sapiens

<400> SEQUENCE: 124

| | |
|---|---|
| aggaucacua ggcccucgg | 19 |

<210> SEQ ID NO 125
<211> LENGTH: 19
<212> TYPE: RNA
<213> ORGANISM: Homo sapiens

<400> SEQUENCE: 125

| | |
|---|---|
| cagugugaaa gacauagcu | 19 |

<210> SEQ ID NO 126
<211> LENGTH: 19
<212> TYPE: RNA
<213> ORGANISM: Homo sapiens

<400> SEQUENCE: 126

| | |
|---|---|
| agcuaugucu uucacacug | 19 |

<210> SEQ ID NO 127
<211> LENGTH: 19
<212> TYPE: RNA
<213> ORGANISM: Homo sapiens

<400> SEQUENCE: 127

| | |
|---|---|
| gaauuccacg cugguugu | 19 |

<210> SEQ ID NO 128
<211> LENGTH: 19
<212> TYPE: RNA
<213> ORGANISM: Homo sapiens

<400> SEQUENCE: 128

| | |
|---|---|
| acaacccagc guggaauuc | 19 |

<210> SEQ ID NO 129
<211> LENGTH: 19
<212> TYPE: RNA
<213> ORGANISM: Homo sapiens

```
<400> SEQUENCE: 129
aauuccacgc uggguuguu                                              19

<210> SEQ ID NO 130
<211> LENGTH: 19
<212> TYPE: RNA
<213> ORGANISM: Homo sapiens

<400> SEQUENCE: 130
aacaacccag cguggaauu                                              19

<210> SEQ ID NO 131
<211> LENGTH: 19
<212> TYPE: RNA
<213> ORGANISM: Homo sapiens

<400> SEQUENCE: 131
acgcuggguu guuaccgcu                                              19

<210> SEQ ID NO 132
<211> LENGTH: 19
<212> TYPE: RNA
<213> ORGANISM: Homo sapiens

<400> SEQUENCE: 132
agcgguaaca acccagcgu                                              19

<210> SEQ ID NO 133
<211> LENGTH: 19
<212> TYPE: RNA
<213> ORGANISM: Homo sapiens

<400> SEQUENCE: 133
cgcuggguug uuaccgcua                                              19

<210> SEQ ID NO 134
<211> LENGTH: 19
<212> TYPE: RNA
<213> ORGANISM: Homo sapiens

<400> SEQUENCE: 134
uagcgguaac aacccagcg                                              19

<210> SEQ ID NO 135
<211> LENGTH: 19
<212> TYPE: RNA
<213> ORGANISM: Homo sapiens

<400> SEQUENCE: 135
cuggguuguu accgcuaca                                              19

<210> SEQ ID NO 136
<211> LENGTH: 19
<212> TYPE: RNA
<213> ORGANISM: Homo sapiens

<400> SEQUENCE: 136
uguagcggua acaacccag                                              19

<210> SEQ ID NO 137
<211> LENGTH: 19
<212> TYPE: RNA
<213> ORGANISM: Homo sapiens
```

<400> SEQUENCE: 137
gguuguuacc gcuacagcu                                                19

<210> SEQ ID NO 138
<211> LENGTH: 19
<212> TYPE: RNA
<213> ORGANISM: Homo sapiens

<400> SEQUENCE: 138
agcuguagcg guaacaacc                                                19

<210> SEQ ID NO 139
<211> LENGTH: 19
<212> TYPE: RNA
<213> ORGANISM: Homo sapiens

<400> SEQUENCE: 139
guuaccgcua cagcuacgu                                                19

<210> SEQ ID NO 140
<211> LENGTH: 19
<212> TYPE: RNA
<213> ORGANISM: Homo sapiens

<400> SEQUENCE: 140
acguagcugu agcgguaac                                                19

<210> SEQ ID NO 141
<211> LENGTH: 19
<212> TYPE: RNA
<213> ORGANISM: Homo sapiens

<400> SEQUENCE: 141
aggaccucau gcucaaacu                                                19

<210> SEQ ID NO 142
<211> LENGTH: 19
<212> TYPE: RNA
<213> ORGANISM: Homo sapiens

<400> SEQUENCE: 142
aguuugagca ugagguccu                                                19

<210> SEQ ID NO 143
<211> LENGTH: 19
<212> TYPE: RNA
<213> ORGANISM: Homo sapiens

<400> SEQUENCE: 143
ucaugcucaa acuccggcu                                                19

<210> SEQ ID NO 144
<211> LENGTH: 19
<212> TYPE: RNA
<213> ORGANISM: Homo sapiens

<400> SEQUENCE: 144
agccggaguu ugagcauga                                                19

<210> SEQ ID NO 145
<211> LENGTH: 19
<212> TYPE: RNA

<213> ORGANISM: Homo sapiens

<400> SEQUENCE: 145
aucaccucgg uguacggcu                                                    19

<210> SEQ ID NO 146
<211> LENGTH: 19
<212> TYPE: RNA
<213> ORGANISM: Homo sapiens

<400> SEQUENCE: 146
agccguacac cgaggugau                                                    19

<210> SEQ ID NO 147
<211> LENGTH: 19
<212> TYPE: RNA
<213> ORGANISM: Homo sapiens

<400> SEQUENCE: 147
accucggugu acggcugca                                                    19

<210> SEQ ID NO 148
<211> LENGTH: 19
<212> TYPE: RNA
<213> ORGANISM: Homo sapiens

<400> SEQUENCE: 148
ugcagccgua caccgaggu                                                    19

<210> SEQ ID NO 149
<211> LENGTH: 19
<212> TYPE: RNA
<213> ORGANISM: Homo sapiens

<400> SEQUENCE: 149
aucauggcgg ucgucugga                                                    19

<210> SEQ ID NO 150
<211> LENGTH: 19
<212> TYPE: RNA
<213> ORGANISM: Homo sapiens

<400> SEQUENCE: 150
uccagacgac cgccaugau                                                    19

<210> SEQ ID NO 151
<211> LENGTH: 19
<212> TYPE: RNA
<213> ORGANISM: Homo sapiens

<400> SEQUENCE: 151
ucauggcggu cgucuggaa                                                    19

<210> SEQ ID NO 152
<211> LENGTH: 19
<212> TYPE: RNA
<213> ORGANISM: Homo sapiens

<400> SEQUENCE: 152
uuccagacga ccgccauga                                                    19

<210> SEQ ID NO 153
<211> LENGTH: 19

<212> TYPE: RNA
<213> ORGANISM: Homo sapiens

<400> SEQUENCE: 153
gcuacuacga ccccuucgu 19

<210> SEQ ID NO 154
<211> LENGTH: 19
<212> TYPE: RNA
<213> ORGANISM: Homo sapiens

<400> SEQUENCE: 154
acgaaggggu cguaguagc 19

<210> SEQ ID NO 155
<211> LENGTH: 19
<212> TYPE: RNA
<213> ORGANISM: Homo sapiens

<400> SEQUENCE: 155
ccgugcagcc gguggucuu 19

<210> SEQ ID NO 156
<211> LENGTH: 19
<212> TYPE: RNA
<213> ORGANISM: Homo sapiens

<400> SEQUENCE: 156
aagaccaccg gcugcacgg 19

<210> SEQ ID NO 157
<211> LENGTH: 19
<212> TYPE: RNA
<213> ORGANISM: Homo sapiens

<400> SEQUENCE: 157
ucuuccaggc cugugaagu 19

<210> SEQ ID NO 158
<211> LENGTH: 19
<212> TYPE: RNA
<213> ORGANISM: Homo sapiens

<400> SEQUENCE: 158
acuucacagg ccuggaaga 19

<210> SEQ ID NO 159
<211> LENGTH: 19
<212> TYPE: RNA
<213> ORGANISM: Homo sapiens

<400> SEQUENCE: 159
gccugugaag ugaaccuga 19

<210> SEQ ID NO 160
<211> LENGTH: 19
<212> TYPE: RNA
<213> ORGANISM: Homo sapiens

<400> SEQUENCE: 160
ucagguucac uucacaggc 19

<210> SEQ ID NO 161
```
<211> LENGTH: 19
<212> TYPE: RNA
<213> ORGANISM: Homo sapiens

<400> SEQUENCE: 161
gugaagugaa ccugacgcu                                                    19

<210> SEQ ID NO 162
<211> LENGTH: 19
<212> TYPE: RNA
<213> ORGANISM: Homo sapiens

<400> SEQUENCE: 162
agcgucaggu ucacuucac                                                    19

<210> SEQ ID NO 163
<211> LENGTH: 19
<212> TYPE: RNA
<213> ORGANISM: Homo sapiens

<400> SEQUENCE: 163
cgcuggacaa caggcucga                                                    19

<210> SEQ ID NO 164
<211> LENGTH: 19
<212> TYPE: RNA
<213> ORGANISM: Homo sapiens

<400> SEQUENCE: 164
ucgagccugu uguccagcg                                                    19

<210> SEQ ID NO 165
<211> LENGTH: 19
<212> TYPE: RNA
<213> ORGANISM: Homo sapiens

<400> SEQUENCE: 165
cuggacaaca ggcucgacu                                                    19

<210> SEQ ID NO 166
<211> LENGTH: 19
<212> TYPE: RNA
<213> ORGANISM: Homo sapiens

<400> SEQUENCE: 166
agucgagccu guguccag                                                     19

<210> SEQ ID NO 167
<211> LENGTH: 19
<212> TYPE: RNA
<213> ORGANISM: Homo sapiens

<400> SEQUENCE: 167
guccucagca ccccguacu                                                    19

<210> SEQ ID NO 168
<211> LENGTH: 19
<212> TYPE: RNA
<213> ORGANISM: Homo sapiens

<400> SEQUENCE: 168
aguacggggu gcugaggac                                                    19
```

```
<210> SEQ ID NO 169
<211> LENGTH: 19
<212> TYPE: RNA
<213> ORGANISM: Homo sapiens

<400> SEQUENCE: 169
uccucagcac cccguacuu                                                  19

<210> SEQ ID NO 170
<211> LENGTH: 19
<212> TYPE: RNA
<213> ORGANISM: Homo sapiens

<400> SEQUENCE: 170
aaguacgggg ugcugagga                                                  19

<210> SEQ ID NO 171
<211> LENGTH: 19
<212> TYPE: RNA
<213> ORGANISM: Homo sapiens

<400> SEQUENCE: 171
agcaccccgu acuucccca                                                  19

<210> SEQ ID NO 172
<211> LENGTH: 19
<212> TYPE: RNA
<213> ORGANISM: Homo sapiens

<400> SEQUENCE: 172
uggggaagua cggggugcu                                                  19

<210> SEQ ID NO 173
<211> LENGTH: 19
<212> TYPE: RNA
<213> ORGANISM: Homo sapiens

<400> SEQUENCE: 173
cagcuacuac ucgccccaa                                                  19

<210> SEQ ID NO 174
<211> LENGTH: 19
<212> TYPE: RNA
<213> ORGANISM: Homo sapiens

<400> SEQUENCE: 174
uuggggcgag uaguagcug                                                  19

<210> SEQ ID NO 175
<211> LENGTH: 19
<212> TYPE: RNA
<213> ORGANISM: Homo sapiens

<400> SEQUENCE: 175
agcuacuacu cgccccaaa                                                  19

<210> SEQ ID NO 176
<211> LENGTH: 19
<212> TYPE: RNA
<213> ORGANISM: Homo sapiens

<400> SEQUENCE: 176
uuuggggcga guaguagcu                                                  19
```

```
<210> SEQ ID NO 177
<211> LENGTH: 19
<212> TYPE: RNA
<213> ORGANISM: Homo sapiens

<400> SEQUENCE: 177
acuacucgcc ccaaaccca                                                    19

<210> SEQ ID NO 178
<211> LENGTH: 19
<212> TYPE: RNA
<213> ORGANISM: Homo sapiens

<400> SEQUENCE: 178
uggguuuggg gcgaguagu                                                    19

<210> SEQ ID NO 179
<211> LENGTH: 19
<212> TYPE: RNA
<213> ORGANISM: Homo sapiens

<400> SEQUENCE: 179
ucgccccaaa cccacugcu                                                    19

<210> SEQ ID NO 180
<211> LENGTH: 19
<212> TYPE: RNA
<213> ORGANISM: Homo sapiens

<400> SEQUENCE: 180
agcagugggu uugggcga                                                     19

<210> SEQ ID NO 181
<211> LENGTH: 19
<212> TYPE: RNA
<213> ORGANISM: Homo sapiens

<400> SEQUENCE: 181
gcuccuggca ccucacggu                                                    19

<210> SEQ ID NO 182
<211> LENGTH: 19
<212> TYPE: RNA
<213> ORGANISM: Homo sapiens

<400> SEQUENCE: 182
accgugaggu gccaggagc                                                    19

<210> SEQ ID NO 183
<211> LENGTH: 19
<212> TYPE: RNA
<213> ORGANISM: Homo sapiens

<400> SEQUENCE: 183
cccucucugg acuacggcu                                                    19

<210> SEQ ID NO 184
<211> LENGTH: 19
<212> TYPE: RNA
<213> ORGANISM: Homo sapiens

<400> SEQUENCE: 184
agccguaguc cagagaggg                                                    19
```

```
<210> SEQ ID NO 185
<211> LENGTH: 19
<212> TYPE: RNA
<213> ORGANISM: Homo sapiens

<400> SEQUENCE: 185
acggcuuggc ccucugguu                                                19

<210> SEQ ID NO 186
<211> LENGTH: 19
<212> TYPE: RNA
<213> ORGANISM: Homo sapiens

<400> SEQUENCE: 186
aaccagaggg ccaagccgu                                                19

<210> SEQ ID NO 187
<211> LENGTH: 19
<212> TYPE: DNA
<213> ORGANISM: Homo sapiens

<400> SEQUENCE: 187
cggcttggcc ctctggttt                                                19

<210> SEQ ID NO 188
<211> LENGTH: 19
<212> TYPE: RNA
<213> ORGANISM: Homo sapiens

<400> SEQUENCE: 188
aaaccagagg gccaagccg                                                19

<210> SEQ ID NO 189
<211> LENGTH: 19
<212> TYPE: RNA
<213> ORGANISM: Homo sapiens

<400> SEQUENCE: 189
gcuuggcccu cugguuuga                                                19

<210> SEQ ID NO 190
<211> LENGTH: 19
<212> TYPE: RNA
<213> ORGANISM: Homo sapiens

<400> SEQUENCE: 190
ucaaaccaga gggccaagc                                                19

<210> SEQ ID NO 191
<211> LENGTH: 19
<212> TYPE: RNA
<213> ORGANISM: Homo sapiens

<400> SEQUENCE: 191
ccucugguuu gaugccuau                                                19

<210> SEQ ID NO 192
<211> LENGTH: 19
<212> TYPE: RNA
<213> ORGANISM: Homo sapiens

<400> SEQUENCE: 192
```

```
auaggcauca aaccagagg                                            19

<210> SEQ ID NO 193
<211> LENGTH: 19
<212> TYPE: RNA
<213> ORGANISM: Homo sapiens

<400> SEQUENCE: 193
cagaaguaug auuugccgu                                            19

<210> SEQ ID NO 194
<211> LENGTH: 19
<212> TYPE: RNA
<213> ORGANISM: Homo sapiens

<400> SEQUENCE: 194
acggcaaauc auacuucug                                            19

<210> SEQ ID NO 195
<211> LENGTH: 19
<212> TYPE: RNA
<213> ORGANISM: Homo sapiens

<400> SEQUENCE: 195
aaguaugauu ugccgugca                                            19

<210> SEQ ID NO 196
<211> LENGTH: 19
<212> TYPE: RNA
<213> ORGANISM: Homo sapiens

<400> SEQUENCE: 196
ugcacggcaa aucauacuu                                            19

<210> SEQ ID NO 197
<211> LENGTH: 19
<212> TYPE: RNA
<213> ORGANISM: Homo sapiens

<400> SEQUENCE: 197
augauuugcc gugcaccca                                            19

<210> SEQ ID NO 198
<211> LENGTH: 19
<212> TYPE: RNA
<213> ORGANISM: Homo sapiens

<400> SEQUENCE: 198
ugggugcacg gcaaaucau                                            19

<210> SEQ ID NO 199
<211> LENGTH: 19
<212> TYPE: RNA
<213> ORGANISM: Homo sapiens

<400> SEQUENCE: 199
acccagggcc aguggacga                                            19

<210> SEQ ID NO 200
<211> LENGTH: 19
<212> TYPE: RNA
<213> ORGANISM: Homo sapiens

<400> SEQUENCE: 200
```
ucguccacug gcccugggu                                              19

<210> SEQ ID NO 201
<211> LENGTH: 19
<212> TYPE: RNA
<213> ORGANISM: Homo sapiens

<400> SEQUENCE: 201
agggccagug gacgaucca                                              19

<210> SEQ ID NO 202
<211> LENGTH: 19
<212> TYPE: RNA
<213> ORGANISM: Homo sapiens

<400> SEQUENCE: 202
uggaucgucc acuggcccu                                              19

<210> SEQ ID NO 203
<211> LENGTH: 19
<212> TYPE: RNA
<213> ORGANISM: Homo sapiens

<400> SEQUENCE: 203
ggccagugga cgauccaga                                              19

<210> SEQ ID NO 204
<211> LENGTH: 19
<212> TYPE: RNA
<213> ORGANISM: Homo sapiens

<400> SEQUENCE: 204
ucuggaucgu ccacuggcc                                              19

<210> SEQ ID NO 205
<211> LENGTH: 19
<212> TYPE: RNA
<213> ORGANISM: Homo sapiens

<400> SEQUENCE: 205
gccaguggac gauccagaa                                              19

<210> SEQ ID NO 206
<211> LENGTH: 19
<212> TYPE: RNA
<213> ORGANISM: Homo sapiens

<400> SEQUENCE: 206
uucuggaucg uccacuggc                                              19

<210> SEQ ID NO 207
<211> LENGTH: 19
<212> TYPE: RNA
<213> ORGANISM: Homo sapiens

<400> SEQUENCE: 207
cagcccuacg ccgagagga                                              19

<210> SEQ ID NO 208
<211> LENGTH: 19
<212> TYPE: RNA
<213> ORGANISM: Homo sapiens

```
<400> SEQUENCE: 208
uccucucggc guagggcug                                                  19

<210> SEQ ID NO 209
<211> LENGTH: 19
<212> TYPE: RNA
<213> ORGANISM: Homo sapiens

<400> SEQUENCE: 209
cggugugcgg gugcacuau                                                  19

<210> SEQ ID NO 210
<211> LENGTH: 19
<212> TYPE: RNA
<213> ORGANISM: Homo sapiens

<400> SEQUENCE: 210
auagugcacc cgcacaccg                                                  19

<210> SEQ ID NO 211
<211> LENGTH: 19
<212> TYPE: RNA
<213> ORGANISM: Homo sapiens

<400> SEQUENCE: 211
gugcgggugc acuauggcu                                                  19

<210> SEQ ID NO 212
<211> LENGTH: 19
<212> TYPE: RNA
<213> ORGANISM: Homo sapiens

<400> SEQUENCE: 212
agccauagug cacccgcac                                                  19

<210> SEQ ID NO 213
<211> LENGTH: 19
<212> TYPE: RNA
<213> ORGANISM: Homo sapiens

<400> SEQUENCE: 213
ugcgggugca cuauggcuu                                                  19

<210> SEQ ID NO 214
<211> LENGTH: 19
<212> TYPE: RNA
<213> ORGANISM: Homo sapiens

<400> SEQUENCE: 214
aagccauagu gcacccgca                                                  19

<210> SEQ ID NO 215
<211> LENGTH: 19
<212> TYPE: RNA
<213> ORGANISM: Homo sapiens

<400> SEQUENCE: 215
gggugcacua uggcuugua                                                  19

<210> SEQ ID NO 216
<211> LENGTH: 19
<212> TYPE: RNA
<213> ORGANISM: Homo sapiens
```

-continued

```
<400> SEQUENCE: 216
uacaagccau agugcaccc                                                    19

<210> SEQ ID NO 217
<211> LENGTH: 19
<212> TYPE: RNA
<213> ORGANISM: Homo sapiens

<400> SEQUENCE: 217
ugcacuaugg cuuguacaa                                                    19

<210> SEQ ID NO 218
<211> LENGTH: 19
<212> TYPE: RNA
<213> ORGANISM: Homo sapiens

<400> SEQUENCE: 218
uuguacaagc cauagugca                                                    19

<210> SEQ ID NO 219
<211> LENGTH: 19
<212> TYPE: RNA
<213> ORGANISM: Homo sapiens

<400> SEQUENCE: 219
ugcccuggag aguccucu                                                     19

<210> SEQ ID NO 220
<211> LENGTH: 19
<212> TYPE: RNA
<213> ORGANISM: Homo sapiens

<400> SEQUENCE: 220
agaggaacuc uccagggca                                                    19

<210> SEQ ID NO 221
<211> LENGTH: 19
<212> TYPE: RNA
<213> ORGANISM: Homo sapiens

<400> SEQUENCE: 221
uggaugagag aaacugcgu                                                    19

<210> SEQ ID NO 222
<211> LENGTH: 19
<212> TYPE: RNA
<213> ORGANISM: Homo sapiens

<400> SEQUENCE: 222
acgcaguuuc ucucaucca                                                    19

<210> SEQ ID NO 223
<211> LENGTH: 19
<212> TYPE: RNA
<213> ORGANISM: Homo sapiens

<400> SEQUENCE: 223
ggacagcaca ugcaucuca                                                    19

<210> SEQ ID NO 224
<211> LENGTH: 19
<212> TYPE: RNA
```

```
<213> ORGANISM: Homo sapiens

<400> SEQUENCE: 224
ugagaugcau gugcugucc                                              19

<210> SEQ ID NO 225
<211> LENGTH: 19
<212> TYPE: RNA
<213> ORGANISM: Homo sapiens

<400> SEQUENCE: 225
acagcacaug caucucacu                                              19

<210> SEQ ID NO 226
<211> LENGTH: 19
<212> TYPE: RNA
<213> ORGANISM: Homo sapiens

<400> SEQUENCE: 226
agugagaugc augugcugu                                              19

<210> SEQ ID NO 227
<211> LENGTH: 19
<212> TYPE: RNA
<213> ORGANISM: Homo sapiens

<400> SEQUENCE: 227
ccaaggucug ugaugggca                                              19

<210> SEQ ID NO 228
<211> LENGTH: 19
<212> TYPE: RNA
<213> ORGANISM: Homo sapiens

<400> SEQUENCE: 228
ugcccaucac agaccuugg                                              19

<210> SEQ ID NO 229
<211> LENGTH: 19
<212> TYPE: RNA
<213> ORGANISM: Homo sapiens

<400> SEQUENCE: 229
augggcagcc ugauugucu                                              19

<210> SEQ ID NO 230
<211> LENGTH: 19
<212> TYPE: RNA
<213> ORGANISM: Homo sapiens

<400> SEQUENCE: 230
agacaaucag gcugcccau                                              19

<210> SEQ ID NO 231
<211> LENGTH: 19
<212> TYPE: RNA
<213> ORGANISM: Homo sapiens

<400> SEQUENCE: 231
ggcagccuga uugucucaa                                              19

<210> SEQ ID NO 232
<211> LENGTH: 19
```

```
<212> TYPE: RNA
<213> ORGANISM: Homo sapiens

<400> SEQUENCE: 232
uugagacaau caggcugcc                                               19

<210> SEQ ID NO 233
<211> LENGTH: 19
<212> TYPE: RNA
<213> ORGANISM: Homo sapiens

<400> SEQUENCE: 233
ccugauuguc ucaacggca                                               19

<210> SEQ ID NO 234
<211> LENGTH: 19
<212> TYPE: RNA
<213> ORGANISM: Homo sapiens

<400> SEQUENCE: 234
ugccguugag acaaucagg                                               19

<210> SEQ ID NO 235
<211> LENGTH: 19
<212> TYPE: RNA
<213> ORGANISM: Homo sapiens

<400> SEQUENCE: 235
ucucaacggc agcgacgaa                                               19

<210> SEQ ID NO 236
<211> LENGTH: 19
<212> TYPE: RNA
<213> ORGANISM: Homo sapiens

<400> SEQUENCE: 236
uucgucgcug ccguugaga                                               19

<210> SEQ ID NO 237
<211> LENGTH: 19
<212> TYPE: RNA
<213> ORGANISM: Homo sapiens

<400> SEQUENCE: 237
ugccaggaag gggugccau                                               19

<210> SEQ ID NO 238
<211> LENGTH: 19
<212> TYPE: RNA
<213> ORGANISM: Homo sapiens

<400> SEQUENCE: 238
auggcacccc uuccuggca                                               19

<210> SEQ ID NO 239
<211> LENGTH: 19
<212> TYPE: RNA
<213> ORGANISM: Homo sapiens

<400> SEQUENCE: 239
ggggugccau gugggacau                                               19

<210> SEQ ID NO 240
```

```
<211> LENGTH: 19
<212> TYPE: RNA
<213> ORGANISM: Homo sapiens

<400> SEQUENCE: 240
augucccaca uggcacccc                                                19

<210> SEQ ID NO 241
<211> LENGTH: 19
<212> TYPE: RNA
<213> ORGANISM: Homo sapiens

<400> SEQUENCE: 241
gugccaugug ggacauuca                                                19

<210> SEQ ID NO 242
<211> LENGTH: 19
<212> TYPE: RNA
<213> ORGANISM: Homo sapiens

<400> SEQUENCE: 242 ugaaugucccc acauggcac                                               19

<210> SEQ ID NO 243
<211> LENGTH: 19
<212> TYPE: RNA
<213> ORGANISM: Homo sapiens

<400> SEQUENCE: 243
caugugggac auucaccuu                                                19

<210> SEQ ID NO 244
<211> LENGTH: 19
<212> TYPE: RNA
<213> ORGANISM: Homo sapiens

<400> SEQUENCE: 244
aaggugaaug ucccacaug                                                19

<210> SEQ ID NO 245
<211> LENGTH: 19
<212> TYPE: RNA
<213> ORGANISM: Homo sapiens

<400> SEQUENCE: 245
cagugugagg accggagcu                                                19

<210> SEQ ID NO 246
<211> LENGTH: 19
<212> TYPE: RNA
<213> ORGANISM: Homo sapiens

<400> SEQUENCE: 246
agcuccgguc cucacacug                                                19

<210> SEQ ID NO 247
<211> LENGTH: 19
<212> TYPE: RNA
<213> ORGANISM: Homo sapiens

<400> SEQUENCE: 247
ugaagaagcc caacccgca                                                19
```

<210> SEQ ID NO 248
<211> LENGTH: 19
<212> TYPE: RNA
<213> ORGANISM: Homo sapiens

<400> SEQUENCE: 248
ugcggguugg gcuucuuca                                          19

<210> SEQ ID NO 249
<211> LENGTH: 19
<212> TYPE: RNA
<213> ORGANISM: Homo sapiens

<400> SEQUENCE: 249
gaagcccaac ccgcagugu                                          19

<210> SEQ ID NO 250
<211> LENGTH: 19
<212> TYPE: RNA
<213> ORGANISM: Homo sapiens

<400> SEQUENCE: 250
acacugcggg uugggcuuc                                          19

<210> SEQ ID NO 251
<211> LENGTH: 19
<212> TYPE: RNA
<213> ORGANISM: Homo sapiens

<400> SEQUENCE: 251 cccccuccagc cgcauuguu                                         19

<210> SEQ ID NO 252
<211> LENGTH: 19
<212> TYPE: RNA
<213> ORGANISM: Homo sapiens

<400> SEQUENCE: 252
aacaaugcgg cuggaggggg                                         19

<210> SEQ ID NO 253
<211> LENGTH: 19
<212> TYPE: RNA
<213> ORGANISM: Homo sapiens

<400> SEQUENCE: 253
cagguucggg gucgacaca                                          19

<210> SEQ ID NO 254
<211> LENGTH: 19
<212> TYPE: RNA
<213> ORGANISM: Homo sapiens

<400> SEQUENCE: 254
ugugucgacc ccgaaccug                                          19

<210> SEQ ID NO 255
<211> LENGTH: 19
<212> TYPE: RNA
<213> ORGANISM: Homo sapiens

<400> SEQUENCE: 255
agguucgggg ucgacacau                                          19

```
<210> SEQ ID NO 256
<211> LENGTH: 19
<212> TYPE: RNA
<213> ORGANISM: Homo sapiens

<400> SEQUENCE: 256
augugucgac cccgaaccu                                                     19

<210> SEQ ID NO 257
<211> LENGTH: 19
<212> TYPE: RNA
<213> ORGANISM: Homo sapiens

<400> SEQUENCE: 257
guucgggguc gacacaucu                                                     19

<210> SEQ ID NO 258
<211> LENGTH: 19
<212> TYPE: RNA
<213> ORGANISM: Homo sapiens

<400> SEQUENCE: 258
agaugugucg accccgaac                                                     19

<210> SEQ ID NO 259
<211> LENGTH: 19
<212> TYPE: RNA
<213> ORGANISM: Homo sapiens

<400> SEQUENCE: 259
cgcugaccgc ugggugaua                                                     19

<210> SEQ ID NO 260
<211> LENGTH: 19
<212> TYPE: RNA
<213> ORGANISM: Homo sapiens

<400> SEQUENCE: 260
uaucacccag cggucagcg                                                     19

<210> SEQ ID NO 261
<211> LENGTH: 19
<212> TYPE: RNA
<213> ORGANISM: Homo sapiens

<400> SEQUENCE: 261
gcugaccgcu gggugauaa                                                     19

<210> SEQ ID NO 262
<211> LENGTH: 19
<212> TYPE: RNA
<213> ORGANISM: Homo sapiens

<400> SEQUENCE: 262
uuaucaccca gcggucagc                                                     19

<210> SEQ ID NO 263
<211> LENGTH: 19
<212> TYPE: RNA
<213> ORGANISM: Homo sapiens

<400> SEQUENCE: 263
ugaccgcugg gugauaaca                                                     19
```

<210> SEQ ID NO 264
<211> LENGTH: 19
<212> TYPE: RNA
<213> ORGANISM: Homo sapiens

<400> SEQUENCE: 264
uguuaucacc cagcgguca                                          19

<210> SEQ ID NO 265
<211> LENGTH: 19
<212> TYPE: RNA
<213> ORGANISM: Homo sapiens

<400> SEQUENCE: 265
ccgcugggug auaacagcu                                          19

<210> SEQ ID NO 266
<211> LENGTH: 19
<212> TYPE: RNA
<213> ORGANISM: Homo sapiens

<400> SEQUENCE: 266
agcuguuauc acccagcgg                                          19

<210> SEQ ID NO 267
<211> LENGTH: 19
<212> TYPE: RNA
<213> ORGANISM: Homo sapiens

<400> SEQUENCE: 267
ugcuguggac cguguuccu                                          19

<210> SEQ ID NO 268
<211> LENGTH: 19
<212> TYPE: RNA
<213> ORGANISM: Homo sapiens

<400> SEQUENCE: 268
aggaacacgg uccacagca                                          19

<210> SEQ ID NO 269
<211> LENGTH: 19
<212> TYPE: RNA
<213> ORGANISM: Homo sapiens

<400> SEQUENCE: 269
guguggcaga acucgcgcu                                          19

<210> SEQ ID NO 270
<211> LENGTH: 19
<212> TYPE: RNA
<213> ORGANISM: Homo sapiens

<400> SEQUENCE: 270
agcgcgaguu cugccacac                                          19

<210> SEQ ID NO 271
<211> LENGTH: 19
<212> TYPE: RNA
<213> ORGANISM: Homo sapiens

<400> SEQUENCE: 271

|  |  |
|---|---|
| uccugcaccc guaccacga | 19 |

<210> SEQ ID NO 272
<211> LENGTH: 19
<212> TYPE: RNA
<213> ORGANISM: Homo sapiens

<400> SEQUENCE: 272

|  |  |
|---|---|
| ucgugguacg ggugcagga | 19 |

<210> SEQ ID NO 273
<211> LENGTH: 19
<212> TYPE: RNA
<213> ORGANISM: Homo sapiens

<400> SEQUENCE: 273

|  |  |
|---|---|
| ccugcacccg uaccacgaa | 19 |

<210> SEQ ID NO 274
<211> LENGTH: 19
<212> TYPE: RNA
<213> ORGANISM: Homo sapiens

<400> SEQUENCE: 274

|  |  |
|---|---|
| uucgugguac gggugcagg | 19 |

<210> SEQ ID NO 275
<211> LENGTH: 19
<212> TYPE: RNA
<213> ORGANISM: Homo sapiens

<400> SEQUENCE: 275

|  |  |
|---|---|
| ugcacccgua ccacgaaga | 19 |

<210> SEQ ID NO 276
<211> LENGTH: 19
<212> TYPE: RNA
<213> ORGANISM: Homo sapiens

<400> SEQUENCE: 276

|  |  |
|---|---|
| ucuucguggu acgggugca | 19 |

<210> SEQ ID NO 277
<211> LENGTH: 19
<212> TYPE: RNA
<213> ORGANISM: Homo sapiens

<400> SEQUENCE: 277

|  |  |
|---|---|
| cgcgcuccca cuucuucga | 19 |

<210> SEQ ID NO 278
<211> LENGTH: 19
<212> TYPE: RNA
<213> ORGANISM: Homo sapiens

<400> SEQUENCE: 278

|  |  |
|---|---|
| ucgaagaagu gggagcgcg | 19 |

<210> SEQ ID NO 279
<211> LENGTH: 19
<212> TYPE: RNA
<213> ORGANISM: Homo sapiens

<400> SEQUENCE: 279
ggccugcacu gcuggauua					19

<210> SEQ ID NO 280
<211> LENGTH: 19
<212> TYPE: RNA
<213> ORGANISM: Homo sapiens

<400> SEQUENCE: 280
uaauccagca gugcaggcc					19

<210> SEQ ID NO 281
<211> LENGTH: 19
<212> TYPE: RNA
<213> ORGANISM: Homo sapiens

<400> SEQUENCE: 281
cacugcugga uuacgggcu					19

<210> SEQ ID NO 282
<211> LENGTH: 19
<212> TYPE: RNA
<213> ORGANISM: Homo sapiens

<400> SEQUENCE: 282
agcccguaau ccagcagug					19

<210> SEQ ID NO 283
<211> LENGTH: 19
<212> TYPE: RNA
<213> ORGANISM: Homo sapiens

<400> SEQUENCE: 283
ggaugugcag uugauccca					19

<210> SEQ ID NO 284
<211> LENGTH: 19
<212> TYPE: RNA
<213> ORGANISM: Homo sapiens

<400> SEQUENCE: 284
ugggaucaac ugcacaucc					19

<210> SEQ ID NO 285
<211> LENGTH: 19
<212> TYPE: RNA
<213> ORGANISM: Homo sapiens

<400> SEQUENCE: 285
ugcagcgagg ucuaucgcu					19

<210> SEQ ID NO 286
<211> LENGTH: 19
<212> TYPE: RNA
<213> ORGANISM: Homo sapiens

<400> SEQUENCE: 286
agcgauagac cucgcugca					19

<210> SEQ ID NO 287
<211> LENGTH: 19
<212> TYPE: RNA
<213> ORGANISM: Homo sapiens

```
<400> SEQUENCE: 287
gcagcgaggu cuaucgcua                                              19

<210> SEQ ID NO 288
<211> LENGTH: 19
<212> TYPE: RNA
<213> ORGANISM: Homo sapiens

<400> SEQUENCE: 288
uagcgauaga ccucgcugc                                              19

<210> SEQ ID NO 289
<211> LENGTH: 19
<212> TYPE: RNA
<213> ORGANISM: Homo sapiens

<400> SEQUENCE: 289 gcggaggucua ucgcuacca                                             19

<210> SEQ ID NO 290
<211> LENGTH: 19
<212> TYPE: RNA
<213> ORGANISM: Homo sapiens

<400> SEQUENCE: 290
ugguagcgau agaccucgc                                              19

<210> SEQ ID NO 291
<211> LENGTH: 19
<212> TYPE: RNA
<213> ORGANISM: Homo sapiens

<400> SEQUENCE: 291
gucuaucgcu accagguga                                              19

<210> SEQ ID NO 292
<211> LENGTH: 19
<212> TYPE: RNA
<213> ORGANISM: Homo sapiens

<400> SEQUENCE: 292
ucaccuggua gcgauagac                                              19

<210> SEQ ID NO 293
<211> LENGTH: 19
<212> TYPE: RNA
<213> ORGANISM: Homo sapiens

<400> SEQUENCE: 293
aggugacgcc acgcaugcu                                              19

<210> SEQ ID NO 294
<211> LENGTH: 19
<212> TYPE: RNA
<213> ORGANISM: Homo sapiens

<400> SEQUENCE: 294
agcaugcgug gcgucaccu                                              19

<210> SEQ ID NO 295
<211> LENGTH: 19
<212> TYPE: RNA
<213> ORGANISM: Homo sapiens
```

```
<400> SEQUENCE: 295
gugacgccac gcaugcugu                                                    19

<210> SEQ ID NO 296
<211> LENGTH: 19
<212> TYPE: RNA
<213> ORGANISM: Homo sapiens

<400> SEQUENCE: 296
acagcaugcg uggcgucac                                                    19

<210> SEQ ID NO 297
<211> LENGTH: 19
<212> TYPE: RNA
<213> ORGANISM: Homo sapiens

<400> SEQUENCE: 297
gacgccacgc augcugugu                                                    19

<210> SEQ ID NO 298
<211> LENGTH: 19
<212> TYPE: RNA
<213> ORGANISM: Homo sapiens

<400> SEQUENCE: 298
acacagcaug cguggcguc                                                    19

<210> SEQ ID NO 299
<211> LENGTH: 19
<212> TYPE: RNA
<213> ORGANISM: Homo sapiens

<400> SEQUENCE: 299
ggcuguggcc ggccuaacu                                                    19

<210> SEQ ID NO 300
<211> LENGTH: 19
<212> TYPE: RNA
<213> ORGANISM: Homo sapiens

<400> SEQUENCE: 300
aguuaggccg gccacagcc                                                    19

<210> SEQ ID NO 301
<211> LENGTH: 19
<212> TYPE: RNA
<213> ORGANISM: Homo sapiens

<400> SEQUENCE: 301
gcuguggccg gccuaacua                                                    19

<210> SEQ ID NO 302
<211> LENGTH: 19
<212> TYPE: RNA
<213> ORGANISM: Homo sapiens

<400> SEQUENCE: 302
uaguuaggcc ggccacagc                                                    19

<210> SEQ ID NO 303
<211> LENGTH: 19
<212> TYPE: RNA
```

```
<213> ORGANISM: Homo sapiens

<400> SEQUENCE: 303
uguggccggc cuaacuacu                                              19

<210> SEQ ID NO 304
<211> LENGTH: 19
<212> TYPE: RNA
<213> ORGANISM: Homo sapiens

<400> SEQUENCE: 304
aguaguuagg ccggccaca                                              19

<210> SEQ ID NO 305
<211> LENGTH: 19
<212> TYPE: RNA
<213> ORGANISM: Homo sapiens

<400> SEQUENCE: 305
ggccuaacua cuucggcgu                                              19

<210> SEQ ID NO 306
<211> LENGTH: 19
<212> TYPE: RNA
<213> ORGANISM: Homo sapiens

<400> SEQUENCE: 306
acgccgaagu aguuaggcc                                              19

<210> SEQ ID NO 307
<211> LENGTH: 19
<212> TYPE: RNA
<213> ORGANISM: Homo sapiens

<400> SEQUENCE: 307
ccuaacuacu ucggcgucu                                              19

<210> SEQ ID NO 308
<211> LENGTH: 19
<212> TYPE: RNA
<213> ORGANISM: Homo sapiens

<400> SEQUENCE: 308
agacgccgaa guaguuagg                                              19

<210> SEQ ID NO 309
<211> LENGTH: 19
<212> TYPE: RNA
<213> ORGANISM: Homo sapiens

<400> SEQUENCE: 309
cuaacuacuu cggcgucua                                              19

<210> SEQ ID NO 310
<211> LENGTH: 19
<212> TYPE: RNA
<213> ORGANISM: Homo sapiens

<400> SEQUENCE: 310
uagacgccga aguaguuag                                              19

<210> SEQ ID NO 311
<211> LENGTH: 19
```

```
<212> TYPE: RNA
<213> ORGANISM: Homo sapiens

<400> SEQUENCE: 311
aacuacuucg gcgucuaca                                                19

<210> SEQ ID NO 312
<211> LENGTH: 19
<212> TYPE: RNA
<213> ORGANISM: Homo sapiens

<400> SEQUENCE: 312
uguagacgcc gaaguaguu                                                19

<210> SEQ ID NO 313
<211> LENGTH: 19
<212> TYPE: RNA
<213> ORGANISM: Homo sapiens

<400> SEQUENCE: 313
acacccgcau cacaggugu                                                19

<210> SEQ ID NO 314
<211> LENGTH: 19
<212> TYPE: RNA
<213> ORGANISM: Homo sapiens

<400> SEQUENCE: 314
acaccuguga ugcgggugu                                                19

<210> SEQ ID NO 315
<211> LENGTH: 19
<212> TYPE: RNA
<213> ORGANISM: Homo sapiens

<400> SEQUENCE: 315
cgcaucacag gugugauca                                                19

<210> SEQ ID NO 316
<211> LENGTH: 19
<212> TYPE: RNA
<213> ORGANISM: Homo sapiens

<400> SEQUENCE: 316
ugaucacacc ugugaugcg                                                19

<210> SEQ ID NO 317
<211> LENGTH: 19
<212> TYPE: RNA
<213> ORGANISM: Homo sapiens

<400> SEQUENCE: 317
gcuggaucca gcaaguggu                                                19

<210> SEQ ID NO 318
<211> LENGTH: 19
<212> TYPE: RNA
<213> ORGANISM: Homo sapiens

<400> SEQUENCE: 318
accacuugcu ggauccagc                                                19

<210> SEQ ID NO 319
```

```
<211> LENGTH: 19
<212> TYPE: RNA
<213> ORGANISM: Homo sapiens

<400> SEQUENCE: 319
ggaacugccc cccugcaaa                                                  19

<210> SEQ ID NO 320
<211> LENGTH: 19
<212> TYPE: RNA
<213> ORGANISM: Homo sapiens

<400> SEQUENCE: 320
uuugcagggg ggcaguucc                                                  19

<210> SEQ ID NO 321
<211> LENGTH: 19
<212> TYPE: RNA
<213> ORGANISM: Homo sapiens

<400> SEQUENCE: 321
aggagguggc aucuugucu                                                  19

<210> SEQ ID NO 322
<211> LENGTH: 19
<212> TYPE: RNA
<213> ORGANISM: Homo sapiens

<400> SEQUENCE: 322
agacaagaug ccaccuccu                                                  19

<210> SEQ ID NO 323
<211> LENGTH: 19
<212> TYPE: RNA
<213> ORGANISM: Homo sapiens

<400> SEQUENCE: 323
agguggcauc uugucucgu                                                  19

<210> SEQ ID NO 324
<211> LENGTH: 19
<212> TYPE: RNA
<213> ORGANISM: Homo sapiens

<400> SEQUENCE: 324
acgagacaag augccaccu                                                  19

<210> SEQ ID NO 325
<211> LENGTH: 19
<212> TYPE: RNA
<213> ORGANISM: Homo sapiens

<400> SEQUENCE: 325
ggcaucuugu cucgucccu                                                  19

<210> SEQ ID NO 326
<211> LENGTH: 19
<212> TYPE: RNA
<213> ORGANISM: Homo sapiens

<400> SEQUENCE: 326
agggacgaga caagaugcc                                                  19
```

```
<210> SEQ ID NO 327
<211> LENGTH: 19
<212> TYPE: RNA
<213> ORGANISM: Homo sapiens

<400> SEQUENCE: 327
caucuugucu cgucccuga                                                   19

<210> SEQ ID NO 328
<211> LENGTH: 19
<212> TYPE: RNA
<213> ORGANISM: Homo sapiens

<400> SEQUENCE: 328
ucagggacga gacaagaug                                                   19

<210> SEQ ID NO 329
<211> LENGTH: 19
<212> TYPE: RNA
<213> ORGANISM: Homo sapiens

<400> SEQUENCE: 329
aucuugucuc gucccugau                                                   19

<210> SEQ ID NO 330
<211> LENGTH: 19
<212> TYPE: RNA
<213> ORGANISM: Homo sapiens

<400> SEQUENCE: 330
aucagggacg agacaagau                                                   19

<210> SEQ ID NO 331
<211> LENGTH: 19
<212> TYPE: RNA
<213> ORGANISM: Homo sapiens

<400> SEQUENCE: 331
cagcuggggg ucaagacgu                                                   19

<210> SEQ ID NO 332
<211> LENGTH: 19
<212> TYPE: RNA
<213> ORGANISM: Homo sapiens

<400> SEQUENCE: 332
acgucuugac ccccagcug                                                   19

<210> SEQ ID NO 333
<211> LENGTH: 19
<212> TYPE: RNA
<213> ORGANISM: Homo sapiens

<400> SEQUENCE: 333
gggggucaag acgucccu                                                    19

<210> SEQ ID NO 334
<211> LENGTH: 19
<212> TYPE: RNA
<213> ORGANISM: Homo sapiens

<400> SEQUENCE: 334
aggggacguc uugaccccc                                                   19
```

```
<210> SEQ ID NO 335
<211> LENGTH: 19
<212> TYPE: RNA
<213> ORGANISM: Homo sapiens

<400> SEQUENCE: 335
gggucaagac gucccuga                                                  19

<210> SEQ ID NO 336
<211> LENGTH: 19
<212> TYPE: RNA
<213> ORGANISM: Homo sapiens

<400> SEQUENCE: 336
ucaggggacg ucuugaccc                                                 19

<210> SEQ ID NO 337
<211> LENGTH: 19
<212> TYPE: RNA
<213> ORGANISM: Homo sapiens

<400> SEQUENCE: 337
ccacugcugc cuaaugcaa                                                 19

<210> SEQ ID NO 338
<211> LENGTH: 19
<212> TYPE: RNA
<213> ORGANISM: Homo sapiens

<400> SEQUENCE: 338
uugcauuagg cagcagugg                                                 19

<210> SEQ ID NO 339
<211> LENGTH: 19
<212> TYPE: RNA
<213> ORGANISM: Homo sapiens

<400> SEQUENCE: 339
ugcugccuaa ugcaaggca                                                 19

<210> SEQ ID NO 340
<211> LENGTH: 19
<212> TYPE: RNA
<213> ORGANISM: Homo sapiens

<400> SEQUENCE: 340
ugccuugcau uaggcagca                                                 19

<210> SEQ ID NO 341
<211> LENGTH: 19
<212> TYPE: RNA
<213> ORGANISM: Homo sapiens

<400> SEQUENCE: 341
cuaaugcaag gcaguggcu                                                 19

<210> SEQ ID NO 342
<211> LENGTH: 19
<212> TYPE: RNA
<213> ORGANISM: Homo sapiens

<400> SEQUENCE: 342
agccacugcc uugcauuag                                                 19
```

```
<210> SEQ ID NO 343
<211> LENGTH: 19
<212> TYPE: RNA
<213> ORGANISM: Homo sapiens

<400> SEQUENCE: 343
cagcaagaau gcugguucu                                                  19

<210> SEQ ID NO 344
<211> LENGTH: 19
<212> TYPE: RNA
<213> ORGANISM: Homo sapiens

<400> SEQUENCE: 344
agaaccagca uucuugcug                                                  19

<210> SEQ ID NO 345
<211> LENGTH: 19
<212> TYPE: RNA
<213> ORGANISM: Homo sapiens

<400> SEQUENCE: 345
gaggugcgcc ccacucugu                                                  19

<210> SEQ ID NO 346
<211> LENGTH: 19
<212> TYPE: RNA
<213> ORGANISM: Homo sapiens

<400> SEQUENCE: 346 acagagtuggg gcgcaccuc                                                 19

<210> SEQ ID NO 347
<211> LENGTH: 19
<212> TYPE: RNA
<213> ORGANISM: Homo sapiens

<400> SEQUENCE: 347
cuucggaagc cccuggucu                                                  19

<210> SEQ ID NO 348
<211> LENGTH: 19
<212> TYPE: RNA
<213> ORGANISM: Homo sapiens

<400> SEQUENCE: 348
agaccagggg cuuccgaag                                                  19

<210> SEQ ID NO 349
<211> LENGTH: 19
<212> TYPE: RNA
<213> ORGANISM: Homo sapiens

<400> SEQUENCE: 349
ucggaagccc cuggucuaa                                                  19

<210> SEQ ID NO 350
<211> LENGTH: 19
<212> TYPE: RNA
<213> ORGANISM: Homo sapiens

<400> SEQUENCE: 350
```

| | |
|---|---|
| uuagaccagg ggcuuccga | 19 |

<210> SEQ ID NO 351
<211> LENGTH: 19
<212> TYPE: RNA
<213> ORGANISM: Homo sapiens

<400> SEQUENCE: 351

| | |
|---|---|
| ggaagccccu ggucuaacu | 19 |

<210> SEQ ID NO 352
<211> LENGTH: 19
<212> TYPE: RNA
<213> ORGANISM: Homo sapiens

<400> SEQUENCE: 352

| | |
|---|---|
| aguuagacca ggggcuucc | 19 |

<210> SEQ ID NO 353
<211> LENGTH: 19
<212> TYPE: RNA
<213> ORGANISM: Homo sapiens

<400> SEQUENCE: 353

| | |
|---|---|
| gaagccccug gucuaacuu | 19 |

<210> SEQ ID NO 354
<211> LENGTH: 19
<212> TYPE: RNA
<213> ORGANISM: Homo sapiens

<400> SEQUENCE: 354

| | |
|---|---|
| aaguuagacc aggggcuuc | 19 |

<210> SEQ ID NO 355
<211> LENGTH: 19
<212> TYPE: RNA
<213> ORGANISM: Homo sapiens

<400> SEQUENCE: 355

| | |
|---|---|
| cccuggucua acuugggau | 19 |

<210> SEQ ID NO 356
<211> LENGTH: 19
<212> TYPE: RNA
<213> ORGANISM: Homo sapiens

<400> SEQUENCE: 356

| | |
|---|---|
| aucccaaguu agaccaggg | 19 |

<210> SEQ ID NO 357
<211> LENGTH: 19
<212> TYPE: RNA
<213> ORGANISM: Homo sapiens

<400> SEQUENCE: 357

| | |
|---|---|
| cuggucuaac uugggaucu | 19 |

<210> SEQ ID NO 358
<211> LENGTH: 19
<212> TYPE: RNA
<213> ORGANISM: Homo sapiens

<400> SEQUENCE: 358
agaucccaag uuagaccag 19

<210> SEQ ID NO 359
<211> LENGTH: 19
<212> TYPE: RNA
<213> ORGANISM: Homo sapiens

<400> SEQUENCE: 359
cuaacuuggg aucgggaa 19

<210> SEQ ID NO 360
<211> LENGTH: 19
<212> TYPE: RNA
<213> ORGANISM: Homo sapiens

<400> SEQUENCE: 360
uucccagauc ccaaguuag 19

<210> SEQ ID NO 361
<211> LENGTH: 19
<212> TYPE: RNA
<213> ORGANISM: Homo sapiens

<400> SEQUENCE: 361
ccaucggagg ggacccuca 19

<210> SEQ ID NO 362
<211> LENGTH: 19
<212> TYPE: RNA
<213> ORGANISM: Homo sapiens

<400> SEQUENCE: 362
ugaggguccc cuccgaugg 19

<210> SEQ ID NO 363
<211> LENGTH: 19
<212> TYPE: RNA
<213> ORGANISM: Homo sapiens

<400> SEQUENCE: 363
ugggccugcu gccacugua 19

<210> SEQ ID NO 364
<211> LENGTH: 19
<212> TYPE: RNA
<213> ORGANISM: Homo sapiens

<400> SEQUENCE: 364
uacaguggca gcaggccca 19

<210> SEQ ID NO 365
<211> LENGTH: 19
<212> TYPE: RNA
<213> ORGANISM: Homo sapiens

<400> SEQUENCE: 365
gggccugcug ccacuguaa 19

<210> SEQ ID NO 366
<211> LENGTH: 19
<212> TYPE: RNA
<213> ORGANISM: Homo sapiens

```
<400> SEQUENCE: 366
uuacaguggc agcaggccc                                                        19

<210> SEQ ID NO 367
<211> LENGTH: 19
<212> TYPE: RNA
<213> ORGANISM: Homo sapiens

<400> SEQUENCE: 367
gcugccacug uaagccaaa                                                        19

<210> SEQ ID NO 368
<211> LENGTH: 19
<212> TYPE: RNA
<213> ORGANISM: Homo sapiens

<400> SEQUENCE: 368
uuuggcuuac aguggcagc                                                        19

<210> SEQ ID NO 369
<211> LENGTH: 19
<212> TYPE: RNA
<213> ORGANISM: Homo sapiens

<400> SEQUENCE: 369
ccacuguaag ccaaaaggu                                                        19

<210> SEQ ID NO 370
<211> LENGTH: 19
<212> TYPE: RNA
<213> ORGANISM: Homo sapiens

<400> SEQUENCE: 370
accuuuuggc uuacagugg                                                        19

<210> SEQ ID NO 371
<211> LENGTH: 19
<212> TYPE: RNA
<213> ORGANISM: Homo sapiens

<400> SEQUENCE: 371 aggugggaa guccugacu                                                         19

<210> SEQ ID NO 372
<211> LENGTH: 19
<212> TYPE: RNA
<213> ORGANISM: Homo sapiens

<400> SEQUENCE: 372
agucaggacu uccccaccu                                                        19

<210> SEQ ID NO 373
<211> LENGTH: 19
<212> TYPE: RNA
<213> ORGANISM: Homo sapiens

<400> SEQUENCE: 373
gaauaaagcu gccugauca                                                        19

<210> SEQ ID NO 374
<211> LENGTH: 19
<212> TYPE: RNA
<213> ORGANISM: Homo sapiens
```

```
<400> SEQUENCE: 374
ugaucaggca gcuuuauuc                                              19

<210> SEQ ID NO 375
<211> LENGTH: 19
<212> TYPE: RNA
<213> ORGANISM: Homo sapiens

<400> SEQUENCE: 375
aauaaagcug ccugaucaa                                              19

<210> SEQ ID NO 376
<211> LENGTH: 19
<212> TYPE: RNA
<213> ORGANISM: Homo sapiens

<400> SEQUENCE: 376
uugaucaggc agcuuuauu                                              19

<210> SEQ ID NO 377
<211> LENGTH: 19
<212> TYPE: RNA
<213> ORGANISM: Homo sapiens

<400> SEQUENCE: 377
agcugccuga ucaaaaaaa                                              19

<210> SEQ ID NO 378
<211> LENGTH: 19
<212> TYPE: RNA
<213> ORGANISM: Homo sapiens

<400> SEQUENCE: 378 uuuuuugau caggcagcu                                               19

<210> SEQ ID NO 379
<211> LENGTH: 19
<212> TYPE: RNA
<213> ORGANISM: Homo sapiens

<400> SEQUENCE: 379
cuacagggcc gaguacgaa                                              19

<210> SEQ ID NO 380
<211> LENGTH: 19
<212> TYPE: RNA
<213> ORGANISM: Homo sapiens

<400> SEQUENCE: 380
uucguacucg gcccuguag                                              19

<210> SEQ ID NO 381
<211> LENGTH: 19
<212> TYPE: RNA
<213> ORGANISM: Homo sapiens

<400> SEQUENCE: 381
ugugaugggg ucaaggacu                                              19

<210> SEQ ID NO 382
<211> LENGTH: 19
<212> TYPE: RNA
```

```
<213> ORGANISM: Homo sapiens

<400> SEQUENCE: 382
aguccuugac cccaucaca                                              19

<210> SEQ ID NO 383
<211> LENGTH: 19
<212> TYPE: RNA
<213> ORGANISM: Homo sapiens

<400> SEQUENCE: 383
cuggagaggu guccuucaa                                              19

<210> SEQ ID NO 384
<211> LENGTH: 19
<212> TYPE: RNA
<213> ORGANISM: Homo sapiens

<400> SEQUENCE: 384
uugaaggaca ccucuccag                                              19

<210> SEQ ID NO 385
<211> LENGTH: 19
<212> TYPE: RNA
<213> ORGANISM: Homo sapiens

<400> SEQUENCE: 385
ggaccgacug gccauguau                                              19

<210> SEQ ID NO 386
<211> LENGTH: 19
<212> TYPE: RNA
<213> ORGANISM: Homo sapiens

<400> SEQUENCE: 386
auacauggcc agucggucc                                              19

<210> SEQ ID NO 387
<211> LENGTH: 19
<212> TYPE: RNA
<213> ORGANISM: Homo sapiens

<400> SEQUENCE: 387
aguugauccc acaggaccu                                              19

<210> SEQ ID NO 388
<211> LENGTH: 19
<212> TYPE: RNA
<213> ORGANISM: Homo sapiens

<400> SEQUENCE: 388
agguccugug ggaucaacu                                              19

<210> SEQ ID NO 389
<211> LENGTH: 19
<212> TYPE: RNA
<213> ORGANISM: Homo sapiens

<400> SEQUENCE: 389
aaaccgccaa agcccagaa                                              19

<210> SEQ ID NO 390
<211> LENGTH: 19
```

```
<212> TYPE: RNA
<213> ORGANISM: Homo sapiens

<400> SEQUENCE: 390
uucugggcuu uggcgguuu                                              19

<210> SEQ ID NO 391
<211> LENGTH: 19
<212> TYPE: RNA
<213> ORGANISM: Homo sapiens

<400> SEQUENCE: 391
ugugugccgg cuaccgcaa                                              19

<210> SEQ ID NO 392
<211> LENGTH: 19
<212> TYPE: RNA
<213> ORGANISM: Homo sapiens

<400> SEQUENCE: 392
uugcgguagc cggcacaca                                              19

<210> SEQ ID NO 393
<211> LENGTH: 19
<212> TYPE: RNA
<213> ORGANISM: Homo sapiens

<400> SEQUENCE: 393
auuccacgcu ggguuguua                                              19

<210> SEQ ID NO 394
<211> LENGTH: 19
<212> TYPE: RNA
<213> ORGANISM: Homo sapiens

<400> SEQUENCE: 394
uaacaaccca gcguggaau                                              19

<210> SEQ ID NO 395
<211> LENGTH: 19
<212> TYPE: RNA
<213> ORGANISM: Homo sapiens

<400> SEQUENCE: 395
ucgcugaccg cugggugau                                              19

<210> SEQ ID NO 396
<211> LENGTH: 19
<212> TYPE: RNA
<213> ORGANISM: Homo sapiens

<400> SEQUENCE: 396
aucacccagc ggucagcga                                              19

<210> SEQ ID NO 397
<211> LENGTH: 19
<212> TYPE: RNA
<213> ORGANISM: Homo sapiens

<400> SEQUENCE: 397
caagcagggg gacaaguau                                              19

<210> SEQ ID NO 398
```

```
<211> LENGTH: 19
<212> TYPE: RNA
<213> ORGANISM: Homo sapiens

<400> SEQUENCE: 398
auacuugucc cccugcuug                                                  19

<210> SEQ ID NO 399
<211> LENGTH: 19
<212> TYPE: RNA
<213> ORGANISM: Homo sapiens

<400> SEQUENCE: 399
ugaugucugc uccagugau                                                  19

<210> SEQ ID NO 400
<211> LENGTH: 19
<212> TYPE: RNA
<213> ORGANISM: Homo sapiens

<400> SEQUENCE: 400
aucacuggag cagacauca                                                  19

<210> SEQ ID NO 401
<211> LENGTH: 19
<212> TYPE: RNA
<213> ORGANISM: Homo sapiens

<400> SEQUENCE: 401
gagguguccu ucaagguga                                                  19

<210> SEQ ID NO 402
<211> LENGTH: 19
<212> TYPE: RNA
<213> ORGANISM: Homo sapiens

<400> SEQUENCE: 402
ucaccuugaa ggacaccuc                                                  19

<210> SEQ ID NO 403
<211> LENGTH: 19
<212> TYPE: RNA
<213> ORGANISM: Homo sapiens

<400> SEQUENCE: 403
aagcaggggg acaaguauu                                                  19

<210> SEQ ID NO 404
<211> LENGTH: 19
<212> TYPE: RNA
<213> ORGANISM: Homo sapiens

<400> SEQUENCE: 404
aauacuuguc ccccugcuu                                                  19

<210> SEQ ID NO 405
<211> LENGTH: 19
<212> TYPE: RNA
<213> ORGANISM: Homo sapiens

<400> SEQUENCE: 405
cuugggaucu gggaaugga                                                  19
```

```
<210> SEQ ID NO 406
<211> LENGTH: 19
<212> TYPE: RNA
<213> ORGANISM: Homo sapiens

<400> SEQUENCE: 406
uccauuccca gaucccaag                                                 19

<210> SEQ ID NO 407
<211> LENGTH: 19
<212> TYPE: RNA
<213> ORGANISM: Homo sapiens

<400> SEQUENCE: 407
gguauuuccu aggguacaa                                                 19

<210> SEQ ID NO 408
<211> LENGTH: 19
<212> TYPE: RNA
<213> ORGANISM: Homo sapiens

<400> SEQUENCE: 408
uuguacccua ggaaauacc                                                 19

<210> SEQ ID NO 409
<211> LENGTH: 19
<212> TYPE: RNA
<213> ORGANISM: Homo sapiens

<400> SEQUENCE: 409
ggcuaccgca agggcaaga                                                 19

<210> SEQ ID NO 410
<211> LENGTH: 19
<212> TYPE: RNA
<213> ORGANISM: Homo sapiens

<400> SEQUENCE: 410
ucuugcccuu gcgguagcc                                                 19

<210> SEQ ID NO 411
<211> LENGTH: 19
<212> TYPE: RNA
<213> ORGANISM: Homo sapiens

<400> SEQUENCE: 411 gcaggggggac aaguauucu                                                19

<210> SEQ ID NO 412
<211> LENGTH: 19
<212> TYPE: RNA
<213> ORGANISM: Homo sapiens

<400> SEQUENCE: 412
agaauacuug uccccugc                                                  19

<210> SEQ ID NO 413
<211> LENGTH: 19
<212> TYPE: RNA
<213> ORGANISM: Homo sapiens

<400> SEQUENCE: 413
gcucagcagc aagaaugcu                                                 19
```

```
<210> SEQ ID NO 414
<211> LENGTH: 19
<212> TYPE: RNA
<213> ORGANISM: Homo sapiens

<400> SEQUENCE: 414
agcauucuug cugcugagc                                            19

<210> SEQ ID NO 415
<211> LENGTH: 19
<212> TYPE: RNA
<213> ORGANISM: Homo sapiens

<400> SEQUENCE: 415
uugggaucug ggaauggaa                                            19

<210> SEQ ID NO 416
<211> LENGTH: 19
<212> TYPE: RNA
<213> ORGANISM: Homo sapiens

<400> SEQUENCE: 416
uuccauuccc agaucccaa                                            19

<210> SEQ ID NO 417
<211> LENGTH: 19
<212> TYPE: RNA
<213> ORGANISM: Homo sapiens

<400> SEQUENCE: 417
ccaaagccca gaagaugcu                                            19

<210> SEQ ID NO 418
<211> LENGTH: 19
<212> TYPE: RNA
<213> ORGANISM: Homo sapiens

<400> SEQUENCE: 418
agcaucuucu gggcuuugg                                            19

<210> SEQ ID NO 419
<211> LENGTH: 19
<212> TYPE: RNA
<213> ORGANISM: Homo sapiens

<400> SEQUENCE: 419
gcuaccgcaa gggcaagaa                                            19

<210> SEQ ID NO 420
<211> LENGTH: 19
<212> TYPE: RNA
<213> ORGANISM: Homo sapiens

<400> SEQUENCE: 420
uucuugcccu ugcgguagc                                            19

<210> SEQ ID NO 421
<211> LENGTH: 19
<212> TYPE: RNA
<213> ORGANISM: Homo sapiens

<400> SEQUENCE: 421
gcucagcugc ccuuuggaa                                            19
```

<210> SEQ ID NO 422
<211> LENGTH: 19
<212> TYPE: RNA
<213> ORGANISM: Homo sapiens

<400> SEQUENCE: 422
uuccaaaggg cagcugagc                                                    19

<210> SEQ ID NO 423
<211> LENGTH: 19
<212> TYPE: RNA
<213> ORGANISM: Homo sapiens

<400> SEQUENCE: 423
ugguggcagg agguggcau                                                    19

<210> SEQ ID NO 424
<211> LENGTH: 19
<212> TYPE: RNA
<213> ORGANISM: Homo sapiens

<400> SEQUENCE: 424
augccaccuc cugccacca                                                    19

<210> SEQ ID NO 425
<211> LENGTH: 19
<212> TYPE: RNA
<213> ORGANISM: Homo sapiens

<400> SEQUENCE: 425
cccacucugu acagaggcu                                                    19

<210> SEQ ID NO 426
<211> LENGTH: 19
<212> TYPE: RNA
<213> ORGANISM: Homo sapiens

<400> SEQUENCE: 426
agccucugua cagaguggg                                                    19

<210> SEQ ID NO 427
<211> LENGTH: 19
<212> TYPE: RNA
<213> ORGANISM: Homo sapiens

<400> SEQUENCE: 427
cucacagccc agacccuca                                                    19

<210> SEQ ID NO 428
<211> LENGTH: 19
<212> TYPE: RNA
<213> ORGANISM: Homo sapiens

<400> SEQUENCE: 428
ugagggucug ggcugugag                                                    19

<210> SEQ ID NO 429
<211> LENGTH: 19
<212> TYPE: RNA
<213> ORGANISM: Homo sapiens

<400> SEQUENCE: 429
ccucucugga cuacggcuu                                                        19

<210> SEQ ID NO 430
<211> LENGTH: 19
<212> TYPE: RNA
<213> ORGANISM: Homo sapiens

<400> SEQUENCE: 430
aagccguagu ccagagagg                                                        19

<210> SEQ ID NO 431
<211> LENGTH: 19
<212> TYPE: RNA
<213> ORGANISM: Homo sapiens

<400> SEQUENCE: 431
guggcaggag guggcaucu                                                        19

<210> SEQ ID NO 432
<211> LENGTH: 19
<212> TYPE: RNA
<213> ORGANISM: Homo sapiens

<400> SEQUENCE: 432
agaugccacc uccugccac                                                        19

<210> SEQ ID NO 433
<211> LENGTH: 19
<212> TYPE: RNA
<213> ORGANISM: Homo sapiens

<400> SEQUENCE: 433
uucggaagcc ccuggucua                                                        19

<210> SEQ ID NO 434
<211> LENGTH: 19
<212> TYPE: RNA
<213> ORGANISM: Homo sapiens

<400> SEQUENCE: 434
uagaccaggg gcuuccgaa                                                        19

<210> SEQ ID NO 435
<211> LENGTH: 19
<212> TYPE: RNA
<213> ORGANISM: Homo sapiens

<400> SEQUENCE: 435
agcucagcug cccuuugga                                                        19

<210> SEQ ID NO 436
<211> LENGTH: 19
<212> TYPE: RNA
<213> ORGANISM: Homo sapiens

<400> SEQUENCE: 436 uccaagggc agcugagcu                                                         19

<210> SEQ ID NO 437
<211> LENGTH: 19
<212> TYPE: RNA
<213> ORGANISM: Homo sapiens

<400> SEQUENCE: 437
ggccuggaug agagaaacu                                                       19

<210> SEQ ID NO 438
<211> LENGTH: 19
<212> TYPE: RNA
<213> ORGANISM: Homo sapiens

<400> SEQUENCE: 438
aguuucucuc auccaggcc                                                       19

<210> SEQ ID NO 439
<211> LENGTH: 19
<212> TYPE: RNA
<213> ORGANISM: Homo sapiens

<400> SEQUENCE: 439
uggcaggagg uggcaucuu                                                       19

<210> SEQ ID NO 440
<211> LENGTH: 19
<212> TYPE: RNA
<213> ORGANISM: Homo sapiens

<400> SEQUENCE: 440
aagaugccac cuccugcca                                                       19

<210> SEQ ID NO 441
<211> LENGTH: 19
<212> TYPE: RNA
<213> ORGANISM: Homo sapiens

<400> SEQUENCE: 441
acugugacug uggccucca                                                       19

<210> SEQ ID NO 442
<211> LENGTH: 19
<212> TYPE: RNA
<213> ORGANISM: Homo sapiens

<400> SEQUENCE: 442
uggaggccac agucacagu                                                       19

<210> SEQ ID NO 443
<211> LENGTH: 19
<212> TYPE: RNA
<213> ORGANISM: Homo sapiens

<400> SEQUENCE: 443
ccccuggucu aacuuggga                                                       19

<210> SEQ ID NO 444
<211> LENGTH: 19
<212> TYPE: RNA
<213> ORGANISM: Homo sapiens

<400> SEQUENCE: 444
ucccaaguua gaccagggg                                                       19

<210> SEQ ID NO 445
<211> LENGTH: 19
<212> TYPE: RNA
<213> ORGANISM: Homo sapiens

```
<400> SEQUENCE: 445
ucagcugccc uuuggaaua                                              19

<210> SEQ ID NO 446
<211> LENGTH: 19
<212> TYPE: RNA
<213> ORGANISM: Homo sapiens

<400> SEQUENCE: 446
uauuccaaag ggcagcuga                                              19

<210> SEQ ID NO 447
<211> LENGTH: 19
<212> TYPE: RNA
<213> ORGANISM: Homo sapiens

<400> SEQUENCE: 447
ucggggucga cacaucugu                                              19

<210> SEQ ID NO 448
<211> LENGTH: 19
<212> TYPE: RNA
<213> ORGANISM: Homo sapiens

<400> SEQUENCE: 448
acagaugugu cgaccccga                                              19

<210> SEQ ID NO 449
<211> LENGTH: 19
<212> TYPE: RNA
<213> ORGANISM: Homo sapiens

<400> SEQUENCE: 449
gucccugaug ucugcucca                                              19

<210> SEQ ID NO 450
<211> LENGTH: 19
<212> TYPE: RNA
<213> ORGANISM: Homo sapiens

<400> SEQUENCE: 450
uggagcagac aucagggac                                              19

<210> SEQ ID NO 451
<211> LENGTH: 19
<212> TYPE: RNA
<213> ORGANISM: Homo sapiens

<400> SEQUENCE: 451
ucaucgcuga ccgcugggu                                              19

<210> SEQ ID NO 452
<211> LENGTH: 19
<212> TYPE: RNA
<213> ORGANISM: Homo sapiens

<400> SEQUENCE: 452
acccagcggu cagcgauga                                              19

<210> SEQ ID NO 453
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 453
ggggugcuac ucugguauut t                                                   21

<210> SEQ ID NO 454
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 454
aauaccagag uagcacccct t                                                   21

<210> SEQ ID NO 455
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 455
ucuucugguu cauucuccat t                                                   21

<210> SEQ ID NO 456
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 456
uggagaauga accagaagat t                                                   21

<210> SEQ ID NO 457
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 457
acgcuggguu guuaccgcut t                                                   21

<210> SEQ ID NO 458
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 458
agcgguaaca acccagcgut t                                              21

<210> SEQ ID NO 459
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 459
cagaaguaug auuugccgut t                                              21

<210> SEQ ID NO 460
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 460
acggcaaauc auacuucugt t                                              21

<210> SEQ ID NO 461
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 461
cgcugaccgc ugggugauat t                                              21

<210> SEQ ID NO 462
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 462
uaucacccag cggucagcgt t                                              21

<210> SEQ ID NO 463
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 463
ucugguauuu ccuaggguat t                                              21

<210> SEQ ID NO 464
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 464
uacccuagga aauaccagat t                                              21

<210> SEQ ID NO 465
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 465
ccuacagggc cgaguacgat t                                              21

<210> SEQ ID NO 466
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 466
ucguacucgg cccuguaggt t                                              21

<210> SEQ ID NO 467
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 467
cgcuggguug uuaccgcuat t                                              21

<210> SEQ ID NO 468
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 468
uagcgguaac aacccagcgt t                                           21

<210> SEQ ID NO 469
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 469
ggccagugga cgauccagat t                                           21

<210> SEQ ID NO 470
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 470
ucuggaucgu ccacuggcct t                                           21

<210> SEQ ID NO 471
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 471
ugaccgcugg gugauaacat t                                           21

<210> SEQ ID NO 472
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 472
uguuaucacc cagcggucat t                                           21
```

```
<210> SEQ ID NO 473
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 473
ggucagccag guguacucat t                                              21

<210> SEQ ID NO 474
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 474
ugaguacacc uggcugacct t                                              21

<210> SEQ ID NO 475
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 475
cuacagggcc gaguacgaat t                                              21

<210> SEQ ID NO 476
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 476
uucguacucg gcccuguagt t                                              21

<210> SEQ ID NO 477
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 477
uuauuccaaa gggcagcugt t                                              21
```

<210> SEQ ID NO 478
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 478
cuggguuguu accgcuacat t        21

<210> SEQ ID NO 479
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 479
uguagcggua acaacccagt t        21

<210> SEQ ID NO 480
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 480
ugcacuaugg cuuguacaat t        21

<210> SEQ ID NO 481
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 481
uuguacaagc cauagugcat t        21

<210> SEQ ID NO 482
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 482
ccuggagagg uguccuucat t        21

<210> SEQ ID NO 483
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 483
ugaaggacac cucuccaggt t                                              21

<210> SEQ ID NO 484
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 484
agccaggugu acucaggcat t                                              21

<210> SEQ ID NO 485
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 485
ugccugagua caccuggcut t                                              21

<210> SEQ ID NO 486
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 486
acagggccga guacgaagut t                                              21

<210> SEQ ID NO 487
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 487
acuucguacu cggcccugut t							21

<210> SEQ ID NO 488
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 488
gguuguuacc gcuacagcut t							21

<210> SEQ ID NO 489
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 489
agcuguagcg guaacaacct t							21

<210> SEQ ID NO 490
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 490
ugugaugggg ucaaggacut t							21

<210> SEQ ID NO 491
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 491
aguccuugac cccaucacat t							21

<210> SEQ ID NO 492
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 492
cuggagaggu guccuucaat t                                              21

<210> SEQ ID NO 493
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 493
uugaaggaca ccucuccagt t                                              21

<210> SEQ ID NO 494
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 494
uccgcaguga aaccgccaat t                                              21

<210> SEQ ID NO 495
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 495
uuggcgguuu cacugcggat t                                              21

<210> SEQ ID NO 496
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 496
gggccgagua cgaaguggat t                                              21

<210> SEQ ID NO 497
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

```
<400> SEQUENCE: 497
uccacuucgu acucggccct t                                              21

<210> SEQ ID NO 498
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 498
ggaccgacug gccauguaut t                                              21

<210> SEQ ID NO 499
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 499
auacauggcc agucggucct t                                              21

<210> SEQ ID NO 500
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 500
caacggccug gaugagagat t                                              21

<210> SEQ ID NO 501
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 501
ucucucaucc aggccguugt t                                              21

<210> SEQ ID NO 502
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 502
aguugauccc acaggaccut t                                              21

<210> SEQ ID NO 503
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 503
agguccugug ggaucaacut t                                              21

<210> SEQ ID NO 504
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 504
ccgcagugaa accgccaaat t                                              21

<210> SEQ ID NO 505
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 505
uuuggcgguu ucacugcggt t                                              21

<210> SEQ ID NO 506
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 506
ccgagggccu agugauccut t                                              21

<210> SEQ ID NO 507
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 507
aggaucacua ggcccucggt t                                              21

<210> SEQ ID NO 508
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 508
uccucagcac cccguacuut t                                              21

<210> SEQ ID NO 509
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 509
aaguacgggg ugcugaggat t                                              21

<210> SEQ ID NO 510
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 510
cagguucggg gucgacacat t                                              21

<210> SEQ ID NO 511
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 511
ugugucgacc ccgaaccugt t                                              21

<210> SEQ ID NO 512
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

-continued

<223> OTHER INFORMATION: Description of Combined DNA/RNA Molecule:
    Synthetic oligonucleotide

<400> SEQUENCE: 512
aggugacgcc acgcaugcut t                                          21

<210> SEQ ID NO 513
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 513
agcaugcgug gcgucaccut t                                          21

<210> SEQ ID NO 514
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 514
aaaccgccaa agcccagaat t                                          21

<210> SEQ ID NO 515
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 515
uucugggcuu uggcgguuut t                                          21

<210> SEQ ID NO 516
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 516
cagugugaaa gacauagcut t                                          21

<210> SEQ ID NO 517
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

```
<220> FEATURE:
<223> OTHER INFORMATION: Description of Combined DNA/RNA Molecule:
      Synthetic oligonucleotide

<400> SEQUENCE: 517
agcuaugucu uucacacugt t                                              21

<210> SEQ ID NO 518
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 518
cccucucugg acuacggcut t                                              21

<210> SEQ ID NO 519
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 519
agccguaguc cagagagggt t                                              21

<210> SEQ ID NO 520
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 520 guucggdgguc gacacaucut t                                             21

<210> SEQ ID NO 521
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 521
agaugugucg accccgaact t                                              21

<210> SEQ ID NO 522
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                           oligonucleotide
<220> FEATURE:
<223> OTHER INFORMATION: Description of Combined DNA/RNA Molecule:
      Synthetic oligonucleotide

<400> SEQUENCE: 522
ugugugccgg cuaccgcaat t                                              21

<210> SEQ ID NO 523
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 523
uugcgguagc cggcacacat t                                              21

<210> SEQ ID NO 524
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 524
gcuucuucug guucauucut t                                              21

<210> SEQ ID NO 525
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 525
agaaugaacc agaagaagct t                                              21

<210> SEQ ID NO 526
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 526
auuccacgcu ggguuguuat t                                              21

<210> SEQ ID NO 527
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 527
uaacaaccca gcguggaaut t                                              21

<210> SEQ ID NO 528
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 528
acggcuuggc ccucugguut t                                              21

<210> SEQ ID NO 529
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 529
aaccagaggg ccaagccgut t                                              21

<210> SEQ ID NO 530
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 530
ucgcugaccg cugggugaut t                                              21

<210> SEQ ID NO 531
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 531
aucacccagc ggucagcgat t                                              21

<210> SEQ ID NO 532
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 532
aguggugacc ugaggaacut t                                              21

<210> SEQ ID NO 533
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 533
aguuccucag gucaccacut t                                              21

<210> SEQ ID NO 534
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 534
caagcagggg gacaaguaut t                                              21

<210> SEQ ID NO 535
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 535
auacuugucc cccugcuugt t                                              21

<210> SEQ ID NO 536
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 536
ugaugucugc uccagugaut t                                              21

<210> SEQ ID NO 537
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 537
aucacuggag cagacaucat t                                              21

<210> SEQ ID NO 538
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 538
cuaacuuggg aucuggaat t                                               21

<210> SEQ ID NO 539
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 539
uucccagauc ccaaguuagt t                                              21

<210> SEQ ID NO 540
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 540
ugguauuucc uaggguacat t                                              21

<210> SEQ ID NO 541
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 541
uguacccuag gaaauaccat t                                              21

<210> SEQ ID NO 542
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 542
gagguguccu ucaaggugat t                                              21

<210> SEQ ID NO 543
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 543
ucaccuugaa ggacaccuct t                                              21

<210> SEQ ID NO 544
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 544
aagcaggggg acaaguauut t                                              21

<210> SEQ ID NO 545
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 545
aauacuuguc ccccugcuut t                                              21

<210> SEQ ID NO 546
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 546
cagcuggggg ucaagacgut t                                              21

<210> SEQ ID NO 547
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 547
acgucuugac ccccagcugt t                                            21

<210> SEQ ID NO 548
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 548
cuugggaucu gggaauggat t                                            21

<210> SEQ ID NO 549
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 549
uccauuccca gaucccaagt t                                            21

<210> SEQ ID NO 550
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 550
gguauuuccu aggguacaat t                                            21

<210> SEQ ID NO 551
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 551
uuguacccua ggaaauacct t                                            21
```

```
<210> SEQ ID NO 552
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 552
ggcuaccgca agggcaagat t                                              21

<210> SEQ ID NO 553
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 553
ucuugcccuu gcgguagcct t                                              21

<210> SEQ ID NO 554
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 554 gcaggggggac aaguauucut t                                             21

<210> SEQ ID NO 555
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 555
agaauacuug uccccugct t                                               21

<210> SEQ ID NO 556
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 556
gcucagcagc aagaaugcut t                                              21
```

<210> SEQ ID NO 557
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 557
agcauucuug cugcugagcu t                                              21

<210> SEQ ID NO 558
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 558
uugggaucug ggaauggaat t                                              21

<210> SEQ ID NO 559
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 559
uuccauuccc agaucccaat t                                              21

<210> SEQ ID NO 560
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 560
ccaaagccca gaagaugcut t                                              21

<210> SEQ ID NO 561
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 561
agcaucuucu gggcuuuggt t                                              21

<210> SEQ ID NO 562
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 562
gcuaccgcaa gggcaagaat t                                              21

<210> SEQ ID NO 563
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 563
uucuugcccu ugcgguagct t                                              21

<210> SEQ ID NO 564
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 564
ugguggcagg agguggcaut t                                              21

<210> SEQ ID NO 565
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 565
augccaccuc cugccaccat t                                              21

<210> SEQ ID NO 566
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 566
cccacucugu acagaggcut t						21

<210> SEQ ID NO 567
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 567
agccucugua cagagugggt t						21

<210> SEQ ID NO 568
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 568
cucacagccc agacccucat t						21

<210> SEQ ID NO 569
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 569
ugagggucug ggcugugagt t						21

<210> SEQ ID NO 570
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 570
ccucucugga cuacggcuut t						21

<210> SEQ ID NO 571
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 571
aagccguagu ccagagaggt t                            21

<210> SEQ ID NO 572
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 572
guggcaggag guggcaucut t                            21

<210> SEQ ID NO 573
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 573
agaugccacc uccugccact t                            21

<210> SEQ ID NO 574
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 574
uucggaagcc ccuggucuat t                            21

<210> SEQ ID NO 575
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 575
uagaccaggg gcuuccgaat t                            21

<210> SEQ ID NO 576
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 576
agcucagcug cccuuuggat t                                              21

<210> SEQ ID NO 577
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 577
uccaaagggc agcugagcut t                                              21

<210> SEQ ID NO 578
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 578
ggccuggaug agagaaacut t                                              21

<210> SEQ ID NO 579
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 579
aguuucucuc auccaggcct t                                              21

<210> SEQ ID NO 580
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 580
uggcaggagg uggcaucuut t                                              21

<210> SEQ ID NO 581
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 581
aagaugccac cuccugccat t    21

<210> SEQ ID NO 582
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 582
ucggaagccc cuggucuaat t    21

<210> SEQ ID NO 583
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 583
uuagaccagg ggcuuccgat t    21

<210> SEQ ID NO 584
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 584
gcucagcugc ccuuuggaat t    21

<210> SEQ ID NO 585
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 585
uuccaaaggg cagcugagct t    21

<210> SEQ ID NO 586
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 586
acugugacug uggccuccat t                                              21

<210> SEQ ID NO 587
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 587
uggaggccac agucacagut t                                              21

<210> SEQ ID NO 588
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 588
aggagguggc aucuugucut t                                              21

<210> SEQ ID NO 589
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 589
agacaagaug ccaccuccut t                                              21

<210> SEQ ID NO 590
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 590
ccccuggucu aacuugggat t                                              21

<210> SEQ ID NO 591
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 591
ucccaaguua gaccaggggt t                                              21

<210> SEQ ID NO 592
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 592
ucagcugccc uuuggaauat t                                              21

<210> SEQ ID NO 593
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 593
uauuccaaag ggcagcugat t                                              21

<210> SEQ ID NO 594
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 594 ucgggucga cacaucugut t                                               21

<210> SEQ ID NO 595
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 595
acagaugugu cgacccgat t                                               21

<210> SEQ ID NO 596
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 596
gucccugaug ucugcuccat t                                              21

<210> SEQ ID NO 597
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 597
uggagcagac aucagggact t                                              21

<210> SEQ ID NO 598
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 598
cccuggucua acuugggaut t                                              21

<210> SEQ ID NO 599
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 599
aucccaaguu agaccagggt t                                              21

<210> SEQ ID NO 600
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 600
cagcugcccu uuggaauaat t                                              21

<210> SEQ ID NO 601
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
          oligonucleotide
<220> FEATURE:
<223> OTHER INFORMATION: Description of Combined DNA/RNA Molecule:
      Synthetic oligonucleotide

<400> SEQUENCE: 601
uuauuccaaa gggcagcugt t                                              21

<210> SEQ ID NO 602
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 602
ucaucgcuga ccgcugggut t                                              21

<210> SEQ ID NO 603
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 603
acccagcggu cagcgaugat t                                              21

<210> SEQ ID NO 604
<211> LENGTH: 19
<212> TYPE: RNA
<213> ORGANISM: Homo sapiens

<400> SEQUENCE: 604
ccuggagagg uguccuuca                                                 19

<210> SEQ ID NO 605
<211> LENGTH: 19
<212> TYPE: RNA
<213> ORGANISM: Homo sapiens

<400> SEQUENCE: 605
ugaaggacac cucuccagg                                                 19

<210> SEQ ID NO 606
<211> LENGTH: 19
<212> TYPE: RNA
<213> ORGANISM: Homo sapiens

<400> SEQUENCE: 606
caacggccug gaugagaga                                                 19

<210> SEQ ID NO 607
<211> LENGTH: 19
<212> TYPE: RNA
<213> ORGANISM: Homo sapiens

<400> SEQUENCE: 607
```

```
ucucucaucc aggccguug                                                19

<210> SEQ ID NO 608
<211> LENGTH: 19
<212> TYPE: RNA
<213> ORGANISM: Homo sapiens

<400> SEQUENCE: 608
aguggugacc ugaggaacu                                                19

<210> SEQ ID NO 609
<211> LENGTH: 19
<212> TYPE: RNA
<213> ORGANISM: Homo sapiens

<400> SEQUENCE: 609
aguuccucag gucaccacu                                                19

<210> SEQ ID NO 610
<211> LENGTH: 19
<212> TYPE: RNA
<213> ORGANISM: Homo sapiens

<400> SEQUENCE: 610
cagcugcccu uuggaauaa                                                19

<210> SEQ ID NO 611
<211> LENGTH: 19
<212> TYPE: RNA
<213> ORGANISM: Homo sapiens

<400> SEQUENCE: 611
uuauuccaaa gggcagcug                                                19
```